(12) United States Patent
Zeng et al.

(10) Patent No.: US 10,858,365 B2
(45) Date of Patent: Dec. 8, 2020

(54) TRIAZOLO-PYRIMIDINE COMPOUNDS AND USES THEREOF

(71) Applicant: Dizal (Jiangsu) Pharmaceutical Co., Ltd., Shanghai (CN)

(72) Inventors: Qingbei Zeng, Shanghai (CN); Changhe Qi, Shanghai (CN); Honchung Tsui, Shanghai (CN); Zhenfan Yang, Shanghai (CN); Xiaolin Zhang, Shanghai (CN)

(*) Notice: Subject to any disclaimer, the term of this patent is extended or adjusted under 35 U.S.C. 154(b) by 0 days.

(21) Appl. No.: 16/910,334

(22) Filed: Jun. 24, 2020

(65) Prior Publication Data
US 2020/0331918 A1    Oct. 22, 2020

Related U.S. Application Data

(63) Continuation of application No. PCT/CN2019/105591, filed on Sep. 12, 2019.

(30) Foreign Application Priority Data

Sep. 12, 2018 (WO) ............... PCT/CN2018/105220

(51) Int. Cl.
| | | |
|---|---|---|
| *C07D 487/04* | (2006.01) | |
| *C07D 519/00* | (2006.01) | |
| *A61K 33/243* | (2019.01) | |
| *A61K 45/06* | (2006.01) | |

(52) U.S. Cl.
CPC ......... *C07D 487/04* (2013.01); *C07D 519/00* (2013.01); *A61K 33/243* (2019.01); *A61K 45/06* (2013.01)

(58) Field of Classification Search
CPC .............................. C07D 48/04; A61K 31/519
USPC ..................................... 544/263; 514/259.31
See application file for complete search history.

(56) References Cited

FOREIGN PATENT DOCUMENTS

| CN | 1596258 A | 3/2005 |
|---|---|---|
| CN | 109535161 A | 3/2019 |
| EP | 0976753 A1 | 2/2000 |
| EP | 1544200 A1 | 6/2005 |
| WO | 2018166493 A1 | 9/2018 |
| WO | 2018184590 A1 | 10/2018 |
| WO | 2019168847 A1 | 9/2019 |
| WO | 2019206336 A1 | 10/2019 |

OTHER PUBLICATIONS

International Search Report of PCT Application No. PCT/CN2019/105591, dated Nov. 28, 2019.
Written Opinion of the International Searching Authority of PCT Application No. PCT/CN2019/105591, dated Nov. 28, 2019.

*Primary Examiner* — Jeffrey H Murray
(74) *Attorney, Agent, or Firm* — Jun He Law Offices P.C.; Zhaohui Wang

(57) ABSTRACT

The present disclosure relates to novel triazolo-pyrimidine compounds targeting adenosine receptors (especially A1 and A2, particularly A2a). The present disclosure also relates to pharmaceutical compositions comprising one or more of the compounds as an active ingredient, and use of the compounds in the treatment of adenosine receptor (AR) associated diseases, for example cancer such as NSCLC, RCC, prostate cancer, and breast cancer.

9 Claims, No Drawings

TRIAZOLO-PYRIMIDINE COMPOUNDS AND USES THEREOF

CROSS-REFERENCE TO RELATED APPLICATIONS

This application is a Continuation of PCT Patent Application No. PCT/CN2019/105591, filed on Sep. 12, 2019, which claims foreign priority of PCT Patent Application No. PCT/2018/105220, filed on Sep. 12, 2018, now abandoned. Each of these applications is hereby incorporated by reference herein in its entirety.

FIELD OF THE DISCLOSURE

The present disclosure relates to novel triazolo-pyrimidine compounds targeting adenosine receptors (especially A1 and A2, particularly A2a). The present disclosure also relates to pharmaceutical compositions comprising one or more of the compounds as an active ingredient, and use of the compounds in the treatment of adenosine receptor (AR) associated diseases, for example cancer such as non-small cell lung cancer (NSCLC), renal cell carcinoma (RCC), prostate cancer, and breast cancer.

BACKGROUND

Adenosine is a naturally occurring nucleoside, which elicits a variety of physiological responses by interacting with a family of adenosine receptors. Four subtypes of adenosine receptors (A1, A2a, A2b, and A3) in humans have been differentiated based on their biochemical and pharmacological properties such as ligand binding characteristics, glycosylations, and functions.

The inflammatory response helps eliminate harmful agents from the body, but inflammation is also a non-specific response that can harm healthy tissue. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma, as well as growth of tumors.

It is reported that adenosine receptors play a non-redundant role in down-regulation of inflammation in vivo by acting as a physiological "STOP" (a termination mechanism) that can limit the immune response and thereby protect normal tissues form excessive immune damage during pathogenesis of different diseases. Adenosine receptors, such as A2a, A2b, and A3, are shown to down-regulate the immune response during inflammation and protect tissues from immune damage. Inhibition of signaling through the adenosine receptor can be used to intensify and prolong the immune response. Adenosine suppresses prolonged inflammation acting through the A2a adenosine receptor (Ohta et al., Nature 2001; 414:916-920). A2b adenosine receptor has been implicated in regulation of cell growth (See Adenosine A2b Receptors as Therapeutic Targets, Drug Dev Res 45:198; Feoktistov et al., Trends Pharmacol Sci 19:148-153).

Therefore, compounds that targeting adenosine receptors are needed as pharmacological tools and are of considerable interest as drugs for treating Adenosine receptor-associated disease such as cancer (e.g., NSCLC, RCC, prostate cancer, or breast cancer), Parkinson disease, epilepsy, cerebral ischemia and stroke, depression, cognitive impairment, HIV, ADA-SCID, AHIF and chronic heart failure, chronic obstructive pulmonary disease (COPD), or asthma.

SUMMARY

In one aspect, the present disclosure provides a compound represented by Formula (I):

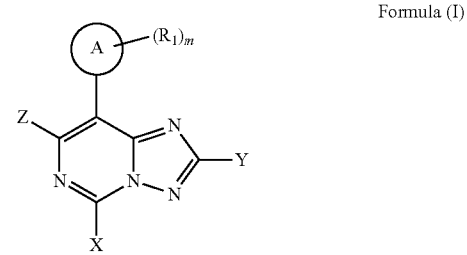

Formula (I)

or a pharmaceutically acceptable salt thereof, wherein X, ring A, Z, Y, $R_1$ and m are as herein defined.

In one aspect, the present disclosure provides a compound represented by Formula (Ia):

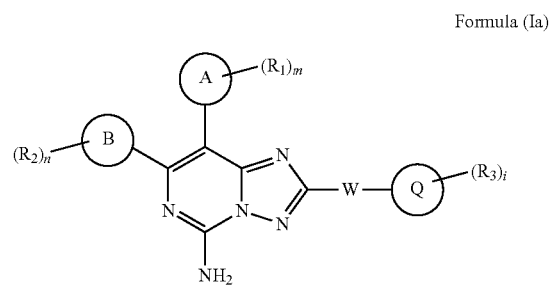

Formula (Ia)

or a pharmaceutically acceptable salt thereof, wherein ring A, ring B, ring Q, W, $R_1$, $R_2$, $R_3$, m, n and i are as herein defined.

In one aspect, the present disclosure provides a compound represented by Formula (Ib):

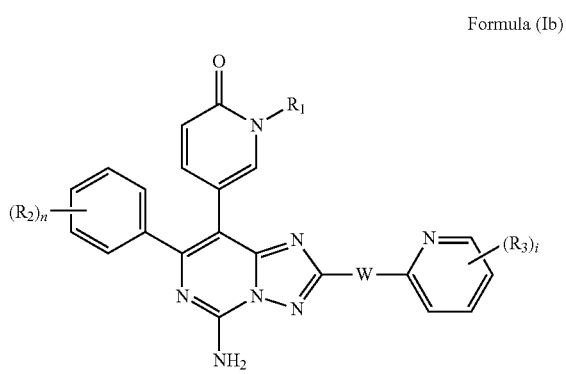

Formula (Ib)

or a pharmaceutically acceptable salt thereof, wherein W, $R_1$, $R_2$, $R_3$, n and i are as herein defined.

In another aspect, the present disclosure also relates to pharmaceutical compositions comprising one or more of the compounds, or a pharmaceutically acceptable salt thereof, as an active ingredient, and use of the compounds, or a pharmaceutically acceptable salt thereof, in the treatment of adenosine receptors (AR) associated diseases, for example cancer such as NSCLC, RCC, prostate cancer, or breast cancer.

DETAILED DESCRIPTION

In one aspect, the present disclosure provides compounds of Formula (I):

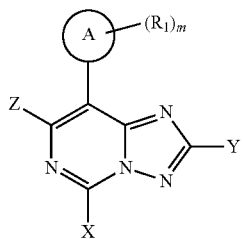

Formula (I)

or a pharmaceutically acceptable salt thereof, wherein:
wherein,
X is selected from amino, halogen, hydroxyl, cyano, $C_{1-12}$ alkoxyl, N—($C_{1-12}$ alkyl)amino, N,N—($C_{1-12}$ alkyl)$_2$amino, $C_{1-12}$ alkanoylamino, ring A is 3-12 membered saturated or unsaturated mono- or poly-cyclic heterocyclyl, Y is —W—V, wherein —W— is bond, O, S, —NH—, —$C_{1-12}$ alkylene-, —$C_{1-12}$ alkylene-NH—, V is hydrogen, $C_{1-12}$ alkyl, $C_{1-12}$ alkoxyl, $C_{1-12}$ alkyl-OH, amino, carbamoyl, urea, carbamate, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, 3-12 membered saturated or unsaturated carbocyclyl, or 3-12 membered saturated or unsaturated heterocyclyl, which can be optionally mono- or independently multi-substituted by $R_3$, Z is selected from hydrogen, halogen, cyano, hydroxyl, amino, carbamoyl, urea, carbamate, $C_{1-12}$ alkyl, N—($C_{1-12}$ alkyl)amino, N,N—($C_{1-12}$ alkyl)$_2$amino, 3-12 membered saturated or unsaturated carbocyclyl, or 3-12 membered saturated or unsaturated heterocyclyl, which can be optionally mono- or independently multi-substituted by $R_2$, each $R_1$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein said 3-10 membered saturated or unsaturated carbocyclyl, or 3-10 membered saturated or unsaturated heterocyclyl can be optionally mono- or independently multi-substituted by $R_4$, each $R_2$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein said 3-10 membered saturated or unsaturated carbocyclyl, or 3-10 membered saturated or unsaturated heterocyclyl can be optionally mono- or independently multi-substituted by $R_5$, each $R_3$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, a 3-10 membered saturated or unsaturated carbocyclyl, or a 3-10 membered saturated or unsaturated heterocyclyl, wherein said 3-10 membered saturated or unsaturated carbocyclyl, or 3-10 membered saturated or unsaturated heterocyclyl can be optionally mono- or independently multi-substituted by $R_6$, wherein each $R_4$, $R_5$ or $R_6$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, m is 0, 1, 2, 3 or 4.

In some embodiments, X is selected from amino, halogen, hydroxyl, cyano, $C_{1-12}$ alkoxyl, N—($C_{1-12}$ alkyl)amino, N,N—($C_{1-12}$ alkyl)$_2$amino, or $C_{1-12}$ alkanoylamino.

In some embodiments, X is amino.

In some embodiments, ring A is 3-12 membered saturated or unsaturated mono- or poly-cyclic heterocyclyl having 1, 2, or 3 heteroatoms selected from N, O, or S.

In some embodiments, ring A is 6-10 membered unsaturated mono- or poly-cyclic heterocyclyl selected from the group consisting of pyridinyl, pyrazinyl, pyrimidinyl, pyridazinyl, triazinyl, pyridonyl, pyrimidonyl, pyrazinonyl, pyrimidonyl, pyridazonyl, triazinonyl, phenyl fused ring or pyridinyl fused ring.

In some embodiments, ring A is 6-10 membered unsaturated mono- or poly-cyclic heterocyclyl selected from

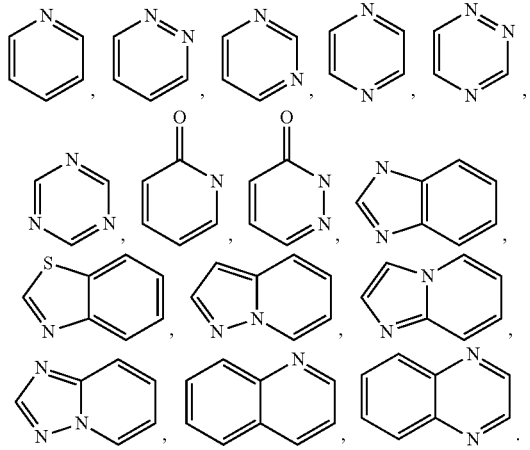

In some embodiments, each $R_1$ is independently selected from: halogen, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, or 3-6 membered saturated carbocyclyl or heterocyclyl. In some embodiments, the 3-6 membered saturated carbocyclyl or heterocyclyl is cyclopropyl, cyclobutyl, oxacyclopentanyl, oxetanyl, or 1,1-dioxothietanyl.

In some embodiments, m is 0.
In some embodiments, m is 1.
In some embodiments, m is 2.

In some embodiments, m is 3.

In some embodiments, m is 4.

In some embodiments, Y is —W—V.

In some embodiments, —W— is $C_{1-12}$ alkylene, $C_{1-12}$ alkylene-NH— or —NH—. In some embodiments, —W— is $C_{1-6}$ alkylene. In some embodiments, —W— is $C_{1-3}$ alkylene.

In some embodiments, —W— is methylene or ethylene.

In some embodiments, —W— is methylene.

In some embodiments, V is halogen, $C_{1-12}$ alkyl, $C_{1-12}$ alkoxyl, $C_{1-12}$ alkyl-OH, amino, carbamoyl, urea, carbamate, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, $C_{1-12}$ alkanoylamino, which can be optionally mono- or independently multi-substituted by $R_3$.

In some embodiments, V is 5-6 membered saturated or unsaturated carbocyclyl, or 5-6 membered saturated or unsaturated heterocyclyl, which can be optionally mono- or independently multi-substituted by $R_3$.

In some embodiments, V is 5-6 membered saturated or unsaturated carbocyclyl, or 5-6 membered saturated or unsaturated heterocyclyl selected from:

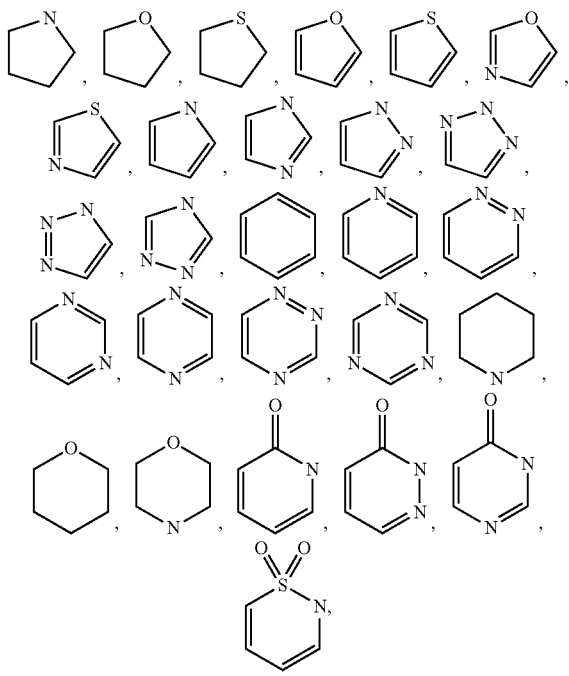

which can be optionally mono- or independently multi-substituted by $R_3$.

In some embodiments, V is pyrrolidyl, tetrahydrofuryl, thienyl, triazolyl, thiazolyl, phenyl, or pyridinyl, which can be optionally mono- or independently multi-substituted by $R_3$.

In some embodiments, each $R_3$ is independently selected from halogen, cyano, amino, $C_{1-12}$ alkyl, $C_{1-12}$ alkoxyl, $C_{1-12}$ haloalkoxyl, N—($C_{1-12}$ alkyl) amino, N,N—($C_{1-12}$ alkyl)$_2$amino, $C_{1-12}$ alkanoylamino, a 3-10 membered saturated or unsaturated carbocyclyl, or a 3-10 membered saturated or unsaturated heterocyclyl, wherein the 3-10 membered saturated or unsaturated carbocyclyl, or 3-10 membered saturated or unsaturated heterocyclyl can be optionally mono- or independently multi-substituted by $R_6$.

In some embodiments, —W— is ethylene, V is $C_{1-12}$ alkoxyl.

In some embodiments, —W— is methylene, V is $C_{1-12}$ alkyl which is further substituted by $C_{1-12}$ alkoxyl.

In some embodiments, —W— is ethylene, V is methoxyl.

In some embodiments, —W— is methylene, V is pyrrolidyl, tetrahydrofuryl, thienyl, triazolyl, thiazolyl, phenyl, or pyridinyl, which can be optionally mono- or independently multi-substituted by $R_3$, wherein each $R_3$ is independently selected from halogen, cyano, amino, $C_{1-12}$ alkyl, $C_{1-12}$ alkoxyl, $C_{1-12}$ haloalkoxyl, N—($C_{1-12}$ alkyl) amino, N,N—($C_{1-12}$ alkyl)$_2$amino, $C_{1-12}$ alkanoylamino.

In some embodiments, Z is hydrogen, halogen, cyano, hydroxyl, amino, carbamoyl, urea, carbamate, N—($C_{1-12}$ alkyl) amino, N,N—($C_{1-12}$ alkyl)$_2$amino, $C_{1-12}$ alkyl, 3-12 membered saturated or unsaturated carbocyclyl, or 3-12 membered saturated or unsaturated heterocyclyl which can be optionally mono- or independently multi-substituted by $R_2$, wherein each $R_2$ is independently selected from halogen, cyano, $C_{1-12}$ alkyl, $C_{1-12}$ haloalkyl, $C_{1-12}$ alkoxyl, or $C_{1-12}$ haloalkoxyl.

In some embodiments, Z is halogen, amino, N—($C_{1-12}$ alkyl) amino, or N,N—($C_{1-12}$ alkyl)$_2$amino.

In some embodiments, Z is 3-12 membered saturated or unsaturated carbocyclyl, or 3-12 membered saturated or unsaturated heterocyclyl which can be optionally mono- or independently multi-substituted by $R_2$.

In some embodiments, Z is 3-12 membered saturated or unsaturated carbocyclyl, or 3-12 membered saturated or unsaturated heterocyclyl selected from:

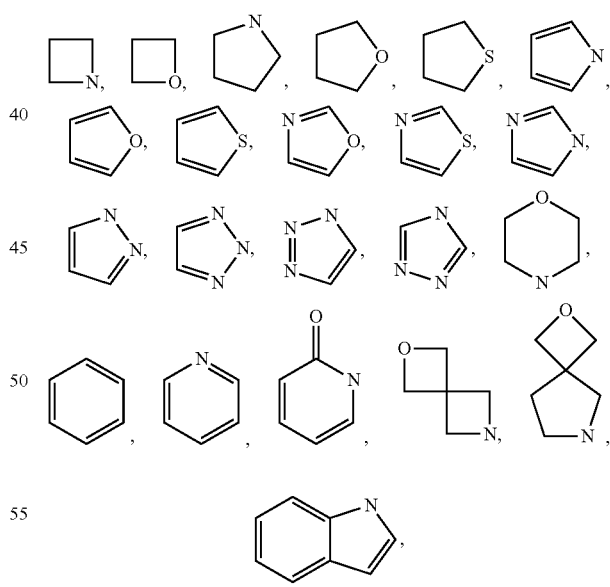

which can be optionally mono- or independently multi-substituted by $R_2$.

In some embodiments, each $R_2$ is independently selected from halogen, cyano, $C_{1-12}$ alkyl, $C_{1-12}$ haloalkyl, $C_{1-12}$ alkoxyl, or $C_{1-12}$ haloalkoxyl.

In another aspect the present disclosure-provides compounds of Formula (Ia):

Formula (Ia)

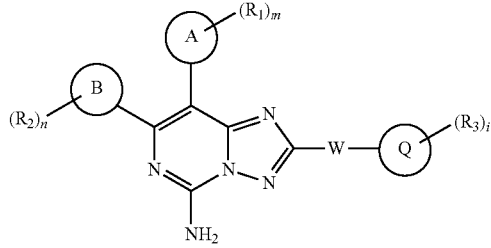

or a pharmaceutically acceptable salt thereof,
wherein, ring A is 6-10 membered unsaturated mono- or polycyclic heterocyclyl having 1, 2, or 3 heteroatoms selected from N, O, or S;

ring B is selected from 3-12 membered saturate saturated or unsaturated carbocyclyl, or 3-12 membered saturated or unsaturated heterocyclyl;

ring Q is 5-6 membered saturated or unsaturated carbocyclyl, or 5-6 membered saturated or unsaturated heterocyclyl;

W is bond, O, S, —NH—, $C_{1-12}$ alkylene, or $C_{1-12}$ alkylene-NH—, each $R_1$ is independently selected from halogen, hydroxyl, cyano, amino, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, carbamoyl, N—($C_{1-12}$ alkyl)carbamoyl, N,N—($C_{1-12}$ alkyl)$_2$carbamoyl, a 3-10 membered saturated or unsaturated carbocyclyl, or a 3-10 membered saturated or unsaturated heterocyclyl, wherein said 3-10 membered saturated or unsaturated carbocyclyl, or 3-10 membered saturated or unsaturated heterocyclyl can be optionally mono- or independently multi-substituted by $R_4$;

each $R_2$ is independently selected from halogen, hydroxyl, cyano, amino, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, carbamoyl, N—($C_{1-12}$ alkyl)carbamoyl, N,N—($C_{1-12}$ alkyl)$_2$carbamoyl;

each $R_3$ is independently selected from halogen, hydroxyl, cyano, amino, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, carbamoyl, N—($C_{1-12}$ alkyl)carbamoyl, N,N—($C_{1-12}$ alkyl)$_2$carbamoyl;

each $R_4$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, carbamoyl, N—($C_{1-12}$ alkyl)carbamoyl, N,N—($C_{1-12}$ alkyl)$_2$carbamoyl, $C_{1-12}$ alkanoylamino;

and m is 0, 1, 2, 3 or 4;

n is 0, 1, 2, 3 or 4;

i is 0, 1, 2, 3 or 4.

In some embodiments, ring A is selected from

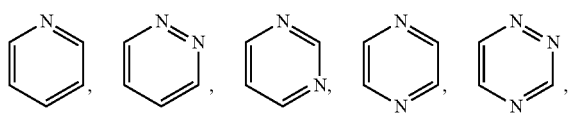

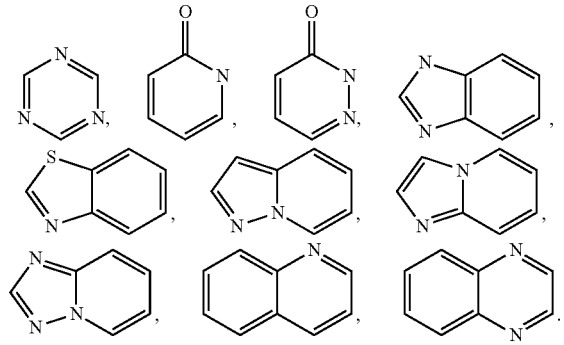

In some embodiments, ring A is selected from the group consisting of: 4-pyridinyl, 4-pyridazinyl, 5-pyridinyl-2-one, imidazo[1,2-a]pyridin-6-yl, [1,2,4]triazolo[4,3-a]pyridin-6-yl, 6-benzimidazolyl, 6-benzthiazolyl, quinolin-6-yl, or quinoxalin-6-yl.

In some embodiments, each $R_1$ is independently selected from hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxyl, ethoxyl, difluoromethoxyl, trifluoromethoxyl, trifluoroethoxyl, methylamino, dimethylamino, ethylamino, isopropanylamino, hydroxymethyl, hydroxyethyl, cyclopropyl, cyclobutyl, 3-oxacyclopentanyl, 3-oxetanyl, or 1,1-dioxothietanyl, which can be optionally further mono- or independently multi-substituted by $R_4$.

In some embodiments, one of $R_1$ is selected from cyclopropyl, cyclobutyl, tetrahydrofuryl, oxetanyl, or 1,1-dioxothietanyl, which can be optionally mono- or independently multi-substituted by $R_4$.

In some embodiments, m is 0, 1 or 2.

In some embodiments, m=0, 1, or 2; each $R_1$ is independently selected from: hydroxyl, fluoro, chloro, bromo, amino, carbamoyl, urea, carbamate, cyano, methyl, ethyl, n-propyl, isopropyl, fluoromethyl, difluoromethyl, trifluoromethyl, fluoroethyl, difluoroethyl, trifluoroethyl, methoxyl, ethoxyl, difluoromethoxyl, trifluoromethoxyl, trifluoroethoxyl, methylamino, dimethylamino, ethylamino, hydroxymethyl, hydroxyethyl, cyclopropyl, 3-oxacyclopentanyl, 3-oxetanyl, or 1,1-dioxothietanyl, which can be optionally further mono- or independently multi-substituted by $R_4$; and each $R_4$ is independently selected from halogen, hydroxyl, cyano, amino, carbamoyl, urea, carbamate, $C_{1-12}$ alkyl, $C_{1-12}$ haloalkyl, $C_{1-12}$ alkoxyl, $C_{1-12}$ haloalkoxyl, $C_{1-12}$ alkyl-OH, N—($C_{1-12}$ alkyl)amino, N,N—($C_{1-12}$ alkyl)$_2$amino, N—($C_{1-12}$ alkyl)carbamoyl, N,N—($C_{1-12}$ alkyl)$_2$carbamoyl, or $C_{1-12}$ alkanoylamino.

In some embodiments, ring A is 4-pyridinyl, 4-pyridazinyl, 5-pyridinyl-2-one, imidazo[1,2-a]pyridin-6-yl, [1,2,4]triazolo[4,3-a]pyridin-6-yl, 6-benzimidazolyl, 6-benzthiazolyl, quinolin-6-yl, or quinoxalin-6-yl; m is 0, 1 or 2; and each $R_1$ is independently selected from fluoro, chloro, cyano, amino, methyl, ethyl, n-propyl, isopropyl, trifluoromethyl, methoxyl, difluoromethoxyl, methylamino, dimethylamino, hydroxyethyl, cyclopropyl, oxacyclopentanyl, 3-oxetanyl, or 1,1-dioxothietanyl.

In some embodiments, ring Q is 5-6 membered saturated or unsaturated carbocyclyl, or 5-6 membered saturated or unsaturated heterocyclyl selected from:

In some embodiments, ring Q is pyrrolidyl, phenyl, or pyridinyl.

In some embodiments, each $R_3$ is independently selected from halogen, cyano, amino, $C_{1-12}$ alkyl, $C_{1-12}$ alkoxyl, $C_{1-12}$ haloalkoxyl, N,N—$(C_{1-12}$ alkyl$)_2$amino, or $C_{1-12}$ alkanoylamino.

In some embodiments, each $R_3$ is independently selected from fluoro, chloro, cyano, amino, methyl, ethyl, n-propyl, isopropyl, methoxyl, fluoromethyl, difluoromethyl, trifluoromethyl, difluoromethoxyl, methylamino, dimethylamino, isopropylamino, ethoxyl, trifluoroethoxy, or ethylamino.

In some embodiments, each $R_3$ is independently selected from: amino, cyano, methyl, fluoro, chloro, difluoromethoxyl, methoxyl, or dimethylamino.

In some embodiments, i is 0.
In some embodiments, i is 1.
In some embodiments, i is 2.
In some embodiments, i is 3.
In some embodiments, i is 4.
In some embodiments, i is 0, 1 or 2.

In some embodiments, i is 0, 1, or 2; each $R_3$ is independently selected from fluoro, chloro, cyano, amino, methyl, ethyl, n-propyl, isopropyl, methoxyl, fluoromethyl, difluoromethyl, trifluoromethyl, difluoromethoxyl, methylamino, dimethylamino, isopropylamino, ethoxyl, trifluoroethoxy, or ethylamino.

In some embodiments, ring Q is pyrrolidyl, phenyl, or pyridinyl; i=0, 1 or 2; and each $R_3$ is independently selected from: amino, cyano, methyl, fluoro, chloro, difluoromethoxyl, methoxyl, or dimethylamino.

In some embodiments, ring B is selected from:

In some embodiments, ring B is selected from 1-azetidinyl, 2-oxa-6-aza-spiro[3.4]octan-5-yl, 1-pyrrolidyl, 1-piperazinyl, 2-oxazolyl, 2-thiazolyl, 1-pyrazolyl, 4-pyrazolyl, 1-[1,2,3]triazolyl, 1-[1,2,5]triazolyl, phenyl, 2-pyridinyl, 3-pyridinyl, 4-morpholinyl, or 5-indolyl.

In some embodiments, each $R_2$ is independently selected from fluoro, chloro, cyano, methyl, amino, ethyl, methoxyl, fluoromethyl, difluoromethyl, trifluoromethyl, difluoromethoxyl, trifluoromethoxyl, ethoxyl, methylamino, dimethylamino, ethylamino, isopropanylamino, hydromethyl, or hydroxyethyl.

In some embodiments, each $R_2$ is independently selected from cyano, chloro, fluoro, methyl, methoxyl, difluoromethyl, trifluoromethyl, or dimethylamino.

In some embodiments, n is 0.
In some embodiments, n is 1.
In some embodiments, n is 2.
In some embodiments, n is 3.
In some embodiments, n is 4.
In some embodiments, n is 0, 1 or 2.

In some embodiments, n is 0, 1, or 2; and each $R_2$ is independently selected from cyano, chloro, fluoro, methyl, methoxyl, difluoromethyl, trifluoromethyl, or dimethylamino.

In some embodiments, ring B is selected from 1-azetidinyl, 2-oxa-6-aza-spiro[3.4]octan-5-yl, 1-pyrrolidyl, 1-piperazinyl, 2-oxazolyl, 2-thiazolyl, 1-pyrazolyl, 4-pyrazolyl, 1-[1,2,3]triazolyl, 1-[1,2,5]triazolyl, phenyl, 2-pyridinyl, 3-pyridinyl, 4-morpholinyl, or 5-indolyl; n is 0, 1, or 2; and each $R_2$ is independently selected from cyano, chloro, fluoro, methyl, methoxyl, difluoromethyl, trifluoromethyl, or dimethylamino.

In yet another aspect, the present disclosure provides compounds of Formula (Ib):

Formula (Ib)

or a pharmaceutically acceptable salt thereof, wherein,

R$_1$ is selected from hydroxyl, cyano, amino, C$_{1-12}$ alkyl, C$_{1-12}$ haloalkyl, C$_{1-12}$ alkoxyl, C$_{1-12}$ haloalkoxyl, C$_{1-12}$ alkyl-OH, N—(C$_{1-12}$ alkyl)amino, N,N—(C$_{1-12}$ alkyl)$_2$ amino, a 3-10 membered saturated or unsaturated carbocyclyl, or a 3-10 membered saturated or unsaturated heterocyclyl, which can be optionally mono- or independently multi-substituted by R$_4$;

each R$_2$ is independently selected from halogen, hydroxyl, cyano, amino, C$_{1-12}$ alkyl, C$_{1-12}$ haloalkyl, C$_{1-12}$ alkoxyl, C$_{1-12}$ haloalkoxyl, C$_{1-12}$ alkyl-OH, N—(C$_{1-12}$ alkyl)amino, or N,N—(C$_{1-12}$ alkyl)$_2$amino;

each R$_3$ is independently selected from halogen, hydroxyl, cyano, amino, C$_{1-12}$ alkyl, C$_{1-12}$ haloalkyl, C$_{1-12}$ alkoxyl, C$_{1-12}$ haloalkoxyl, C$_{1-12}$ alkyl-OH, N—(C$_{1-12}$ alkyl)amino, or N,N—(C$_{1-12}$ alkyl)$_2$amino;

each R$_4$ is independently selected from halogen, hydroxyl, cyano, amino, C$_{1-12}$ alkyl, C$_{1-12}$ haloalkyl, C$_{1-12}$ alkoxyl, C$_{1-12}$ haloalkoxyl, C$_{1-12}$ alkyl-OH, N—(C$_{1-12}$ alkyl) amino, N,N—(C$_{1-12}$ alkyl)$_2$amino, or C$_{1-12}$ alkanoylamino;

W is bond, O, S, —NH—, C$_{1-12}$ alkylene, or C$_{1-12}$ alkylene-NH—, and n is 0, 1, 2, 3 or 4;

i is 0, 1, 2, 3 or 4.

In some embodiments, R$_1$ is C$_{1-12}$ alkyl.

In some embodiments, R$_1$ is methyl.

In some embodiments, R$_1$ is isopropyl.

In some embodiments, n=1.

In some embodiments, R$_2$ is halogen.

In some embodiments, R$_2$ is fluoro.

In some embodiments, R$_2$ is halogen, and n=1.

In some embodiments, R$_2$ is fluoro, and n=1.

In some embodiments, R$_3$ is halogen.

In some embodiments, R$_3$ is fluoro.

In some embodiments, R$_3$ is halogen, and i=1.

In some embodiments, R$_3$ is fluoro, and i=1.

In some embodiments, W is methylene.

In one aspect, the present disclosure provides a compound of Formula (I) selected from:

8-(2,6-dimethylpyridin-4-yl)-7-(4-fluorophenyl)-2-[(3-fluoropyridin-2-yl)methyl]-[1,2,4]triazolo[1,5-c]pyrimidin-5-amine, 7-(4-fluorophenyl)-2-((3-fluoropyridin-2-yl)methyl)-8-(2-methylpyridin-4-yl)-[1,2,4]triazolo[1,5-c]pyrimidin-5-amine, 8-(2-chloropyridin-4-yl)-7-(4-fluorophenyl)-2-((3-fluoropyridin-2-yl)methyl)-[1,2,4]triazolo[1,5-c]pyrimidin-5-amine, 2-[(2,6-difluorophenyl)methyl]-7-(4-fluorophenyl)-8-[2-(trifluoromethyl)pyridin-4-yl]-[1,2,4]triazolo[1,5-c]pyrimidin-5-amine, 2-(2,6-difluorobenzyl)-7-(4-fluorophenyl)-8-(2-methoxypyridin-4-yl)-[1,2,4]triazolo[1,5-c]pyrimidin-5-amine, 2-(2,6-difluorobenzyl)-7-(4-fluorophenyl)-8-(pyridazin-4-yl)-[1,2,4]triazolo[1,5-c]pyrimidin-5-amine, 7-(4-fluorophenyl)-8-(2-methylpyridin-4-yl)-2-[(1,3-thiazol-4-yl)methyl]-[1,2,4]triazolo[1,5-c]pyrimidin-5-amine, 2-[(3-chlorophenyl)methyl]-7-(4-fluorophenyl)-8-(2-methylpyridin-4-yl)-[1,2,4]triazolo[1,5-c]pyrimidin-5-amine, 5-(5-amino-2-(2,6-difluorobenzyl)-7-(4-fluorophenyl)-[1,2,4]triazolo[1,5-c]pyrimidin-8-yl)-1-methylpyridin-2(1H)-one, 2-(2,6-difluorobenzyl)-8-(2-(dimethylamino)pyridin-4-yl)-7-(4-fluorophenyl)-[1,2,4]triazolo[1,5-c]pyrimidin-5-amine, 7-(4-fluorophenyl)-8-(2-methylpyridin-4-yl)-2-[(1,3-thiazol-4-yl)methyl]-[1,2,4]triazolo[1,5-c]pyrimidin-5-amine, 2-[1-(2,6-difluorophenyl)ethyl]-7-(4-fluorophenyl)-8-(2-methylpyridin-4-yl)-[1,2,4]triazolo[1,5-c]pyrimidin-5-amine, 2-[(2,6-difluorophenyl)methyl]-8-(2,5-dimethylpyridin-4-yl)-7-(4-fluorophenyl)-[1,2,4]triazolo[1,5-c]pyrimidin-5-amine, 8-(2,6-dimethylpyridin-4-yl)-7-(4-fluorophenyl)-2-((3-fluoropyridin-2-yl)methyl)-[1,2,4]triazolo[1,5-c]pyrimidin-5-amine, 2-[(6-chloropyridin-2-yl)methyl]-7-(4-fluorophenyl)-8-(2-methylpyridin-4-yl)-[1,2,4]triazolo[1,5-c]pyrimidin-5-amine, 2-(2,6-difluorobenzyl)-8-(2,3-dimethylpyridin-4-yl)-7-(4-fluorophenyl)-[1,2,4]triazolo[1,5-c]pyrimidin-5-amine, 2-((6-(dimethylamino)pyridin-2-yl)methyl)-7-(4-fluorophenyl)-8-(2-methylpyridin-4-yl)-[1,2,4]triazolo[1,5-f]pyrimidin-5-amine, 8-(2-chloro-6-methylpyridin-4-yl)-7-(4-fluorophenyl)-2-((3-fluoropyridin-2-yl)methyl)-[1,2,4]triazolo[1,5-c]pyrimidin-5-amine, 6-((5-amino-7-(4-fluorophenyl)-8-(2-methylpyridin-4-yl)-[1,2,4]triazolo[1,5-f]pyrimidin-2-yl)methyl)picolinonitrile, 5-(5-amino-2-[[3-(difluoromethoxy)pyridin-2-yl]methyl]-7-(4-fluorophenyl)-[1,2,4]triazolo[1,5-c]pyrimidin-8-yl)-1-methyl-1,2-dihydropyridin-2-one, 5-(5-amino-2-((3-fluoropyridin-2-yl)methyl)-7-(oxazol-2-yl)-[1,2,4]triazolo[1,5-c]pyrimidin-8-yl)-1-methylpyridin-2(1H)-one, 5-(5-amino-2-(2,6-difluorobenzyl)-7-(oxazol-2-yl)-[1,2,4]triazolo[1,5-c]pyrimidin-8-yl)-1-methylpyridin-2(1H)-one, 5-[5-amino-7-(4-fluorophenyl)-2-[(3-fluoropyridin-2-yl) methyl]-[1,2,4]triazolo[1,5-c]pyrimidin-8-yl]-1-[(3S)-oxolan-3-yl]-1,2-dihydropyridin-2-one, 5-[5-amino-2-[(2,6-difluorophenyl)methyl]-7-(6-methylpyridin-3-yl)-[1,2,4]triazolo[1,5-c]pyrimidin-8-yl]-1-methyl-1,2-dihydropyridin-2-one, 5-[5-amino-2-[(2,6-difluorophenyl)methyl]-7-(2H-1,2,3-triazol-2-yl)-[1,2,4]triazolo[1,5-c]pyrimidin-8-yl]-1-methyl-1,2-dihydropyridin-2-one, 5-(5-amino-2-(2,6-difluorobenzyl)-7-(5-methyloxazol-2-yl)-[1,2,4]triazolo[1,5-c]pyrimidin-8-yl)-1-methylpyridin-2(1H)-one, 5-(5-amino-2-(2,6-difluorobenzyl)-7-(4-methyloxazol-2-yl)-[1,2,4]triazolo[1,5-c]pyrimidin-8-yl)-1-methylpyridin-2(1H)-one, 5-(5-amino-7-chloro-2-(2,6-difluorobenzyl)-[1,2,4]triazolo[1,5-c]pyrimidin-8-yl)-1-methylpyridin-2(1H)-one, 5-(5-amino-7-(4-fluorophenyl)-2-((3-fluoropyridin-2-yl) methyl)-[1,2,4]triazolo[1,5-c]pyrimidin-8-yl)-1,3-dimethylpyridin-2(1H)-one, 6-(5-amino-7-(4-fluorophenyl)-2-((3-fluoropyridin-2-yl) methyl)-[1,2,4]triazolo[1,5-f]pyrimidin-8-yl)-2-methylpyridazin-3(2H)-one, 2-((3-fluoropyridin-2-yl)methyl)-8-(imidazo[1,2-a]pyridin-6-yl)-7-(oxazol-2-yl)-[1,2,4]triazolo[1,5-c]pyrimidin-5-amine, 7-(4-fluorophenyl)-2-((3-fluoropyridin-2-yl)methyl)-8-(imidazo[1,2-a]pyridin-6-yl)-[1,2,4]triazolo[1,5-c]pyrimidin-5-amine, 2-[(2,6-difluorophenyl)methyl]-8-(2,6-dimethylpyridin-4-yl)-7-(1,3-oxazol-2-yl)-[1,2,4]triazolo[1,5-c]pyrimidin-5-amine,
5-(5-amino-7-(4-fluorophenyl)-2-((3-fluoropyridin-2-yl)methyl)-[1,2,4]triazolo[1,5-c]pyrimidin-8-yl)-1-ethylpyridin-2(1H)-one,
5-(5-amino-2-((6-aminopyridin-2-yl)methyl)-7-(4-fluorophenyl)-[1,2,4]triazolo[1,5-c]pyrimidin-8-yl)-1-methylpyridin-2(1H)-one,
5-(5-amino-2-(2,6-difluorobenzyl)-7-(oxazol-2-yl)-[1,2,4]triazolo[1,5-c]pyrimidin-8-yl)-1-methylpyridin-2(1H)-one,
6-[[5-amino-7-(4-fluorophenyl)-8-[imidazo[1,2-a]pyridin-6-yl]-[1,2,4]triazolo[1,5-c]pyrimidin-2-yl]methyl]pyridin-2-amine,
8-(2-aminopyridin-4-yl)-7-(4-fluorophenyl)-2-((3-fluoropyridin-2-yl)methyl)-[1,2,4]triazolo[1,5-c]pyrimidin-5-amine,
5-[5-amino-7-(3,4-difluorophenyl)-2-[(3-fluoropyridin-2-yl)methyl]-[1,2,4]triazolo[1,5-c]pyrimidin-8-yl]-1-methyl-1,2-dihydropyridin-2-one,
5-(5-amino-7-(3-fluorophenyl)-2-((3-fluoropyridin-2-yl)methyl)-[1,2,4]triazolo[1,5-c]pyrimidin-8-yl)-1-methylpyridin-2(1H)-one,
5-(5-amino-7-(4-(difluoromethyl)phenyl)-2-((3-fluoropyridin-2-yl)methyl)-[1,2,4]triazolo[1,5-c]pyrimidin-8-yl)-1-methylpyridin-2(1H)-one,
5-[5-amino-7-(4-fluorophenyl)-2-[(1,3-thiazol-2-yl)methyl]-[1,2,4]triazolo[1,5-c]pyrimidin-8-yl]-1-methyl-1,2-dihydropyridin-2-one,
7-(4-fluorophenyl)-2-((3-fluoropyridin-2-yl)methyl)-8-(2-(methylamino) pyridin-4-yl)-[1,2,4]triazolo[1,5-c]pyrimidin-5-amine,
5-(5-amino-2-(2,6-difluorobenzyl)-7-(thiazol-2-yl)-[1,2,4]triazolo[1,5-c]pyrimidin-8-yl)-1-methylpyridin-2(1H)-one,
7-(4-fluorophenyl)-2-((6-methylpyridin-2-yl)methyl)-8-(2-methylpyridin-4-yl)-[1,2,4]triazolo[1,5-c]pyrimidin-5-amine,
7-(4-fluorophenyl)-8-(2-methylpyridin-4-yl)-N2-(pyridin-2-yl)-[1,2,4]triazolo[1,5-c]pyrimidine-2,5-diamine,
7-(4-fluorophenyl)-2-((6-methylpyridin-2-yl)methyl)-8-(2,6-dimethylpyridin-4-yl)-[1,2,4]triazolo[1,5-c]pyrimidin-5-amine,
2-(2,6-difluorobenzyl)-8-(2,6-dimethylpyridin-4-yl)-7-(4-fluorophenyl)-[1,2,4]triazolo[1,5-c]pyrimidin-5-amine,
3-amino-N-(2-(difluoromethoxy)benzyl)-5-(4-fluorophenyl)-6-(1-methyl-6-oxo-1,6-dihydropyridin-3-yl)pyrazine-2-carboxamide,
8-(2,6-dimethylpyridin-4-yl)-7-(4-fluorophenyl)-2-((3-methoxypyridin-2-yl)methyl)-[1,2,4]triazolo[1,5-c]pyrimidin-5-amine,
8-(2-amino-6-methylpyridin-4-yl)-2-(2,6-difluorobenzyl)-7-(4-fluorophenyl)-[1,2,4]triazolo[1,5-c]pyrimidin-5-amine,
5-[5-amino-7-(4-fluorophenyl)-2-[(3-fluoropyridin-2-yl)methyl]-[1,2,4]triazolo[1,5-c]pyrimidin-8-yl]-1-(propan-2-yl)-1,2-dihydropyridin-2-one,
5-(5-amino-7-(4-chlorophenyl)-2-((3-fluoropyridin-2-yl)methyl)-[1,2,4]triazolo[1,5-c]pyrimidin-8-yl)-1-methylpyridin-2(1H)-one,
4-(5-amino-2-((3-fluoropyridin-2-yl)methyl)-8-(1-methyl-6-oxo-1,6-dihydropyridin-3-yl)-[1,2,4]triazolo[1,5-c]pyrimidin-7-yl)benzonitrile,
5-[5-amino-7-(4-fluorophenyl)-2-[(1,3-thiazol-4-yl)methyl]-[1,2,4]triazolo[1,5-c]pyrimidin-8-yl]-1-methyl-1,2-dihydropyridin-2-one,
5-(5-amino-2-((3-fluoropyridin-2-yl)methyl)-7-(1-methyl-1H-pyrazol-4-yl)-[1,2,4]triazolo[1,5-c]pyrimidin-8-yl)-1-methylpyridin-2(1H)-one,
5-(5-amino-2-(2,6-difluorobenzyl)-7-(4-fluorophenyl)-[1,2,4]triazolo[1,5-c]pyrimidin-8-yl)-1-(1,1-dioxidothietan-3-yl)pyridin-2(1H)-one,
5-(5-amino-2-((3-fluoropyridin-2-yl)methyl)-7-(4-methoxyphenyl)-[1,2,4]triazolo[1,5-c]pyrimidin-8-yl)-1-methylpyridin-2(1H)-one,
5-(5-amino-2-((3-fluoropyridin-2-yl)methyl)-7-(4-(trifluoromethyl)phenyl)-[1,2,4]triazolo[1,5-c]pyrimidin-8-yl)-1-methylpyridin-2(1H)-one,
5-[5-amino-2-[(3-fluoropyridin-2-yl)methyl]-7-(1H-pyrazol-1-yl)-[1,2,4]triazolo[1,5-c]pyrimidin-8-yl]-1-methyl-1,2-dihydropyridin-2-one,
5-(5-amino-7-(2,4-difluorophenyl)-2-((3-fluoropyridin-2-yl)methyl)-[1,2,4]triazolo[1,5-c]pyrimidin-8-yl)-1-methylpyridin-2(1H)-one,
7-(4-fluorophenyl)-2-((3-fluoropyridin-2-yl)methyl)-8-(1-methyl-1H-benzo[d]imidazol-6-yl)-[1,2,4]triazolo[1,5-c]pyrimidin-5-amine,
7-(4-fluorophenyl)-2-((3-fluoropyridin-2-yl)methyl)-8-(1-methyl-1H-benzo[d]imidazol-6-yl)-[1,2,4]triazolo[1,5-c]pyrimidin-5-amine,
5-(5-amino-2-(2,6-difluorobenzyl)-7-(oxazol-2-yl)-[1,2,4]triazolo[1,5-c]pyrimidin-8-yl)-1-methylpyridin-2(1H)-one,
7-(4-fluorophenyl)-8-[imidazo[1,2-a]pyridin-6-yl]-2-[(2-methyl-1,3-thiazol-4-yl)methyl]-[1,2,4]triazolo[1,5-c]pyrimidin-5-amine,
7-(4-fluorophenyl)-2-((3-fluoropyridin-2-yl)methyl)-8-(1-methyl-1H-benzo[d]imidazol-6-yl)-[1,2,4]triazolo[1,5-c]pyrimidin-5-amine,
5-(5-amino-7-(3-chlorophenyl)-2-((3-fluoropyridin-2-yl)methyl)-[1,2,4]triazolo[1,5-c]pyrimidin-8-yl)-1-methylpyridin-2(1H)-one,
5-(5-amino-2-[[3-(difluoromethoxy)pyridin-2-yl]methyl]-7-(1,3-oxazol-2-yl)-[1,2,4]triazolo[1,5-c]pyrimidin-8-yl)-1-methyl-1,2-dihydropyridin-2-one,
5-(5-amino-2-(2,6-difluorobenzyl)-7-(oxazol-2-yl)-[1,2,4]triazolo[1,5-c]pyrimidin-8-yl)-1-methylpyridin-2(1H)-one,
2-((3-(difluoromethoxy)pyridin-2-yl)methyl)-7-(4-fluorophenyl)-8-(imidazo[1,2-a]pyrid in-6-yl)-[1,2,4]triazolo[1,5-c]pyrimidin-5-amine,
2-((3-(difluoromethoxy)pyridin-2-yl)methyl)-8-(imidazo[1,2-a]pyridin-6-yl)-7-(oxazol-2-yl)-[1,2,4]triazolo[1,5-c]pyrimidin-5-amine,
8-(1H-benzo[d]imidazol-6-yl)-7-(4-fluorophenyl)-2-((3-fluoropyridin-2-yl)methyl)-[1,2,4]triazolo[1,5-c]pyrimidin-5-amine,
5-(5-amino-7-(3,5-difluorophenyl)-2-((3-fluoropyridin-2-yl)methyl)-[1,2,4]triazolo[1,5-c]pyrimidin-8-yl)-1-methylpyridin-2(1H)-one,
5-(5-amino-2-((3-fluoropyridin-2-yl)methyl)-7-(3-methoxyphenyl)-[1,2,4]triazolo[1,5-c]pyrimidin-8-yl)-1-methylpyridin-2(1H)-one,
5-(5-amino-7-(2-chlorophenyl)-2-((3-fluoropyridin-2-yl)methyl)-[1,2,4]triazolo[1,5-c]pyrimidin-8-yl)-1-methylpyridin-2(1H)-one,
5-(5-amino-2-(2,6-difluorobenzyl)-7-(oxazol-2-yl)-[1,2,4]triazolo[1,5-c]pyrimidin-8-yl)-1-isopropylpyridin-2(1H)-one,
5-(5-amino-2-((3-fluoropyridin-2-yl)methyl)-7-(oxazol-2-yl)-[1,2,4]triazolo[1,5-c]pyrimidin-8-yl)-1-isopropylpyridin-2(1H)-one, 8-(2-amino-6-methylpyridin-4-yl)-2-(2,6-difluorobenzyl)-7-(oxazol-2-yl)-[1,2,4]triazolo[1,5-c]pyrimidin-5-amine, 8-(2-chloro-6-methylpyridin-4-yl)-2-((3-fluoropyridin-2-yl)methyl)-7-(oxazol-2-yl)-[1,2,4]triazolo[1,5-c]pyrimidin-5-amine, 4-(5-amino-2-(2,6-difluorobenzyl)-7-(oxazol-2-yl)-[1,2,4]triazolo[1,5-c]pyrimidin-8-yl)-6-methylpicolinonitrile, 8-(2-cyclopropyl-6-methylpyridin-4-yl)-2-(2,6-difluorobenzyl)-7-(oxazol-2-yl)-[1,2,4]triazolo[1,5-c]pyrimidin-5-amine, 2-(2,6-difluorobenzyl)-8-(2-(difluoromethoxy)pyridin-4-yl)-7-(oxazol-2-yl)-[1,2,4]triazolo[1,5-c]pyrimidin-5-amine, 8-(2-(difluoromethoxy)pyridin-4-yl)-2-((3-fluoropyridin-2-yl)methyl)-7-(oxazol-2-yl)-[1,2,4]triazolo[1,5-c]pyrimidin-5-amine, 8-(2-(difluoromethoxy)-6-methylpyridin-4-yl)-2-((3-fluoropyridin-2-yl)methyl)-7-(oxazol-2-yl)-[1,2,4]triazolo[1,5-c]pyrimidin-5-amine, 8-(benzo[d]thiazol-6-yl)-7-(4-fluorophenyl)-2-((3-fluoropyridin-2-yl)methyl)-[1,2,4]triazolo[1,5-c]pyrimidin-5-amine, 7-(4-fluorophenyl)-2-((3-fluoropyridin-2-yl)methyl)-8-(quinolin-6-yl)-[1,2,4]triazolo[1,5-c]pyrimidin-5-amine, 2-((3-fluoropyridin-2-yl)methyl)-8-(1-methyl-1H-benzo[d]imidazol-6-yl)-7-(oxazol-2-yl)-[1,2,4]triazolo[1,5-c]pyrimidin-5-amine, 2-(2,6-difluorobenzyl)-8-(1-methyl-1H-benzo[d]imidazol-6-yl)-7-(oxazol-2-yl)-[1,2,4]triazolo[1,5-c]pyrimidin-5-amine, 5-[5-amino-2-[(2,6-difluorophenyl)methyl]-7-(pyridin-2-yl)-[1,2,4]triazolo[1,5-c]pyrimidin-8-yl]-1-methyl-1,2-dihydropyridin-2-one, 2-((3-fluoropyridin-2-yl)methyl)-8-(imidazo[1,2-a]pyridin-6-yl)-7-(1H-1,2,3-triazol-1-yl)-[1,2,4]triazolo[1,5-c]pyrimidin-5-amine, 2-[(3-fluoropyridin-2-yl)methyl]-8-[imidazo[1,2-a]pyridin-6-yl]-7-(2H-1,2,3-triazol-2-yl)-[1,2,4]triazolo[1,5-c]pyrimidin-5-amine, 5-(5-amino-7-(4-fluorophenyl)-2-((3-fluoropyridin-2-yl)methyl)-[1,2,4]triazolo[1,5-c]pyrimidin-8-yl)-1-(2-hydroxyethyl)pyridin-2(1H)-one 7-(4-fluorophenyl)-2-((3-fluoropyridin-2-yl)methyl)-8-(quinoxalin-6-yl)-[1,2,4]triazolo[1,5-c]pyrimidin-5-amine, 5-(5-amino-2-((3-fluoropyridin-2-yl)methyl)-7-(1-methyl-1H-indol-5-yl)-[1,2,4]triazolo[1,5-c]pyrimidin-8-yl)-1-methylpyridin-2(1H)-one, 5-(5-amino-2-((3-fluoropyridin-2-yl)methyl)-7-(2-methoxyphenyl)-[1,2,4]triazolo[1,5-c]pyrimidin-8-yl)-1-methylpyridin-2(1H)-one, 2-((3-fluoropyridin-2-yl)methyl)-8-(3-methylimidazo[1,2-a]pyridin-6-yl)-7-(oxazol-2-yl)-[1,2,4]triazolo[1,5-c]pyrimidin-5-amine, 2-((3-fluoropyridin-2-yl)methyl)-N7,N7-dimethyl-8-(3-methylimidazo[1,2-a]pyridin-6-yl)-[1,2,4]triazolo[1,5-c]pyrimidine-5,7-diamine, 2-((3-fluoropyridin-2-yl)methyl)-8-(3-methylimidazo[1,2-a]pyridin-6-yl)-7-(pyrrolidin-1-yl)-[1,2,4]triazolo[1,5-c]pyrimidin-5-amine, 2-((3-fluoropyridin-2-yl)methyl)-8-(3-methylimidazo[1,2-a]pyridin-6-yl)-7-morpholino-[1,2,4]triazolo[1,5-c]pyrimidin-5-amine, (S)-7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine, (R)-7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine, 7-(4-fluorophenyl)-8-(3-methylimidazo[1,2-a]pyridin-6-yl)-2-((tetrahydrofuran-3-yl)methyl)-[1,2,4]triazolo[1,5-c]pyrimidin-5-amine (isomer 1), 7-(4-fluorophenyl)-8-(3-methylimidazo[1,2-a]pyridin-6-yl)-2-((tetrahydrofuran-3-yl)methyl)-[1,2,4]triazolo[1,5-c]pyrimidin-5-amine (isomer 2), 8-(3-methylimidazo[1,2-a]pyridin-6-yl)-7-(oxazol-2-yl)-2-((tetrahydrofuran-2-yl)methyl)-[1,2,4]triazolo[1,5-c]pyrimidin-5-amine (isomer 1), 8-(3-methylimidazo[1,2-a]pyridin-6-yl)-7-(oxazol-2-yl)-2-((tetrahydrofuran-2-yl)methyl)-[1,2,4]triazolo[1,5-c]pyrimidin-5-amine (isomer 2), 8-(3-methylimidazo[1,2-a]pyridin-6-yl)-7-(oxazol-2-yl)-2-((tetrahydrofuran-3-yl)methyl)-[1,2,4]triazolo[1,5-c]pyrimidin-5-amine (isomer 1), 8-(3-methylimidazo[1,2-a]pyridin-6-yl)-7-(oxazol-2-yl)-2-((tetrahydrofuran-3-yl)methyl)-[1,2,4]triazolo[1,5-c]pyrimidin-5-amine (isomer 2), 2-(2,6-difluorobenzyl)-8-(3-methylimidazo[1,2-a]pyridin-6-yl)-7-(4-methylpiperazin-1-yl)-[1,2,4]triazolo[1,5-c]pyrimidin-5-amine, 2-(2,6-difluorobenzyl)-7-(3-methoxyazetidin-1-yl)-8-(3-methylimidazo[1,2-a]pyridin-6-yl)-[1,2,4]triazolo[1,5-c]pyrimidin-5-amine, 2-((3-fluoropyridin-2-yl)methyl)-8-(3-methylimidazo[1,2-a]pyridin-6-yl)-7-(2-oxa-6-azaspiro[3.4]octan-6-yl)-[1,2,4]triazolo[1,5-c]pyrimidin-5-amine, 2-((3-fluoropyridin-2-yl)methyl)-8-(3-methylimidazo[1,2-a]pyridin-6-yl)-7-(2-methylmorpholino)-[1,2,4]triazolo[1,5-c]pyrimidin-5-amine (isomer 1), 2-((3-fluoropyridin-2-yl)methyl)-8-(3-methylimidazo[1,2-a]pyridin-6-yl)-7-(2-methylmorpholino)-[1,2,4]triazolo[1,5-c]pyrimidin-5-amine (isomer 2), 2-((3-fluoropyridin-2-yl)methyl)-8-(3-methylimidazo[1,2-a]pyridin-6-yl)-7-(3-methylmorpholino)-[1,2,4]triazolo[1,5-c]pyrimidin-5-amine (isomer 1), 2-((3-fluoropyridin-2-yl)methyl)-8-(3-methylimidazo[1,2-a]pyridin-6-yl)-7-(3-methylmorpholino)-[1,2,4]triazolo[1,5-c]pyrimidin-5-amine (isomer 2), 7-(4-fluorophenyl)-2-(2-methoxyethyl)-8-(3-methylimidazo[1,2-a]pyridin-6-yl)-[1,2,4]triazolo[1,5-c]pyrimidin-5-amine, 7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine, 7-(3-fluoro-1H-pyrazol-1-yl)-2-((3-fluoropyridin-2-yl)methyl)-8-(3-methylimidazo[1,2-a]pyridin-6-yl)-[1,2,4]triazolo[1,5-c]pyrimidin-5-amine, 7-(4-fluoro-1H-pyrazol-1-yl)-2-((3-fluoropyridin-2-yl)methyl)-8-(3-methylimidazo[1,2-a]pyridin-6-yl)-[1,2,4]triazolo[1,5-c]pyrimidin-5-amine, 2-((3-fluoropyridin-2-yl)methyl)-8-(3-methylimidazo[1,2-a]pyridin-6-yl)-7-(2-oxa-6-azaspiro[3.3]heptan-6-yl)-[1,2,4]triazolo[1,5-c]pyrimidin-5-amine, 7-(azetidin-1-yl)-2-((3-fluoropyridin-2-yl)methyl)-8-(3-methylimidazo[1,2-a]pyridin-6-yl)-[1,2,4]triazolo[1,5-c]pyrimidin-5-amine, 2-(2-(dimethylamino)ethyl)-7-(4-fluorophenyl)-8-(3-methylimidazo[1,2-a]pyridin-6-yl)-[1,2,4]triazolo[1,5-c]pyrimidin-5-amine, 2-(2,6-difluorobenzyl)-8-(3-methylimidazo[1,2-a]pyridin-6-yl)-7-morpholino-[1,2,4]triazolo[1,5-c]pyrimidin-5-amine, (S)-7-(4-fluorophenyl)-8-(3-methylimidazo[1,2-a]pyridin-6-yl)-2-((1-methylpyrrolidin-2-yl)methyl)-[1,2,4]triazolo[1,5-c]pyrimidin-5-amine,
2-(2,6-difluorobenzyl)-8-(3-methylimidazo[1,2-a]pyridin-6-yl)-7-(pyrrolidin-1-yl)-[1,2,4]triazolo[1,5-c]pyrimidin-5-amine,
7-(azetidin-1-yl)-2-(2,6-difluorobenzyl)-8-(3-methylimidazo[1,2-a]pyridin-6-yl)-[1,2,4]triazolo[1,5-c]pyrimidin-5-amine,
(R)-7-(4-fluorophenyl)-8-(3-methylimidazo[1,2-a]pyridin-6-yl)-2-((1-methylpyrrolidin-2-yl)methyl)-[1,2,4]triazolo[1,5-c]pyrimidin-5-amine,
2-(2-methoxyethyl)-8-(3-methylimidazo[1,2-a]pyridin-6-yl)-7-(oxazol-2-yl)-[1,2,4]triazolo[1,5-c]pyrimidin-5-amine, or
a pharmaceutically acceptable salt thereof.

Exemplary compounds 1-126 of Formula (I) are set forth in Table 1 below.

TABLE 1

Exemplary Compounds 1-126

| Compound number | Compound structure | Compound name |
| --- | --- | --- |
| 1 | 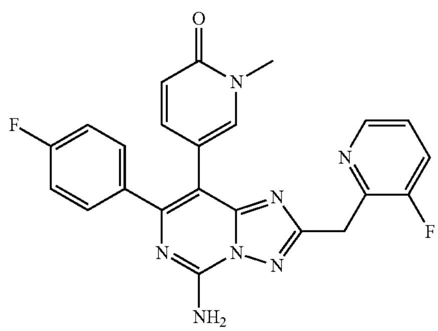 [SMILES: Cn1cc(-c2c(-c3ccc(F)cc3)nc(N)n3nc(Cc4ncccc4F)nc23)ccc1=O] | 8-(2,6-dimethylpyridin-4-yl)-7-(4-fluorophenyl)-2-[(3-fluoropyridin-2-yl)methyl]-[1,2,4]triazolo[1,5-c]pyrimidin-5-amine |
| 2 | 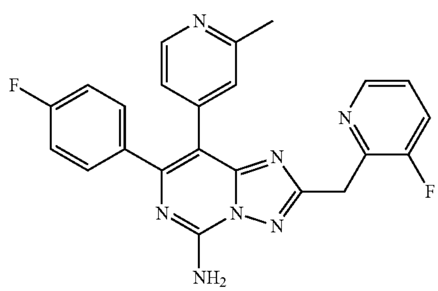 [SMILES: Cc1cc(-c2c(-c3ccc(F)cc3)nc(N)n3nc(Cc4ncccc4F)nc23)ccn1] | 7-(4-fluorophenyl)-2-((3-fluoropyridin-2-yl)methyl)-8-(2-methylpyridin-4-yl)-[1,2,4]triazolo[1,5-c]pyrmidin-5-amine |
| 3 | 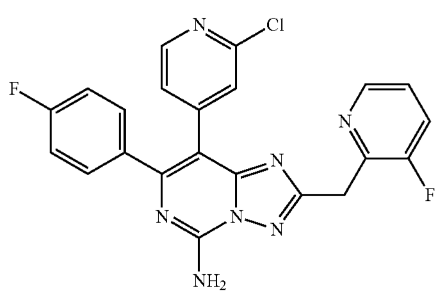 [SMILES: Nc1nc(-c2ccc(F)cc2)c(-c2ccnc(Cl)c2)c2nc(Cc3ncccc3F)nn12] | 8-(2-chloropyridin-4-yl)-7-(4-fluorophenyl)-2-((3-fluoropyridin-2-yl)methyl)-[1,2,4]triazolo[1,5-c]pyrmidin-5-amine |
| 4 | 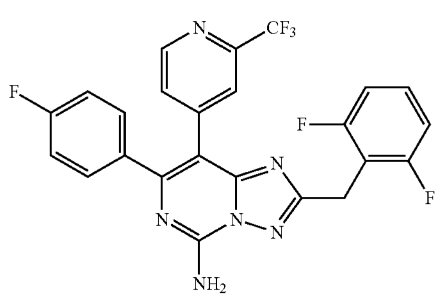 [SMILES: Nc1nc(-c2ccc(F)cc2)c(-c2ccnc(C(F)(F)F)c2)c2nc(Cc3c(F)cccc3F)nn12] | 2-[(2,6-difluorophenyl)methyl]-7-(4-fluorophenyl)-8-[2-(trfluoromethyl)pyridin-4-y]-[1,2,4]triazolo[1,5-c]pyrimidin-5-amine |

TABLE 1-continued

Exemplary Compounds 1-126

| Compound number | Compound structure | Compound name |
|---|---|---|
| 5 | 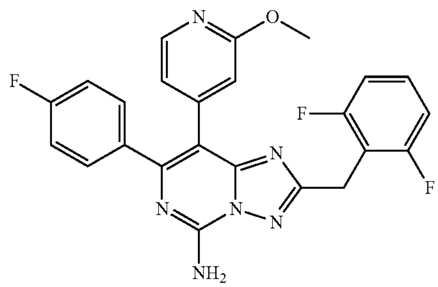 [SMILES: COc1cc(-c2c(-c3ccc(F)cc3)nc(N)n3nc(Cc4c(F)cccc4F)nc23)ccn1] | 2-(2,6-difluorobenzyl)-7-(4-fluorophenyl)-8-(2-methoxypyridin-4-yl)-[1,2,4]triazolo[1,5-c]pyrimidin-5-amine |
| 6 | 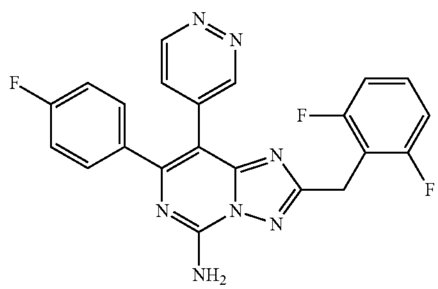 [SMILES: Nc1nc(-c2ccc(F)cc2)c(-c2ccnnc2)c2nc(Cc3c(F)cccc3F)nn12] | 2-(2,6-difluorobenzyl)-7-(4-fluorophenyl)-8-(pyridazin-4-yl)-[1,2,4]triazolo[1,5-c]pyrimidin-5-amine |
| 7 | 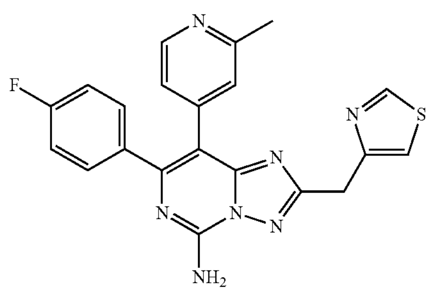 [SMILES: Cc1cc(-c2c(-c3ccc(F)cc3)nc(N)n3nc(Cc4cscn4)nc23)ccn1] | 17-(4-fluorophenyl)-8-(2-methylpyridin-4-yl)-2-[(1,3-thiazol-4-yl)methyl]-[1,2,4]triazolo[1,5-c]pyrimidin-5-amine |
| 8 | 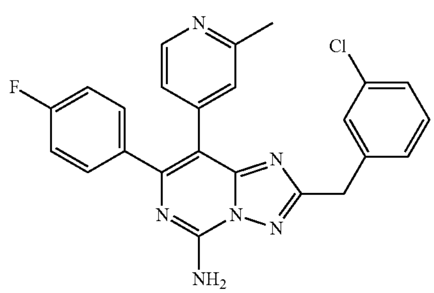 [SMILES: Cc1cc(-c2c(-c3ccc(F)cc3)nc(N)n3nc(Cc4cccc(Cl)c4)nc23)ccn1] | 2-[(3-chlorophenyl)methyl]-7-(4-fluorophenyl)-8-(2-methylpyridin-4-yl)-[1,2,4]triazolo[1,5-c]pyrimidin-5-amine |
| 9 | 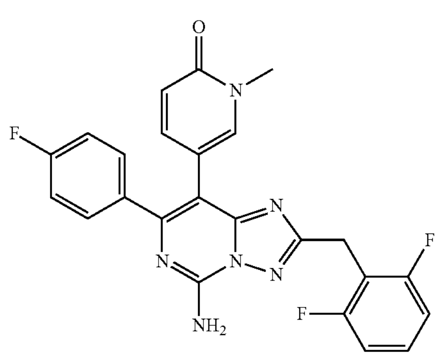 [SMILES: Cn1cc(-c2c(-c3ccc(F)cc3)nc(N)n3nc(Cc4c(F)cccc4F)nc23)ccc1=O] | 5-(5-amino-2-(2,6-difluorobenzyl)-7-(4-fluorophenyl)-[1,2,4]triazolo[1,5-c]pyrimidin-8-yl)-1-methylpyridin-2(1H)-one |

TABLE 1-continued

Exemplary Compounds 1-126

| Compound number | Compound structure | Compound name |
| --- | --- | --- |
| 10 | 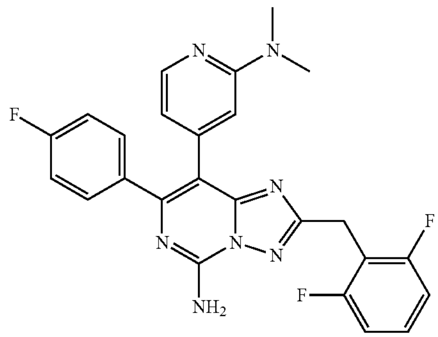 [SMILES: CN(C)c1cc(-c2c(-c3ccc(F)cc3)nc(N)n3nc(Cc4c(F)cccc4F)nc23)ccn1] | 2-(2,6-difluorobenzyl)-8-(2-(dimethylamino) pyridin-4-yl)-7-(4-fluorophenyl)-[1,2,4]triazolo [1,5-c]pyrmidin-5-amine |
| 11 | 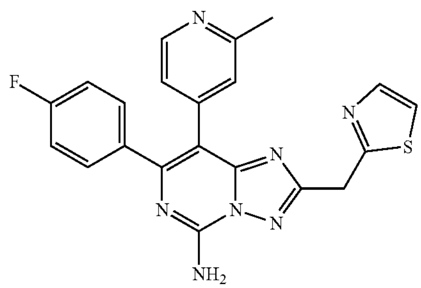 [SMILES: Cc1cc(-c2c(-c3ccc(F)cc3)nc(N)n3nc(Cc4nccs4)nc23)ccn1] | 7-(4-fluorophenyl)-8-(2-methylpyridin-4-yl)-2-[(1,3-thiazol-4-yl)methyl]-[1,2,4]triazolo[1,5-c] pyrimidin-5-amine |
| 12 | 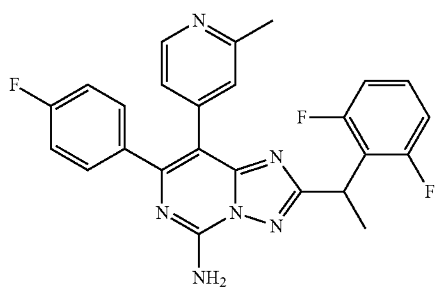 [SMILES: Cc1cc(-c2c(-c3ccc(F)cc3)nc(N)n3nc(C(C)c4c(F)cccc4F)nc23)ccn1] | 2-[1-(2,6-difluorophenyl)ethyl]-7-(4-fluoropheny l)-8-(2-methylpyridin-4-yl)-[1,2,4]triazolo[1,5-c] pyrimidin-5-amine |
| 13 | 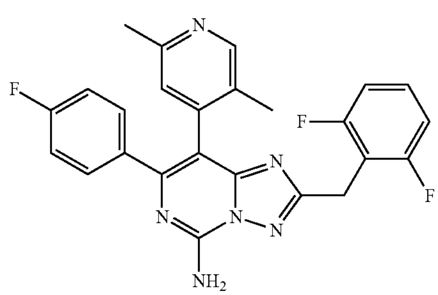 [SMILES: Cc1cc(-c2c(-c3ccc(F)cc3)nc(N)n3nc(Cc4c(F)cccc4F)nc23)c(C)cn1] | 2-[(2,6-difluorophenyl)methyl]-8-(2,5-dimethylp yridin-4-yl)-7-(4-fluorophenyl)-[1,2,4]triazolo [1,5-c]pyrimidin-5-amine |
| 14 | 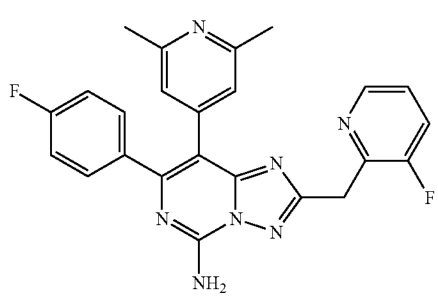 | 8-(2,6-dimethylpyridin-4-yl)-7-(4-fluorophenyl)-2-((3-fluoropyridin-2-yl)methyl)-[1,2,4]triazolo [1,5-c]pyrimidin-5-amine |

TABLE 1-continued

Exemplary Compounds 1-126

| Compound number | Compound structure | Compound name |
|---|---|---|
| 15 | 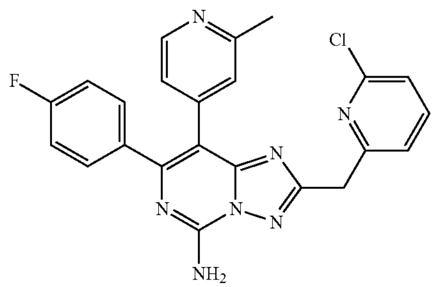 | 2-[(6-chloropyridin-2-yl)methyl]-7-(4-fluorophenyl)-8-(2-methylpyridin-4-yl)-[1,2,4]triazolo[1,5-c]pyrimidin-5-amine |
| 16 | 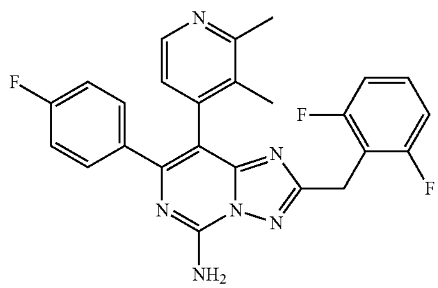 [SMILES: Cc1nccc(-c2c(-c3ccc(F)cc3)nc(N)n3nc(Cc4c(F)cccc4F)nc23)c1C] | 2-(2,6-difluorobenzyl)-8-(2,3-dimethylpyridin-4-yl)-7-(4-fluorophenyl)-[1,2,4]triazolo[1,5-c]pyrimidin-5-amine |
| 17 | 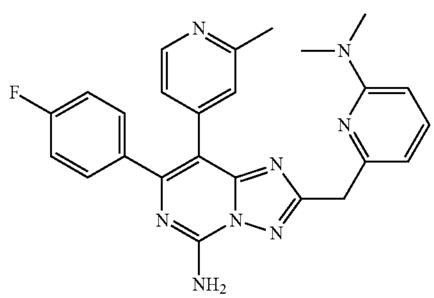 [SMILES: Cc1cc(-c2c(-c3ccc(F)cc3)nc(N)n3nc(Cc4cccc(N(C)C)n4)nc23)ccn1] | 2-((6-(dimethylamino)pyridin-2-yl)methyl)-7-(4-fluorophenyl)-8-(2-methylpyridin-4-yl)-[1,2,4]triazolo[1,5-f]pyrimidin-5-amine |
| 18 | 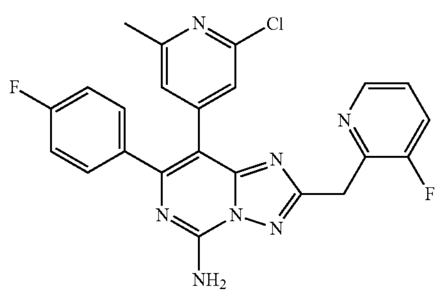 | 8-(2-chloro-6-methylpyridin-4-yl)-7-(4-fluorophenyl)-2-((3-fluoropyridin-2-yl)methyl)-[1,2,4]triazolo[1,5-c]pyrimidin-5-amine |
| 19 | 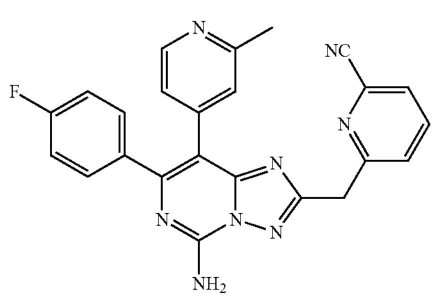 | 6-((5-amino-7-(4-fluorophenyl)-8-(2-methylpyridin-4-yl)-[1,2,4]triazolo[1,5-f]pyrimidin-2-yl)methyl)picolinonitrile |

TABLE 1-continued

Exemplary Compounds 1-126

| Compound number | Compound structure | Compound name |
|---|---|---|
| 20 | 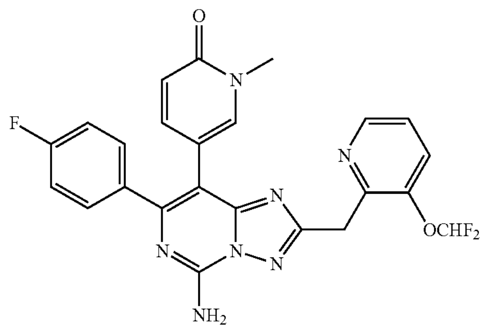 [SMILES: Cn1cc(-c2c(-c3ccc(F)cc3)nc(N)n3nc(Cc4ncccc4OC(F)F)nc23)ccc1=O] | 5-(5-amino-2-[[3-(difluoromethoxy)pyridin-2-yl]methyl]-7-(4-fluorophenyl)-[1, 2,4]triazolo[1,5-c]pyrimidin-8-yl)-1-methyl-1,2-dihydropyridin-2-one |
| 21 | 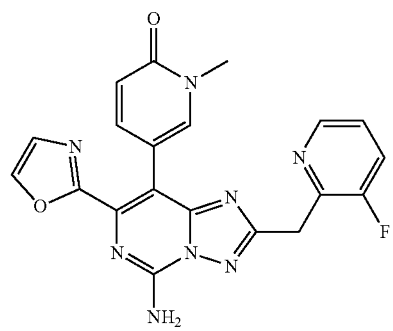 [SMILES: Cn1cc(-c2c(-c3ncco3)nc(N)n3nc(Cc4ncccc4F)nc23)ccc1=O] | 5-(5-amino-2-((3-fluoropyridin-2-yl)methyl)-7-(oxazol-2-yl)-[1,2,4]triazolo[1,5-c]pyrimidin-8-yl)-1-methylpyridin-2(1H)-one |
| 22 | 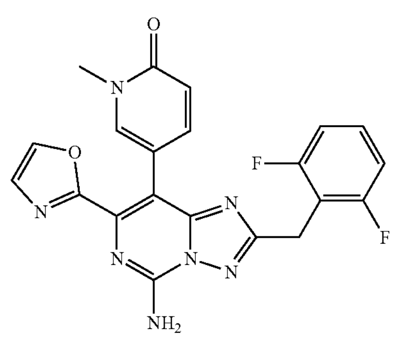 [SMILES: Cn1cc(-c2c(-c3ncco3)nc(N)n3nc(Cc4c(F)cccc4F)nc23)ccc1=O] | 5-(5-amino-2-(2,6-difluorobenzyl)-7-(oxazol-2-yl)-[1,2,4]triazolo[1,5-c]pyrimidin-8-yl)-1-methylpyridin-2(1H)-one |
| 23 | 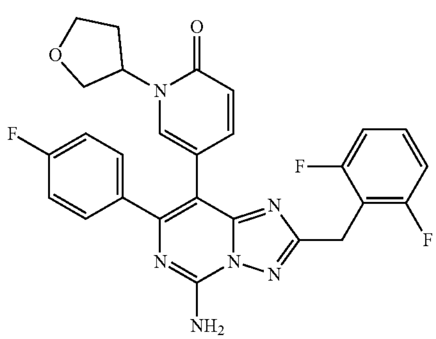 [SMILES: Nc1nc(-c2ccc(F)cc2)c(-c2ccc(=O)n(C3CCOC3)c2)c2nc(Cc3c(F)cccc3F)nn12] | 5-[5-amino-7-(4-fluorophenyl)-2-[(3-fluoropyridin-2-yl)methyl]-[1,2,4]triazolo[1,5-c]pyrimidin-8-yl]-1-[(3S)-oxolan-3-yl]-1,2-dihydropyridin-2-one |

TABLE 1-continued

Exemplary Compounds 1-126

| Compound number | Compound structure | Compound name |
|---|---|---|
| 24 | 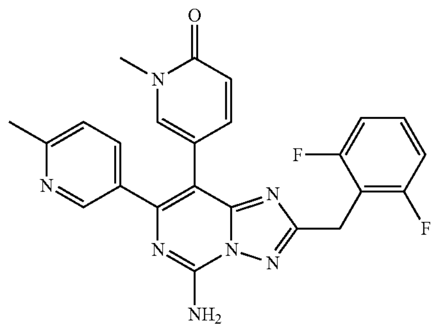 [SMILES: Cc1ccc(-c2nc(N)n3nc(Cc4c(F)cccc4F)nc3c2-c2ccc(=O)n(C)c2)cn1] | 5-[5-amino-2-[(2,6-difluorophenyl)methyl]-7-(6-methylpyridin-3-yl)-[1,2,4]triazolo[1,5-c]pyrimidin-8-yl]-1-methyl-1,2-dihydropyridin-2-one |
| 25 | 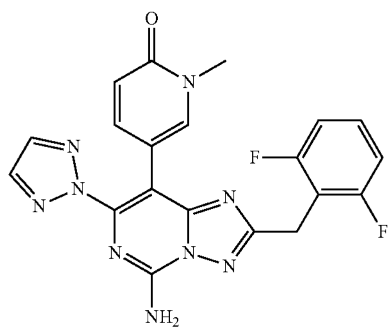 [SMILES: Cn1cc(-c2c(-n3nccn3)nc(N)n3nc(Cc4c(F)cccc4F)nc23)ccc1=O] | 5-[5-amino-2-[(2,6-difluorophenyl)methyl]-7-(2H-1,2,3-triazol-2-yl)-[1,2,4]triazolo[1,5-c]pyrimidin-8-yl]-1-methyl-1,2-dihydropyridin-2-one |
| 26 | 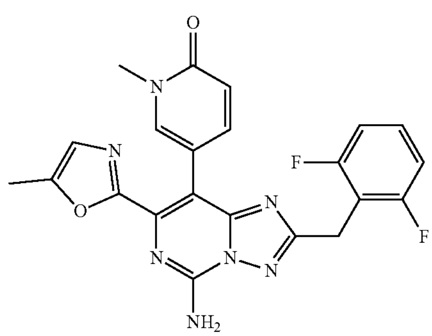 [SMILES: Cc1cnc(-c2nc(N)n3nc(Cc4c(F)cccc4F)nc3c2-c2ccc(=O)n(C)c2)o1] | 5-(5-amino-2-(2,6-difluorobenzyl)-7-(5-methyloxazol-2-yl)-[1,2,4]triazolo[1,5-c]pyrimidin-8-yl)-1-methylpyridin-2(1H)-one |
| 27 | 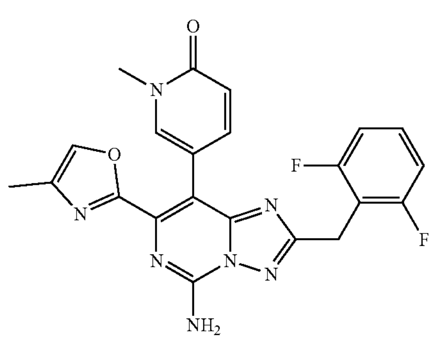 [SMILES: Cc1coc(-c2nc(N)n3nc(Cc4c(F)cccc4F)nc3c2-c2ccc(=O)n(C)c2)n1] | 5-(5-amino-2-(2,6-difluorobenzyl)-7-(4-methyloxazol-2-yl)-[1,2,4]triazolo[1,5-c]pyrimidin-8-yl)-1-methylpyridin-2(1H)-one |

TABLE 1-continued

Exemplary Compounds 1-126

| Compound number | Compound structure | Compound name |
|---|---|---|
| 28 | 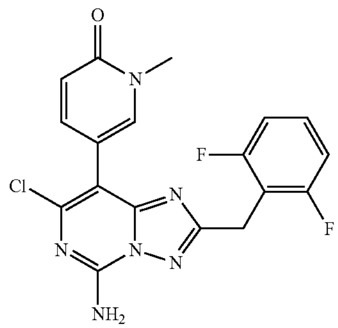 [SMILES: Cn1cc(-c2c(Cl)nc(N)n3nc(Cc4c(F)cccc4F)nc23)ccc1=O] | 5-(5-amino-7-chloro-2-(2,6-difluorobenzyl)-[1,2,4]triazolo[1,5-c]pyrimidin-8-yl)-1-methylpyridin-2(1H)-one |
| 29 | 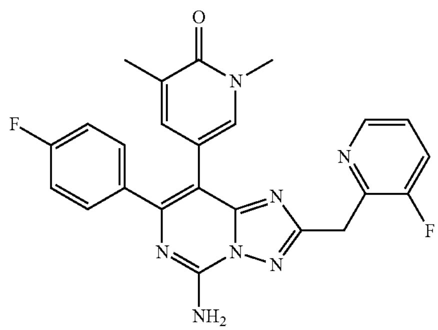 [SMILES: Cc1cc(-c2c(-c3ccc(F)cc3)nc(N)n3nc(Cc4ncccc4F)nc23)cn(C)c1=O] | 5-(5-amino-7-(4-fluorophenyl)-2-((3-fluoropyridin-2-yl)methyl)-[1,2,4]triazolo[1,5-c]pyrimidin-8-yl)-1,3-dimethylpyridin-2(1H)-one |
| 30 | 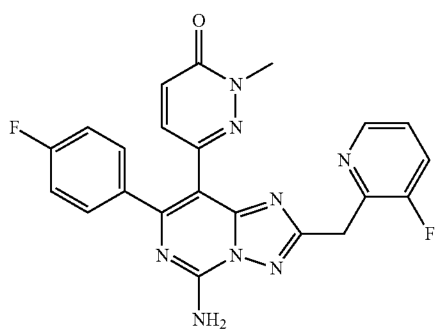 | 6-(5-amino-7-(4-fluorophenyl)-2-((3-fluoropyridin-2-yl)methyl)-[1,2,4]triazolo[1,5-f]pyrimidin-8-yl)-2-methylpyridazin-3(2H)-one |
| 31 | 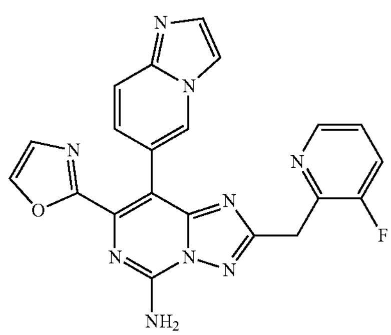 [SMILES: Nc1nc(-c2ncco2)c(-c2ccc3nccn3c2)c2nc(Cc3ncccc3F)nn12] | 2-((3-fluoropyridin-2-yl)methyl)-8-(imidazo[1,2-a]pyrdin-6-yl)-7-(oxazol-2-yl)-[1,2,4]triazolo[1,5-c]pyrimidin-5-amine |

TABLE 1-continued

Exemplary Compounds 1-126

| Compound number | Compound structure | Compound name |
|---|---|---|
| 32 | 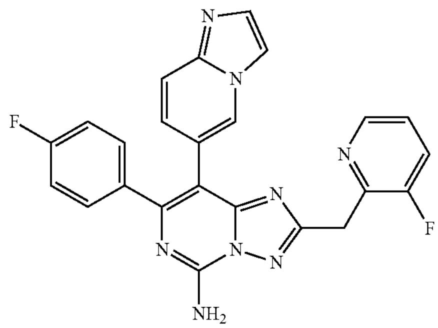 [SMILES: Nc1nc(-c2ccc(F)cc2)c(-c2ccc3nccn3c2)c2nc(Cc3ncccc3F)nn12] | 7-(4-fluorophenyl)-2-((3-fluoropyridin-2-yl)methyl)-8-(imidazo[1,2-a]pyridin-6-yl)-[1,2,4]triazolo[1,5-c]pyrimidin-5-amine |
| 33 | 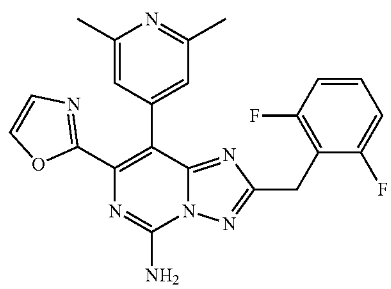 [SMILES: Cc1cc(-c2c(-c3ncco3)nc(N)n3nc(Cc4c(F)cccc4F)nc23)cc(C)n1] | 2-[(2,6-difluorophenyl)methyl]-8-(2,6-dimethylpyridin-4-yl)-7-(1,3-oxazol-2-yl)-[1,2,4]triazolo[1,5-c]pyrimidin-5-amine |
| 34 | 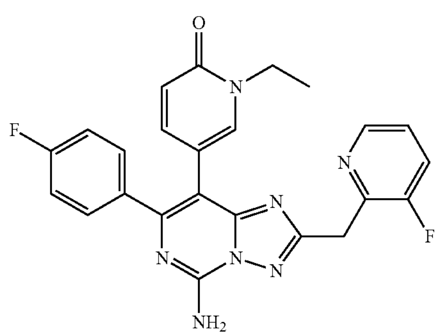 | 5-(5-amino-7-(4-fluorophenyl)-2-((3-fluoropyridin-2-yl)methyl)-[1,2,4]triazolo[1,5-c]pyrimidin-8-yl)-1-ethylpyridin-2(1H)-one |
| 35 | 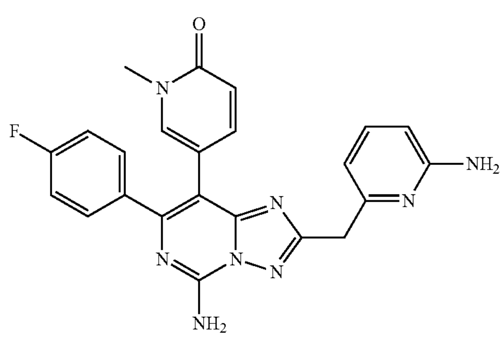 [SMILES: Cn1cc(-c2c(-c3ccc(F)cc3)nc(N)n3nc(Cc4cccc(N)n4)nc23)ccc1=O] | 5-(5-amino-2-((6-aminopyridin-2-yl)methyl)-7-(4-fluorophenyl)-[1,2,4]triazolo[1,5-c]pyrimidin-8-yl)-1-methylpyridin-2(1H)-one |

TABLE 1-continued

Exemplary Compounds 1-126

| Compound number | Compound structure | Compound name |
|---|---|---|
| 36 | 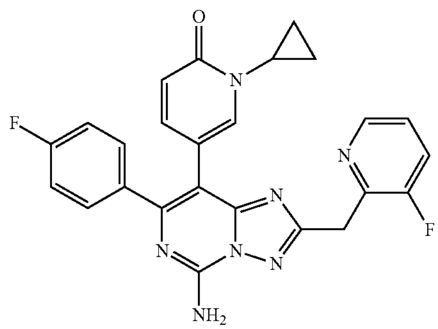 [SMILES: Nc1nc(-c2ccc(F)cc2)c(-c2ccc(=O)n(C3CC3)c2)c2nc(Cc3ncccc3F)nn12] | 5-(5-amino-2-(2,6-difluorobenzyl)-7-(oxazol-2-yl)-[1,2,4]triazolo[1,5-c]pyrimidin-8-yl)-1-methyl pyridin-2(1H)-one |
| 37 | 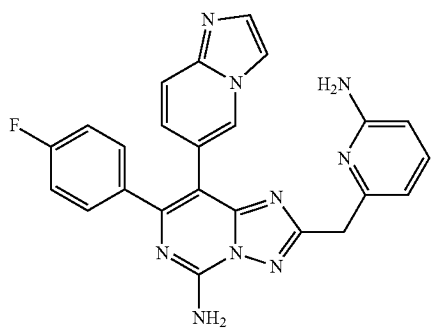 [SMILES: Nc1cccc(Cc2nc3c(-c4ccc5nccn5c4)c(-c4ccc(F)cc4)nc(N)n3n2)n1] | 6-[[5-amino-7-(4-fluorophenyl)-8-[imidazo[1,2-a]pyridin-6-yl]-[1,2,4]triazolo[1,5-c]pyrimidin-2-yl]methyl]pyridin-2-amine |
| 38 | 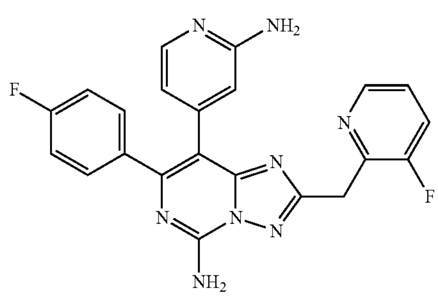 | 8-(2-aminopyridin-4-yl)-7-(4-fluorophenyl)-2-((3-fluoropyridin-2-yl)methyl)-[1,2,4]triazolo[1,5-c]pyrmidin-5-amine |
| 39 | 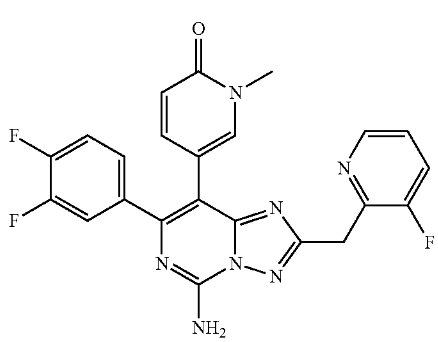 [SMILES: Cn1cc(-c2c(-c3ccc(F)c(F)c3)nc(N)n3nc(Cc4ncccc4F)nc23)ccc1=O] | 5-[5-amino-7-(3,4-difluorophenyl)-2-[(3-fluoropyridin-2-yl)methyl]-[1,2,4]triazolo[1,5-c]pyrimidin-8-yl]-1-methyl-1,2-dihydropyridin-2-one |

TABLE 1-continued

Exemplary Compounds 1-126

| Compound number | Compound structure | Compound name |
| --- | --- | --- |
| 40 | 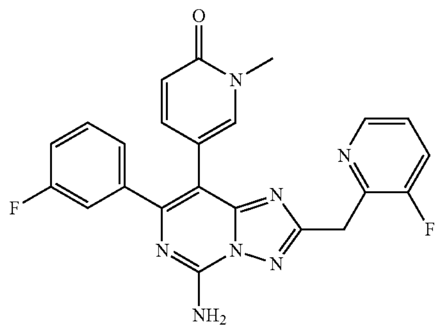 [SMILES: Cn1cc(-c2c(-c3cccc(F)c3)nc(N)n3nc(Cc4ncccc4F)nc23)ccc1=O] | 5-(5-amino-7-(3-fluorophenyl)-2-((3-fluoropyridin-2-yl)methyl)-[1,2,4]triazolo[1,5-c]pyrimidin-8-yl)-1-methylpyridin-2(1H)-one |
| 41 | 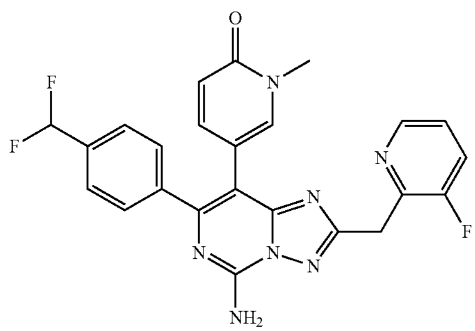 [SMILES: Cn1cc(-c2c(-c3ccc(C(F)F)cc3)nc(N)n3nc(Cc4ncccc4F)nc23)ccc1=O] | 5-(5-amino-7-(4-(difluoromethyl)phenyl)-2-((3-fluoropyridin-2-yl)methyl)-[1,2,4]triazolo[1,5-c]pyrimidin-8-yl)-1-methylpyridin-2(1H)-one |
| 42 | 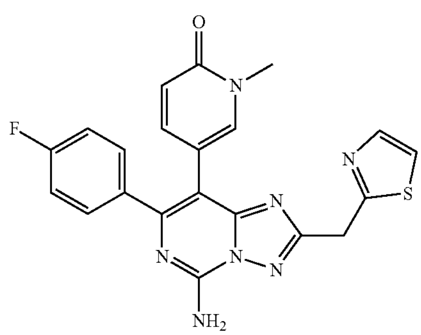 [SMILES: Cn1cc(-c2c(-c3ccc(F)cc3)nc(N)n3nc(Cc4nccs4)nc23)ccc1=O] | 5-[5-amino-7-(4-nuorophenyl)-2-[(1,3-thiazol-2-yl)methyl]-[1,2,4]triazolo[1,5-c]pyrimidin-8-yl]-1-methyl-1,2-dihydropyridin-2-one |
| 43 | 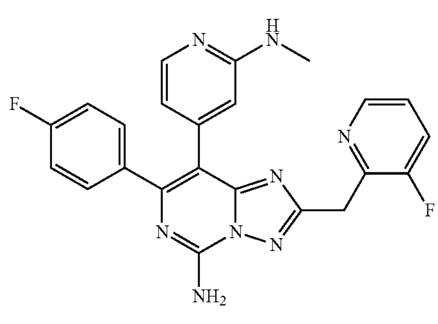 [SMILES: CNc1cc(-c2c(-c3ccc(F)cc3)nc(N)n3nc(Cc4ncccc4F)nc23)ccn1] | 7-(4-fluorophenyl)-2-((3-fluoropyridin-2-yl)methyl)-8-(2-(methylamino)pyridin-4-yl)-[1,2,4]triazolo[1,5-c]pyrimidin-5-amine |

TABLE 1-continued

Exemplary Compounds 1-126

| Compound number | Compound structure | Compound name |
| --- | --- | --- |
| 44 | 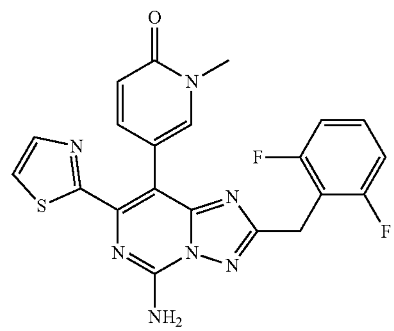 [SMILES: Cn1cc(-c2c(-c3nccs3)nc(N)n3nc(Cc4c(F)cccc4F)nc23)ccc1=O] | 5-(5-amino-2-(2,6-difluorobenzyl)-7-(thiazol-2-yl)-[1,2,4]triazolo[1,5-c]pyrimidin-8-yl)-1-methyl pyridin-2(1H)-one |
| 45 | 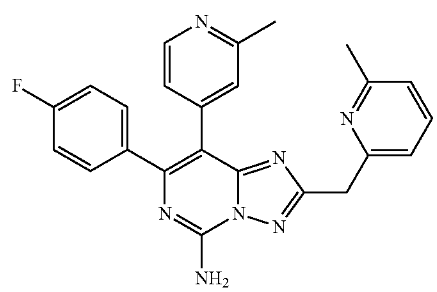 [SMILES: Cc1cc(-c2c(-c3ccc(F)cc3)nc(N)n3nc(Cc4cccc(C)n4)nc23)ccn1] | 7-(4-fluorophenyl)-2-((6-methylpyridin-2-yl)methyl)-8-(2-methylpyridin-4-yl)-[1,2,4]triazolo[1,5-c]pyrimidin-5-amine |
| 46 | 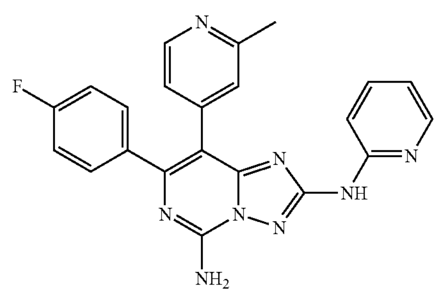 [SMILES: Cc1cc(-c2c(-c3ccc(F)cc3)nc(N)n3nc(Nc4ccccn4)nc23)ccn1] | 7-(4-fluorophenyl)-8-(2-methylpyridin-4-yl)-N2-(pyridin-2-yl)-[1,2,4]triazolo[1,5-c]pyrimidine-2,5-diamine |
| 47 | 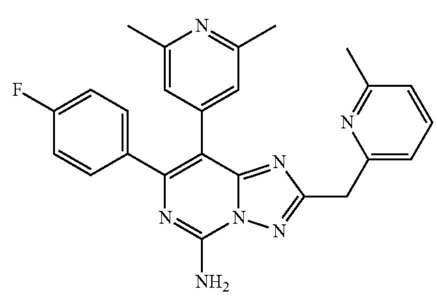 [SMILES: Cc1cc(-c2c(-c3ccc(F)cc3)nc(N)n3nc(Cc4cccc(C)n4)nc23)cc(C)n1] | 7-(4-fluorophenyl)-2-((6-methylpyridin-2-yl)methyl)-8-(2,6-dimethylpyridin-4-yl)-[1,2,4]triazolo[1,5-c]pyrimidin-5-amine |
| 48 | 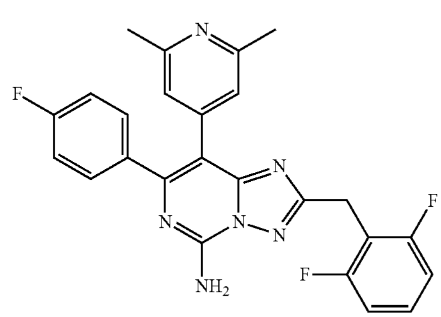 [SMILES: Cc1cc(-c2c(-c3ccc(F)cc3)nc(N)n3nc(Cc4c(F)cccc4F)nc23)cc(C)n1] | 2-(2,6-difluorobenzyl)-8-(2,6-dimethylpyridin-4-yl)-7-(4-fluorophenyl)-[1,2,4]triazolo[1,5-c]pyrimidin-5-amine |

TABLE 1-continued

Exemplary Compounds 1-126

| Compound number | Compound structure | Compound name |
|---|---|---|
| 50 | 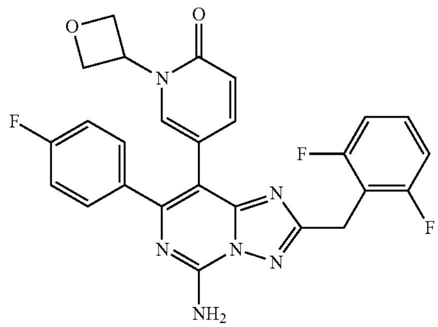 [SMILES: Nc1nc(-c2ccc(F)cc2)c(-c2ccc(=O)n(C3COC3)c2)c2nc(Cc3c(F)cccc3F)nn12] | 3-amino-N-(2-(difluoromethoxy)benzyl)-5-(4-fluorophenyl)-6-(1-methyl-6-oxo-1,6-dihydropyridin-3-yl)pyrazine-2-carboxamide |
| 51 | 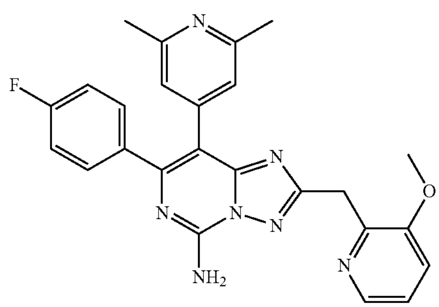 [SMILES: COc1cccnc1Cc1nc2c(-c3cc(C)nc(C)c3)c(-c3ccc(F)cc3)nc(N)n2n1] | 8-(2,6-dimethylpyridin-4-yl)-7-(4-fluorophenyl)-2-((3-methoxypyridin-2-yl)methyl)-[1,2,4]triazolo[1,5-c]pyrimidin-5-amine |
| 52 | 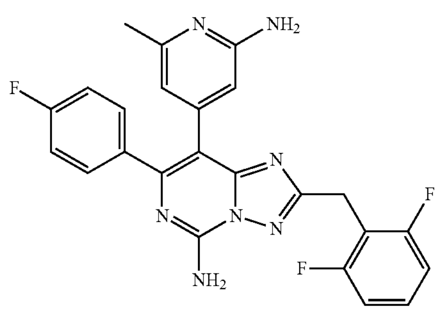 [SMILES: Cc1cc(-c2c(-c3ccc(F)cc3)nc(N)n3nc(Cc4c(F)cccc4F)nc23)cc(N)n1] | 8-(2-amino-6-methylpyridin-4-yl)-2-(2,6-difluorobenzyl)-7-(4-fluorophenyl)-[1,2,4]triazolo[1,5-c]pyrimidin-5-amine |
| 55 | 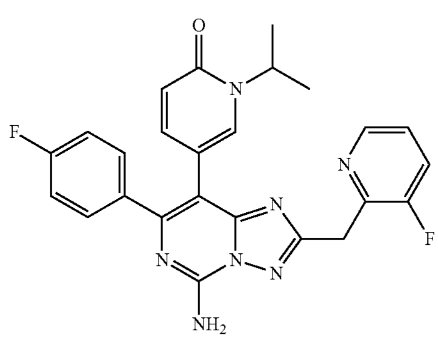 [SMILES: CC(C)n1cc(-c2c(-c3ccc(F)cc3)nc(N)n3nc(Cc4ncccc4F)nc23)ccc1=O] | 5-[5-amino-7-(4-fluorophenyl)-2-[(3-fluoropyridin-2-yl)methyl]-[1,2,4]triazolo[1,5-c]pyrimidin-8-yl]-1-(propan-2-yl)-1,2-dihydropyridin-2-one |

TABLE 1-continued

Exemplary Compounds 1-126

| Compound number | Compound structure | Compound name |
|---|---|---|
| 56 | 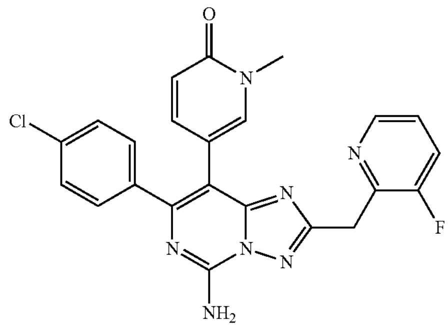 [SMILES: Cn1cc(-c2c(-c3ccc(Cl)cc3)nc(N)n3nc(Cc4ncccc4F)nc23)ccc1=O] | 5-(5-amino-7-(4-chlorophenyl)-2-((3-fluoropyridin-2-yl)methyl)-[1,2,4]triazolo[1,5-c]pyrimidin-8-yl)-l-methylpyridin-2(1H)-one |
| 57 | 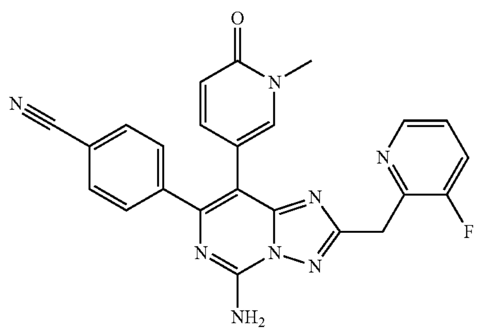 [SMILES: Cn1cc(-c2c(-c3ccc(C#N)cc3)nc(N)n3nc(Cc4ncccc4F)nc23)ccc1=O] | 4-(5-amino-2-((3-fluoropyridin-2-yl)methyl)-8-(1-methyl-6-oxo-1,6-dihydropyridin-3-yl)-[1,2,4]triazolo[1,5-c]pyrimidin-7-yl)benzonitrile |
| 58 | 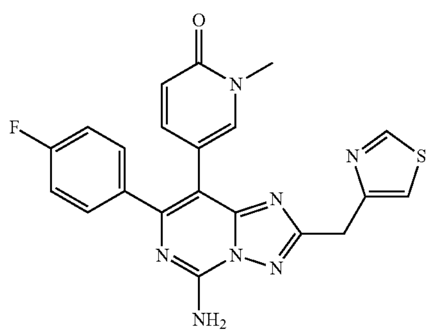 [SMILES: Cn1cc(-c2c(-c3ccc(F)cc3)nc(N)n3nc(Cc4cscn4)nc23)ccc1=O] | 5-[5-amino-7-(4-fluorophenyl)-2-[(1,3-thiazol-4-yl)methyl]-[1,2,4]triazolo[1,5-c]pyrimidin-8-yl]-1-methyl-1,2-dihydropyridin-2-one |
| 59 | 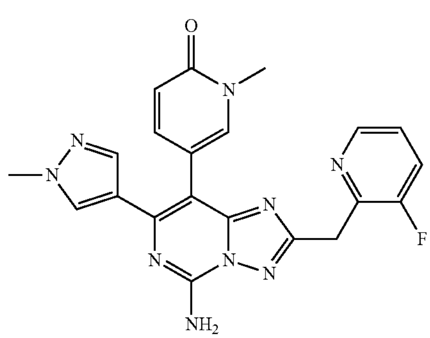 [SMILES: Cn1cc(-c2nc(N)n3nc(Cc4ncccc4F)nc3c2-c2ccc(=O)n(C)c2)cn1] | 5-(5-amino-2-((3-fluoropyridin-2-yl)methyl)-7-(1-methyl-1H-pyrazol-4-yl)-[1,2,4]triazolo[1,5-c]pyrirridin-8-yl)-l-methylpyridin-2(1H)-one |

TABLE 1-continued

Exemplary Compounds 1-126

| Compound number | Compound structure | Compound name |
|---|---|---|
| 60 | 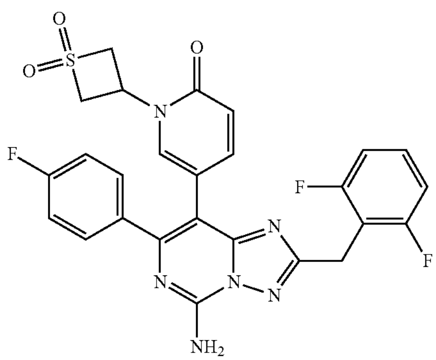 [SMILES: Nc1nc(-c2ccc(F)cc2)c(-c2ccc(=O)n(C3CS(=O)(=O)C3)c2)c2nc(Cc3c(F)cccc3F)nn12] | 5-(5-amino-2-(2,6-difluorobenzyl)-7-(4-fluorophenyl)-[1,2,4]triazolo[1,5-c]pyrimidin-8-yl)-1-(1,1-dioxidothietan-3-yl)pyridin-2(1H)-one |
| 61 | 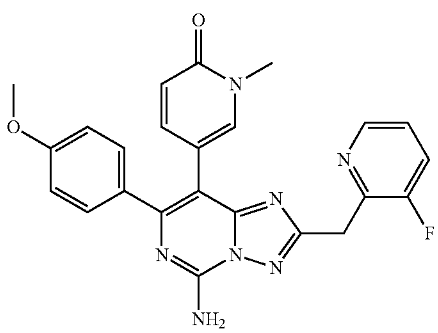 [SMILES: COc1ccc(-c2nc(N)n3nc(Cc4ncccc4F)nc3c2-c2ccc(=O)n(C)c2)cc1] | 5-(5-amino-2-((3-fluoropyridin-2-yl)methyl)-7-(4-methoxyphenyl)-[1,2,4]triazolo[1,5-c]pyrimidin-8-yl)-1-methylpyridin-2(1H)-one |
| 62 | 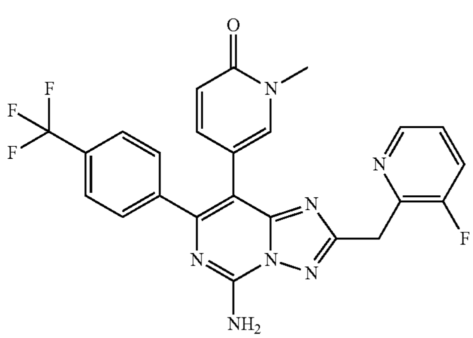 [SMILES: Cn1cc(-c2c(-c3ccc(C(F)(F)F)cc3)nc(N)n3nc(Cc4ncccc4F)nc23)ccc1=O] | 5-(5-amino-2-((3-fluoropyridin-2-yl)methyl)-7-(4-(trifluoromethyl)phenyl)-[1,2,4]triazolo[1,5-c]pyrimidin-8-yl)-1-methylpyridin-2(1H)-one |
| 63 | 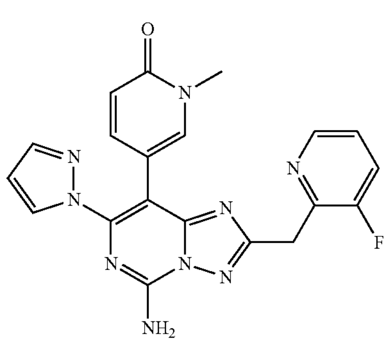 [SMILES: Cn1cc(-c2c(-n3cccn3)nc(N)n3nc(Cc4ncccc4F)nc23)ccc1=O] | 5-[5-amino-2-[(3-fluoropyridin-2-yl)methyl]-7-(1H-pyrazol-1-yl)-[1,2,4]triazolo[1,5-c]pyrimidin-8-yl]-1-methyl-1,2-dihydropyridin-2-one |

TABLE 1-continued

Exemplary Compounds 1-126

| Compound number | Compound structure | Compound name |
|---|---|---|
| 64 | 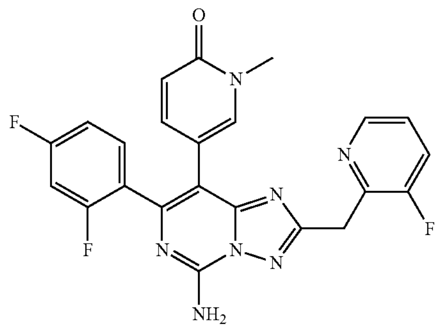 [SMILES: Cn1cc(-c2c(-c3ccc(F)cc3F)nc(N)n3nc(Cc4ncccc4F)nc23)ccc1=O] | 5-(5-amino-7-(2,4-difluorophenyl)-2-((3-fluorop yridin-2-yl)methyl)-[1,2,4]triazolo[1,5-c]pyrimid in-8-yl)-l-methylpyridin-2(1H)-one |
| 65 | 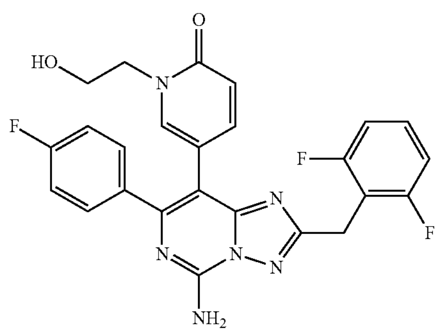 [SMILES: Nc1nc(-c2ccc(F)cc2)c(-c2ccc(=O)n(CCO)c2)c2nc(Cc3c(F)cccc3F)nn12] | 7-(4-fluorophenyl)-2-((3-fluoropyridin-2-yl) methyl)-8-(1-methyl-1H-benzo[d]imidazol-6-yl)- [1,2,4]triazolo[l,5-c]pyrimidin-5-amine |
| 66 | 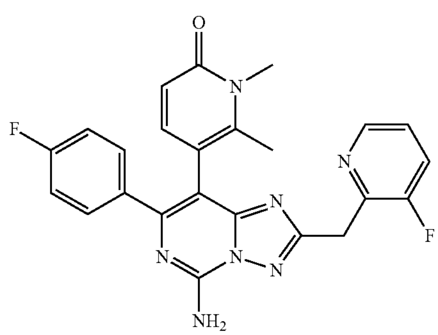 [SMILES: Cc1c(-c2c(-c3ccc(F)cc3)nc(N)n3nc(Cc4ncccc4F)nc23)ccc(=O)n1C] | 7-(4-fluorophenyl)-2-((3-fluoropyridin-2-yl) methyl)-8-(1-methyl-1H-benzo[d]imidazol-6-yl)- [1,2,4]triazolo[l,5-c]pyrimidin-5-amine |
| 67 | 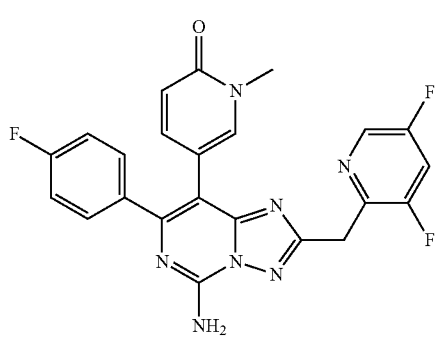 [SMILES: Cn1cc(-c2c(-c3ccc(F)cc3)nc(N)n3nc(Cc4ncc(F)cc4F)nc23)ccc1=O] | 5-(5-amino-2-(2,6-difluorobenzyl)-7-(oxazol-2- yl)-[1,2,4]triazolo[1,5-c]pyrimidin-8-yl)-1-methyl pyridin-2(1H)-one |

TABLE 1-continued

Exemplary Compounds 1-126

| Compound number | Compound structure | Compound name |
| --- | --- | --- |
| 68 | 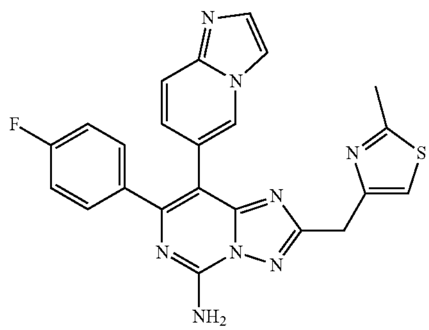 [SMILES: Cc1nc(Cc2nc3c(-c4ccc5nccn5c4)c(-c4ccc(F)cc4)nc(N)n3n2)cs1] | 7-(4-fluorophenyl)-8-[imidazo[1,2-a]pyridin-6-yl]-2-[(2-methyl-1,3-thiazol-4-yl)methyl]-[1,2,4]triazolo[1,5-c]pyrimidin-5-amine |
| 69 | 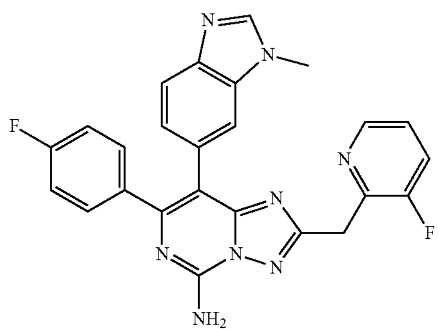 | 7-(4-fluorophenyl)-2-((3-fluoropyridin-2-yl)methyl)-8-(1-methyl-1H-benzo[d]imidazol-6-yl)-[1,2,4]triazolo[1,5-c]pyrimidin-5-amine |
| 70 | 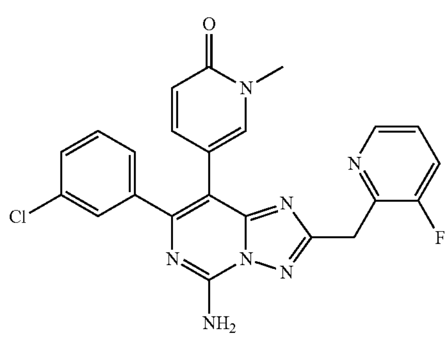 [SMILES: Cn1cc(-c2c(-c3cccc(Cl)c3)nc(N)n3nc(Cc4ncccc4F)nc23)ccc1=O] | 5-(5-amino-7-(3-chlorophenyl)-2-((3-fluoropyridin-2-yl)methyl)-[1,2,4]triazolo[1,5-c]pyrimidin-8-yl)-1-methylpyridin-2(1H)-one |
| 71 | 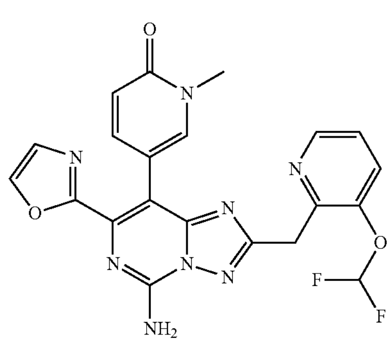 [SMILES: Cn1cc(-c2c(-c3ncco3)nc(N)n3nc(Cc4ncccc4OC(F)F)nc23)ccc1=O] | 5-(5-amino-2-[[3-(difluoromethoxy)pyridin-2-yl]methyl]-7-(1,3-oxazol-2-yl)-[1,2,4]triazolo[1,5-c]pyrimidin-8-yl)-1-methyl-1,2-dihydropyridin-2-one |

TABLE 1-continued

Exemplary Compounds 1-126

| Compound number | Compound structure | Compound name |
|---|---|---|
| 72 | 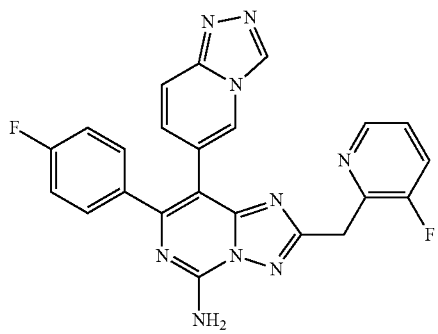 [SMILES: Nc1nc(-c2ccc(F)cc2)c(-c2ccc3nncn3c2)c2nc(Cc3ncccc3F)nn12] | 5-(5-amino-2-(2,6-difluorobenzyl)-7-(oxazol-2-yl)-[1,2,4]triazolo[1,5-c]pyrimidin-8-yl)-1-methyl pyridin-2(1H)-one |
| 73 | 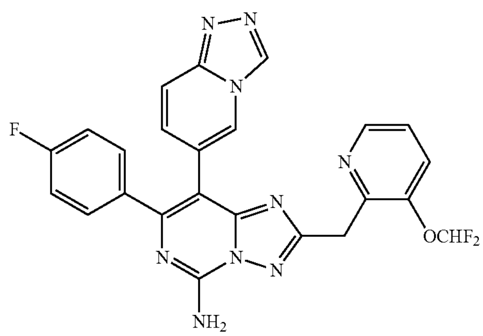 [SMILES: Nc1nc(-c2ccc(F)cc2)c(-c2ccc3nncn3c2)c2nc(Cc3ncccc3OC(F)F)nn12] | 2-((3-(difluoromethoxy)pyridin-2-yl)methyl)-7-(4-fluorophenyl)-8-(imidazo[1,2-a]pyridin-6-yl)-[1,2,4 triazolo[1,5-c]pyrimidin-5-amine |
| 74 | 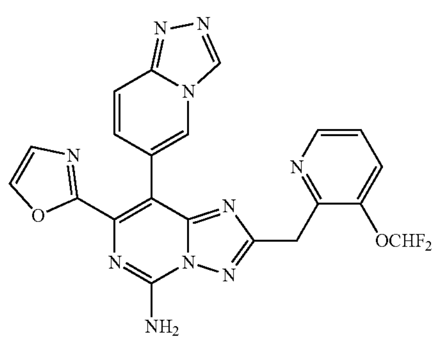 [SMILES: Nc1nc(-c2ncco2)c(-c2ccc3nncn3c2)c2nc(Cc3ncccc3OC(F)F)nn12] | 2-((3-(difluoromethoxy)pyridin-2-yl)methyl)-8-(imidazo[1,2-a]pyridin-6-yl)-7-(oxazol-2-yl)-[1,2,4]triazolo[1,5-c]pyrimidin-5-amine |
| 75 | 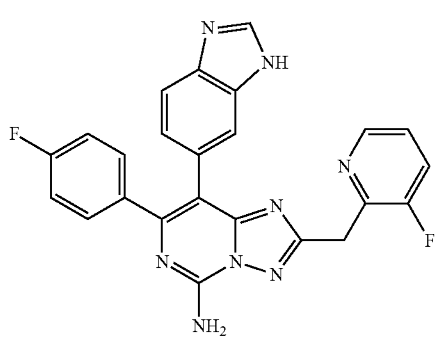 [SMILES: Nc1nc(-c2ccc(F)cc2)c(-c2ccc3nc[nH]c3c2)c2nc(Cc3ncccc3F)nn12] | 8-(1H-benzo[d]imidazol-6-yl)-7-(4-fluorophenyl)-2-((3-fluoropyridin-2-yl)methyl)-[1,2,4]triazolo[1,5-c]pyrimidin-5-amine |

TABLE 1-continued

Exemplary Compounds 1-126

| Compound number | Compound structure | Compound name |
|---|---|---|
| 76 | 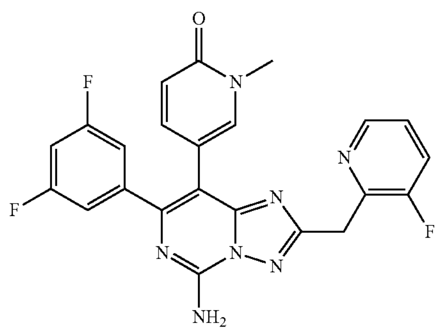 [SMILES: Cn1cc(-c2c(-c3cc(F)cc(F)c3)nc(N)n3nc(Cc4ncccc4F)nc23)ccc1=O] | 5-(5-amino-7-(3,5-difliiorophenyl)-2-((3-fluoropyridin-2-yl)methyl)-[1,2,4]triazolo[1,5-c]pyrimidin-8-yl)-1-methylpyridin-2(1H)-one |
| 77 | 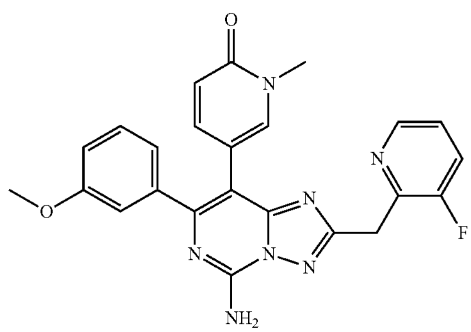 [SMILES: COc1cccc(-c2nc(N)n3nc(Cc4ncccc4F)nc3c2-c2ccc(=O)n(C)c2)c1] | 5-(5-amino-2-((3-fluoropyridin-2-yl)methyl)-7-(3-methoxyphenyl)-[1,2,4]triazolo[1,5-c]pyrimidin-8-yl)-1-methylpyridin-2(1H)-one |
| 78 | 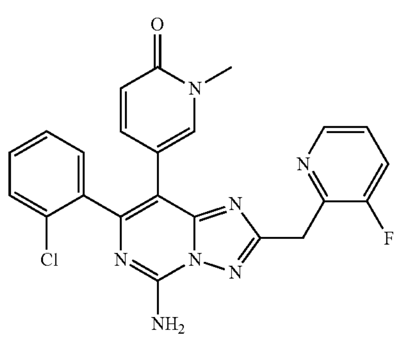 | 5-(5-amino-7-(2-chlorophenyl)-2-((3-fluoropyridin-2-yl)methyl)-[1,2,4]triazolo[1,5-c]pyrimidin-8-yl)-l-methylpyridin-2(1H)-one |
| 79 | 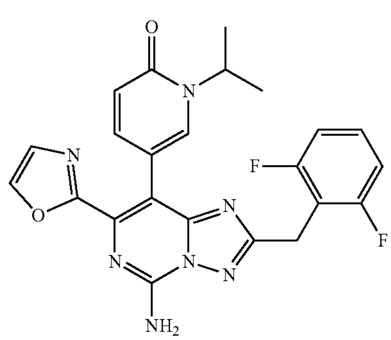 [SMILES: CC(C)n1cc(-c2c(-c3ncco3)nc(N)n3nc(Cc4c(F)cccc4F)nc23)ccc1=O] | 5-(5-am i no-2-(2,6-difluorobenzy1)-7-(oxazol-2-yl)-[1,2,4]triazolo[1,5-c]pyrimidin-8-yl)-l-isopropylpyrdin-2(1H)-one |

TABLE 1-continued

Exemplary Compounds 1-126

| Compound number | Compound structure | Compound name |
|---|---|---|
| 80 | 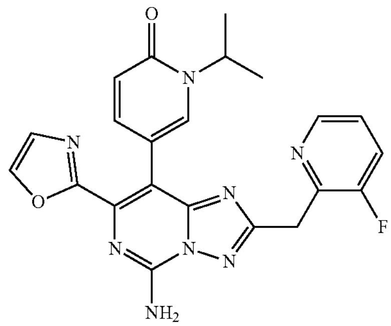 [SMILES: CC(C)n1cc(-c2c(-c3ncco3)nc(N)n3nc(Cc4ncccc4F)nc23)ccc1=O] | 5-(5-amino-2-((3-fluoropyridin-2-yl)methyl)-7-(oxazol-2-yl)-[1,2,4]triazolo[1,5-c]pyrimidin-8-yl)-1-isopropylpyridin-2(1H)-one |
| 81 | 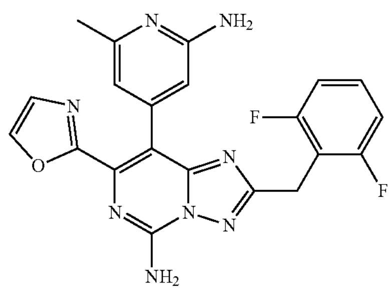 [SMILES: Cc1cc(-c2c(-c3ncco3)nc(N)n3nc(Cc4c(F)cccc4F)nc23)cc(N)n1] | 8-(2-amino-6-methylpyridin-4-yl)-2-(2,6-difluorobenzyl)-7-(oxazol-2-yl)-[1,2,4]triazolo[1,5-c]pyrimidin-5-amine |
| 82 | 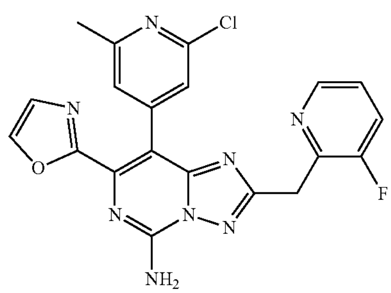 [SMILES: Cc1cc(-c2c(-c3ncco3)nc(N)n3nc(Cc4ncccc4F)nc23)cc(Cl)n1] | 8-(2-chloro-6-methylpyridin-4-yl)-2-((3-fluoropyridin-2-yl)methyl)-7-(oxazol-2-yl)-[1,2,4]triazolo[1,5-c]pyrimidin-5-amine |
| 83 | 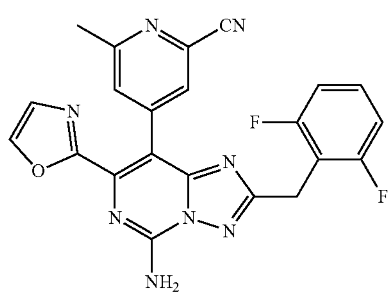 [SMILES: Cc1cc(-c2c(-c3ncco3)nc(N)n3nc(Cc4c(F)cccc4F)nc23)cc(C#N)n1] | 4-(5-amino-2-(2,6-difluorobenzyl)-7-(oxazol-2-yl)-[1,2,4]triazolo[1,5-c]pyrimidin-8-yl)-6-methylpicolinonitrile |
| 84 | 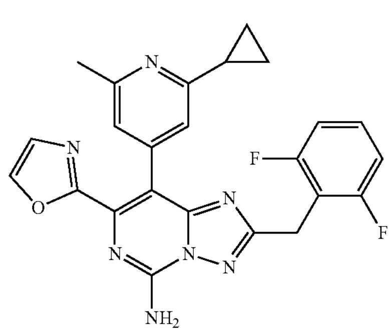 [SMILES: Cc1cc(-c2c(-c3ncco3)nc(N)n3nc(Cc4c(F)cccc4F)nc23)cc(C2CC2)n1] | 8-(2-cyclopropyl-6-methylpyridin-4-yl)-2-(2,6-difluorobenzyl)-7-(oxazol-2-yl)-[1,2,4]triazolo[1,5-c]pyrimidin-5-amine |

TABLE 1-continued

Exemplary Compounds 1-126

| Compound number | Compound structure | Compound name |
|---|---|---|
| 85 | 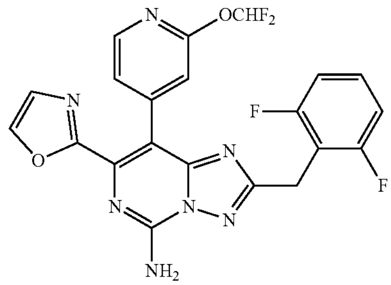 [SMILES: Nc1nc(-c2ncco2)c(-c2ccnc(OC(F)F)c2)c2nc(Cc3c(F)cccc3F)nn12] | 2-(2,6-difluorobenzyl)-8-(2-(difluoromethoxy) pyridin-4-yl)-7-(oxazol-2-yl)-[1,2,4]triazolo[1,5-c] pyrimidin-5-amine |
| 86 | 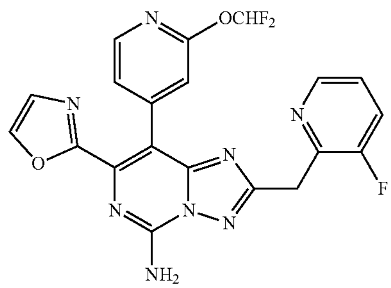 [SMILES: Nc1nc(-c2ncco2)c(-c2ccnc(OC(F)F)c2)c2nc(Cc3ncccc3F)nn12] | 8-(2-(difluoromethoxy)pyridin-4-yl)-2-((3-fluoro pyridin-2-yl)methyl)-7-(oxazol-2-yl)-[1,2,4]triaz olo[1,5-c]pyrimidin-5-amine |
| 87 | 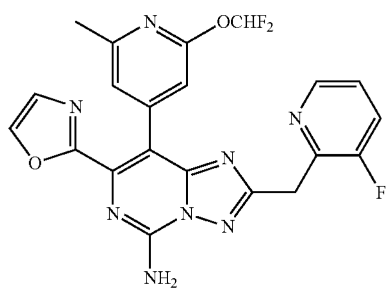 [SMILES: Cc1cc(-c2c(-c3ncco3)nc(N)n3nc(Cc4ncccc4F)nc23)cc(OC(F)F)n1] | 8-(2-(difluoromethoxy)-6-methylpyridin-4-yl)-2-((3-fluoropyridin-2-yl)methyl)-7-(oxazol-2-yl)-[1,2,4 triazolo[l,5-c]pyrimidin-5-amine |
| 88 | 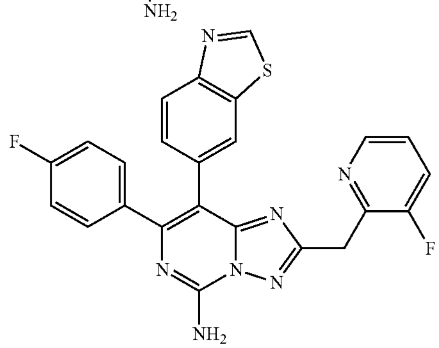 | 8-(benzo[d]thiazol-6-yl)-7-(4-fluorophenyl)-2-((3-fluoropyridin-2-yl)methyl)-[1,2,4]triazolo[1,5-c]pyrmidin-5-amine |
| 89 | 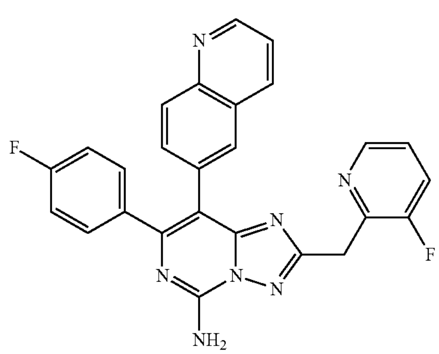 [SMILES: Nc1nc(-c2ccc(F)cc2)c(-c2ccc3ncccc3c2)c2nc(Cc3ncccc3F)nn12] | 7-(4-fluorophenyl)-2-((3-fluoropyridin-2-yl) methyl)-8-(quinolin-6-yl)-[1,2,4]triazolo[l,5-c] pyrimidin-5-amine |

TABLE 1-continued

Exemplary Compounds 1-126

| Compound number | Compound structure | Compound name |
|---|---|---|
| 90 | 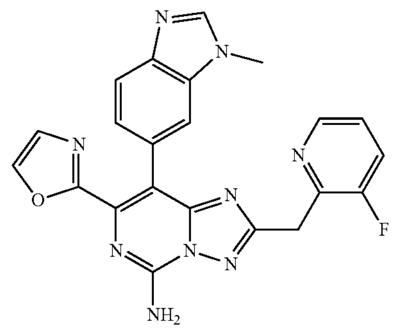 [SMILES: Cn1cnc2ccc(-c3c(-c4ncco4)nc(N)n4nc(Cc5ncccc5F)nc34)cc21] | 2-((3-fluoropyridin-2-yl)methyl)-8-(1-methyl-1H-benzo[d]imidazol-6-yl)-7-(oxazol-2-yl)-[1,2,4]triazolo[1,5-c]pyrimidin-5-amine |
| 91 | 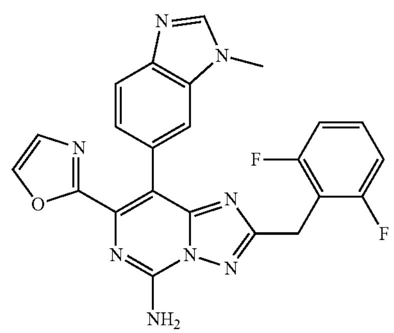 [SMILES: Cn1cnc2ccc(-c3c(-c4ncco4)nc(N)n4nc(Cc5c(F)cccc5F)nc34)cc21] | 2-(2,6-difluorobenzyl)-8-(1-methyl-1H-benzo[d]imidazol-6-yl)-7-(oxazol-2-yl)-[1,2,4]triazolo[1,5-c]pyrimidin-5-amine |
| 92 | 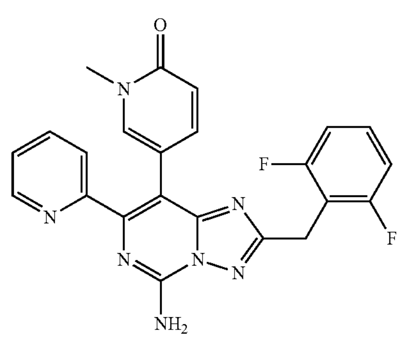 [SMILES: Cn1cc(-c2c(-c3ccccn3)nc(N)n3nc(Cc4c(F)cccc4F)nc23)ccc1=O] | 5-[5-amino-2-[(2,6-difluorophenyl)methyl]-7-(pyridin-2-yl)-[1,2,4]triazolo[1,5-c]pyrimidin-8-yl]-1-methyl-1,2-dihydropyridin-2-one |
| 93 | 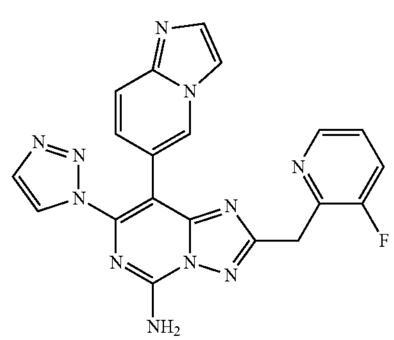 | 2-((3-fluoropyridin-2-yl)methyl)-8-(imidazo[1,2-a]pyrdin-6-yl)-7-(1H-1,2,3-triazol-1-yl)-[1,2,4]triazolo[1,5-c]pyrimidin-5-amine |

TABLE 1-continued

Exemplary Compounds 1-126

| Compound number | Compound structure | Compound name |
|---|---|---|
| 94 | 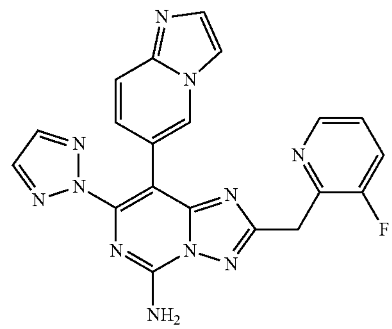 [SMILES: Nc1nc(-n2nccn2)c(-c2ccc3nccn3c2)c2nc(Cc3ncccc3F)nn12] | 2-[(3-fluoropyridin-2-yl)methyl]-8-[imidazo[1,2-a]pyrdin-6-yl]-7-(2H-1,2,3-triazol-2-yl)-[1,2,4]triazolo[1,5-c]pyrimidin-5-amine |
| 95 | 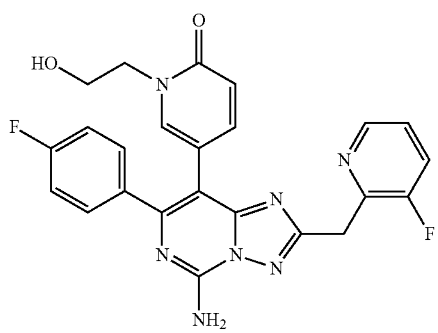 [SMILES: Nc1nc(-c2ccc(F)cc2)c(-c2ccc(=O)n(CCO)c2)c2nc(Cc3ncccc3F)nn12] | 5-(5-amino-7-(4-fluorophenyl)-2-((3-fluoropyridin-2-yl)methyl)-[1,2,4]triazolo[1,5-c]pyrimidin-8-yl)-1-(2-hydroxyethyl)pyridin-2(1H)-one |
| 96 | 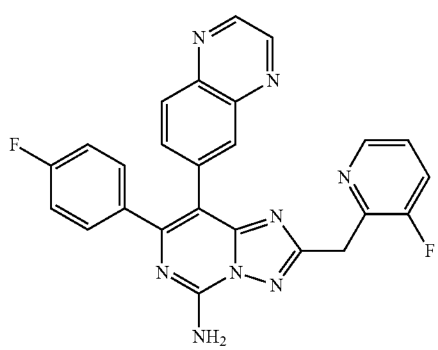 [SMILES: Nc1nc(-c2ccc(F)cc2)c(-c2ccc3nccnc3c2)c2nc(Cc3ncccc3F)nn12] | 7-(4-fluorophenyl)-2-((3-fluoropyridin-2-yl)methyl)-8-(quinoxalin-6-yl)-[1,2,4]triazolo[1,5-c]pyrimidin-5-amine |
| 97 | 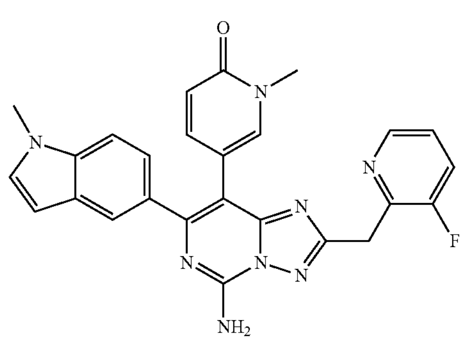 [SMILES: Cn1cc(-c2c(-c3ccc4c(ccn4C)c3)nc(N)n3nc(Cc4ncccc4F)nc23)ccc1=O] | 5-(5-amino-2-((3-fluoropyridin-2-yl)methyl)-7-(1-methyl-1H-indol-5-yl)-[1,2,4]triazolo[1,5-c]pyrimidin-8-yl)-1-methylpyridin-2(1H)-one |

TABLE 1-continued

Exemplary Compounds 1-126

| Compound number | Compound structure | Compound name |
|---|---|---|
| 98 | 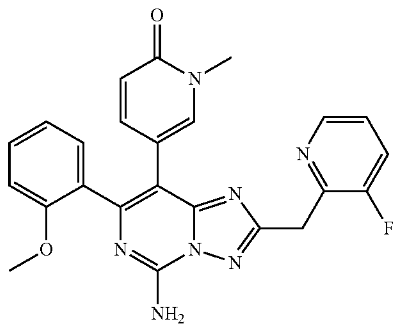 [SMILES: COc1ccccc1-c1nc(N)n2nc(Cc3ncccc3F)nc2c1-c1ccc(=O)n(C)c1] | 5-(5-amino-2-((3-fluoropyridin-2-yl)methyl)-7-(2-methoxyphenyl)-[1,2,4]triazolo[1,5-c]pyrimidin-8-yl)-1-methylpyridin-2(1H)-one |
| 99 | 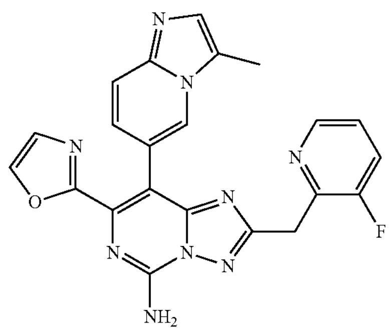 [SMILES: Cc1cnc2ccc(-c3c(-c4ncco4)nc(N)n4nc(Cc5ncccc5F)nc34)cn12] | 2-((3-fluoropyridin-2-yl)methyl)-8-(3-methylimidazo[1,2-a]pyridin-6-yl)-7-(oxazol-2-yl)-[1,2,4]triazolo[1,5-c]pyrimidin-5-amine |
| 100 | 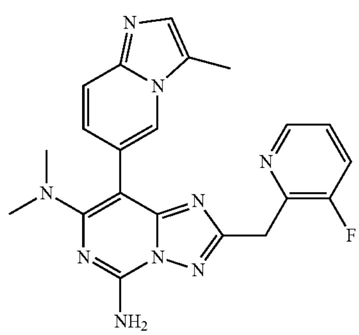 [SMILES: Cc1cnc2ccc(-c3c(N(C)C)nc(N)n4nc(Cc5ncccc5F)nc34)cn12] | 2-((3*fluoropyridin-2-yl)methyl)-N7,N7-dimethyl-8-(3-methylimidazo[1,2-a]pyridin-6-yl)-[1,2,4]triazolo[1,5-c]pyrimidine-5,7-diamine |
| 101 | 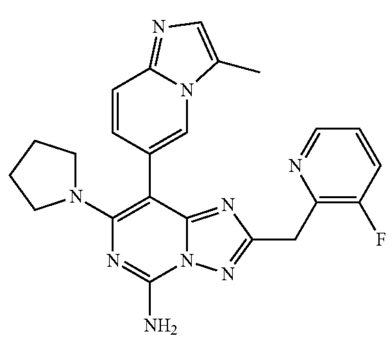 [SMILES: Cc1cnc2ccc(-c3c(N4CCCC4)nc(N)n4nc(Cc5ncccc5F)nc34)cn12] | 2-((3*fluoropyridin-2-yl)methyl)-8-(3-methylimidazo[1,2-a]pyridin-6-yl)-7-(pyrrolidin-1-yl)-[1,2,4]triazolo[1,5-c]pyrimidin-5-amine |

TABLE 1-continued

Exemplary Compounds 1-126

| Compound number | Compound structure | Compound name |
|---|---|---|
| 102 | 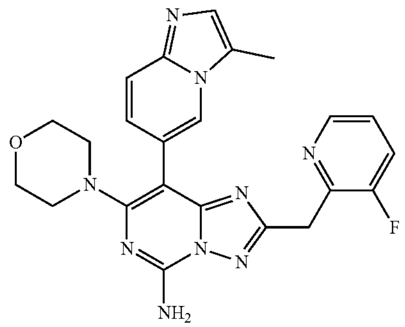 [SMILES: Cc1cnc2ccc(-c3c(N4CCOCC4)nc(N)n4nc(Cc5ncccc5F)nc34)cn12] | 2-((3-fluoropyridin-2-yl)methyl)-8-(3-methylimidazo[1,2-a]pyridin-6-yl)-7-morpholino-[1,2,4]triazolo[1,5-c]pyrimidin-5-amine |
| 103 | 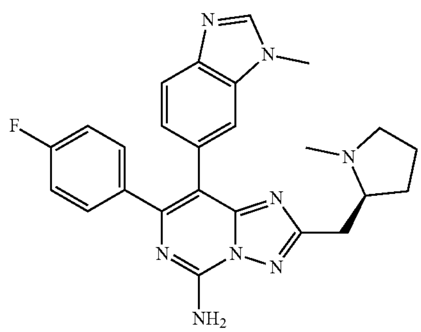 [SMILES: CN1CCC[C@H]1Cc1nc2c(-c3ccc4ncn(C)c4c3)c(-c3ccc(F)cc3)nc(N)n2n1] | (S)-7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine |
| 104 | 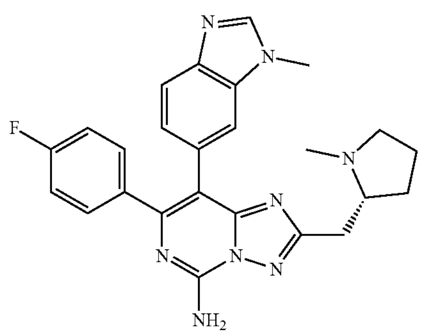 [SMILES: CN1CCC[C@@H]1Cc1nc2c(-c3ccc4ncn(C)c4c3)c(-c3ccc(F)cc3)nc(N)n2n1] | (R)-7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine |
| 105-1 | 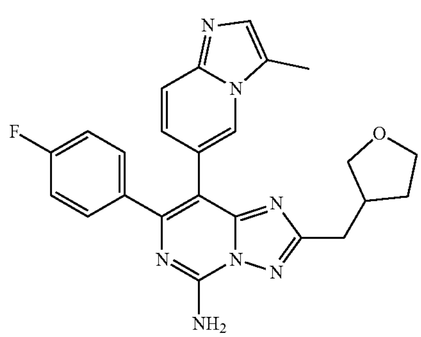 [SMILES: Cc1cnc2ccc(-c3c(-c4ccc(F)cc4)nc(N)n4nc(CC5CCOC5)nc34)cn12] | 7-(4-fluorophenyl)-8-(3-methylimidazo[1,2-a]pyridin-6-yl)-2-((tetrahydrofuran-3-yl)methyl)-[1,2,4]triazolo[1,5-c]pyrimidin-5-amine(isomer 1) |

TABLE 1-continued

Exemplary Compounds 1-126

| Compound number | Compound structure | Compound name |
|---|---|---|
| 105-2 | 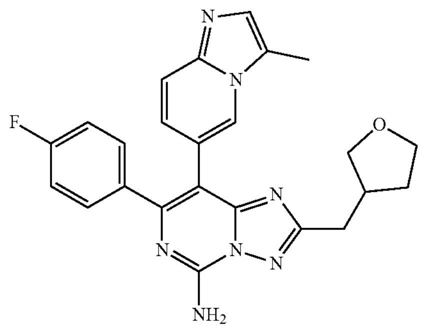 [SMILES: Cc1cnc2ccc(-c3c(-c4ccc(F)cc4)nc(N)n4nc(CC5CCOC5)nc34)cn12] | 7-(4-fluorophenyl)-8-(3-methylimidazo[1,2-a]pyridin-6-yl )-2-((tetrahydrofuran-3-yl)methyl)-[1,2,4]triazolo[1,5-c]pyrimidin-5-amine(isomer 2) |
| 106-1 | 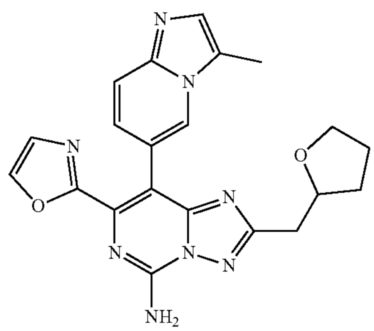 [SMILES: Cc1cnc2ccc(-c3c(-c4ncco4)nc(N)n4nc(CC5CCCO5)nc34)cn12] | 8-(3-methyiimidazo[1,2-a]pyridin-6-yl)-7-(oxazol-2-yl)-2-((tetrahydrofuran-2-yl)methyl)-[1,2,4]triazolo[1,5-c]pyrimidin-5-amine (isomer 1) |
| 106-2 | 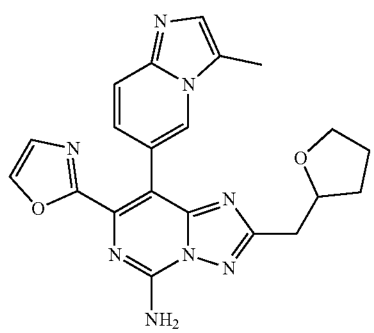 [SMILES: Cc1cnc2ccc(-c3c(-c4ncco4)nc(N)n4nc(CC5CCCO5)nc34)cn12] | 8-(3-methylimidazo[1,2-a]pyridin-6-yl)-7-(oxazol-2-yl)-2-((tetrahydrofuran-2-yl)methyl)-[1,2,4]triazolo[1,5-c]pyrimidin-5-amine (isomer 2) |
| 107-1 | 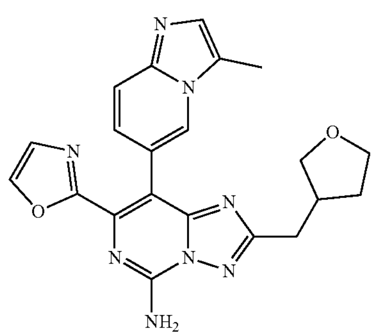 [SMILES: Cc1cnc2ccc(-c3c(-c4ncco4)nc(N)n4nc(CC5CCOC5)nc34)cn12] | 8-(3-methylimidazo[1,2-a]pyridin-6-yl)-7-(oxazol-2-yl)-2-((tetrahydrofuran-3-yl)methyl)-[1,2,4]triazolo[1,5-c]pyrimidin-5-amine (isomer 1) |

TABLE 1-continued

Exemplary Compounds 1-126

| Compound number | Compound structure | Compound name |
|---|---|---|
| 107-2 | 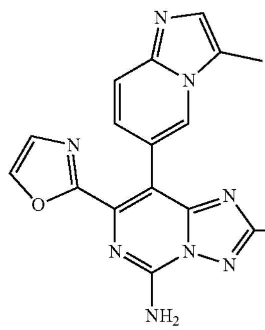 | 8-(3-methylimidazo[1,2-a]pyridin-6-yl)-7-(oxazol-2-yl)-2-((tetrahydrofuran-3-yl)methyl)-[1,2,4]triazolo[1,5-c]pyrimidin-5-amine (isomer 2) |
| 108 | 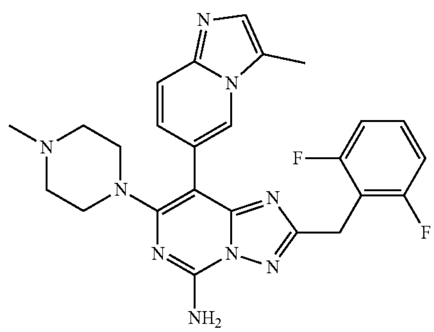 [SMILES: Cc1cnc2ccc(-c3c(N4CCN(C)CC4)nc(N)n4nc(Cc5c(F)cccc5F)nc34)cn12] | 2-(2,6-difluorobenzyl)-8-(3-methylimidazo[1,2-a]pyridin-6-yl)-7-{4-methylpiperazin-1-yl)-[1,2,4]triazolo[1,5-c]pyrimidin-5-amine |
| 109 | 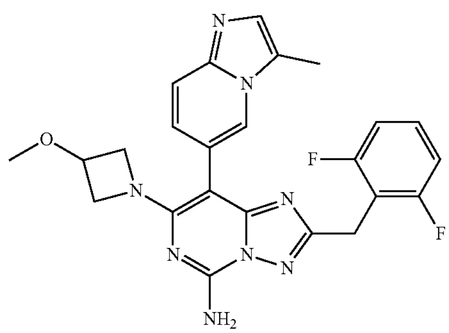 [SMILES: COC1CN(c2nc(N)n3nc(Cc4c(F)cccc4F)nc3c2-c2ccc3ncc(C)n3c2)C1] | 2-(2,6-difluorobenzyl)-7-(3-methoxyazetidin-1-yl)-8-(3-methylimidazo[1,2-a]pyridin-6-yl)-[1,2,4]triazolo[1,5-c]pyrimidin-5-amine |
| 110 | 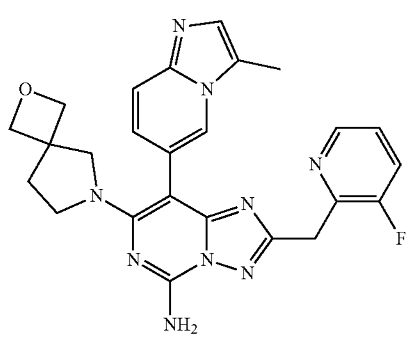 [SMILES: Cc1cnc2ccc(-c3c(N4CCC5(COC5)C4)nc(N)n4nc(Cc5ncccc5F)nc34)cn12] | 2-((3-fluoropyridin-2-yl)methyl)-8-(3-methylimidazo[1,2-a]pyridin-6-yl)-7-(2-oxa-6-azaspiro[3.4]octan-6-yl)-[1,2,4]triazolo[1,5-c]pyrimidin-5-amine |

TABLE 1-continued

Exemplary Compounds 1-126

| Compound number | Compound structure | Compound name |
| --- | --- | --- |
| 112-1 | 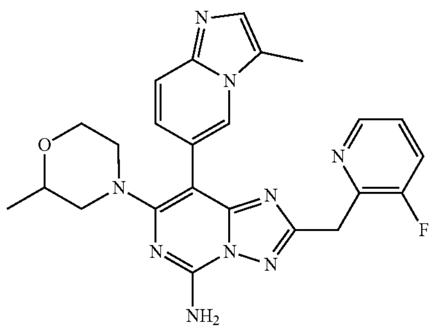 [SMILES: Cc1cnc2ccc(-c3c(N4CCOC(C)C4)nc(N)n4nc(Cc5ncccc5F)nc34)cn12] | 2-((3-fluoropyridin-2-yl)methyl)-8-(3-methylimidazo[1,2-a]pyridin-6-yl)-7-(2-methylmorpholino)-[1,2,4]triazolo[1,5-c]pyrimidin-5-amine (isomer 1) |
| 112-2 | 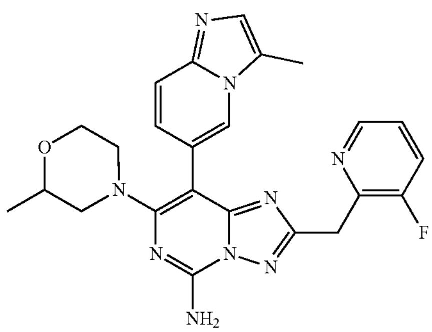 [SMILES: Cc1cnc2ccc(-c3c(N4CCOC(C)C4)nc(N)n4nc(Cc5ncccc5F)nc34)cn12] | 2-((3-fluoropyridin-2-yl)methyl)-8-(3-methylimidazo[1,2-a]pyridin-6-yl)-7-(2-methylmorpholino)-[1,2,4]triazolo[1,5-c]pyrimidin-5-amine (isomer 2) |
| 113-1 | 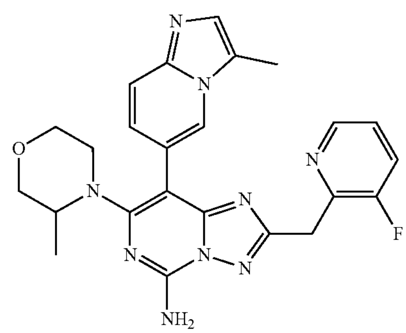 [SMILES: Cc1cnc2ccc(-c3c(N4CCOCC4C)nc(N)n4nc(Cc5ncccc5F)nc34)cn12] | 2-((3-fluoropyridin-2-yl)methyl)-8-(3-methylimidazo[1,2-a]pyridin-6-yl)-7-(3-methylmorpholino)-[1,2,4]triazolo[1,5-c]pyrimidin-5-amine (isomer 1) |
| 113-2 | 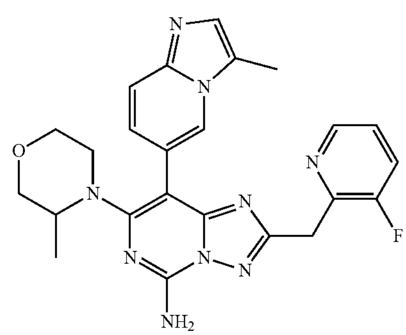 [SMILES: Cc1cnc2ccc(-c3c(N4CCOCC4C)nc(N)n4nc(Cc5ncccc5F)nc34)cn12] | 2-((3-fluoropyridin-2-yl)methyl)-8-(3-methylimidazo[1,2-a]pyridin-6-yl)-7-(3-methylmorpholino)-[1,2,4]triazolo[1,5-c]pyrimidin-5-amine (isomer 2) |

TABLE 1-continued

Exemplary Compounds 1-126

| Compound number | Compound structure | Compound name |
| --- | --- | --- |
| 114 | 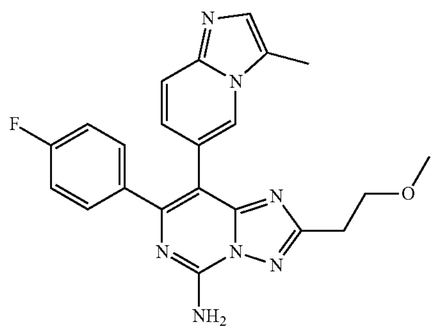 | 7-(4-fluorophenyl)-2-(2-methoxyethyl)-8-(3-methylimidazo[1,2-a]pyridin-6-yl)-[1,2,4]triazolo[1,5-c]pyrimidin-5-amine |
| 115 | 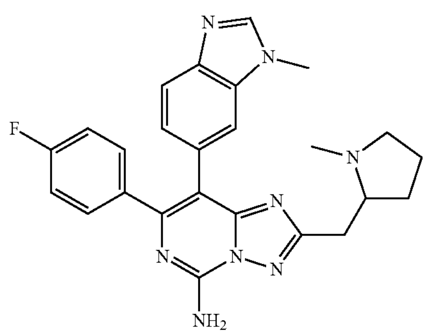 [SMILES: CN1CCCC1Cc1nc2c(-c3ccc4ncn(C)c4c3)c(-c3ccc(F)cc3)nc(N)n2n1] | (±)7-(4-fluorophenyl)-8-(1-methyl-1H-benzo[d]imidazol-6-yl)-2-((l-methylpyrrolidin-2-yl)methyl)-[1,2,4]triazolo[1,5-c]pyrimidin-5-amine |
| 116 | 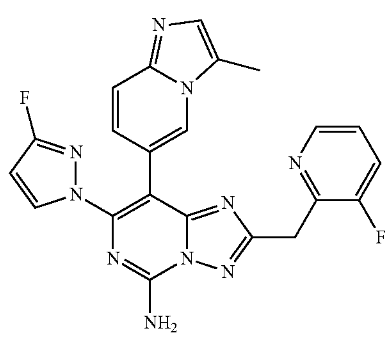 [SMILES: Cc1cnc2ccc(-c3c(-n4ccc(F)n4)nc(N)n4nc(Cc5ncccc5F)nc34)cn12] | 7-(3-fluoro-1H-pyrazol-1-yl)-2-((3-fluoropyridin-2-yl)methyl)-8-(3-methylimidazo[l,2-a]pyridin-6-yl)-[l,2,4]triazolo[l,5-c]pyrimidin-5-amine |
| 117 | 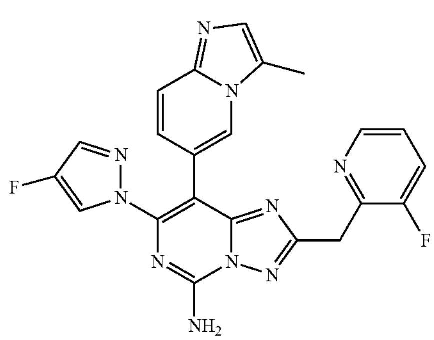 [SMILES: Cc1cnc2ccc(-c3c(-n4cc(F)cn4)nc(N)n4nc(Cc5ncccc5F)nc34)cn12] | 7-(4-fluoro-1H-pyrazol-1-yl)-2-((3-fluoropyridin-2-yl)methyl)-8-(3-methylimidazo[l,2-a]pyridin-6-yl)-[1,2,4]triazolo[1,5-c]pyrimidin-5-amine |

TABLE 1-continued

Exemplary Compounds 1-126

| Compound number | Compound structure | Compound name |
|---|---|---|
| 118 | 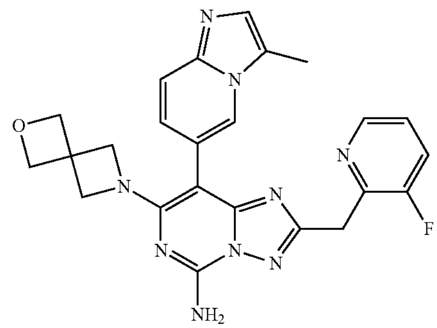 [SMILES: Cc1cnc2ccc(-c3c(N4CC5(COC5)C4)nc(N)n4nc(Cc5ncccc5F)nc34)cn12] | 2-((3-fluoropyridin-2-yl)methyl)-8-(3-methylimidazo[1,2-a]pyridin-6-yl)-7-(2-oxa-6-azaspiro[3.3]heptan-6-yl)-[1,2,4]triazolo[1,5-c]pyrimidin-5-amine |
| 119 | 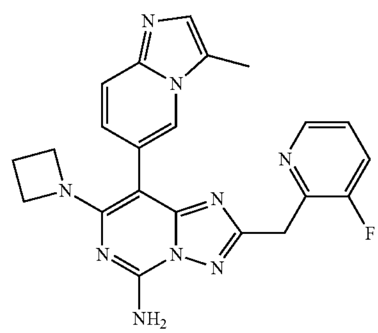 [SMILES: Cc1cnc2ccc(-c3c(N4CCC4)nc(N)n4nc(Cc5ncccc5F)nc34)cn12] | 7-(azetidin-1-yl)-2-((3-fluoropyridin-2-yl)methyl)-8-(3-methylimidazo[1,2-a]pyridin-6-yl)-[1,2,4]triazolo[1,5-c]pyrimidin-5-amine |
| 120 | 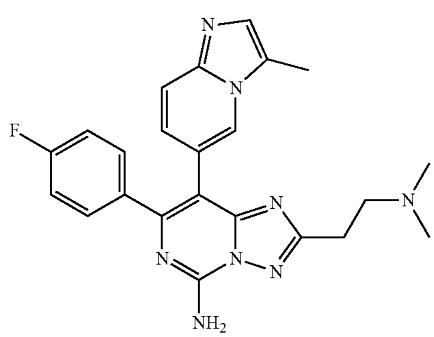 [SMILES: Cc1cnc2ccc(-c3c(-c4ccc(F)cc4)nc(N)n4nc(CCN(C)C)nc34)cn12] | 2-(2-(dimethylamino)ethyl)-7-(4-fluorophenyl)-8-(3-methylimidazo[1,2-a]pyridin-6-yl)-[1,2,4]triazolo[1,5-c]pyrimidin-5-amine |
| 121 | 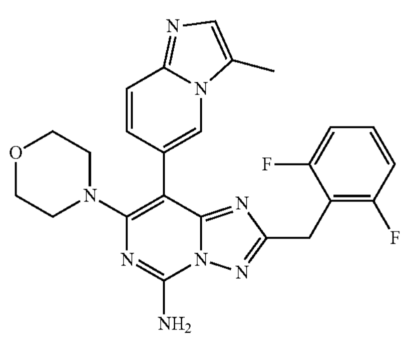 [SMILES: Cc1cnc2ccc(-c3c(N4CCOCC4)nc(N)n4nc(Cc5c(F)cccc5F)nc34)cn12] | 2-(2,6-difluorobenzyl)-8-(3-methylimidazo[1,2-a]pyridin-6-yl)-7-morpholino-[1,2,4]triazolo[1,5-c]pyrimidin-5-amine |

TABLE 1-continued

Exemplary Compounds 1-126

| Compound number | Compound structure | Compound name |
|---|---|---|
| 122 | 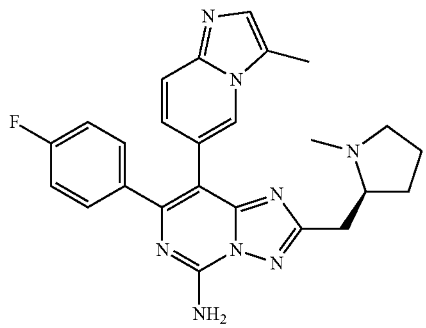 [SMILES: Cc1cnc2ccc(-c3c(-c4ccc(F)cc4)nc(N)n4nc(C[C@@H]5CCCN5C)nc34)cn12] | (S)-7-(4-fluorophenyl)-8-(3-methylimidazo[1,2-a]pyridin-6-yl)-2-((1-methylpyrrolidin-2-yl)methyl)-[1,2,4]triazolo[1,5-c]pyrimidin-5-amine |
| 123 | 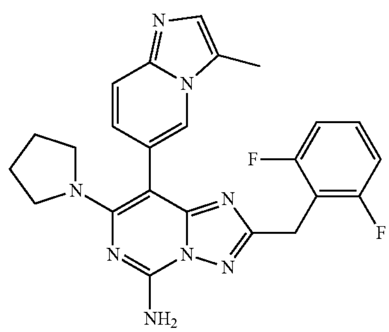 [SMILES: Cc1cnc2ccc(-c3c(N4CCCC4)nc(N)n4nc(Cc5c(F)cccc5F)nc34)cn12] | 2-(2,6-difluorobenzyl)-8-(3-methylimidazo[1,2-a]pyridin-6-yl)-7-(pyrrolidin-1-yl)-[1,2,4]triazolo[1,5-c]pyrimidin-5-amine |
| 124 | 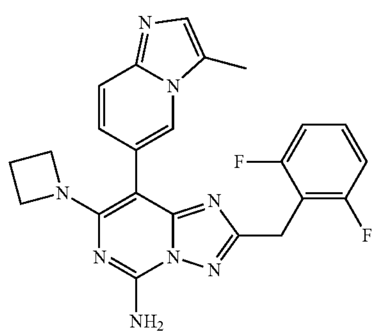 [SMILES: Cc1cnc2ccc(-c3c(N4CCC4)nc(N)n4nc(Cc5c(F)cccc5F)nc34)cn12] | 7-(azetidin-1-yl)-2-(2,6-difluorobenzyl)-8-(3-methylimidazo[1,2-a]pyridin-6-yl)-[1,2,4]triazolo[1,5-c]pyrimidin-5-amine |
| 125 | 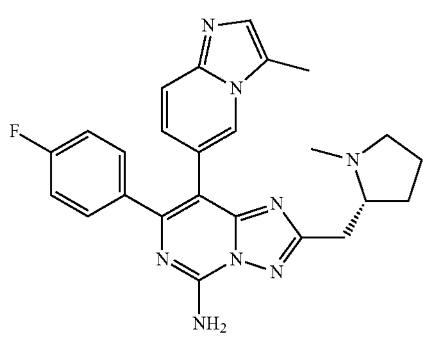 [SMILES: Cc1cnc2ccc(-c3c(-c4ccc(F)cc4)nc(N)n4nc(C[C@H]5CCCN5C)nc34)cn12] | (R)-7-(4-fluorophenyl)-8-(3-methylimidazo[1,2-a]pyrdin-6-yl)-2-((1-methylpyrrolidin-2-yl)methyl)-[1,2,4]triazolo[1,5-c]pyrimidin-5-amine |

TABLE 1-continued

Exemplary Compounds 1-126

| Compound number | Compound structure | Compound name |
|---|---|---|
| 126 | 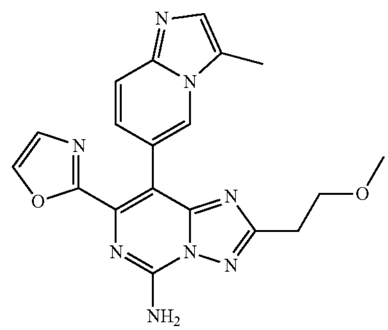 [SMILES: COCCc1nc2c(-c3ccc4ncc(C)n4c3)c(-c3ncco3)nc(N)n2n1] | 2-(2-methoxyethyl)-8-(3-methylimidazo[1,2-a]pyridin-6-yl)-7-(oxazol-2-yl)-[1,2,4]triazolo[1,5-c]pyrimidin-5-amine |

It is appreciated that certain features of the present disclosure, which are, for clarity, described in the context of separate embodiments, can also be provided in combination in a single embodiment. Conversely, various features of the present disclosure, which are, for brevity, described in the context of a single embodiment, can also be provided separately or in any suitable sub combination.

At various places in the present disclosure, linking substituents are described. Where the structure clearly requires a linking group, the Markush variables listed for that group are understood to be linking groups. For example, if the structure requires a linking group and the Markush group definition for that variable lists "alkyl", then it is understood that the "alkyl" represents a linking alkylene group.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate, fused to, a parent group. As used herein, the term "optionally substituted" or "optionally . . . substituted" means that the chemical group may have no substituents (i.e. unsubstituted) or may have one or more substituents (i.e. substituted). It is to be understood that substitution at a given atom is limited by valency.

As used herein, the term "$C_{i-j}$" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{1-12}$" indicates 1 to 12, including 1 to 10, 1 to 8, 1 to 6, 1 to 5, 1 to 4, 1 to 3 or 1 to 2 carbon atoms.

As used herein, the term "alkyl", whether as part of another term or used independently, refers to a saturated or unsaturated hydrocarbon chain, while the latter may be further subdivided into hydrocarbon chain having at least one double or triple bonds (alkenyl or alkynyl). In some embodiments, alkyl refers to a saturated hydrocarbon chain. The hydrocarbon chain mentioned above may be straight-chain or branched-chain. The term "$C_{i-j}$ alkyl" refers to an alkyl having i to j carbon atoms. Examples of saturated alkyl group include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of unsaturated alkyl groups include, but are not limited to, ethenyl, n-propenyl, isopropenyl, n-butenyl, sec-butenyl, ethynyl, propyn-1-yl, propyn-2-yl, and the like. Examples of "$C_{1-12}$ alkyl" are methyl, ethyl, propyl, isopropyl and butyl. Examples of "$C_{1-3}$ alkyl" are methyl, ethyl, propyl and isopropyl.

As used herein, the term "alkylene", whether as part of another term or used independently, refers to a divalent alkyl. Examples of alkylene groups include, but are not limited to, methylene, 1,1-ethylene, 1,2-ethylene, 1,1-propylene, 1,2-propylene, 1,3-propylene, 2,2-propylene, and the like.

As used herein the terms "halo" and "halogen" refer to an atom selected from fluorine, chlorine, bromine or iodine.

As used herein, the term "alkoxy", whether as part of another term or used independently, refers to a group of formula —O-alkyl. The term "$C_{i-j}$ alkoxy" means that the alkyl moiety of the alkoxy group has i to j carbon atoms. Examples of alkoxy groups include, but are not limited to, methoxyl, ethoxyl, propoxyl (e.g. n-propoxy and iso-propoxy), t-butoxy, and the like. Examples of "$C_{1-12}$ alkoxyl" are methoxyl, ethoxyl and propoxyl.

As used herein, the term "$C_{i-j}$ alky-OH", refers to a group of formula "—$C_{1-12}$ alkyl-OH", wherein the alkyl moiety of the group has i to j carbon atoms, and one or more hydroxyl groups may be linked to any carbon atoms in the alkyl moiety. In some embodiments, "C j alky-OH" has one hydroxyl group. Examples of "$C_{1-12}$ alkyl-OH" are hydroxymethyl, 1-hydroxyethyl, 2-hydroxyethyl and 1-hydroxyisopropyl.

As used herein, the term "C j haloalkyl", refers to a halogen substituted (mono- or multi-substituted) $C_{i-j}$ alkyl group. Examples of "$C_{1-12}$ haloalkyl" are fluoromethyl, difluoromethyl, trifluoromethyl, fluoroethyl, difluoroethyl, trifluoroethyl, chloroethyl and bromoisopropyl. Examples of "difluoroethyl" are 1,1-difluoroethyl. Examples of "trifluoroethyl" are 2,2,2-trifluoroethyl and 1,2,2-trifluoroethlyl.

Examples of "$C_{1-3}$ haloalkoxyl" are fluoromethoxyl, difluoromethoxyl, or trifluoromethoxyl. Examples of "trifluoroethoxy" are 2,2,2-trifluoroethoxy and 1,2,2-trifluoroethoxy.

Examples of "N—($C_{1-12}$ alkyl)amino" are methylamino and ethylamino.

Examples of "N—($C_{1-12}$ haloalkyl)amino" are fluoromethylamino, difluoromethylamino, trifluoromethylamino, 2-chloroethylamino and 1-bromoisopropylamino.

As used herein, the term "$C_{i-j}$ alkanoyl" refers to $C_{i-j}$ alkylcarbonyl. Examples of "$C_{1-12}$ alkanoyl" are propionyl and acetyl.

Examples of "$C_{1-12}$ alkanoylamino" are formamido, acetamido and propionylamino.

Examples of "$C_{1-12}$ alkanoyloxy" are acetoxy.

Examples of "$C_{1-12}$ alkoxycarbonyl" are methoxycarbonyl, ethoxycarbonyl, n- and t-butoxycarbonyl As used herein, the term "carbamoyl" refers to aminocarbonyl group. Examples of "N—($C_{1-12}$ alkyl)carbamoyl" are methylaminocarbonyl and ethylaminocarbonyl. Examples of "N,N—($C_{1-12}$ alkyl)$_2$carbamoyl" are dimethylaminocarbonyl and methylethylaminocarbonyl.

Examples of "N,N—($C_{1-12}$ alkyl)$_2$amino" are di-(N-methyl)amino, di-(N-ethyl)amino and N-ethyl-N-methylamino.

As used herein, the term "carbocyclyl", whether as part of another term or used independently, refers to any ring, including mono- or poly-cyclic ring(s) (e.g. having 2 or 3 fused, bridged or spiro rings), in which all the ring atoms are carbon and which contains at least three ring forming carbon atoms. In some embodiments, the carbocyclyl may contain 3 to 12 ring forming carbon atoms (i.e. 3-12 membered carbon atoms), 3 to 10 ring forming carbon atoms, 3 to 9 ring forming carbon atoms or 4 to 8 ring forming carbon atoms. Carbocyclyl groups may be saturated, partially unsaturated or fully unsaturated. In some embodiments, the carbocyclyl group may be a saturated cyclic alkyl group. In some embodiments, the carbocyclyl group may be an unsaturated cyclic alkyl group that contains at least one double bond in its ring system. In some embodiments, an unsaturated carbocyclyl group may contains one or more aromatic rings. In some embodiments, one or more ring forming —CH$_2$— group of the saturated or unsaturated carbocyclyl may be replaced by a —C(O)— group.

In some embodiments, the carbocyclyl group is a monocyclic alkyl group. In some embodiments, the carbocyclyl group is a saturated monocyclic alkyl group. Examples of monocyclic saturated or unsaturated carbocyclyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, and the like.

As used herein, the term "spiro" rings refers to ring systems having two rings connected through one single common atom; the term "fused" rings refers to ring systems having two rings sharing two adjacent atoms; and the term "bridged" rings refers to ring systems with two rings sharing three or more atoms.

A 3-12, 3-10 or 5-6 "membered saturated or unsaturated carbocyclyl" is a saturated, partially unsaturated or fully unsaturated mono- or poly-cyclic ring system having 3 to 12, 3 to 10, or 5 to 6 ring forming carbon atoms respectively, wherein one or more ring forming —CH$_2$— group can optionally be replaced by a —C(O)— group.

Examples of "3-12 membered saturated or unsaturated carbocyclyl" are $C_{3-4}$ cycloalkyl, cyclohexyl, cyclohexenyl, cyclopentyl, phenyl, naphthyl and bicyclo[1.1.1]pentan-1-yl.

Examples of "$C_{3-4}$ cycloalkyl" are cyclopropyl and cyclobutyl. Examples of "5-6 membered saturated or unsaturated carbocyclyl" are cyclopentyl and phenyl.

As used herein, the term "heterocyclyl" refers to a carbocyclyl group, wherein one or more (e.g. 1, 2 or 3) ring atoms are replaced by heteroatoms, which include, but are not limited to, O, S, N, P, and the like. In some embodiments, the heterocyclyl is a saturated heterocyclyl. In some embodiments, the heterocyclyl is an unsaturated heterocyclyl having one or more double bonds in its ring system. In some embodiments, the heterocyclyl is a partially unsaturated heterocyclyl. In some embodiments, the heterocyclyl is a fully unsaturated heterocyclyl. In some embodiments, an unsaturated heterocyclyl group may contain one or more aromatic rings. In some embodiments, one or more ring forming —CH$_2$— group of the heterocyclyl can optionally be replaced by a —C(O)—, a —S—, a —S(O)—, or a —S(O)$_2$— group. In some embodiments, where the heterocyclyl contains a sulphur in its ring system, said ring forming sulphur atom may be optionally oxidised to form the S-oxides. In some embodiments the heterocyclyl is linked to the other portion of a compound through its ring forming carbon. In some embodiments the heterocyclyl is linked to the other portion of a compound through its ring forming nitrogen.

In some embodiments, 3-12 membered saturated or unsaturated mono- or poly-cyclic heterocyclyl having 1, 2, or 3 heteroatoms selected from N, O, or S.

A 3-12, 3-10 or 5-6 "membered saturated or unsaturated heterocyclyl" is a saturated, partially unsaturated or fully unsaturated mono- or poly-cyclic ring(s) (e.g. having 2 or 3 fused, bridged or spiro rings) system having 3 to 12, 3 to 10, or 5 to 6 ring forming atoms respectively, of which at least one ring forming atom is chosen from nitrogen, sulphur or oxygen, which may, unless otherwise specified, linked to the other portion of a compound through its ring forming carbon or nitrogen, wherein one or more ring forming —CH$_2$— group of the saturated or unsaturated heterocyclyl may be replaced by a —C(O)—, a —S—, a —S(O)—, or a —S(O)$_2$— group, and wherein when the heterocyclyl contains a sulphur in its ring system, said ring sulphur atom may be optionally oxidised to form the S-oxides.

Exemplary monocyclic heterocyclyl groups include, but are not limited to oxetanyl,1,1-dioxothietanylpyrrolidyl, tetrahydrofuryl, tetrahydrothienyl, pyrrolyl, furanyl, thienyl, pyrazolyl, imidazolyl, triazolyl, oxazolyl, thiazolyl, piperidyl, piperidyl, piperazinyl, morpholinyl, pyridinyl, pyrazinyl, pyrimidinyl, pyridazinyl, triazinyl, pyridonyl, pyrimidonyl, pyrazinonyl, pyrimidonyl, pyridazonyl, triazinonyl, and the like.

Examples of spiro heterocyclyl include, but are not limited to, spiropyranyl, spirooxazinyl, and the like. Examples of fused heterocyclyl include, but are not limited to, phenyl fused ring or pyridinyl fused ring, such as quinolinyl, isoquinolinyl, quinoxalinyl, quinolizinyl, quinazolinyl, azaindolizinyl, pteridinyl, chromenyl, isochromenyl, indolyl, isoindolyl, indolizinyl, indazolyl, purinyl, benzofuranyl, isobenzofuranyl, benzimidazolyl, benzothienyl, benzothiazolyl, carbazolyl, phenazinyl, phenothiazinyl, phenanthridinyl, imidazo[1,2-a]pyridinyl, [1,2,4]triazolo[4,3-a]pyridinyl, [1,2,3]triazolo[4,3-a]pyridinyl groups, and the like. Examples of bridged heterocyclyl include, but are not limited to, morphanyl, hexamethylenetetraminyl, 8-aza-bicyclo[3.2.1]octane, 1-aza-bicyclo[2.2.2]octane, 1,4-diazabicyclo[2.2.2]octane (DABCO), and the like.

The "compound" of present disclosure is intended to encompass all stereoisomers, geometric isomers, and tautomers of the structures depicted unless otherwise specified.

The term "stereoisomer" refers to any of the various stereoisomeric configurations (e.g. enantiomers, diastereomers and racemates) of an asymmetric compound (e.g. those having one or more asymmetrically substituted carbon atoms or "asymmetric centers"). Compounds of the present disclosure that contain asymmetric centers can be isolated in optically active (enantiomers or diastereomers) or optically inactive (racemic) forms. The term "enantiomer" includes pairs of stereoisomers that are non-superimposable mirror images of each other. A 1:1 mixture of a pair of enantiomers is a "racemic mixture". The terms "diastereomers" or "diastereoisomers" include stereoisomers that have at least two asymmetric atoms, but which are not mirror images of each other. Certain compounds containing one or more asymmetric centers may give rise to enantiomers, diastereomers or other stereoisomeric forms that may be defined, in terms of absolute configuration, as (R)- or (S)- at each asymmetric center according to the Cahn-Ingold-Prelog R—S system. Resolved compounds whose absolute configuration is unknown can be designated using the term "or" at the asymmetric center. Methods on how to prepare optically active forms from racemic mixtures are known in the art, such as resolution by HPLC or stereoselective synthesis.

The terms "geometric isomers" or "cis and trans isomers" refer to compounds with same formula but their functional groups are rotated into a different orientation in three-dimensional space.

The term "tautomers" include prototropic tautomers that are isomeric protonation states of compounds having the same formula and total charge. Examples of prototropic tautomers include, but are not limited to, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomers can be in equilibrium or sterically locked into one form by appropriate substitution. Compounds of the present disclosure identified by name or structure as one particular tautomeric form are intended to include other tautomeric forms unless otherwise specified.

The "compound" of the present disclosure is also intended to encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^1$H, $^2$H, $^3$H, $^{11}$C, $^{12}$C, $^{13}$C, $^{14}$C, $^{14}$N, $^{15}$N, $^{16}$O, $^{17}$O, $^{18}$O, $^{31}$P, $^{32}$P, $^{32}$S, $^{33}$S, $^{34}$S, $^{36}$S, $^{17}$F, $^{19}$F, $^{35}$Cl, $^{37}$Cl, $^{79}$Br, $^{81}$Br, $^{127}$I and $^{131}$I. In some embodiments, hydrogen includes protium, deuterium and tritium. In some embodiments, the term "substituted by deuterium" or "deuterium substituted" to replace the other isoform of hydrogen (e.g. protium) in the chemical group with deuterium. In some embodiments, carbon includes $^{12}$C and $^{13}$C. In some embodiments, "compound" of the present disclosure only encompasses the isotopes of hydrogen in the compound. In some embodiments, "compound" of the present disclosure only encompasses the isotopes of atoms in natural abundance.

It is also to be understood that the "compound" of present disclosure can exist in solvated as well as unsolvated forms, such as, for example, hydrated forms, solid forms, and the present disclosure is intended to encompass all such solvated and unsolvated forms.

It is further to be understood that the "compound" of present disclosure can exist in forms of pharmaceutically acceptable salts.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, "pharmaceutically acceptable salts" refers to derivatives of the compounds of present disclosure wherein the parent compound is modified by converting an existing acidic moiety (e.g. carboxyl and the like) or base moiety (e.g. amine, alkali and the like) to its salt form. In many cases, compounds of present disclosure are capable of forming acid and/or base salts by virtue of the presence of amino and/or carboxyl groups or groups similar thereto. The pharmaceutically acceptable salts are acid and/or base salts that retain biological effectiveness and properties of the parent compound, which typically are not biologically or otherwise undesirable. Suitable pharmaceutically acceptable salts of a compound of the present disclosure includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). In some embodiments, the pharmaceutically acceptable salt of the compound of the present disclosure is a formic acid salt. In some embodiments, the pharmaceutically acceptable salt of the compound of the present disclosure is a TFA salt.

Suitable pharmaceutically acceptable salts of a compound of the present disclosure also include, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. Those skilled in the art would appreciate that adding acids or bases for forming acid/base-addition salts other than those shown in the examples may also be possible. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002). In some embodiments, Suitable pharmaceutically acceptable salts of a compound of the present disclosure is inorganic bases salt.

The present disclosure also includes active intermediates, active metabolites and prodrugs of the compounds of present disclosure. As used herein, an "active intermediate" refer to intermediate compound in the synthetic process, which exhibits the same or essentially the same biological activity as the final synthesized compound.

As used herein, an "active metabolite" refers to a breakdown or end product of a compound of the present disclosure or its salt or prodrug produced through metabolism or biotransformation in the animal or human body, which exhibits the same or essentially the same biological activity as the specified compound. Such metabolites may result from, for example, oxidation, reduction, hydrolysis, amidation, deamidation, esterification, deesterification, enzymatic cleavage, and the like, of the administered compound or salt or prodrug.

As used herein, "prodrugs" refer to any compounds or conjugates which release the active parent drug when administered to an animal or human subject. Prodrugs can be prepared by modifying functional groups present in the compounds in such a way that the modifications are cleavable, either in routine manipulation or in vivo, from the parent compounds. Prodrugs include compounds wherein hydroxyl, amino, sulfhydryl, or carboxyl group is bonded to any group that, when administered to a mammalian subject, is cleavable to form a free hydroxyl, amino, sulfhydryl, or carboxyl group respectively. Examples of prodrugs include, but are not limited to, acetate, formate and benzoate derivatives of alcohol and amine functional groups in the compounds of the present disclosure. Preparation and use of prodrugs is discussed in T. Higuchi and V. Stella, "Pro-drugs as Novel Delivery Systems", Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Synthetic Method

Synthesis of the compounds provided herein, including pharmaceutically acceptable salts thereof, are illustrated in the synthetic schemes in the examples. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized for the purposes of research and potentially submission to regulatory agencies.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g. temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by one skilled in the art.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g. $^1$H or $^{13}$C), infrared spectroscopy, spectrophotometry (e.g. UV-visible), mass spectrometry, or by chromatographic methods such as high performance liquid chromatography (HPLC), liquid chromatography-mass spectroscopy (LCMS), or thin layer chromatography (TLC). Compounds can be purified by one skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety), and normal phase silica chromatography.

The structures of the compounds in the examples are characterized by nuclear magnetic resonance (NMR) or/and liquid chromatography-mass spectrometry (LC-MS). NMR chemical shift (δ) is given in the unit of $10^{-6}$ (ppm). $^1$H-NMR spectra is recorded in dimethyl sulfoxide-d6 (DMSO-d6) or CDCl3 or CD3OD or D2O or Acetone_$d_6$ or $CD_3CN$ (from Innochem or Sigma-Aldrich or Cambridge Isotope Lab., Inc.) on Bruker AVANCE NMR (300 MHz or 400 MHz) spectrometers using ICON-NMR (under TopSpin program control) with tetramethylsilane as an internal standard.

MS measurement is carried out using Shimadzu 2020 Mass Spectrometer with an electrospray source at positive and negative ion mode.

High Performance Liquid Chromatography (HPLC) measurement is carried out on Shimadzu LC-20AD systems or Shimadzu LC-20ADXR systems or Shimadzu LC-30AD systems using Shim-pack XR-ODS C18 column (3.0*50 mm, 2.2 μm), or Ascentis Express C18 column (2.1*50 mm, 2.7 μm), or Agilent Poroshell HPH-C18 column (3.0*50 mm, 2.7 μm).

Thin layer chromatography is carried out using Sinopharm Chemical Reagent Beijing Co., Ltd. and Xinnuo Chemical silica gel plates. The silica gel plates used for thin layer chromatography (TLC) are 175-225 μm. The silica gel plates used for separating and purifying products by TLC are 1.0 mm.

Purified chromatographic column uses the silica gel as the carrier (100~200, 200~300 or 300~400 mesh, produced by Rushanshi Shangbang Xincailiao Co., Ltd. or Rushan Taiyang Desiccant Co., Ltd. etc.), or flash column (reversed phase C18 column 20-45 μm, produced by Agela Technologies) in Agela Technologies flash system. The size of columns are adjusted according to the amount of compounds.

The known starting materials of the present disclosure can be synthesized by using or according to the known methods in the art, or can be purchased from Alfa Aesar, TCI, Sigma-Aldrich, Bepharm, Bide pharmatech, PharmaBlock, Enamine, Innochem and JW&Y PharmLab etc.

Unless otherwise specified, the reactions are all carried out under argon or nitrogen atmosphere. Argon or nitrogen atmosphere refers to that the reaction flask is connected to an argon or nitrogen balloon with a volume of about 1 L. Hydrogenation is usually carried out under pressure. Unless otherwise specified, the reaction temperature in the examples is ambient temperature, which is 10° C.-30° C.

The reaction progress are monitored by TLC or/and LC-MS. The eluent systems used for the reactions include dichloromethane-methanol system and petroleum ether-ethyl acetate system. The volume ratios of the solvents are adjusted according to the different polarities of compounds.

The elution system of column chromatography used for purifying compounds and eluent system of TLC include dichloromethane-methanol system and petroleum ether-ethyl acetate system. The volume ratios of the solvents are adjusted according to the different polarities of compounds. A small amount of alkaline or acidic agents (0.1%1%) such as formic acid, or acetic acid, or TFA, or ammonia can be added for adjustment.

Abbreviations for chemicals used in the synthesis of the compounds provided herein are listed below:

| | |
|---|---|
| AcOH | Acetic acid |
| AcOK | Potassium acetate |
| BnSH | Benzyl mercaptan |
| $Br_2$ | Bromine |
| BSA | N,O-Bis(trimethylsilyl)acetamide |
| $CH_3CN$ | Acetonitrile |
| $ClCH_2CH_2Cl$ | 1,2-Dichloroethane |
| $Cs_2CO_3$ | Caesium carbonate |
| $Cu(OAc)_2$ | Cupric Acetate |
| DCM | Dichloromethane |
| DIEA | N,N-Diisopropylethylamine |
| DMF | N,N-Dimethylformamide |
| DMSO | Dimethyl sulfoxide |
| dtbpf | 1,1'-Bis(di-t-butylphosphino)ferrocene |
| EtOAc | Ethyl acetate |
| EtOH | Ethanol |
| HATU | 1-[Bis(dimethylamino)methylene]-1H-1,2,3-triazolo[4,5-b]pyridinium 3-oxid hexafluorophosphate |
| ICl | Iodine monochloride |
| $K_2CO_3$ | Potassium carbonate |
| $K_3PO_4$ | Tripotassium phosphate |
| KF | Potassium fluoride |
| LiCl | Lithium chloride |
| LiOH | Lithium hydroxide |
| MeOH | Methanol |
| MTBE | Methyl tert-butyl ether |
| $Na_2CO_3$ | Sodium Carbonate |
| NaCl | Sodium chloride |
| NaOH | Sodium hydroxide |
| NBS | N-Bromosuccinimide |
| n-BuOH | Butyl alcohol |
| $NH_2NH_2$—$H_2O$ | Hydrazine hydrate |
| NIS | N-iodosuccinimide |
| NMP | N-Methyl pyrrolidone |
| Pd(amphos)$Cl_2$ | Bis(di-tert-butyl(4-dimethylaminophenyl)phosphine)dichloropalladium(II) |
| Pd(dppf)$Cl_2$ | [1,1'-Bis(diphenylphosphino)ferrocene]dichloropalladium(II) |
| Pd(PPh$_3$)$_4$ | Tetrakis(triphenylphosphine)palladium |
| PE | Petroleum ether |
| $POCl_3$ | Phosphoric trichloride |
| $T_3P$ | 1,3,5,2,4,6-Trioxatriphosphorinane, 2,4,6-tripropyl-, 2,4,6-trioxide |
| TEA | Triethylamine |
| TFA | Trifluoroacetic acid |
| THF | Tetrahydrofuran |
| $ZnCl_2$ | Zinc chloride |

Pharmaceutical Composition

The present disclosure provides pharmaceutical compositions comprising at least one compound of the present disclosure, or a pharmaceutically acceptable salt thereof. In some embodiments, the pharmaceutical composition comprises more than one compound of the present disclosure, or a pharmaceutically acceptable salt thereof. In some embodiments, the pharmaceutical composition comprises one or more compounds of the present disclosure, or a pharmaceutically acceptable salt thereof, and a pharmaceutical acceptable carrier.

In general, the pharmaceutically acceptable carriers are conventional medicinal carriers in the art which can be prepared in a manner well known in the pharmaceutical art. In some embodiments, the compounds of the present disclosure, or a pharmaceutically acceptable salt thereof, may be admixed with pharmaceutically acceptable carrier for the preparation of pharmaceutical composition.

The form of pharmaceutical compositions depends on a number of criteria, including, but not limited to, route of administration, extent of disease, or dose to be administered. The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, powder, granule, sachets, cachets, lozenges, suspensions, emulsions, solutions, syrups, aerosols (as a solid or in a liquid medium), spray, ointment, paste, cream, lotion, gel, patch, inhalant, or suppository.

In certain embodiments, the pharmaceutical compositions comprise about 1 mg to about 1000 mg of the compounds of the present disclosure, or a pharmaceutically acceptable salt thereof.

In some embodiments, the pharmaceutical compositions comprise one or more compounds of the present disclosure, or a pharmaceutically acceptable salt thereof, as a first active ingredient, and further comprise a second active ingredient. The second active ingredient can be any immunomodulator or anti-tumour agent known in the art, including without limitation, chemotherapeutics, immunotherapeutics, cell signal transduction inhibitors, cell signal transduction inhibitors, alkylating agents, topoisomerase inhibitors, mitosis inhibitors, antihormonal agents, etc. Examples of such immunomodulators or anti-tumour agents are, platinum based chemotherapeutics (e.g., Cisplatin (DDP), Carboplatin (CBP), Sulfato-1,2-diaminocyclohexane platinum (SHP), Nedaplatin, Oxaliplatin (OXA), Laboplatin), Docetaxel, Paclitaxel, Doxorubicin, Etoposide, Mitoxantrone, CTLA-4 inhibitors, anti-CTLA-4 antibodies, PD-1 inhibitors, PD-L1 inhibitors, anti-PD-1/PD-L1 antibodies, CD39 inhibitors, anti-CD39 antibodies, CD73 inhibitors, anti-CD73 antibodies, CCR2 inhibitors, anti-CCR2 antibodies, EGFR inhibitors, CDK 4/6 inhibitors, MELK inhibitors, OX40 agonists, antiandrogen inhibitors, IgG4 isotype antibodies, tyrosine kinase inhibitors, DNA methyltransferase inhibitors, Hsp90 inhibitors, FGFR inhibitors, mTOR inhibitors, aromatase inhibitors, VEGF inhibitors, LHRH antagonists, PI3K inhibitors, AKT inhibitors, aurora kinase inhibitors, MEK inhibitors, HDAC inhibitors, BET inhibitors, PIK3CA inhibitors, proteasome inhibitors, other SERDs, farnesyltransferase inhibitors, VEGF-A antibodies, ErbB3 (Her3) antibodies, proteasome inhibitors, protein kinase C inhibitors, anti-IGF-1R antibodies, anti-HER2 antibodies, SERMs, IGF inhibitors, anti-IgG antibodies and the like. Representative examples of the anti tumour agents for treating cancers or tumors may include, but are not limited to, cisplatin, carboplatin, SHP, nedaplatin, oxaliplatin, laboplatin, docetaxel, paclitaxel, doxorubicin, etoposide, mitoxantrone, vincristine, vinblastine, gemcitabine, cyclophosphamide, chlormabucil, carmustine, methotrexate, fluorouracil, actinomycin, epirubicin, anthracycline, bleomycin, mitomycin-C, irinotecan, topotecan, teniposide interleukin, interferon, tremelimumab, ipilimumab, pembrolizumab, nivolumab, avelumab, durvalumab, atezolizumab, IPH 52, IPH 53, CPI-006, plozalizumab, MLN1202, cetuximab, lapatinib, erlotinib, gefitinib, neratinib, trastuzumab, ado-trastuzumab emtansine, pertuzumab, MCLA-128, anastrazole, raloxifene, G1T38, tamoxifen, goserelin, enzalutamide, vorinostat, entinostat, sunitinib, pazopanib, bevacizumab, ranibizumab, pegaptanib, cediranib, dasatinib, GDC-0980, gedatolisib, alpelisib, BKM120, copanlisib, AZD8835, GDC-0941, taselisib, temsirolimus, everolimus, sapanisertib, AZD5363, MK2206, panitumumab, pembrolizumab, sorafenib, palbociclib, abemaciclib, ribociclib, crizotinib, dovitinib, ruxolitinib, azacitidine, CC-486, HSP90 ganetespib, Debio 1347, erdafitinib, vitusertib, alisertib, selumetinib, GS-5829, GSK525762, MLN9708, GDC-0810, AFP464, tipifarnib, seribantumab, bortezomib, enzastaurin, AVE1642, xentuzumab, dalotuzumab, AMG 479, and the like.

The treatment of Adenosine receptor-associated diseases defined hereinafter may be applied as a sole therapy or may involve, in addition to the compound of the invention, conventional surgery or radiotherapy or chemotherapy or immunotherapy. Such chemotherapy may include one or more of the following chemotherapeutics: Cisplatin (DDP), Carboplatin (CBP), Sulfato-1,2-diaminocyclohexane platinum (SHP), Nedaplatin, Oxaliplatin (OXA), Laboplatin, Docetaxel, Paclitaxel, Doxorubicin, Etoposide, or Mitoxantrone. Such immunotherapeutics may include one or more of the following anti-tumour agents: (i) an anti-CTLA-4 antibody; (ii) an anti-PD-1 antibody; (iii) an anti-PD-L1 antibody; (iv) an anti-CD73 antibody; (v) an anti-CD39 antibody; or (vi) an anti-CCR2 antibody.

Particularly an anti-CTLA-4 antibody is tremelimumab (as disclosed in U.S. Pat. No. 6,682,736). In another aspect of the invention, particularly an anti-CTLA-4 antibody is ipilimumab (marketed by Bristol Myers Squib as YERVOY®).

Particularly an anti-PD-L1 antibody is an antibody as disclosed in US 20130034559 (MedImmune). In another aspect of the invention, particularly an anti-PD-L1 antibody is an antibody as disclosed US 2010/0203056 (Genentech/Roche). In another aspect of the invention, particularly an anti-PD-L1 antibody is an antibody as disclosed US 20090055944 (Medarex). In another aspect of the invention, particularly an anti-PD-L1 antibody is an antibody as disclosed US 20130323249 (Sorrento Therapeutics).

Particularly an anti-PD-1 antibody is MRK-3475 (Merck). In another aspect of the invention, particularly an anti-PD-1 antibody is Nivolumab, or an anti-PD-1 antibody as disclosed in WO 2006/121168 or U.S. Pat. No. 8,008,449 (Medarex). In another aspect of the invention, particularly an anti-PD-1 antibody is an antibody as disclosed in WO2009/101611 (CureTech). In another aspect of the invention, particularly an anti-PD-1 antibody is an antibody as disclosed in WO2012/145493 (Amplimmune). In another aspect of the invention, particularly an anti-PD-1 antibody is an antibody as disclosed in U.S. Pat. No. 7,488,802 (Wyeth/MedImmune). In another aspect of the invention, particularly an anti-PD-1 antibody is an antibody as disclosed in US 20130280275 (Board of Regents, Univ. of Texas). In another aspect of the invention, particularly an anti-PD-1 antibody is an antibody as disclosed in WO 99/42585 (Agonox), WO 95/12673 and WO 95/21915.

Particularly an anti-CD39 antibody is IPH52 (Innate Pharmaceuticals).

Particularly an anti-CD73 antibody is CPI-006 (Corvus Pharmaceuticals) or IPH53 (Innate Pharmaceuticals).

Particularly an anti-CCR2 antibody is plozalizumab (Takeda Pharmaceuticals International Co.) or MLN1202 (Millennium Pharmaceuticals).

According to this aspect of the invention, there is provided a combination suitable for use in the treatment of an Adenosine receptor-associated disease, especially cancer, comprising a compound of formula (I) as defined hereinbefore or a pharmaceutically acceptable salt thereof and any one or more of the chemotherapeutics listed above and/or any one or more of the immonotherapeutics listed under (i)-(vi) above.

For example, the compounds of present disclosure may be provided in combination with an anti-PD1/PD-L1 antibody. In some specific embodiments, the compounds of present disclosure may be provided in combination with an anti-PD1/PD-L1 antibody and further in combination of an anti-CTLA-4, CD38, CD73, or CCR2 antibody.

According to this aspect of the present disclosure, there is provided a combination suitable for use in the treatment of cancer comprising a compound of formula (I) as defined hereinbefore or a pharmaceutically acceptable salt thereof and any one of the immunomodulators or anti tumour agents listed above.

Therefore in a further aspect of the present disclosure, there is provided a compound of formula (I) or a pharmaceutically acceptable salt thereof in combination with an immunomodulator or chemotherapeutics selected from one listed above.

Herein, where the term "combination" is used, it is to be understood that this refers to simultaneous, separate or sequential administration. In some embodiments, "combination" refers to simultaneous administration. In another aspect of the present disclosure, "combination" refers to separate administration. In a further aspect of the present disclosure, "combination" refers to sequential administration. Where the administration is sequential or separate, the delay in administering the second component should not be such as to lose the beneficial effect of the combination.

According to a further aspect of the present disclosure, there is provided a pharmaceutical composition which comprises a compound of formula (I) or a pharmaceutically acceptable salt thereof in combination with an immunomodulator or anti-tumour agent selected from those listed above, in association with a pharmaceutically acceptable diluent or carrier.

According to a further aspect of the present disclosure, there is provided a pharmaceutical composition which comprises a compound of formula (I) or a pharmaceutically acceptable salt thereof in combination with an immunomodulator or anti-tumour agent selected from one listed above, in association with a pharmaceutically acceptable diluent or carrier for use in producing an immunomodulating or anti-cancer effect.

According to a further aspect of the present disclosure, there is provided a pharmaceutical composition which comprises a compound of formula (I) or a pharmaceutically acceptable salt thereof in combination with an immunomodulator or anti-tumour agent selected from one listed above, in association with a pharmaceutically acceptable diluent or carrier for use in treating NSCLC, RCC, prostate cancer, or breast cancer (etc.).

According to a further aspect of the present disclosure, there is provided a kit comprising a compound of formula (I) or a pharmaceutically acceptable salt thereof in combination with an immunomodulator or anti-tumour agent selected from one listed above.

According to a further aspect of the present disclosure, there is provided a kit comprising:

a) a compound of formula (I) or a pharmaceutically acceptable salt thereof in a first unit dosage form;

b) an immunomodulator or anti-tumour agent selected from one listed above in a second unit dosage form; and c) container for containing said first and second dosage forms.

In addition to their use in therapeutic medicine, the compounds of formula (I), or a pharmaceutically acceptable salt thereof, are also useful as pharmacological tools in the development and standardisation of in vitro and in vivo test systems for the evaluation of the activity or the expression of adenosine receptors in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the present disclosure, described herein also apply.

Method for Treatment

The present disclosure provides a method of treating a disease associated with adenosine receptors (including, for example, A1, A2a, and/or A2b, particularly A2a) by administering to a subject a therapeutically effective amount of one or more compounds, pharmaceutically acceptable salts thereof or the pharmaceutical composition of the present disclosure.

As used herein, the term "disease associated with adenosine receptors" or "AR associated disease" refers to a disease whose onset or development or both is associated with the genomic alterations, expression, over-expression, degradation or activity of AR (including, for example, A1, A2a, and/or A2b, especially A2a), as the case may be. Examples include but are not limited to, inflammatory disorders, cancer, Parkinson disease, epilepsy, cerebral ischemia and stroke, sepression, cognitive impairment, HIV, ADA-SCID, acute heart failure (AHF) and chronic heart failure, chronic obstructive pulmonary disease (COPD), asthma, and other diseases. In certain embodiments, AR associated disease refers to a disease that will be treated by inhibition of the effect of Adenosine receptor.

In some embodiments, the AR associated disease is cancer, preferably an AR-expressing cancer, or AR-overexpressing cancer. An "AR-expressing cancer" is one that involves cancer cells or tumor cells having AR protein, such as A2a, A1 and/or A2b, present at their cell surface. An "AR-overexpressing cancer" is one which has significantly higher levels of AR protein, such as A2a, A1 and/or A2b, at the cell surface of a cancer or tumor cell, compared to a noncancerous cell of the same tissue type. Such overexpression may be caused by gene amplification or by increased transcription or translation. Adenosine receptor expression or overexpression may be determined in a diagnostic or prognostic assay by evaluating increased levels of the AR proteins present on the surface of a cell (e.g. via an immunohistochemistry assay; IHC). Alternatively, or additionally, one may measure levels of AR-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR)(Methods 132: 73-80 (1990)). Aside from the above assays, various in vivo assays are available to one skilled in the art. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

In particular, the cancers include but are not limited to, lung cancer (e.g. non-small cell lung cancer (NSCLC), small cell lung cancer, lung adenocarcinoma, large cell lung cancer, squamous cell lung cancer), renal cell carcinoma (RCC), prostate cancer, breast cancer, ovarian cancer, endometrial cancer, cervical cancer, bone cancer, uterine cancer, colon cancer, leukemia, glioblastoma, melanoma, chondrosarcoma, brain cancer, cholangiocarcinoma, osteosarcoma, lymphoma, adenoma, myeloma, hepatocellular carcinoma, adrenocortical carcinoma, pancreatic cancer, bladder cancer, liver cancer, gastric cancer, colorectal cancer, esophageal cancer, testicular cancer, skin cancer, kidney cancers, mesothelioma, neuroblastoma, thyroid cancer, head and neck cancers, esophageal cancers, eye cancers, nasopharyngeal cancer, or oral cancer. In some embodiments, the cancer is NSCLC, RCC, prostate cancer, or breast cancer. The cancer as mentioned herein can be at any stage, unless otherwise specified. In some embodiments, the cancer is early stage cancer. In some embodiments the cancer is locally advanced cancer. In some embodiments the cancer is locally advanced and/or metastatic cancer. In some embodiments the cancer is invasive cancer. In some embodiments the cancer is a cancer resistant to existing therapies.

In some embodiments, the compounds, or pharmaceutically acceptable salts thereof, of the present disclosure possess potency of treating cancer (e.g., NSCLC, RCC, prostate cancer, breast cancer). In addition, the compounds of the present disclosure, or pharmaceutically acceptable salts thereof may also be useful in the treatment of other Adenosine receptor-associated diseases, for example Parkinson disease, epilepsy, cerebral ischemia and stroke, sepression, cognitive impairment, HIV, ADA-SCID, AHF and chronic heart failure, Chronic obstructive pulmonary disease (COPD), or Asthma.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g. in light of a history of symptoms and/or in light of genetic or other susceptibility factors). Treatment may also be continued after symptoms have resolved, for example to present or delay their recurrence.

The therapeutically effective amount of a compound or a pharmaceutically acceptable salts thereof as provided herein will depend on various factors known in the art, such as body weight, age, past medical history, present medications, state of health of the subject and potential for cross-reaction, allergies, sensitivities and adverse side-effects, as well as the administration route and extent of disease development. Dosages may be proportionally reduced or increased by one skilled in the art (e.g. physician or veterinarian) as indicated by these and other circumstances or requirements.

Use of Compounds

In certain embodiments, the present disclosure provides use of the compounds, pharmaceutically acceptable salts thereof, or pharmaceutical composition of the present disclosure in the manufacture of medicaments for the treatment of AR associated diseases. Exemplary AR associated diseases include but are not limited to cancer (e.g. NSCLC, RCC, prostate, or breast cancer), and other diseases.

In such situation, the present disclosure also provides a method of screening patient suitable for treating with the compounds or pharmaceutical composition of the present disclosure alone or combined with other ingredients (e.g. a second active ingredient, e.g. anti-tumour agent). The method includes sequencing the tumor samples from patients and detecting the accumulation or activation of AR.

According to another aspect of the present disclosure, there is therefore provided a compound of formula (I), or a pharmaceutically acceptable salt thereof, as defined hereinbefore for use as a medicament.

According to a further aspect of the present disclosure, there is provided the use of a compound of formula (I), or a pharmaceutically acceptable salt thereof, as defined hereinbefore in the manufacture of a medicament for modulating adenosine receptors in a warm-blooded animal such as man.

The term "modulate", "modulating" or "modulation" when used in connection with adenosine receptors, refers to an action or result of changing the expression, degradation, and/or activity of the adenosine receptors.

According to a further aspect of the present disclosure, there is provided the use of a compound of formula (I), or a pharmaceutically acceptable salt thereof, as defined hereinbefore in the manufacture of a medicament for the treatment of AR associated diseases in a warm-blooded animal such as man.

According to this aspect of the present disclosure, there is provided the use of a compound of formula (I), or a pharmaceutically acceptable salt thereof, as defined hereinbefore in the manufacture of a medicament for the production of an anti-cancer effect in a warm-blooded animal such as man.

According to a further feature of the present disclosure, there is provided the use of a compound of formula (I), or a pharmaceutically acceptable salt thereof, as defined hereinbefore in the manufacture of a medicament for use in the treatment of NSCLC, RCC, prostate, or breast cancer According to a further feature of the present disclosure, there is provided the use of a compound of formula (I), or a pharmaceutically acceptable salt thereof, as defined hereinbefore in the manufacture of a medicament for use in the treatment of breast cancer.

According to a further feature of this aspect of the present disclosure, there is provided a method of modulating adenosine receptors in a warm-blooded animal, such as man, in need of such treatment, which comprises administering to said animal an effective amount of a compound of formula (I), or a pharmaceutically acceptable salt thereof, as defined hereinbefore.

According to a further feature of this aspect of the present disclosure, there is provided a method of treating AR associated diseases in a warm-blooded animal, such as man, in need of such treatment, which comprises administering to said animal an effective amount of a compound of formula (I), or a pharmaceutically acceptable salt thereof, as defined hereinbefore.

According to a further feature of this aspect of the present disclosure, there is provided a method for producing an anti-cancer effect in a warm-blooded animal, such as man, in need of such treatment, which comprises administering to said animal an effective amount of a compound of formula (I), or a pharmaceutically acceptable salt thereof, as defined hereinbefore.

According to a further feature of this aspect of the present disclosure, there is provided a method of producing an anti-cancer effect in a warm-blooded animal, such as man, in need of such treatment, which comprises (1) determining whether or not the warm blooded animal has an AR-expressing cancer and (2) if so administering to said animal an effective amount of the compound of formula (I), or a pharmaceutically acceptable salt thereof, as defined hereinbefore.

According to an additional feature of this aspect of the present disclosure, there is provided a method of treating NSCLC, RCC, prostate, or breast cancer, in a warm-blooded animal, such as man, in need of such treatment, which comprises administering to said animal an effective amount of a compound of formula (I), or a pharmaceutically acceptable salt thereof, as defined hereinbefore.

According to a further aspect of the present disclosure, there is provided a compound of formula (I), or a pharmaceutically acceptable salt thereof, as defined hereinbefore, for use in modulating AR in a warm-blooded animal such as man.

According to a further aspect of the present disclosure, there is provided a compound of formula (I), or a pharmaceutically acceptable salt thereof, as defined hereinbefore, for use in the treatment of AR associated diseases in a warm-blooded animal such as man.

According to this aspect of the present disclosure, there is provided a compound of formula (I), or a pharmaceutically acceptable salt thereof, as defined hereinbefore, for use in the production of an anti-cancer effect in a warm-blooded animal such as man.

According to a further feature of the present disclosure, there is provided a compound of formula (I), or a pharmaceutically acceptable salt thereof, as defined hereinbefore, for use in the treatment of NSCLC, RCC, prostate, or breast cancer.

EXAMPLES

The followings further explain the general methods of the present disclosure. The compounds of the present disclosure may be prepared by the methods known in the art. The following illustrates the detailed preparation methods of the preferred compounds of the present disclosure. However, they are by no means limiting the preparation methods of the compounds of the present disclosure.

Example 1

Preparation of 5-(5-amino-7-(4-fluorophenyl)-2-((3-fluoropyridin-2-yl)methyl)-[1,2,4]triazolo[1,5-c]pyrimidin-8-yl)-1-methylpyridin-2(1H)-one (Cmpd. 1)

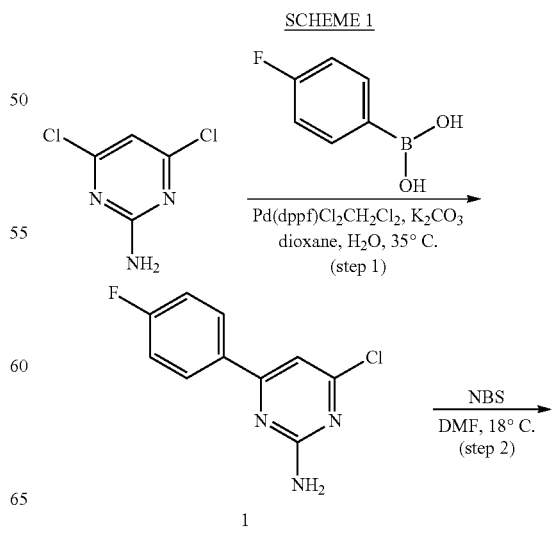

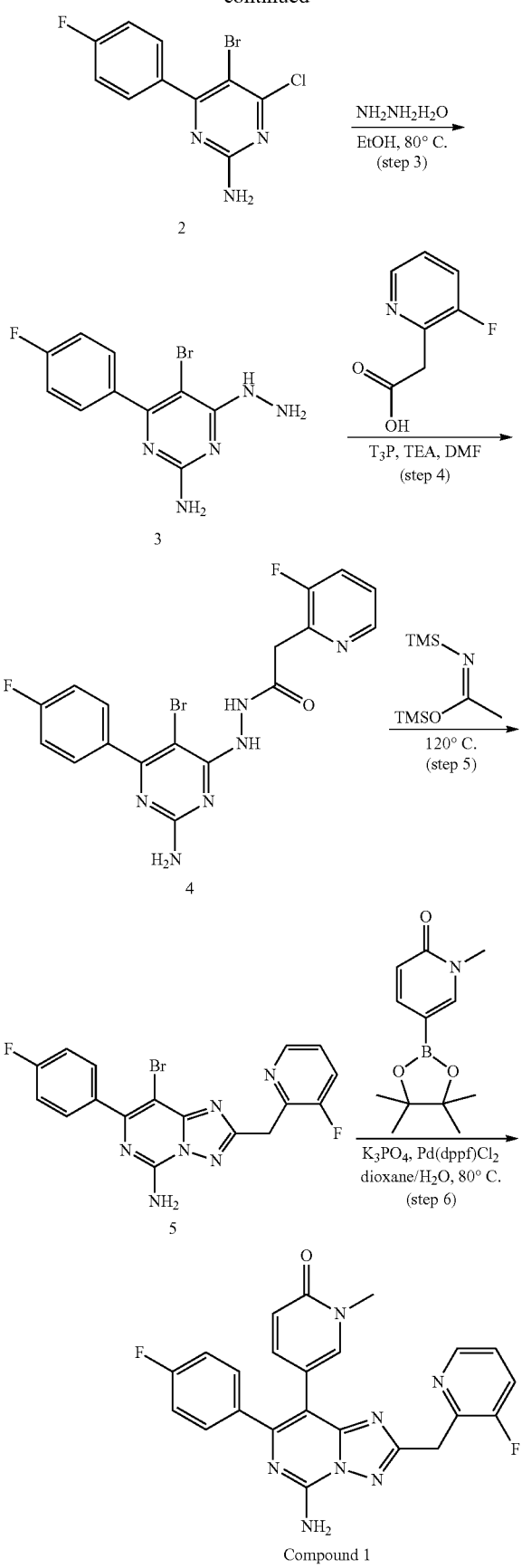

Step 1.
4-chloro-6-(4-fluorophenyl)pyrimidin-2-amine

Into a 2-L round-bottom flask purged and maintained with an inert atmosphere of nitrogen, was placed 4,6-dichloropyrimidin-2-amine (30 g, 182.9 mmol, 1 equiv), (4-fluorophenyl)boronic acid (25.6 g, 182.9 mmol, 1.00 equiv), $K_2CO_3$ (50.8 g, 367.7 mmol, 2.0 equiv), Pd(dppf)Cl$_2$ CH$_2$Cl$_2$ (14.9 g, 18.3 mmol, 0.10 equiv), 1,4-dioxane (1000 mL), H$_2$O (140 mL). The resulting solution was stirred for 5 hours at 35° C. The solvent was removed and the resulting solution was diluted with 500 mL of water. The resulting solution was extracted with 3×500 mL of ethyl acetate and the organic layers were combined. The resulting solution was washed with 2×800 mL of sat. NaCl and the organic layers were combined and dried over anhydrous sodium sulfate. The crude product was re-crystallized from DCM:MeOH in the ratio of 10:1. This resulted in 30 g (60.86%) of 4-chloro-6-(4-fluorophenyl) pyrimidin-2-amine as a brown solid. LCMS: m/z (ESI), [M+H]+=224.0. $^1$H NMR: (300 MHz, Chloroform-d) δ 7.03 (1H, s), 7.22-7.10 (2H, m), 8.03-7.93 (2H, m).

Step 2. 5-bromo-4-chloro-6-(4-fluorophenyl)pyrimidin-2-amine

Into a 2-L round-bottom flask purged and maintained with an inert atmosphere of nitrogen, was placed DMF (1200 mL, 15506.1 mmol, 76.2 equiv), 4-chloro-6-(4-fluorophenyl) pyrimidin-2-amine (45.5 g, 203.5 mmol, 1 equiv), NBS (43.5 g, 244.4 mmol, 1.2 equiv). The resulting solution was stirred for 5 hours at 18° C. The reaction was then quenched by the addition of 1000 mL of water. The reaction was filtered and the filter cake was combined. This resulted in 31.5 g (46.1%) of 5-bromo-4-chloro-6-(4-fluorophenyl) pyrimidin-2-amine as a grey solid. LCMS: m/z (ESI), M+=304.0. $^1$H NMR: (300 MHz, Methanol-d$_4$) δ7.26-7.11 (2H, m), 7.69 (2H, ddd).

Step 3. 5-bromo-4-(4-fluorophenyl)-6-hydrazinylpyrimidin-2-amine

Into a 1-L round-bottom flask purged and maintained with an inert atmosphere of nitrogen, was placed EtOH (500 mL, 8606.8 mmol, 82.7 equiv), 5-bromo-4-chloro-6-(4-fluorophenyl) pyrimidin-2-amine (31.5 g, 104.1 mmol, 1 equiv), hydrazine hydrate (15.6 mL, 321.0 mmol, 3.1 equiv). The resulting solution was stirred for 5 hours at 75° C. in an oil bath. The solids were collected by filtration. The solid was slurried with MTBE and collected by filtration. This resulted in 28 g (88.40%) of 5-bromo-4-(4-fluorophenyl)-6-hydrazinylpyrimidin-2-amine as a grey solid. LCMS: m/z (ESI), M+=298.0. $^1$H NMR: (400 MHz, Methanol-d$_4$) δ7.24-7.11 (2H, m), 7.63-7.50 (2H, m).

Step 4. N'-(2-amino-5-bromo-6-(4-fluorophenyl) pyrimidin-4-yl)-2-(3-fluoropyridin-2-yl)acetohydrazide A mixture of 5-bromo-4-(4-fluorophenyl)-6-hydrazinylpyrimidin-2-amine (20 g, 67.1 mmol, 1 equiv), T3P (42.7 g, 134.2 mmol, 2 equiv), TEA (20.4 g, 201.3 mmol, 3 equiv) and 5-bromo-4-(4-fluorophenyl)-6-hydrazinylpyrimidin-2-amine (20 g, 67.1 mmol, 1 equiv) in DMF (300 mL) was stirred for 2 hours at room temperature under nitrogen atmosphere. The residue was adjusted to pH 9 with saturated NaHCO$_3$ (aq.). The resulting mixture was diluted with water (250 mL). The precipitated solid was collected by filtration and washed with PE to afford N-[2-amino-5-bromo-6-(4- fluorophenyl)pyrimidin-4-yl]-2-(3-fluoropyridin-2-yl)acetohydrazide (16.3 g, 55.8%) as a white solid. LCMS: m/z (ESI), [M+H]⁺=435.1.

Step 5. 8-bromo-7-(4-fluorophenyl)-2-[(3-fluoropyridin-2-yl)methyl]-[1,2,4]triazolo[1,5-c]pyrimidin-5-amine Into a 40 ml Vessel were added N-[2-amino-5-bromo-6-(1,3-oxazol-2-yl)pyrimidin-4-yl]-2-(3-fluoropyridin-2-yl)acetohydrazide (1.0 g, 2.5 mmol, 1 equiv) and (E)-(trimethylsilyl N-(trimethylsilyl)ethanimidate) (5.0 mL, 24.6 mmol, 10.0 equiv) at room temperature, stirred for 2 hours at 120° C., cooled to room temperature, added methanol (5.0 ml), concentrated, washed with i-Pr-O-Methyl ether/methanol (10/1) afford to 8-bromo-7-(4-fluorophenyl)-2-[(3-fluoropyridin-2-yl)methyl]-[1,2,4]triazolo[1,5-c]pyrimidin-5-amine (850 mg) as an off-white sold. LCMS: m/z (ESI), [M+H]⁺=417.1.

Step 6. Preparation of 5-[5-amino-7-(4-fluorophenyl)-2-[(3-fluoropyridin-2-yl)methyl]-[1,2,4]triazolo[1,5-c]pyrimidin-8-yl]-1-methyl-1,2-dihydropyridin-2-one (Cmpd. 1)

Into a 10 mL sealed tube were added 8-bromo-7-(4-fluorophenyl)-2-[(3-fluoropyridin-2-yl)methyl]-[1,2,4]triazolo[1,5-c]pyrimidin-5-amine (120 mg, 0.29 mmol, 1 equiv), 6-methyl-4-(4,4,5,5-tetramethyl-1,3,2-dioxaborolan-2-yl)cyclohexa-2,4-dien-1-one (134.7 mg, 0.58 mmol, 2 equiv), K₃PO₄ (122.1 mg, 0.58 mmol, 2 equiv) and Pd(dppf)Cl₂·CH₂Cl₂ (23.5 mg, 0.03 mmol, 0.1 equiv) in 1,4-dioxane (10 mL) and water (1 mL) at 80° C. for 2 hours. Desired product could be detected by LCMS. The crude product (80 mg) was purified by Prep-HPLC with the following conditions (Column: XBridge Prep OBD C18 Column 30×150 mm 5 μm; Mobile Phase A: Water (0.05% NH₃H₂O), Mobile Phase B: ACN; Flow rate: 60 mL/min; Gradient: 25% B to 34% B in 7 min; 254/220 nm; Rt: 6.25 min) to afford 5-[5-amino-7-(4-fluorophenyl)-2-[(3-fluoropyridin-2-yl)methyl]-[1,2,4]triazolo[1,5-c]pyrimidin-8-yl]-1-methyl-1,2-dihydropyridin-2-one (Cmpd. 1) (20 mg, 15.6%) as a white solid. LCMS: m/z (ESI), [M+H]⁺=446. ¹H NMR (400 MHz, Methanol-d4) δ 3.57 (3H, s), 4.50 (2H, d), 6.43 (1H, d), 7.04-7.15 (2H, m), 7.19 (1H, dd), 7.42 (1H, dt), 7.51-7.61 (2H, m), 7.66 (1H, ddd), 7.80 (1H, d), 8.33 (1H, dt).

Compounds listed in the table below were prepared using methods described in Example 1.

| Example/Compound number | Structure | LCMS [M + H]⁺ | ¹H NMR |
|---|---|---|---|
| 2 | 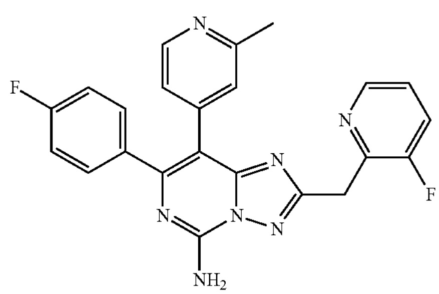 [SMILES: Cc1cc(-c2c(-c3ccc(F)cc3)nc(N)n3nc(Cc4ncccc4F)nc23)ccn1] | 430.2 | ¹H NMR (400 MHz, Methanol-d₄) δ 2.46 (s, 3H), 4.49 (s, 2H), 7.10 - 7.01 (m, 3H), 7.31 (s, 1H), 7.45-7.39(d, m, 3H), 7.67-7.62 (m, 1H), 8 28 (d, J = 9.2 Hz, 1H), 8.32 (d, J = 4 4 Hz, 1H). |
| 3 | 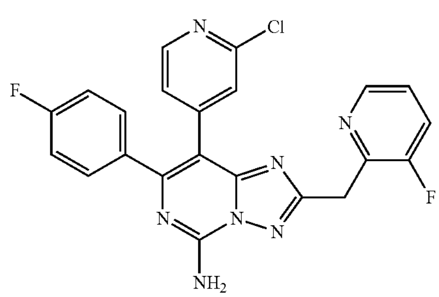 [SMILES: Nc1nc(-c2ccc(F)cc2)c(-c2ccnc(Cl)c2)c2nc(Cc3ncccc3F)nn12] | 450.2 | ¹H NMR (400 MHz, Melhanol-d₄) δ 4.50 (s, 2H), 7.09 - 7.04 (m, 2H), 7.24-7.20 (m, 1H), 7.46-7.39(m, 4H), 7.65 (d, J = 8.4 Hz, lH), 8.23 (d, J = 5.2 Hz, lH), 8.32 (d, J = 5.2 Hz, lH). |
| 14 | 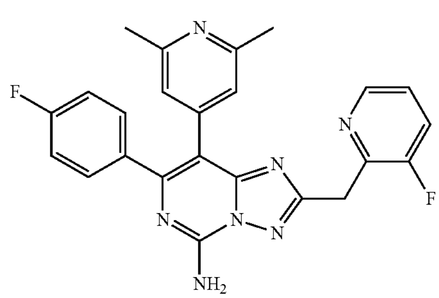 [SMILES: Cc1cc(-c2c(-c3ccc(F)cc3)nc(N)n3nc(Cc4ncccc4F)nc23)cc(C)n1] | 444.2 | ¹H NMR (400 MHz, Methanol-d₄) δ 2.41 (s, 6H), 4,49 (s, 2H), 7,05 - 7.01 (m, 4H), 7.45-7.40 (m, 3H), 7.65 (d, J = 8 4 Hz lH), 8.32 (d, J = 4.8 Hz, lH). |

-continued

| Example/ Compound number | Structure | LCMS [M + H]+ | 1H NMR |
|---|---|---|---|
| 18 | 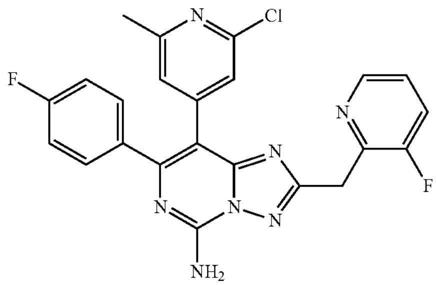 | 464.2 | 1H NMR (400 MHz, DMS0-d4) δ 2.33 (3 H, s), 4.43 (2 H, d), 7.09 (1 H, d), 7.12 - 7.24 (3 H, m), 7.33 - 7.45 (3 H, m), 7.72 (1 H, ddd), 8.23 (2 H, s), 8.33(1 H, dt). |
| 29 | 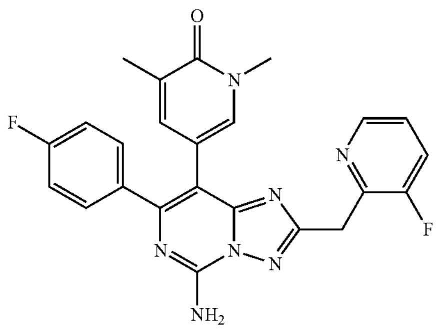 [SMILES: Cc1cc(-c2c(-c3ccc(F)cc3)nc(N)n3nc(Cc4ncccc4F)nc23)cn(C)c1=O] | 460.3 | 1H NMR (300 MHz, DMSO-d6) δ1.90 (3 H, s), 3.34 (3 H, s), 4.42 (2 H, d), 7.07 (1 H, dd), 7.12 - 7.26 (2 H, m), 7.34 - 7.55 (4 H, m), 7.71 (1 H, ddd), 7.96 (2 H, s), 8.34 (1 H, dt). |
| 32 | 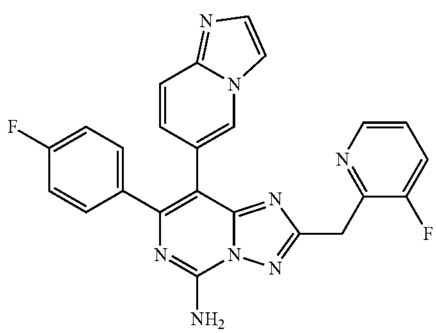 [SMILES: Nc1nc(-c2ccc(F)cc2)c(-c2ccc3nccn3c2)c2nc(Cc3ncccc3F)nn12] | 455.2 | 1H NMR (300 MHz, DMSO-d6) δ 4 41 (1H, d), 6.91 (1H, dd), 7.07 - 7.22 (2H, m), 7.34 - 7.51 (4H, m), 7.56 (1H, d), 7.70 (1H, ddd), 7.88 - 8.19 (3H, m), 8 32 (1H, dt), 8.53 (1H,t) |
| 38 | 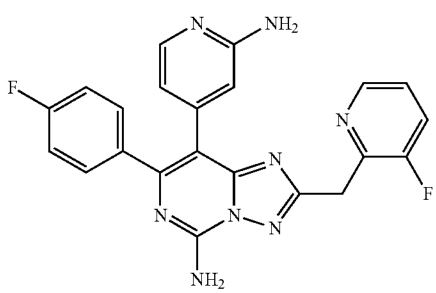 | 431.2 | 1H NMR (400 MHz, Deuterium Oxide): δ 5.88 (d, J = 2.1 Hz, 2H), 7.84 (d, J = 5.3 Hz, 1H), 8.01 (s, 1H), 8.44 (t, J = 8.8 Hz, 2H), 8 79 - 8.86 (m, 1H), 8.90 (t, J = 6.9 Hz, 2H), 9.04 (d, J = 8 8 Hz, 1H), 9.19 (d, J = 5.4 Hz, IH), 9.72 (s, 1H). |
| 69 | 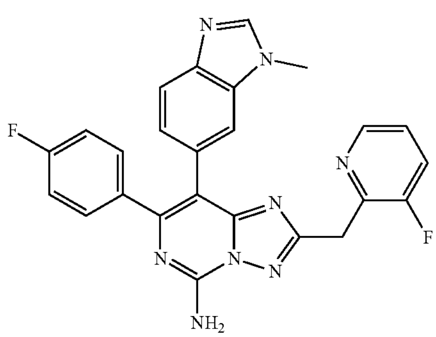 | 469.2 | 1H NMR (300 MHz, Methanol-d4) δ: 3.34 (s, 1H), 3.78 (t, J = 5.3 Hz, 4H), 4.06 (t, J = 5.3 Hz, 4H), 4.29 (s, 4H), 6.45 (d, J = 9.3 Hz, 2H), 6.94 - 7.07 (m, 4H), 7.08 (d, J = 8.8 Hz, 2H), 7.25 (dd, J = 9.3, 2.5 Hz, 2H), 7.26 - 7.40 (m, IH), 7.54 (dd, J = 8.8, 5.4 Hz, 3H), 7.68 (d, J = 2.4 Hz, 2H). |

-continued

| Example/ Compound number | Structure | LCMS [M + H]+ | 1H NMR |
|---|---|---|---|
| 75 | 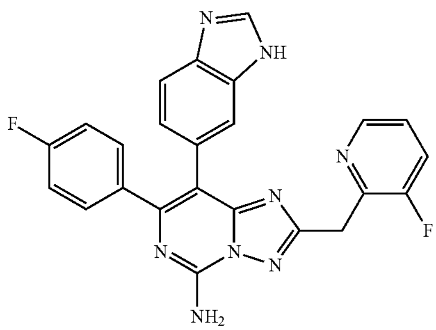 | 455.3 | 1H NMR (300 MHz, DMSO-d6) δ 4.37 (d, J = 2.1 Hz, 2H), 6.88 - 7.09 (m, 3H), 7.27 - 7.58 (m, 5H), 7.66 (ddd, .7=9.9, 8.3, 1.4 Hz, 1H), 7.89 (s, 2H), 8.17 (s, 1H), 8.29 (dt, .7=4.7, 1.6 Hz, IH). |
| 88 | 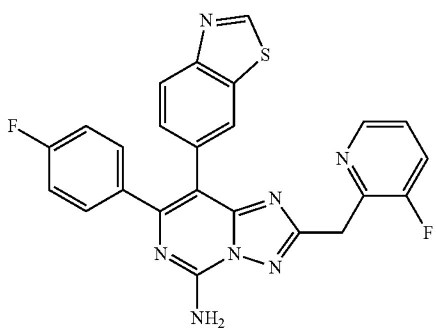 | 472.2 | 1H NMR (300 MHz, DMSO-d6) δ 4.38 (d, J = 2.1 Hz, 2H), 7.00 - 7.11 (m, 2H), 7.25 - 7.41 (m, 4H), 7.61 - 7.72 (m, 1H), 7.91 - 8 04 (m, 3H), 8.07 (d, J = 1.7 Hz, 1H), 8.29 (dt, J = 4.5, 1.6 Hz, 1H), 9.35 (s, 1H). |
| 95 | 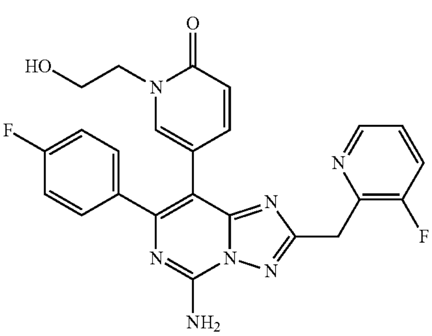 [SMILES: Nc1nc(-c2ccc(F)cc2)c(-c2ccc(=O)n(CCO)c2)c2nc(Cc3ncccc3F)nn12] | 476.2 | 1H NMR (300 MHz, Methanol -d4) δ: 3.34 (s, 2H), 3.77 (t, J = 5.3 Hz, 2H), 4.05 (t, J = 5.3 Hz, 2H), 6.44 (d, J = 9.3 Hz, 1H), 7.07 (t, J = 8.8 Hz, 2H), 7.24 (dd, J = 9.3, 2.5 Hz, 1H), 7.40 (dt, J = 8.7, 4.5 Hz, 1H), 7.49 - 7.58 (m, 2H), 7.59 (d, J = 11.6 Hz, 1H), 7.61 - 7.71 (m, IH), 8.31 (d, J = 4.7 Hz, 1H). |
| 96 | 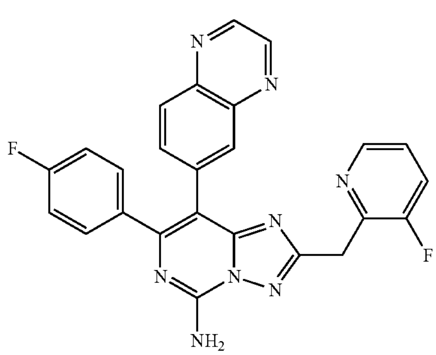 [SMILES: Nc1nc(-c2ccc(F)cc2)c(-c2ccc3nccnc3c2)c2nc(Cc3ncccc3F)nn12] | 467.2 | 1H NMR (400 MHz, DMS0-d6) δ: 4.40 (d, J = 2.0 Hz, 2H), 7.06 (t, J = 8.9 Hz, 2H), 7.36 (td, J = 8.5, 8.1, 5.0 Hz, 3H), 7.60 (dd, J = 8.7, 2.0 Hz, 1H), 7.61 - 7.74 (m, IH), 7.94 (d, J = 8.7 Hz, 1H), 8.04 (d, J = 2.0 Hz, 1H), 8.11 (s, 2H), 8.30 (dt, J =4.7, 1.5 Hz, 1H), 8.89 (q, J = 1.9 Hz, 2H). |

Example 4

Preparation of 2-[(2,6-difluorophenyl)methyl]-7-(4-fluorophenyl)-8-[2-(trifluoromethyl)pyridin-4-yl]-[1,2,4]triazolo[1,5-c]pyrimidin-5-amine (Cmpd. 4)

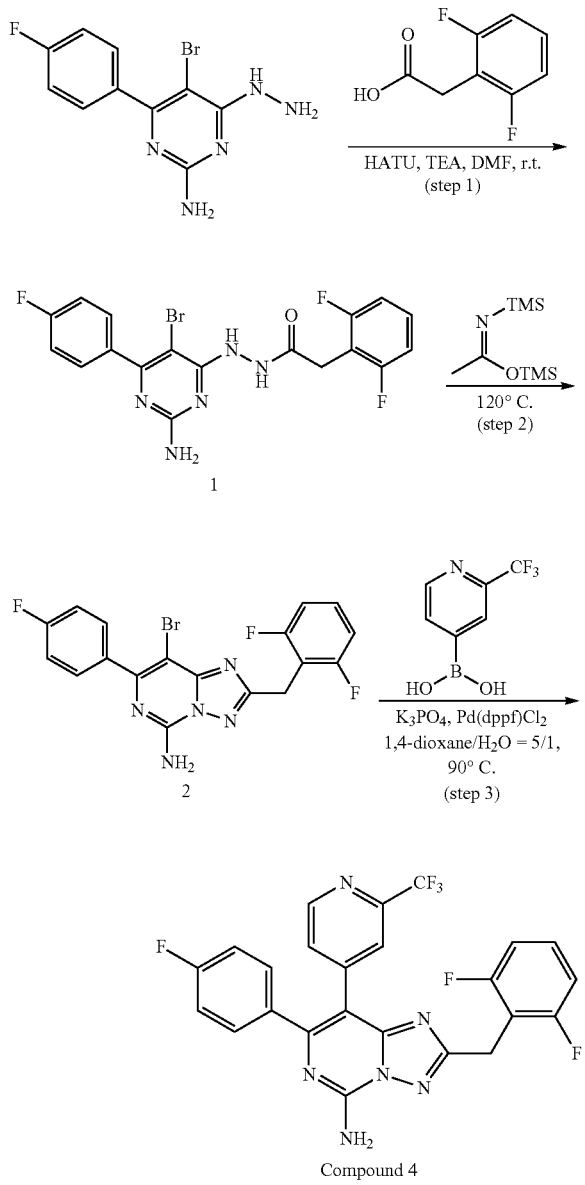

SCHEME 2

Compound 4

Step 1. N'-(2-amino-5-bromo-6-(4-fluorophenyl)pyrimidin-4-yl)-2-(2,6-difluorophenyl)acetohydrazide A mixture of 5-bromo-4-(4-fluorophenyl)-6-hydrazinylpyrimidin-2-amine (2.1 g, 7.04 mmol, 1 equiv), HATU (5.4 g, 14.1 mmol, 2.0 equiv), TEA (2.9 g, 28.18 mmol, 4.0 equiv) and 2-(2,6-difluorophenyl)acetic acid (1.8 g, 10.6 mmol, 1.5 equiv) in DMF (25 mL) was stirred for 3 hours at room temperature under nitrogen atmosphere. The reaction was quenched by the addition of water (50 mL) at room temperature. The product was collected by filtration and dried in vacuum to afford N-[2-amino-5-bromo-6-(4-fluorophenyl)pyrimidin-4-yl]-2-(2,6-difluorophenyl)acetohydrazide (2 g, 62.8%) as a grey solid. LCMS: m/z (ESI), [M+H]$^+$=451.9. $^1$H NMR: (400 MHz, DMSO-d$_6$) δ 6.38 (1H, s), 6.93-7.14 (3H, m), 7.20-7.33 (2H, m), 7.33-7.44 (1H, m), 7.48-7.65 (2H, m), 8.59-8.75 (1H, m), 10.09-10.16 (1H, m).

Step 2. 8-bromo-2-[(2,6-difluorophenyl)methyl]-7-(4-fluorophenyl)-[1,2,4]triazolo[1,5-c]pyrimidin-5-amine A mixture of N-[2-amino-5-bromo-6-(4-fluorophenyl)pyrimidin-4-yl]-2-(2,6-difluorophenyl)acetohydrazide (1.9 g, 4.3 mmol, 1 equiv) and (E)-(trimethylsilyl N-(trimethylsilyl)ethanimidate) (4.4 g, 21.6 mmol, 5.0 equiv) in toluene (35 mL) was stirred for 12 hours at 110° C. under nitrogen atmosphere. The resulting mixture was concentrated under reduced pressure. The crude product was re-crystallized from ethyl acetate/PE (5:1) to afford 8-bromo-2-[(2,6-difluorophenyl)methyl]-7-(4-fluorophenyl)-[1,2,4]triazolo[1,5-c]pyrimidin-5-amine (1.3 g, 69.4%) as a grey solid. LCMS: m/z (ESI), [M+H]$^+$=436.1. $^1$H NMR (400 MHz, DMSO-d$_6$) δ 3.55 (1H, s), 7.11 (3H, dt), 7.24-7.36 (2H, m), 7.36-7.47 (1H, m), 7.67-7.77 (2H, m), 8.06 (2H, s).

Step 3. 2-[(2,6-difluorophenyl)methyl]-7-(4-fluorophenyl)-8-[2-(trifluoromethyl)pyridin-4-yl]-[1,2,4]triazolo[1,5-c]pyrimidin-5-amine (Cmpd. 4)

A mixture of 8-bromo-2-[(2,6-difluorophenyl)methyl]-7-(4-fluorophenyl)-[1,2,4]triazolo[1,5-c]pyrimidin-5-amine (100 mg, 0.2 mmol, 1 equiv) and [2-(trifluoromethyl)pyridin-4-yl]boronic acid (87.9 mg, 0.5 mmol, 2.0 equiv) and Pd(dppf)Cl$_2$(33.7 mg, 0.05 mmol, 0.2 equiv) and K$_3$PO$_4$ (146.7 mg, 0.69 mmol, 3 equiv) in dioxane/H$_2$O (2.4 mL) was stirred for 10 hours at 90° C. under nitrogen atmosphere. The residue was purified by Prep-TLC (PE:EtOAc=2:1 to 1:1), then the crude product (28 mg) was purified by Prep-HPLC to afford 2-[(2,6-difluorophenyl)methyl]-7-(4-fluorophenyl)-8-[2-(trifluoromethyl)pyridin-4-yl]-[1,2,4]triazolo[1,5-c]pyrimidin-5-amine (Cmpd. 4) (12 mg, 10.20%) as a white solid. LCMS: m/z (ESI), [M-$^t$Bu+H]$^+$=501.3. $^1$H NMR (400 MHz, Methanol-d$_4$) δ 1.30 (s, 1H), 4.32 (s, 2H), 6.96-7.11 (m, 3H), 7.31-7.38 (m, 1H), 7.39-7.45 (m, 2H), 7.59 (d, J=5.0 Hz, 1H), 7.74 (d, J=1.4 Hz, 1H), 8.59 (d, J=5.1 Hz, 1H).

Compounds listed in the table below were prepared using methods described in Example 4.

| Example/ Compound number | Structure | LCMS [M + H]+ | 1H NMR |
|---|---|---|---|
| 5 | 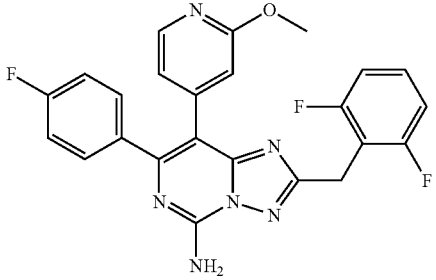 [SMILES: COc1cc(-c2c(-c3ccc(F)cc3)nc(N)n3nc(Cc4c(F)cccc4F)nc23)ccn1] | 463.0 | 1H NMR (400 MHz, Methanol-d4) δ 3.90 (s, 3H), 4.30 (s, 2H), 6.81 (dd, J = 5.3, 1.5 Hz, 1H), 6.84 (d, J = 1.1 Hz, 1H), 7.03 (q, J = 8.4, 7.8 Hz, 4H), 7.36 (t, J = 8.3 Hz, 1H), 7.43 ~ 7.48 (m, 2H), 8.03 (d, J = 5.5 Hz, 1H). |
| 6 | 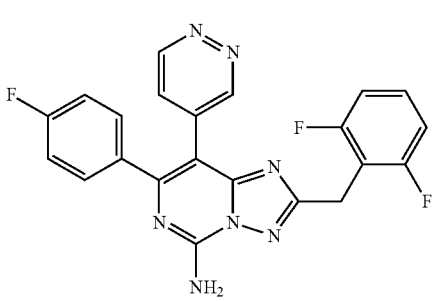 [SMILES: Nc1nc(-c2ccc(F)cc2)c(-c2ccnnc2)c2nc(Cc3c(F)cccc3F)nn12] | 434.0 | 1H NMR (400 MHz, Methanol-d4) δ 4.33 (s, 2H), 7.01 (t, J = 7.9 Hz, 2H), 7.09 (t, J = 8.8 Hz, 2H), 7.33 ~ 7.39 (m, 1H), 7.43 ~ 7.49 (m, 2H), 7.78 (dd, J = 5.4, 2.4 Hz, 1H), 9.01 (dd, J = 2.3, 1.2 Hz, 1H), 9.10 (dd, J = 5.4, 1.2 Hz, 1H). |
| 9 | 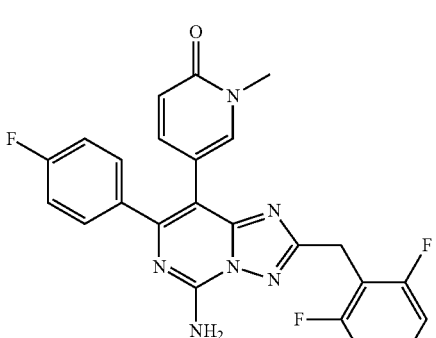 | 463.2 | 1H NMR (400 MHz, Methanol-d$_4$) δ3.29 - 3.40 (m, 1H), 3.57 (s, 3H), 4.31 (s, 2H), 6.44 (d, J = 9.3 Hz, 1H), 7.01 (t, J = 7.9 Hz, 2H), 7.09 (t, J = 8.8 Hz, 2H), 7.21 (dd, J = 9.3, 2.6 Hz, 1H), 7.36 (ddd, J = 14.9, 8 4, 6.5 Hz, 1H), 7.51 - 7.60 (m, 2H), 7.78 (d, J = 2.6 Hz, 1H). |
| 10 | 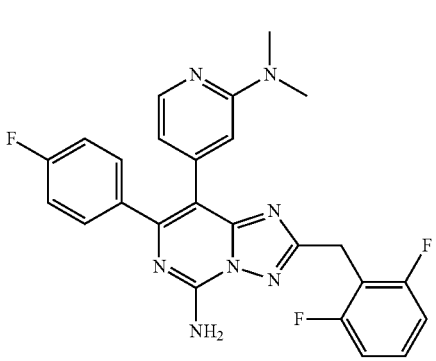 [SMILES: CN(C)c1cc(-c2c(-c3ccc(F)cc3)nc(N)n3nc(Cc4c(F)cccc4F)nc23)ccn1] | 476.2 | 1H NMR (400 MHz, Methanol-d$_4$) δ 2.99 (s, 3H), 3.36 (s, 3H), 4.30 (s, 1H), 6.42 - 6.54 (m, 1H), 6.65 (s, 1H), 7.02 (q, J = 8.3, 7.8 Hz, 2H), 7 48 (dd, J = 8.6, 5.5 Hz, 1H), 7.94 (d, J = 5.3 Hz, 1H). |

Example 7

Preparation of 7-(4-fluorophenyl)-8-(2-methylpyridin-4-yl)-2-[(1,3-thiazol-4-yl)methyl]-[1,2,4]triazolo[1,5-c]pyrimidin-5-amine (Cmpd. 7)

SCHEME 3

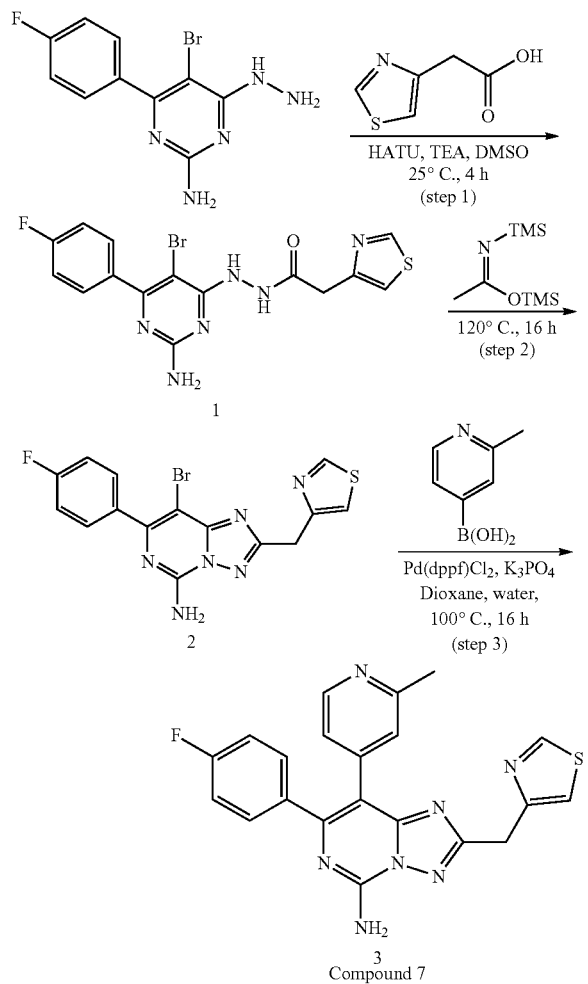

Step 1. N-[2-amino-5-bromo-6-(4-fluorophenyl)pyrimidin-4-yl]-2-(1,3-thiazol-4-yl)acetohydrazide To a solution of 5-bromo-4-(4-fluorophenyl)-6-hydrazinylpyrimidin-2-amine (400 mg, 1.3 mmol), 2-(1,3-thiazol-4-yl)acetic acid (384 mg, 2.7 mmol), TEA (543 mg, 5.4 mmol) in DMSO (10 mL) was added HATU (1.27 g, 3.4 mmol). Stirred at 25° C. for 4 hours. The resulting mixture was poured into 100 mL water and filtered. The solid was dried in vacuum to afford N-[2-amino-5-bromo-6-(4-fluorophenyl)pyrimidin-4-yl]-2-(1,3-thiazol-4-yl)acetohydrazide (326 mg, 57.4%) as a light brown solid. LCMS: m/z (ESI), [M+H]$^+$=425.1.

Step 2. 8-bromo-7-(4-fluorophenyl)-2-[(1,3-thiazol-4-yl)methyl]-[1,2,4]triazolo[1,5-c]pyrimidin-5-amine A mixture of N-[2-amino-5-bromo-6-(4-fluorophenyl)pyrimidin-4-yl]-2-(1,3-thiazol-4-yl)acetohydrazide (326 mg, 0.8 mmol) in trimethylsilyl N-(trimethylsilyl) ethanimidate (4 mL) was stirred at 120° C. for 16 hours. The resulting solution was quenched with 15 mL water. Extracted with EtOAc (3×15 mL). The organic layer was dried over Na$_2$SO$_4$, filtered and concentrated to dryness. The residual solid was washed with EtOAc/MeOH (5/1, 10 mL) and filtered. The solid was dried in vacuum to afford 8-bromo-7-(4-fluorophenyl)-2-[(1,3-thiazol-4-yl)methyl]-[1,2,4]triazolo[1,5-c]pyrimidin-5-amine (164 mg, 52.5%) as a brown solid. LCMS: m/z (ESI), [M+H]$^+$=405.4. $^1$H NMR (300 MHz, DMSO-d$_6$) δ 4.40 (s, 2H), 7.33 (dd, 2H), 7.56 (d, 1H), 7.66-7.79 (m, 2H), 8.15 (s, 2H), 9.05 (d, 1H).

Step 3. 7-(4-fluorophenyl)-8-(2-methylpyridin-4-yl)-2-[(1,3-thiazol-4-yl)methyl]-[1,2,4]triazolo[1,5-c]pyrimidin-5-amine A mixture of 8-bromo-7-(4-fluorophenyl)-2-[(pyrazin-2-yl)methyl]-[1,2,4]triazolo [1,5-c]pyrimidin-5-amine (144 mg, 0.4 mmol), (2-methylpyridin-4-yl)boronic acid (110 mg, 0.8 mmol), Pd(dppf)Cl$_2$.CH$_2$Cl$_2$ (66 mg, 0.1 mmol), K$_3$PO$_4$ (258 mg, 1.2 mmol) in dioxane (20 mL) and water (5 mL) was stirred at 100° C. for 16 hours. Concentrated to dryness. The residue was purified by silica gel column chromatography, eluted with CH$_2$Cl$_2$/MeOH (10:1) to afford a crude product. The crude product was purified by Prep-HPLC with the following conditions (Column: XBridge Prep OBD C18 Column 19*250 mm, 5 μm; Mobile Phase A: Water (10 mmol/L NH$_4$HCO$_3$+0.1% NH$_3$.H$_2$O), Mobile Phase B: ACN; Flow rate: 20 mL/min; Gradient: 30% B to 55% B in 7 min; 220/254 nm; Rt: 6.42 min) to afford 7-(4-fluorophenyl)-8-(2-methylpyridin-4-yl)-2-[(1,3-thiazol-4-yl)methyl]-[1,2,4]triazolo[1,5-c]pyrimidin-5-amine (Cmpd. 7) (44.5 mg, 26%) as an white solid. LCMS: m/z (ESI), [M+H]$^+$=418.2. $^1$H NMR (300 MHz, DMSO-d$_6$) δ 2.38 (s, 3H), 4.37 (s, 2H), 7.01 (dd, 1H), 7.08-7.22 (m, 3H), 7.31-7.42 (m, 2H), 7.51 (dd, 1H), 8.16 (s, 2H), 8.33 (d, 1H), 9.03 (d, 1H).

Example 8

Preparation of 2-[(3-chlorophenyl)methyl]-7-(4-fluorophenyl)-8-(2-methylpyridin-4-yl)-[1,2,4]triazolo[1,5-c]pyrimidin-5-amine (Cmpd. 8)

SCHEME 4

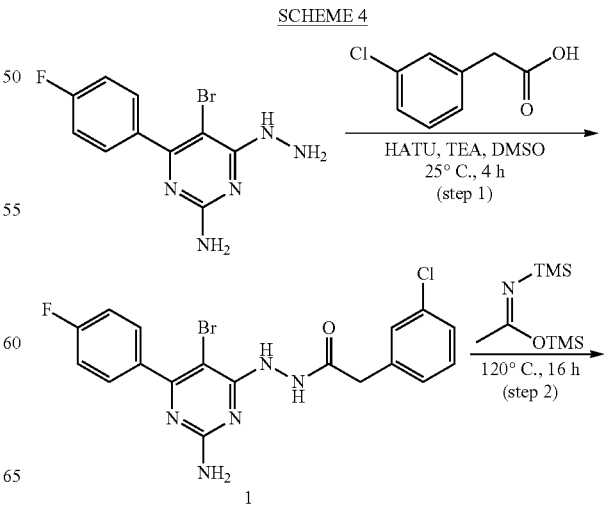

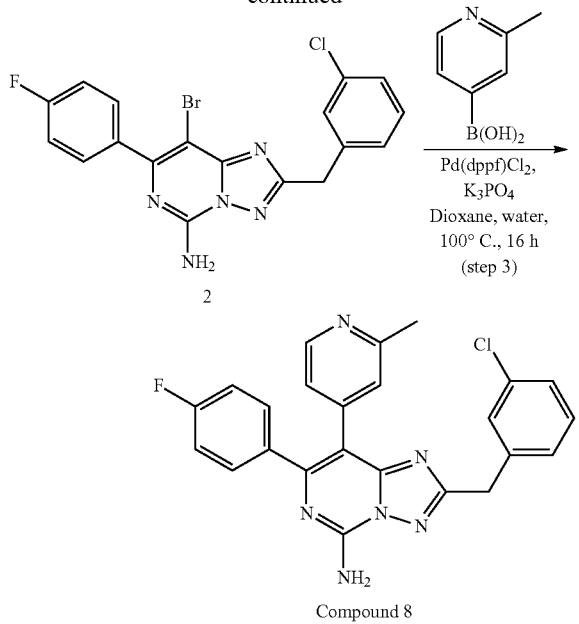

Step 1. N-[2-amino-5-bromo-6-(4-fluorophenyl)pyrimidin-4-yl]-2-(3-chlorophenyl)acetohydrazide To a solution of 5-bromo-4-(4-fluorophenyl)-6-hydrazinylpyrimidin-2-amine (400 mg, 1.3 mmol), 2-(3-chlorophenyl)acetic acid (458 mg, 2.7 mmol), TEA (543 mg, 5.4 mmol) in DMSO (10 mL) was added HATU (1.3 g, 3.4 mmol). The mixture was stirred at 25° C. for 4 hours, then poured into 100 mL water and filtered. The solid was dried in vacuum to afford N-[2-amino-5-bromo-6-(4-fluorophenyl)pyrimidin-4-yl]-2-(3-chlorophenyl)acetohydrazide (560 mg, 92%) as a grey-green solid. LCMS: m/z (ESI), [M+H]$^+$=452.1.

Step 2. 8-bromo-2-[(3-chlorophenyl)methyl]-7-(4-fluorophenyl)-[1,2,4]triazolo[1,5-c]pyrimidin-5-amine A mixture of N-[2-amino-5-bromo-6-(4-fluorophenyl)pyrimidin-4-yl]-2-(3-chlorophenyl)acetohydrazide (663 mg) in trimethylsilyl N-(trimethylsilyl) ethanimidate (4 mL) was stirred at 120° C. for 16 hours. The resulting solution was quenched with 15 mL water. Extracted with EtOAc (3×15 mL). The organic layer was dried over Na$_2$SO$_4$, filtered and concentrated to dryness. The residual solid was washed with EtOAc/MeOH (5/1, 12 mL) and filtered. The solid was dried in vacuum to afford 8-bromo-2-[(3-chlorophenyl)methyl]-7-(4-fluorophenyl)-[1,2,4]triazolo[1,5-c]pyrimidin-5-amine (305 mg, 48%) as a dark-grey solid. LCMS: m/z (ESI), [M+H]$^+$=434.1.

Step 3. 2-[(3-chlorophenyl)methyl]-7-(4-fluorophenyl)-8-(2-methylpyridin-4-yl)-[1,2,4]triazolo[1,5-c]pyrimidin-5-amine A mixture of 8-bromo-2-[(3-chlorophenyl)methyl]-7-(4-fluorophenyl)-[1,2,4] triazolo [1,5-c]pyrimidin-5-amine (150 mg, 0.35 mmol), (2-methylpyridin-4-yl) boronic acid (95 mg, 0.7 mmol), Pd(dppf)Cl$_2$·CH$_2$Cl$_2$ (57 mg, 0.1 mmol), K$_3$PO$_4$ (220.8 mg, 1.0 mmol) in dioxane (20 mL) and water (5 mL) was stirred at 100° C. for 16 hours. Concentrated to dryness. The residue was purified by silica gel column chromatography, eluted with CH$_2$Cl$_2$/MeOH (30:1) to afford a crude product. The crude product was purified by Prep-HPLC with the following conditions (Column: XBridge Prep OBD C18 Column 30×150 mm 5 μm; Mobile Phase A: Water (0.05% NH$_3$H$_2$O), Mobile Phase B: ACN; Flow rate: 60 mL/min; Gradient: 40% B to 60% B in 7 min; 254/220 nm; Rt: 5.83 min) to afford 2-[(3-chlorophenyl)methyl]-7-(4-fluorophenyl)-8-(2-methylpyridin-4-yl)-[1,2,4]triazolo[1,5-c]pyrimidin-5-amine (Cmpd. 8) (6.8 mg, 4.4%) as a white solid. LCMS: m/z (ESI), [M+H]+=445.2. $^1$H NMR (300 MHz, DMSO-d$_6$) δ 2.39 (s, 3H), 4.23 (s, 2H), 7.00 (dd, 1H), 7.08-7.21 (m, 3H), 7.24-7.46 (m, 6H), 8.16 (s, 2H), 8.33 (d, 1H).

Example 11

Preparation of 7-(4-fluorophenyl)-8-(2-methylpyridin-4-yl)-2-(thiazol-2-ylmethyl)-[1,2,4]triazolo[1,5-c]pyrimidin-5-amine (Cmpd. 11)

SCHEME 5

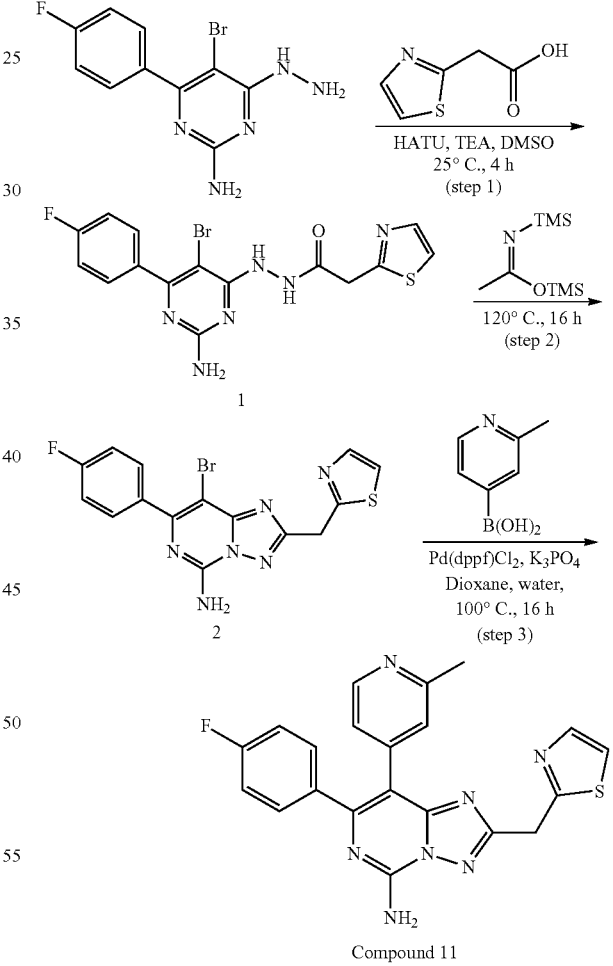

Step 1. N-[2-amino-5-bromo-6-(4-fluorophenyl)pyrimidin-4-yl]-2-(1,3-thiazol-2-yl)acetohydrazide To a solution of 5-bromo-4-(4-fluorophenyl)-6-hydrazinylpyrimidin-2-amine (400 mg, 1.3 mmol), 2-(1,3-thiazol-2-yl)acetic acid (384 mg, 2.7 mmol), TEA (543 mg, 5.4 mmol) in DMSO (10 mL) was added HATU (1.3 g, 3.4 mmol). Stirred at 25° C. for 4 hours. The resulting mixture was poured into 100 mL water and filtered. The solid was dried in vacuum to afford N-[2-amino-5-bromo-6-(4-fluorophenyl)pyrimidin-4-yl]-2-(1,3-thiazol-2-yl)acetohydrazide (336 mg, 59%) as a dark-grey solid. LCMS: m/z (ESI), [M+H]⁺=423.4. ¹H NMR (300 MHz, DMSO-d₆) δ 4.05 (s, 2H), 6.42 (s, 2H), 7.28 (t, 2H), 7.54-7.70 (m, 3H), 7.75 (d, 1H), 8.75 (s, 1H), 10.22 (s, 1H).

Step 2. 8-bromo-7-(4-fluorophenyl)-2-[(1,3-thiazol-2-yl)methyl]-[1,2,4]triazolo[1,5-c]pyrimidin-5-amine A mixture of N-[2-amino-5-bromo-6-(4-fluorophenyl)pyrimidin-4-yl]-2-(1,3-thiazol-2-yl)acetohydrazide (336 mg) in trimethylsilyl N-(trimethylsilyl)ethanimidate (4 mL) was stirred at 120° C. for 16 hours. The resulting solution was quenched with 15 mL water. Extracted with EtOAc (3×15 mL). The organic layer was dried over Na₂SO₄, filtered and concentrated to dryness. The residual solid was washed with EtOAc/MeOH (5/1, 12 mL) and filtered. The solid was dried in vacuum to afford 8-bromo-7-(4-fluorophenyl)-2-[(1,3-thiazol-2-yl)methyl]-[1,2,4]triazolo[1,5-c]pyrimidin-5-amine (126 mg, 39%) as a light brown solid. LCMS: m/z (ESI), [M+H]⁺=405.4. ¹H NMR (300 MHz, DMSO) δ 4.65 (s, 2H), 7.26-7.40 (m, 2H), 7.63-7.80 (m, 4H), 8.18 (s, 2H).

Step 3. 7-(4-fluorophenyl)-8-(2-methylpyridin-4-yl)-2-(thiazol-2-ylmethyl)-[1,2,4]triazolo[1,5-c]pyrimidin-5-amine (Cmpd. 11)

A mixture of 8-bromo-7-(4-fluorophenyl)-2-[(1,3-thiazol-2-yl)methyl]-[1,2,4]triazolo [1,5-c]pyrimidin-5-amine (126 mg, 0.31 mmol), (2-methylpyridin-4-yl)boronic acid (85.2 mg, 0.62 mmol), Pd(dppf)Cl₂.CH₂Cl₂ (50.8 mg, 0.06 mmol), K₃PO₄ (198.0 mg, 0.93 mmol) in dioxane (20 mL) and water (5 mL) was stirred at 100° C. for 16 hours. Concentrated to dryness. The residue was purified by silica gel column chromatography, eluted with CH₂Cl₂/MeOH (10:1) to afford a crude product. The crude product was purified by Prep-HPLC with the following conditions (Column: XBridge Prep OBD C18 Column 30×150 mm 5 μm; Mobile Phase A: Water (0.05% NH₃H₂O), Mobile Phase B: ACN; Flow rate: 60 mL/min; Gradient: 30% B to 35% B in 7 min; 254/220 nm; Rt: 5.77 min) to afford 7-(4-fluorophenyl)-8-(2-methylpyridin-4-yl)-2-(thiazol-2-ylmethyl)-[1,2,4]triazolo[1,5-c]pyrimidin-5-amine (Cmpd. 11) (25.7 mg, 15%) as a white solid. LCMS: m/z (ESI), [M+H]⁺=418.2. ¹H NMR (300 MHz, DMSO-d₆) δ 2.39 (s, 4H), 4.62 (s, 2H), 6.97-7.05 (m, 1H), 7.09-7.22 (m, 3H), 7.32-7.44 (m, 2H), 7.62-7.78 (m, 2H), 8.22 (s, 2H), 8.33 (dd, 1H).

Example 12

Preparation of 2-[1-(2,6-difluorophenyl)ethyl]-7-(4-fluorophenyl)-8-(2-methylpyridin-4-yl)-[1,2,4]triazolo[1,5-c]pyrimidin-5-amine (Cmpd. 12)

SCHEME 6

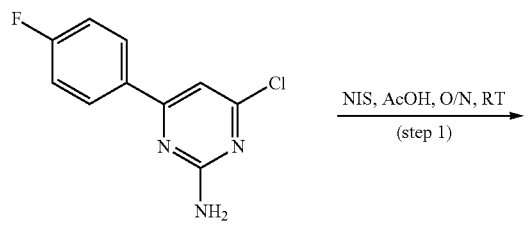

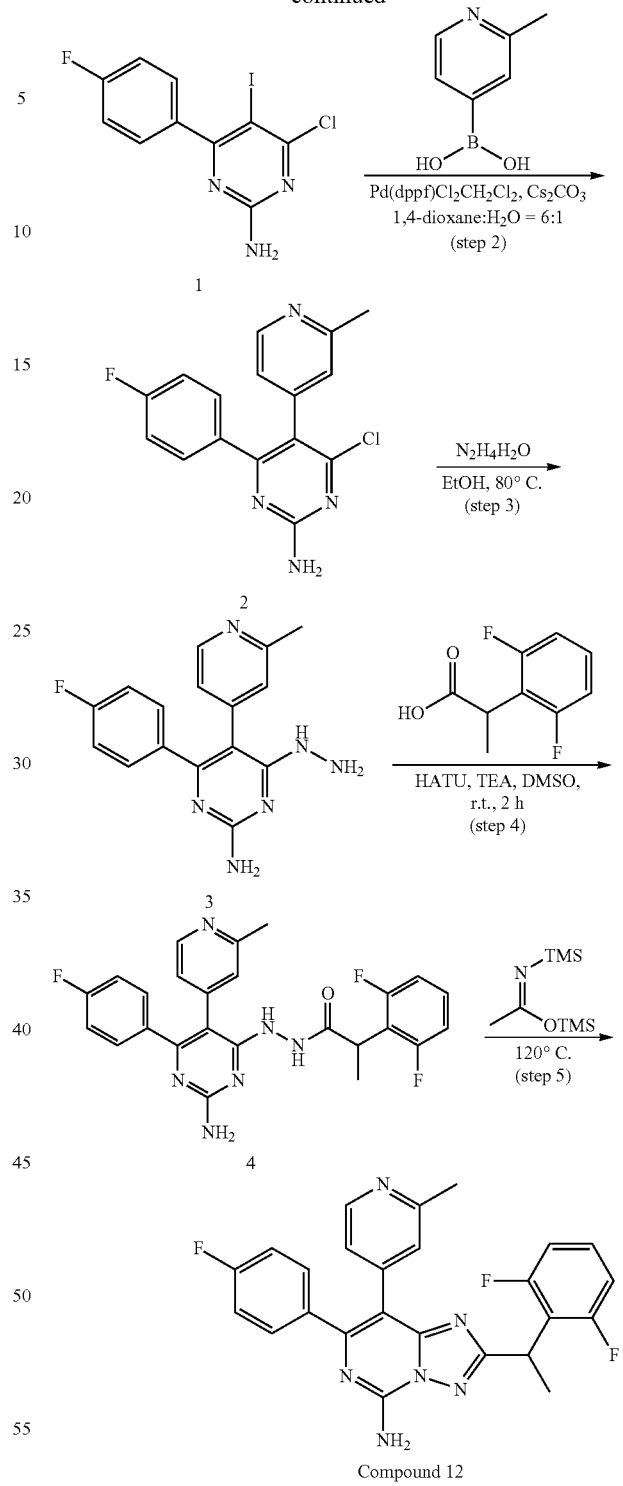

Compound 12

Step 1. 4-chloro-6-(4-fluorophenyl)-5-iodopyrimidin-2-amine

To a stirred mixture of 4-chloro-6-(4-fluorophenyl)pyrimidin-2-amine (2 g, 8.94 mmol, 1 equiv) in AcOH (30 mL) was added NIS (4.0 g, 17.89 mmol, 2 equiv) in portions at room temperature. The resulting mixture was stirred for 2 days at room temperature. The reaction was monitored by LCMS. The resulting mixture was diluted with water (100 mL). The precipitated solid was collected by filtration and washed with water (2×50 mL) and dried under vacuum. The residue was purified by silica gel column chromatography, eluted with CH$_2$Cl$_2$/MeOH (97:3) to afford 4-chloro-6-(4-fluorophenyl)-5-iodopyrimidin-2-amine (2 g, 64.0%) as a white solid. LCMS: m/z (ESI), [M+H]$^+$=350.0. $^1$H NMR: (300 MHz, DMSO-d$_6$) δ 7.24-7.36 (m, 4H), 7.51-7.73 (m, 2H).

Step 2. 4-chloro-6-(4-fluorophenyl)-5-(2-methylpyridin-4-yl)pyrimidin-2-amine

To a stirred mixture of 4-chloro-6-(4-fluorophenyl)-5-iodopyrimidin-2-amine (900 mg, 2.57 mmol, 1 equiv), (2-methylpyridin-4-yl)boronic acid (705.3 mg, 5.2 mmol, 2.0 equiv) and Cs$_2$CO$_3$ (2516.8 mg, 7.7 mmol, 3 equiv) in 1,4-dioxane (30 mL) and H$_2$O (5 mL) was added Pd(dppf)Cl$_2$(188.4 mg, 0.26 mmol, 0.1 equiv) in portions at room temperature under nitrogen atmosphere. The resulting mixture was stirred at 45° C. under nitrogen atmosphere overnight. The reaction was monitored by LCMS. The resulting mixture was concentrated under reduced pressure. The residue was purified by silica gel column chromatography, eluted with CH$_2$C2/MeOH (97:3) to afford 4-chloro-6-(4-fluorophenyl)-5-(2-methylpyridin-4-yl)pyrimidin-2-amine (800 mg, 98.71%) as a Brown yellow State. LCMS: m/z (ESI), [M+H]$^+$=315.2.

Step 3. 4-(4-fluorophenyl)-6-hydrazinyl-5-(2-methylpyridin-4-yl)pyrimidin-2-amine A mixture of 4-chloro-6-(4-fluorophenyl)-5-(2-methylpyridin-4-yl)pyrimidin-2-amine (460 mg, 1.5 mmol), NH$_2$NH$_2$.H$_2$O (219 mg, 4.4 mmol) in EtOH (20 mL) was stirred at 80° C. for 3 hours. Concentrated to dryness. The residue was diluted with EtOAc/MeOH (5/1, 12 mL) and filtered. The solid was dried in vacuum to afford 4-(4-fluorophenyl)-6-hydrazinyl-5-(2-methylpyridin-4-yl)pyrimidin-2-amine (420 mg, 92%) as an off-white solid. LCMS: m/z (ESI), [M+H]$^+$=311.2.

Step 4. N-[2-amino-6-(4-fluorophenyl)-5-(2-methylpyridin-4-yl)pyrimidin-4-yl]-2-(2,6-difluorophenyl)propanehydrazide To a solution of 4-(4-fluorophenyl)-6-hydrazinyl-5-(2-methylpyridin-4-yl)pyrimidin-2-amine (140 mg, 0.45 mmol), 2-(2,6-difluorophenyl)propanoic acid (168 mg, 0.9 mmol), TEA (183 mg, 1.8 mmol) in DMSO (6 mL) was added HATU (429 mg, 1.1 mmol). Stirred at 25° C. for 1 hour. Quenched with water (30 mL) and sat. NaHCO$_3$ (30 mL) and filtered. The solid was dried in vacuum to afford N-[2-amino-6-(4-fluorophenyl)-5-(2-methylpyridin-4-yl)pyrimidin-4-yl]-2-(2,6-difluorophenyl)propanehydrazide (160 mg, 74.12%) as a dark-yellow solid. LCMS: m/z (ESI), [M+H]$^+$=479.3.

Step 5. 2-[1-(2,6-difluorophenyl)ethyl]-7-(4-fluorophenyl)-8-(2-methylpyridin-4-yl)-[1,2,4]triazolo[1,5-c]pyrimidin-5-amine (Cmpd. 12)

A mixture of N-[2-amino-6-(4-fluorophenyl)-5-(2-methylpyridin-4-yl)pyrimidin-4-yl]-2-(2,6-difluorophenyl)propanehydrazide (90 mg, 0.18 mmol) in trimethylsilyl N-(trimethylsilyl)ethanimidate (3 mL) was stirred at 120° C. for 16 hours. Quenched with 15 mL water. Extracted with DCM (3×15 mL). The organic layer was dried over Na$_2$SO$_4$, filtered and concentrated to dryness. The residue was purified by Prep-TLC (CH$_2$Cl$_2$/MeOH 30/1) to afford crude product. The crude product was purified by Prep-HPLC with the following conditions (Column: XBridge Prep OBD C18 Column 30×150 mm 5 μm; Mobile Phase A: Water (0.05% NH$_3$H$_2$O), Mobile Phase B: ACN; Flow rate: 60 mL/min; Gradient: 40% B to 60% B in 7 min; 254/220 nm; Rt: 6.27 min) to afford 2-[1-(2,6-difluorophenyl)ethyl]-7-(4-fluorophenyl)-8-(2-methylpyridin-4-yl)-[1,2,4]triazolo[1,5-c]pyrimidin-5-amine (Cmpd. 12) (21.1 mg, 24%) as a white solid. LCMS: m/z (ESI), [M+H]$^+$=461.2. $^1$H NMR (300 MHz, DMSO-d$_6$) δ 1.77 (d, 3H), 2.34 (s, 3H), 4.71 (d, 1H), 6.95-7.20 (m, 6H), 7.35 (ddt, 3H), 8.06 (s, 2H), 8.30 (d, 1H).

Example 13

Preparation of 2-[(2,6-difluorophenyl)methyl]-8-(2,5-dimethylpyridin-4-yl)-7-(4-fluorophenyl)-[1,2,4]triazolo[1,5-c]pyrimidin-5-amine (Cmpd. 13)

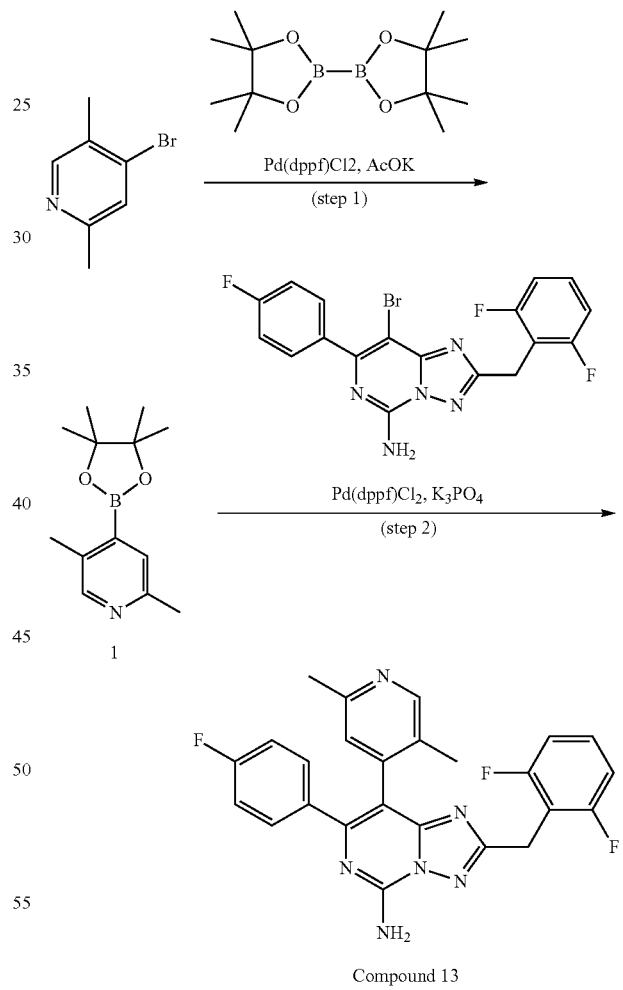

Compound 13

Step 1. 2,5-dimethyl-4-(4,4,5,5-tetramethyl-1,3,2-dioxaborolan-2-yl)pyridine

A solution/mixture of 4-bromo-2,5-dimethylpyridine (530 mg, 2.8 mmol, 1 equiv) and 4,4,5,5-tetramethyl-2-(4,4,5,5-tetramethyl-1,3,2-dioxaborolan-2-yl)-1,3,2-dioxaborolane (1085.1 mg, 4.2 mmol, 1.5 equiv), AcOK (838.7 mg, 8.5 mmol, 3 equiv), Pd(dppf)Cl$_2$ (208.4 mg, 0.3 mmol, 0.1 equiv) in dioxane (10 mL) was stirred for 1 min at 90° C. under nitrogen atmosphere. The residue was purified by Prep-TLC (CH$_2$Cl$_2$/MeOH 10:1) to afford 2,5-dimethyl-4-(4,4,5,5-tetramethyl-1,3,2-dioxaborolan-2-yl)pyridine (389 mg, 46.9%) as a white semi-solid. LCMS: m/z (ESI), [M+H]$^+$=234.3.

Step 2. 2-[(2,6-difluorophenylmethyl]-8-(2,5-dimethylpyridin-4-yl)-7-(4-fluorophenyl)-[1,2,4]triazolo[1,5-c]pyrimidin-5-amine (Cmpd. 13)

To a solution of 8-bromo-2-[(2,6-difluorophenyl)methyl]-7-(4-fluorophenyl)-[1,2,4]triazolo[1,5-c]pyrimidin-5-amine (100 mg, 0.23 mmol, 1 equiv) and 2,5-dimethyl-4-(4,4,5,5-tetramethyl-1,3,2-dioxaborolan-2-yl)pyridine (80.5 mg, 0.35 mmol, 1.50 equiv) in dioxane (9 mL) and water (1 mL) were added K$_3$PO$_4$ (146.7 mg, 0.69 mmol, 3 equiv) and Pd(dppf)Cl$_2$(16.9 mg, 0.02 mmol, 0.1 equiv). After stirring for 2 min at 90° C. under a nitrogen atmosphere, the resulting mixture was concentrated under reduced pressure. The crude product (100 mg) was purified by Prep-HPLC with the following conditions to afford 2-[(2,6-difluorophenyl)methyl]-8-(2,5-dimethylpyridin-4-yl)-7-(4-fluorophenyl)-[1,2,4]triazolo[1,5-c]pyrimidin-5-amine (Cmpd. 13) (5.8 mg, 5.4%) as a light yellow solid. LCMS: m/z (ESI), [M+H]$^+$=461.2. $^1$H NMR: (400 MHz, Methanol-d$_4$) δ 2.1 (s, 3H), 2.7 (s, 3H), 4.3 (s, 2H), 6.9-7.1 (m, 3H), 7.3 (ddd, J=15.0, 8.4, 6.5 Hz, 1H), 7.4-7.4 (m, 2H), 7.7 (s, 1H), 8.5 (s, 1H).

Compound listed in the table below was prepared using methods described in Example 13.

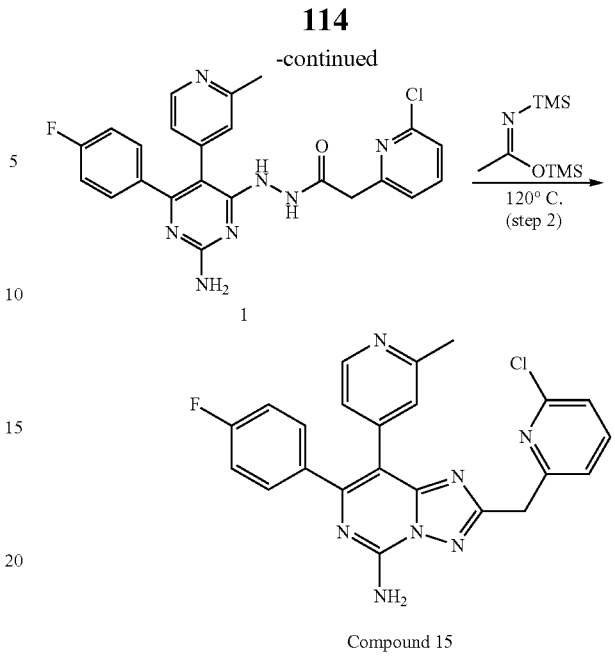

Compound 15

Step 1. N-[2-amino-6-(4-fluorophenyl)-5-(2-methylpyridin-4-yl)pyrimidin-4-yl]-2-(6-chloropyridin-2-yl)acetohydrazide To a solution of 4-(4-fluorophenyl)-6-hydrazinyl-5-(2-methylpyridin-4-yl)pyrimidin-2-amine (530 mg, 1.7 mmol),

| Example/ Compound number | Structure | LCMS [M + H]$^+$ | $^1$H NMR |
|---|---|---|---|
| 16 | 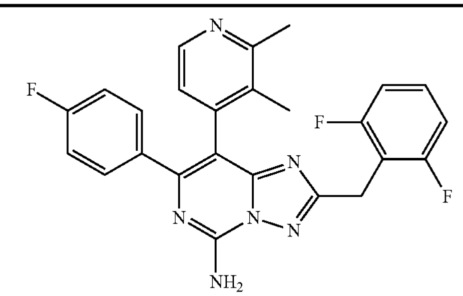 | 461 | $^1$H NMR: (300 MHz, Methanol-d$_4$) δ 2.2 (s, 3H), 2.7 (s, 3H), 4.3 (d, J = 1.2 Hz, 2H), 6.9-7.1 (m, 4H), 7.3-7.5 (m, 3H), 7.6 (d, J = 6.1 Hz, 1H), 8.4 (d, J = 6.1 Hz, 1H). |

Example 15

Preparation of 2-[(6-chloropyridin-2-yl)methyl]-7-(4-fluorophenyl)-8-(2-methylpyridin-4-yl)-[1,2,4]triazolo[1,5-c]pyrimidin-5-amine (Cmpd. 15)

SCHEME 8

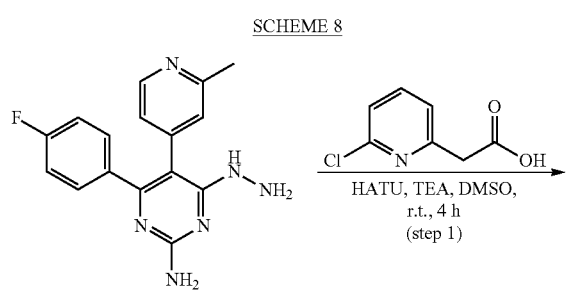

HATU, TEA, DMSO, r.t., 4 h
(step 1)

2-(6-chloropyridin-2-yl)acetic acid (586 mg, 3.4 mmol), TEA (691 mg, 6.8 mmol) in DMSO (4 mL) was added HATU (1.6 g, 4.3 mmol). The mixture was stirred at 25° C. for 2 hours. Quenched with 100 mL water. 20 mL sat. NaHCO$_3$ was added, then filtered. The solid was dried in vacuum to afford N-[2-amino-6-(4-fluorophenyl)-5-(2-methylpyridin-4-yl)pyrimidin-4-yl]-2-(6-chloropyridin-2-yl)acetohydrazide (600 mg, 75%) as a brown solid. LCMS: m/z (ESI), [M+H]$^+$=464.2.

Step 2. 2-[(6-chloropyridin-2-yl)methyl]-7-(4-fluorophenyl)-8-(2-methylpyridin-4-yl)-[1,2,4]triazolo[1,5-c]pyrimidin-5-amine (Cmpd. 15)

A mixture of N-[2-amino-6-(4-fluorophenyl)-5-(2-methylpyridin-4-yl)pyrimidin-4-yl]-2-(6-chloropyridin-2-yl)acetohydrazide (600 mg, 1.3 mmol) in trimethylsilyl N-(trimethylsilyl)ethanimidate (4 mL) was stirred at 120° C. for 16 hours. The resulting mixture was quenched with 15 mL water. Extracted with DCM (3×15 mL). The organic layer was separated and dried over Na$_2$SO$_4$, filtered and concentrated to dryness. The residue was purified by Prep-TLC (CH$_2$Cl$_2$/MeOH=30/1) to afford 2-[(6-chloropyridin-2-yl)methyl]-7-(4-fluorophenyl)-8-(2-methylpyridin-4-yl)-[1,2,4]triazolo [1,5-c]pyrimidin-5-amine (330 mg) as a light brown solid. 50 mg of this crude product was purified by Prep-HPLC with the following conditions: (Column: XBridge Prep OBD C18 Column 30×150 mm 5 μm; Mobile Phase A: Water (0.05% NH$_3$H$_2$O), Mobile Phase B: ACN; Flow rate: 60 mL/min; Gradient: 35% B to 40% B in 7 min; 254/220 nm; Rt: 6.57 min) to afford 2-[(6-chloropyridin-2-yl)methyl]-7-(4-fluorophenyl)-8-(2-methylpyridin-4-yl)-[1,2,4]triazolo [1,5-c]pyrimidin-5-amine (Cmpd. 15) (20 mg) as a white solid. LCMS: m/z (ESI), [M+H]$^+$=446.2. $^1$H NMR (300 MHz, DMSO-d$_6$) δ 2.37 (s, 3H), 4.35 (s, 2H), 7.00 (dd, 1H), 7.08-7.20 (m, 3H), 7.29-7.43 (m, 4H), 7.81 (t, 1H), 8.17 (s, 2H), 8.32 (d, 1H).

Example 17

Preparation of 2-((6-(dimethylamino)pyridin-2-yl)methyl)-7-(4-fluorophenyl)-8-(2-methylpyridin-4-yl)-[1,2,4]triazolo[1,5-f]pyrimidin-5-amine (Cmpd. 17)

SCHEME 9

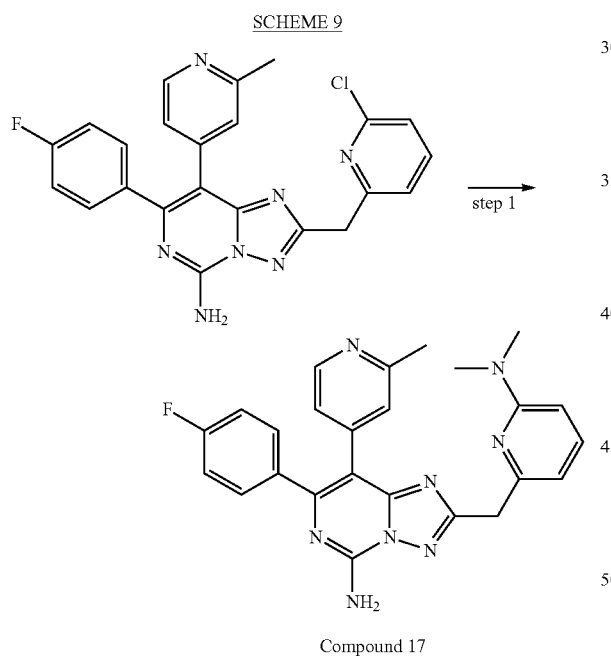

Compound 17

Step 1. 2-((6-(dimethylamino)pyridin-2-yl)methyl)-7-(4-fluorophenyl)-8-(2-methylpyridin-4-yl)-[1,2,4]triazolo[1,5-f]pyrimidin-5-amine (Cmpd. 17)

Into a solution of 2-[(6-chloropyridin-2-yl)methyl]-7-(4-fluorophenyl)-8-(2-methylpyridin-4-yl)-[1,2,4]triazolo [1,5-c]pyrimidin-5-amine (Cmpd. 15, 80 mg, 0.18 mmol, 1 equiv) in DMF (2 mL) were added dimethylamine (1 mL, 2.00 mmol, 11.15 equiv) in THF (1 mL). The final reaction mixture was irradiated with microwave radiation for 90 min at 190° C. The resulting solution was diluted with 15 mL of EA. The resulting mixture was washed with 3×10 ml of water and 2×10 ml of saturated brine. The organic layer was dried over anhydrous sodium sulfate. The crude product (20 mg) was purified by Prep-HPLC with the following conditions: (Column: XBridge Prep OBD C18 Column 19*250 mm, 5 μm; Mobile Phase A: Water (10 MMOL/L NH$_4$HCO$_3$+0.1% NH$_3$.H$_2$O), Mobile Phase B: ACN; Flow rate: 20 mL/min). This resulted in 10 mg (12.26%) of 6-[[5-amino-7-(4-fluorophenyl)-8-(2-methylpyridin-4-yl)-[1,2,4]triazolo[1,5-c]pyrimidin-2-yl]methyl]-N,N-dimethylpyridin-2-amine as a solid. LCMS: m/z (ESI), [M+H]$^+$=455.2. $^1$H NMR (300 MHz, DMSO-d$_6$) δ 2.37 (3H, s), 2.98 (6H, s), 4.15 (2H, s), 6.45 (2H, d), 7.00 (1H, d), 7.08-7.22 (3H, m), 7.31-7.46 (3H, m), 8.16 (2H, s), 8.32 (1H, d).

Example 19

Preparation of 6-((5-amino-7-(4-fluorophenyl)-8-(2-methylpyridin-4-yl)-[1,2,4]triazolo[1,5-f]pyrimidin-2-yl)methyl)picolinonitrile (Cmpd. 19)

SCHEME 10

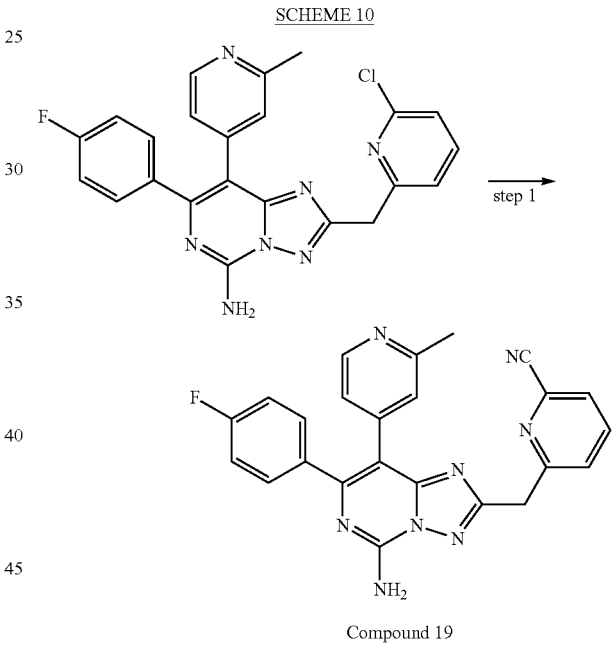

Compound 19

Step 1. 6-((5-amino-7-(4-fluorophenyl)-8-(2-methylpyridin-4-yl)-[1,2,4]triazolo[1,5-f]pyrimidin-2-yl)methyl)picolinonitrile (Cmpd. 19)

Into a 8-mL vial, was placed a solution of 2-[(6-chloropyridin-2-yl)methyl]-7-(4-fluorophenyl)-8-(2-methylpyridin-4-yl)-[1,2,4]triazolo [1,5-c]pyrimidin-5-amine (40 mg, 0.09 mmol, 1 equiv) in THF/H$_2$O (6/2 mL), zincdicarbonitrile (8.4 mg, 0.07 mmol, 0.80 equiv), tBuXPhos Pd G3 (14.3 mg, 0.02 mmol, 0.20 equiv), tBuXphos (18.6 mg, 0.03 mmol, 0.30 equiv). The resulting solution was stirred for 12 hours at 70° C. The resulting mixture was concentrated under vacuum. The mixture was purified by TLC (DCM: MeOH=20:1) to afford a yellow solid (50 mg). The residue was purified by Prep-HPLC Column: XBridge Prep OBD C18 Column 19*250 mm, 5 μm; Mobile Phase A: Water (10

MMOL/L NH₄HCO₃+0.1% NH₃.H₂O), Mobile Phase B: ACN; Flow rate: 20 mL/min; Gradient: 40% B to 50% B in 7 min; 254,220 nm; Rt: 6.85 min. The fractions containing the product was evaporated to afford 6-[[5-amino-7-(4-fluorophenyl)-8-(2-methylpyridin-4-yl)-[1,2,4]triazolo[1,5-c]pyrimidin-2-yl]methyl]pyridine-2-carbonitrilen (15 mg, 38.31%) as a white solid. LCMS: m/z (ESI), [M+H]⁺=437.0. H-NMR (400 MHz, MeOD-d₄) δ 2.47 (3H, s), 4.48 (2H, s), 6.98-7.06 (2H, m), 7.07-7.11 (1H, m), 7.27-7.32 (1H, m), 7.39-7.45 (2H, m), 7.74 (2H, ddd), 7.94 (1H, t), 8.29 (1H, dd).

Example 20

Preparation of 5-(5-amino-2-[[3-(difluoromethoxy)pyridin-2-yl]methyl]-7-(4-fluorophenyl)-[1,2,4]triazolo[1,5-c]pyrimidin-8-yl)-1-methyl-1,2-dihydropyridin-2-one (Cmpd. 20)

SCHEME 11

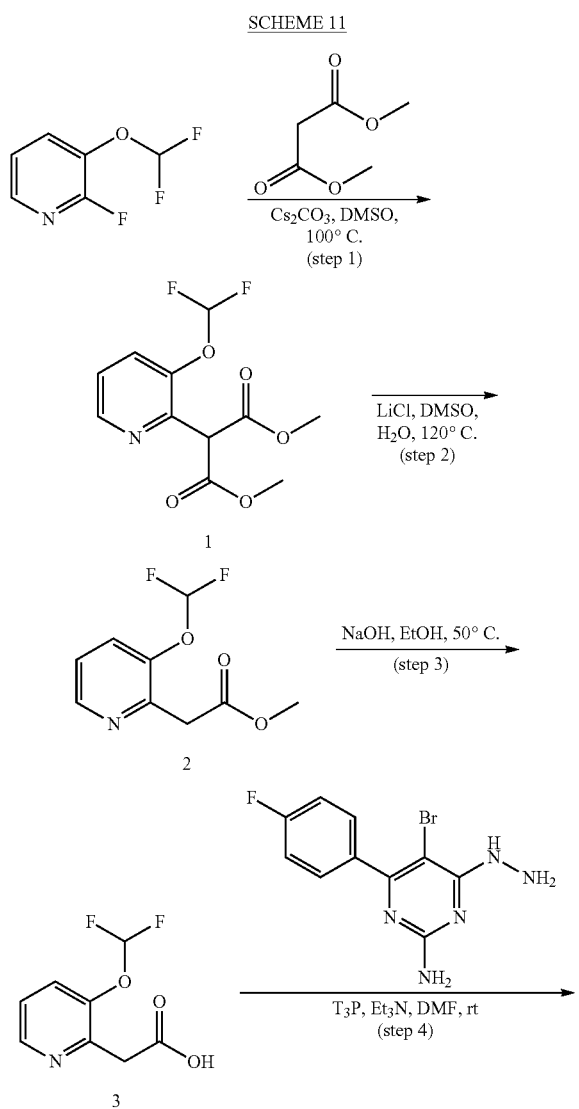

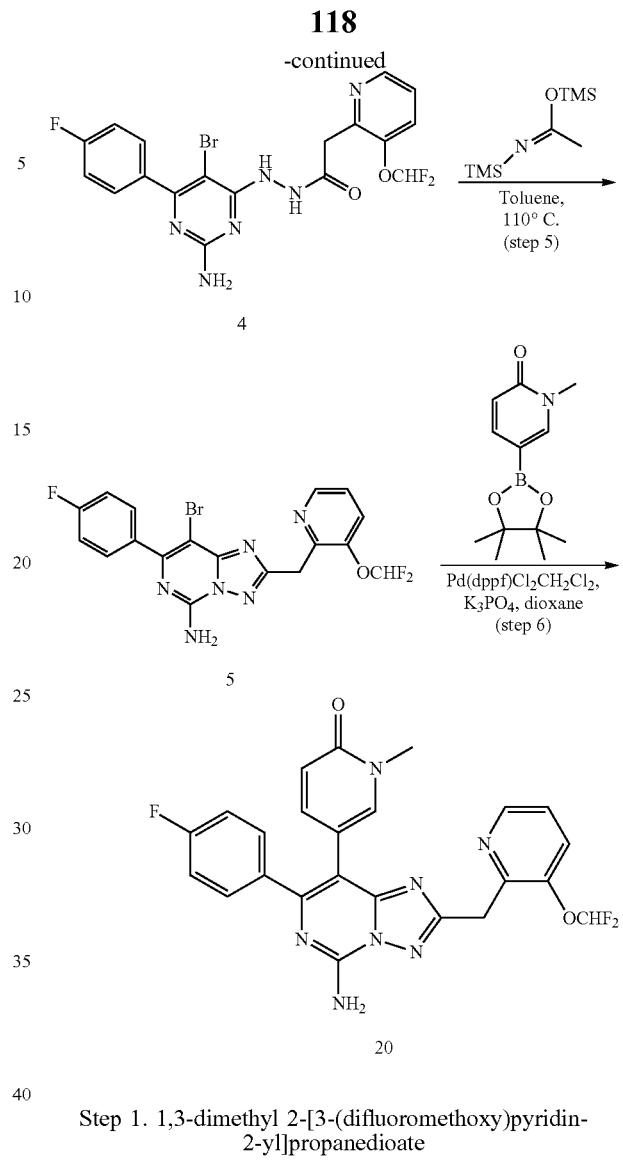

Step 1. 1,3-dimethyl 2-[3-(difluoromethoxy)pyridin-2-yl]propanedioate

Into a 50 mL round-bottom flask purged and maintained with an inert atmosphere of nitrogen, was placed DMSO (20 mL), 3-(difluoromethoxy)-2-fluoropyridine (1.1 g, 6.7 mmol, 1 equiv), 1,3-dimethyl propanedioate (1.1 g, 8.1 mmol, 1.2 equiv), Cs₂CO₃ (6.6 g, 20.2 mmol, 3 equiv). The resulting solution was stirred for 16 hours at 100° C. in an oil bath. The reaction was then quenched by the addition of 50 mL of water. The resulting solution was extracted with 2×100 mL of ethyl acetate and the organic layers combined. The resulting solution was washed with 3×100 mL of brine and the organic layers were combined and dried over anhydrous sodium sulfate and concentrated under vacuum. The residue was applied onto a silica gel column with ethyl acetate/petroleum ether (1:3). This resulted in 1 g (51.7%) of 1,3-dimethyl 2-[3-(difluoromethoxy)pyridin-2-yl]propanedioate as yellow oil. LCMS: m/z (ESI), [M+H]⁺=276.0. ¹H NMR: (400 MHz, DMSO-d₆) δ 3.71 (6H, s), 5.21 (1H, s), 7.29 (1H, t), 7.52 (1H, dd), 7.72 (1H, dq), 8.41 (1H, dd).

Step 2. methyl 2-[3-(difluoromethoxy)pyridin-2-yl]acetate

Into a 50 mL round-bottom flask purged and maintained with an inert atmosphere of nitrogen, was placed DMSO (20 mL), 1,3-dimethyl 2-[3-(difluoromethoxy)pyridin-2-yl]propanedioate (950 mg, 3.45 mmol, 1 equiv), LiCl (365.9 mg, 8.6 mmol, 2.5 equiv), H$_2$O (62.2 mg, 3.5 mmol, 1 equiv). The resulting solution was stirred for 5 hours at 120° C. in an oil bath. The reaction was then quenched by the addition of 50 mL of water. The resulting solution was extracted with 3×50 mL of ethyl acetate and the organic layers combined. The resulting solution was washed with 3×50 mL of brine and the organic layers combined and dried over anhydrous sodium sulfate. The residue was purified by silica gel column with ethyl acetate/petroleum ether (1:2). This resulted in 480 mg (61.5%) of methyl 2-[3-(difluoromethoxy)pyridin-2-yl]acetate as yellow oil. LCMS: m/z (ESI), [M+H]$^+$=218.0. $^1$H NMR: (400 MHz, DMSO-d$_6$) δ 3.63 (3H, s), 3.89 (2H, s), 7.06-7.43 (1H, m), 7.44 (1H, dd), 7.67 (1H, dq), 8.39 (1H, dd).

Step 3. sodium 2-[3-(difluoromethoxy)pyridin-2-yl]acetate

Into a 50 mL round-bottom flask purged and maintained with an inert atmosphere of nitrogen, was placed EtOH (20 mL), methyl 2-[3-(difluoromethoxy)pyridin-2-yl]acetate (210 mg, 1.0 mmol, 1 equiv), NaOH (58.0 mg, 1.5 mmol, 1.5 equiv). The resulting solution was stirred for 2 hours at 50° C. The mixture solution was filtered and the filter cake was dried under vacuum. This resulted in 160 mg (72.0%) of sodium 2-[3-(difluoromethoxy)pyridin-2-yl]acetate as a white solid. LCMS: m/z (ESI), [M+H]$^+$=204.0. $^1$H NMR: (400 MHz, D$_2$O) δ 3.67 (2H, s), 6.71 (1H, t), 7.30 (1H, dd), 7.59 (1H, d), 8.21 (1H, dd).

Step 4. N-[2-amino-5-bromo-6-(4-fluorophenyl)pyrimidin-4-yl]-2-[3-(difluoromethoxy)pyridin-2-yl]acetohydrazide Into a 100 mL round-bottom flask purged and maintained with an inert atmosphere of nitrogen, was placed DMF (20 mL), EtOAc (20 mL), 5-bromo-4-(4-fluorophenyl)-6-hydrazinylpyrimidin-2-amine (251.6 mg, 0.8 mmol, 1.0 equiv), sodium 2-[3-(difluoromethoxy)pyridin-2-yl]acetate (190 mg, 0.8 mmol, 1 equiv), T3P (537.1 mg, 1.7 mmol, 2 equiv), Et$_3$N (170.8 mg, 1.7 mmol, 2 equiv). The resulting solution was stirred for 16 hours at 15° C. The solvent was removed under vacuum and water (20 mL) was added, the mixture was filtered and the filter cake was combined. This resulted in 186 mg (44.2%) of N-[2-amino-5-bromo-6-(4-fluorophenyl)pyrimidin-4-yl]-2-[3-(difluoromethoxy)pyridin-2-yl]acetohydrazide as a grey solid. LCMS: m/z (ESI), [M+H]$^+$=485.1. $^1$H NMR: (400 MHz, DMSO-d$_6$) δ 3.83 (1H, s), 6.44 (1H, s), 7.22-7.53 (2H, m), 7.51-7.74 (2H, m), 8.41 (1H, d), 8.68 (1H, s), 10.10 (1H, s).

Step 5. 8-bromo-2-[[3-(difluoromethoxy)pyridin-2-yl]methyl]-7-(4-fluorophenyl)-[1,2,4]triazolo[1,5-c]pyrimidin-5-amine Into a 50 mL round-bottom flask purged and maintained with an inert atmosphere of nitrogen, was placed Toluene (20 mL, 187.9 mmol, 516.1 equiv), N-[2-amino-5-bromo-6-(4-fluorophenyl)pyrimidin-4-yl]-2-[3-(difluoromethoxy)pyridin-2-yl]acetohydrazide (176 mg, 0.4 mmol, 1 equiv), (Z)-(trimethylsilyl N-(trimethylsilyl)ethanimidate) (222.3 mg, 1.1 mmol, 3 equiv). The resulting solution was stirred for 16 hours at 110° C. in an oil bath. The solvent was removed and the residue was purified by recrystallization with DCM:PE (1:1). 150 mg (92% purity) of 8-bromo-2-[[3-(difluoromethoxy)pyridin-2-yl]methyl]-7-(4-fluorophenyl)-[1,2,4]triazolo[1,5-c]pyrimidin-5-amine as a brown solid. LCMS: m/z (ESI), [M+H]$^+$=465.0. $^1$H NMR: (400 MHz, DMSO-d$_6$) δ 4.42 (1H, s), 6.70 (3H, s), 7.33 (5H, t), 7.73 (2H, d), 8.13 (1H, s), 8.38 (1H, d).

Step 6. 5-(5-amino-2-[[3-(difluoromethoxy)pyridin-2-yl]methyl]-7-(4-fluorophenyl)-[1,2,4]triazolo[1,5-c]pyrimidin-8-yl)-1-methyl-1,2-dihydropyridin-2-one (Cmpd. 20)

Into a 20 mL vial purged and maintained with an inert atmosphere of nitrogen, was placed dioxane (12 mL), H$_2$O (2 mL), 8-bromo-2-[[3-(difluoromethoxy)pyridin-2-yl]methyl]-7-(4-fluorophenyl)-[1,2,4]triazolo[1,5-c]pyrimidin-5-amine (140 mg, 0.3 mmol, 1 equiv), 1-methyl-5-(4,4,5,5-tetramethyl-1,3,2-dioxaborolan-2-yl)-1,2-dihydropyridin-2-one (141.5 mg, 0.60 mmol, 2.00 equiv), Pd(dppf)Cl$_2$·CH$_2$Cl$_2$ (24.6 mg, 0.03 mmol, 0.1 equiv), K$_3$PO$_4$ (191.6 mg, 0.9 mmol, 3 equiv). The resulting solution was stirred for 6 hours at 80° C. The resulting solution was extracted with 3×50 mL of dichloromethane and the organic layers combined and dried over anhydrous sodium sulfate. The residue was dissolved in 5 mL of DCM. The crude product was purified by Prep-TLC (DCM:MeOH, 12:1) and Prep-HPLC with the following conditions: Column: XBridge Prep Phenyl OBD Column 5 μm, 19*250 mm; Mobile Phase A: Water (10 MMOL/L NH4HCO$_3$+0.1% NH$_3$.H$_2$O), Mobile Phase B: ACN; Flow rate: 20 mL/min; Gradient: 32% B to 45% B in 7 min; 254, 220 nm; Rt: 6.93 min. This resulted in 12 mg (7.9%) of 5-(5-amino-2-[[3-(difluoromethoxy)pyridin-2-yl]methyl]-7-(4-fluorophenyl)-[1,2,4]triazolo[1,5-c]pyrimidin-8-yl)-1-methyl-1,2-dihydropyridin-2-one (Cmpd. 20) as a white solid. LCMS: m/z (ESI), [M+H]$^+$=494.2. $^1$H NMR: (400 MHz, MeOD) δ 3.56 (3H, s), 4.50 (2H, s), 6.42 (1H, d), 6.97 (3H, s), 7.09 (2H, m), 7.19 (1H, m), 7.42 (1H, dd), 7.55 (2H, m), 7.70 (1H, m), 7.78 (1H, d), 8.35 (1H, dd).

Compound listed in the table below were prepared using methods described in Example 20.

| Example/Compound number | Structure | LCMS [M + H]$^+$ | $^1$H NMR |
|---|---|---|---|
| 73 | (structure shown) | 503.2 | $^1$H NMR (400 MHz, Methanol-d$_6$) δ4.39 (s, 2H), 6.90 (dd, J = 9.3, 1.8 Hz, 1H), 7.05-7.18 (m, 2H), 7.36-7.43 (m, 1H), 7.43-7.51 (m, 3H), 7.55 (d, J = 1.2 Hz, 1H), 7.61-7.68 (m, 1H), 7.91 (s, 1H), 8.03 (s, 1H), 8.34 (dd, J = 4.7, 1.4 Hz, 1H), 8.53 (t, J = 1.4 Hz, 1H). |

Example 21

Preparation of 5-(5-amino-2-((3-fluoropyridin-2-yl)methyl)-7-(oxazol-2-yl)-[1,2,4]triazolo[1,5-c]pyrimidin-8-yl)-1-methylpyridin-2(1H)-one (Cmpd. 21)

SCHEME 12

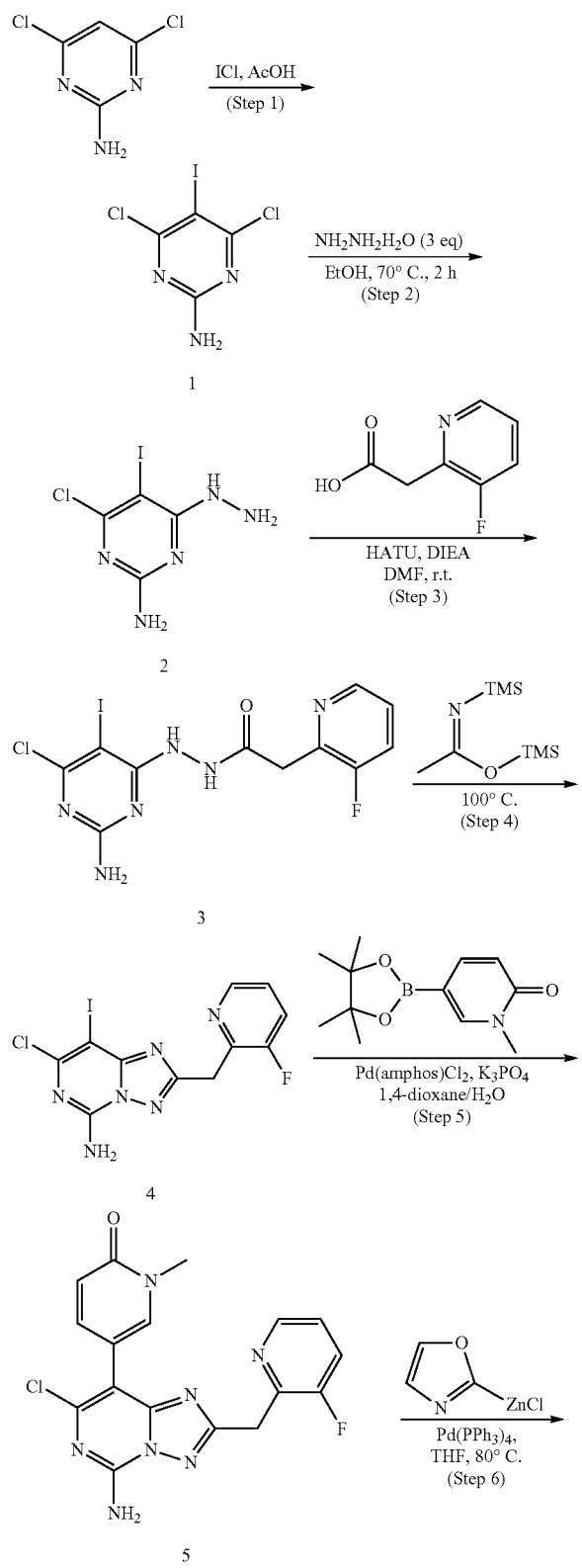

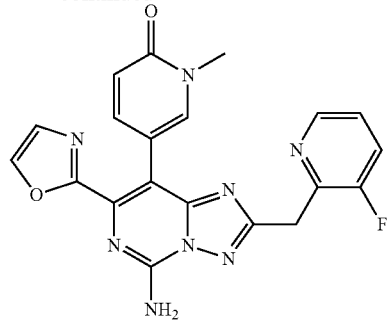

Compound 21

Step 1. 4,6-dichloro-5-iodopyrimidin-2-amine

To a stirred mixture of 4,6-dichloropyrimidin-2-amine (40 g, 243.9 mmol) in AcOH (300 mL) was added ICl (79.2 g, 487.8 mmol) in AcOH (100 mL) dropwise at room temperature under nitrogen atmosphere. The resulting mixture was stirred for overnight at room temperature under nitrogen atmosphere. The reaction was quenched with water/ice at room temperature. The resulting mixture was filtered, the filter cake was washed with ethanol (3×200 mL). The filtrate was concentrated under reduced pressure to afford 4,6-dichloro-5-iodopyrimidin-2-amine (50 g, 70.7%) as an off-white solid. LCMS: m/z (ESI), [M+H]$^+$=290.0.

Step 2. 4-chloro-6-hydrazineyl-5-iodopyrimidin-2-amine

To a stirred mixture of 4,6-dichloro-5-iodopyrimidin-2-amine (10 g, 34.5 mmol) in EtOH (80 mL) was added hydrazine (3.3 mg, 0.1 mmol) dropwise at room temperature under nitrogen atmosphere. The resulting mixture was stirred for 5 hours at 80° C. under nitrogen atmosphere. The mixture was allowed to cool down to room temperature. The precipitated solids were collected by filtration and washed with EtOH (3×50 mL) to afford 4-chloro-6-hydrazinyl-5-iodopyrimidin-2-amine (8 g, 81.2%) as an off-white solid. LCMS: m/z (ESI), [M+H]$^+$=286.0.

Step 3. N'-(2-amino-6-chloro-5-iodopyrimidin-4-yl)-2-(3-fluoropyridin-2-yl) acetohydrazide To a stirred mixture of 4-chloro-6-hydrazinyl-5-iodopyrimidin-2-amine (10 g, 35 mmol) and 2-(3-fluoropyridin-2-yl)acetic acid (6.5 g, 42 mmol) in DMF (100 mL) were added DIEA (13.6 g, 105.1 mmol) and HATU (20 g, 52.6 mmol) in portions at 0° C. under nitrogen atmosphere. The resulting mixture was stirred for 3 hours at room temperature under nitrogen atmosphere. The reaction was quenched by the addition of water (500 mL) at room temperature. The precipitated solids were collected by filtration and washed with MeOH (50 mL) and EtOAc (3×50 mL) to afford N-(2-amino-6-chloro-5-iodopyrimidin-4-yl)-2-(3-fluoropyridin-2-yl)acetohydrazide (7 g, 47.3%) as a grey solid. LCMS: m/z (ESI), [M+H]$^+$=423.1.

Step 4. 7-chloro-2-((3-fluoropyridin-2-yl)methyl)-8-iodo-[1,2,4]triazolo[1,5-c]pyrimidin-5-amine To a stirred mixture of N-(2-amino-6-chloro-5-iodopyrimidin-4-yl)-2-(3-fluoropyridin-2-yl)acetohydrazide (10 g, 0.02 mol) in (Z)-(trimethylsilyl N-(trimethylsilyl)ethanimidate) (40 mL) at room temperature under nitrogen atmosphere. The resulting mixture was stirred for 3 hours at 100° C. under nitrogen atmosphere. The mixture was allowed to cool down to room temperature. The reaction was quenched with water/ice at room temperature. The precipitated solids were collected by filtration and washed with ethanol (2×20 mL) and EA (3×50 mL) to afford 7-chloro-2-[(3-fluoropyridin-2-yl)methyl]-8-iodo-[1,2,4]triazolo[1,5-c]pyrimidin-5-amine (6 g, 62.7%) as a grey solid. LCMS: m/z (ESI), [M+H]$^+$=405.0.

Step 5. 5-(5-amino-7-chloro-2-((3-fluoropyridin-2-yl)methyl)-[1,2,4]triazolo[1,5-c]pyrimidin-8-yl)-1-methylpyridin-2(1H)-one To a stirred mixture of 7-chloro-2-[(3-fluoropyridin-2-yl)methyl]-8-iodo-[1,2,4]triazolo[1,5-c]pyrimidin-5-amine (1 g, 2.5 mmol) and 1-methyl-5-(4,4,5,5-tetramethyl-1,3,2-dioxaborolan-2-yl)-1,2-dihydropyridin-2-one (871.6 mg, 3.7 mmol) in 1,4-dioxane (10 mL) and H$_2$O (2 mL) were added K$_3$PO$_4$ (1.6 g, 7.4 mmol) and Pd(amphos)Cl$_2$ (350 mg, 0.5 mmol) in portions at room temperature under nitrogen atmosphere. The resulting mixture was stirred for 2 hours at 100° C. under nitrogen atmosphere. The resulting mixture was concentrated under reduced pressure. The residue was purified by Prep-TLC (CH$_2$Cl$_2$/MeOH 10:1) to afford 5-[5-amino-7-chloro-2-[(3-fluoropyridin-2-yl)methyl]-[1,2,4]triazolo[1,5-c]pyrimidin-8-yl]-1-methyl-1,2-dihydropyridin-2-one (500 mg, 52.4%) as an off-white solid. LCMS: m/z (ESI), [M+H]$^+$=386.2.

Step 6. 5-[5-amino-2-[(3-fluoropyridin-2-yl)methyl]-7-(1,3-oxazol-2-yl)-[1,2,4]triazolo[1,5-c]pyrimidin-8-yl]-1-methyl-1,2-dihydropyridin-2-one (Cmpd. 21)

To a stirred solution of 1,3-oxazole (200 mg, 2.9 mmol, 4.0 eq.) in THF (3.0 ml) was added n-butyllithium (1.3 mL, 3.2 mmol, 4.4 eq.) dropwise at −78° C. under nitrogen atmosphere, stirred for 30 min, added ZnCl$_2$(1 M in THF, 5.8 mL, 5.8 mmol, 8.0 eq.) dropwise at −78° C., stirred for 1 hour at −30° C., warmed to room temperature, added 5-[5-amino-7-chloro-2-[(3-fluoropyridin-2-yl)methyl]-[1,2,4]triazolo[1,5-c]pyrimidin-8-yl]-1-methyl-1,2-dihydropyridin-2-one (100 mg, 0.73 mmol, 1 eq.) and Pd(PPh$_3$)$_4$ (60 mg, 1.4 mmol, 0.2 eq.), degassed under nitrogen, heated for 15 hours at 80° C. The mixture was allowed to cool down to room temperature. The residue was purified by Prep-TLC (DCM/MeOH=30/1), and washed with ethanol to afford 5-[5-amino-2-[(3-fluoropyridin-2-yl)methyl]-7-(1,3-oxazol-2-yl)-[1,2,4]triazolo[1,5-c]pyrimidin-8-yl]-1-methyl-1,2-dihydropyridin-2-one (Cmpd. 21) (30 mg, 27.7%) as an off-white solid. LCMS: m/z (ESI), [M+H]$^+$=419.2. $^1$H NMR: (400 MHz, DMSO-d6) δ 3.41 (s, 3H), 4.43 (s, 2H), 6.36 (d, j=9.6 Hz, 1H), 7.29-7.26 (m, 1H), 7.42-7.34 (m, 2H), 7.75-7.70 (m, 2H), 8.20-8.16 (brs, 2H), 8.21 (s, 1H), 8.33 (d, J=4.8 Hz, 1H).

Example 22

Preparation of 5-(5-amino-2-(2,6-difluorobenzyl)-7-(oxazol-2-yl)-[1,2,4]triazolo[1,5-c]pyrimidin-8-yl)-1-methylpyridin-2(1H)-one (Cmpd. 22)

SCHEME 13

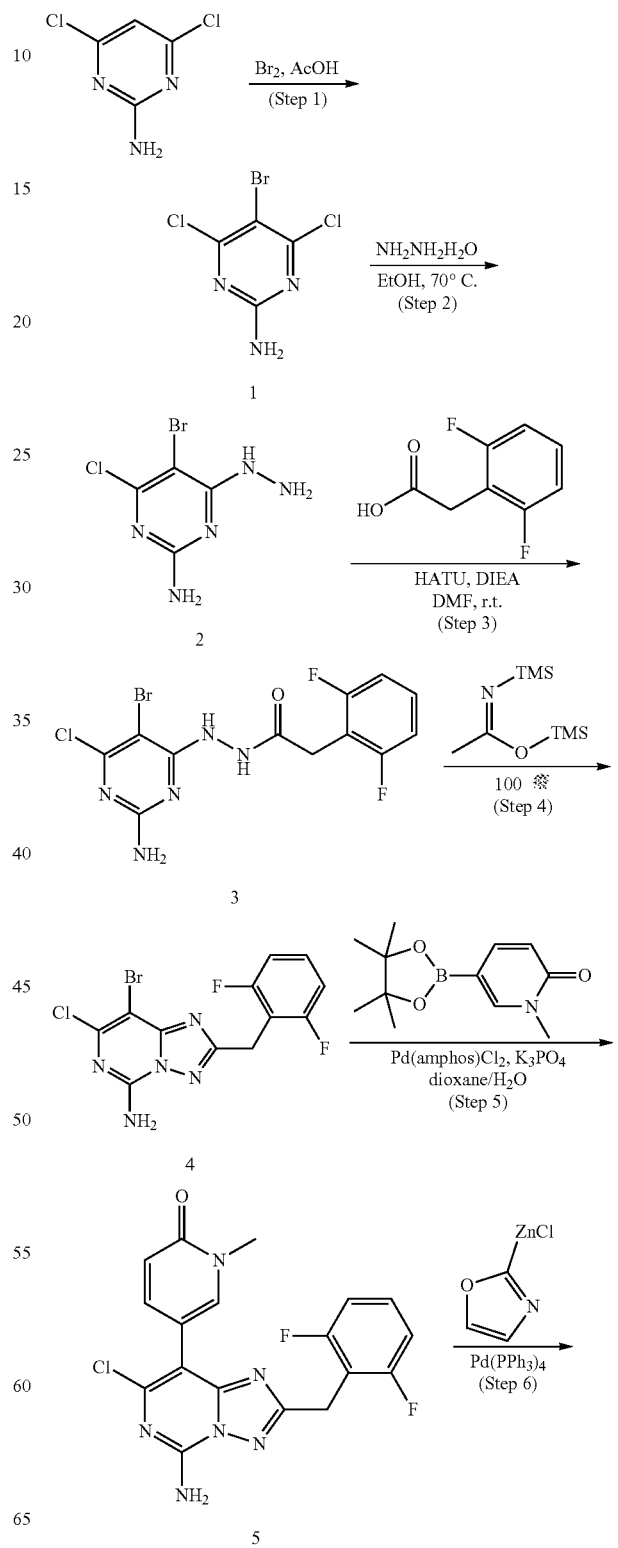

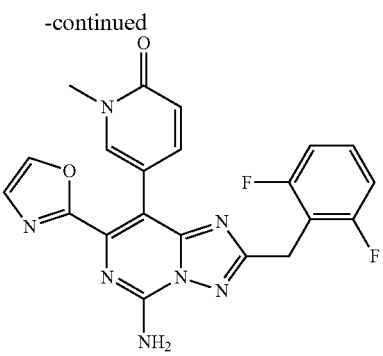

Compound 22

Step 1. 5-bromo-4,6-dichloropyrimidin-2-amine

To a stirred mixture of 4,6-dichloropyrimidin-2-amine (2.46 g, 1 equiv), NaOAc (6.15 g) in AcOH (150 mL) was added Br$_2$(3.24 g) dropwise at room temperature under nitrogen atmosphere. The resulting mixture was stirred at 60° C. for 2 hours under nitrogen atmosphere. The reaction was monitored by LCMS. The resulting mixture was concentrated under reduced pressure. The crude product was precipitated by the addition of water (300 mL) and stirred for 1 hour. The precipitated solids were collected by filtration and washed with MTBE (2×50 mL). The resulting solid was dried under vacuum to afford 5-bromo-4,6-dichloropyrimidin-2-amine (3.4 g, 93.32%) as a white solid. LCMS: m/z (ESI), [M+H]$^+$=242.0. $^1$H NMR: (300 MHz, DMSO-d$_6$) δ 7.69 (s, 2H).

Step 2. 5-bromo-4-chloro-6-hydrazineylpyrimidin-2-amine

A mixture of 5-bromo-4,6-dichloropyrimidin-2-amine (1.9 g, 7.82 mmol, 1 equiv), NH$_2$NH$_2$.H$_2$O (1.2 g, 23.97 mmol, 3.06 equiv) in EtOH (30 mL) was stirred at 80° C. for 2 hours. Concentrated to dryness. The residue was diluted with MTBE (50 mL) and filtered. The solid was dried in vacuum to afford 5-bromo-4-chloro-6-hydrazinylpyrimidin-2-amine (1.9 g, 93.71%) as an off-white solid. LCMS: m/z (ESI), [M+H]$^+$=238.1.

Step 3. N'-(2-amino-5-bromo-6-chloropyrimidin-4-yl)-2-(2,6-difluorophenyl)acetohydrazide To a mixture of 5-bromo-4-chloro-6-hydrazinylpyrimidin-2-amine (1.9 g, 8.0 mmol, 1 equiv), 2-(2,6-difluorophenyl)acetic acid (2.7 g, 15.9 mmol, 2 equiv), TEA (3.2 g, 31.9 mmol, 4 equiv) in DMSO (10 mL) was added HATU (6.1 g, 15.9 mmol, 2 equiv). Stirred at 25° C. for 2 hours. Poured into 150 mL water. 50 mL sat. NaHCO$_3$ was added to the mixture and filtered. The solid was dried in vacuum to afford N-(2-amino-5-bromo-6-chloropyrimidin-4-yl)-2-(2,6-difluorophenyl)acetohydrazide (1.6 g, 51.2%) as a light brown solid. LCMS: m/z (ESI), [M+H]$^+$=392.0

Step 4. 8-bromo-7-chloro-2-(2,6-difluorobenzyl)-[1,2,4]triazolo[1,5-c]pyrimidin-5-amine A mixture of N-(2-amino-5-bromo-6-chloropyrimidin-4-yl)-2-(2,6-difluorophenyl)acetohydrazide (0.6 g, 1.5 mmol, 1 equiv) in (E)-(trimethylsilyl N-(trimethylsilyl)ethanimidate) (10 mL) was stirred at 120° C. for 4 hours. The mixtures were cooled to room temperature and poured into water, then filtered. The solid was dried in vacuum to afford 8-bromo-7-chloro-2-[(2,6-difluorophenyl)methyl]-[1,2,4]triazolo[1,5-c]pyrimidin-5-amine (450 mg, 78.6%) as a brown solid. LCMS: m/z (ESI), [M+H]$^+$=374.0

Step 5. 5-(5-amino-7-chloro-2-(2,6-difluorobenzyl)-[1,2,4]triazolo[1,5-c]pyrimidin-8-yl)-1-methylpyridin-2(1H)-one To a stirred solution of 8-bromo-7-chloro-2-[(2,6-difluorophenyl)methyl]-[1,2,4]triazolo[1,5-c]pyrimidin-5-amine (5.0 g, 13.35 mmol, 1 equiv) and 1-methyl-5-(4,4,5,5-tetramethyl-1,3,2-dioxaborolan-2-yl)-1,2-dihydropyridin-2-one (7845.3 mg, 33.37 mmol, 2.50 equiv) in dioxane/H$_2$O=10:1 (50.0 mL) were added K$_3$PO$_4$ (639.3 mg, 26.70 mmol, 2.0 equiv) and PdAMPHOS (7561.4 mg, 10.68 mmol, 0.8 equiv) in portions at 90° C. under nitrogen atmosphere. The residue was purified by silica gel column chromatography, eluted with CH$_2$Cl$_2$/EtOAc (3:1) to afford 5-[5-amino-7-chloro-2-[(2,6-difluorophenyl)methyl]-[1,2,4]triazolo[1,5-c]pyrimidin-8-yl]-1-methyl-1,2-dihydropyridin-2-one (1.5 g, 27.9%) as a white solid. LCMS: m/z (ESI), [M+H]$^+$=403.2

Step 6. 5-(5-amino-2-(2,6-difluorobenzyl)-7-(oxazol-2-yl)-[1,2,4]triazolo[1,5-c]pyrimidin-8-yl)-1-methylpyridin-2(1H)-one (Cmpd. 22)

To a stirred solution of 1,3-oxazole (100 mg, 1.5 mmol) in THF (2.0 mL) was added n-butyllithium (0.7 mL, 1.6 mmol) dropwise at −78° C. under N$_2$. After stirring for 30 min, ZnCl$_2$(1 M in THF, 2.9 mL, 2.9 mmol) was added dropwise at −78° C. The mixture was stirred for 1 hour at −30° C. Then 5-[7-chloro-2-[(3-fluoropyridin-2-yl)methyl]-[1,2,4]triazolo[1,5-a]pyridin-8-yl]-1-methyl-1,2-dihydropyridin-2-one (100 mg, 0.25 mmol) and Pd(PPh$_3$)$_4$ (57.4 mg, 0.05 mmol) was added thereto. The mixture was stirred for 15 hours at 80° C. under N$_2$. The mixture was allowed to cool down to room temperature and purified by Prep-TLC (DCM/MeOH=30/1). The crude was washed with ethanol and dried to afford 5-(5-amino-2-(2,6-difluorobenzyl)-7-(oxazol-2-yl)-[1,2,4]triazolo[1,5-c]pyrimidin-8-yl)-1-methylpyridin-2(1H)-one (Cmpd. 22) (20 mg, 18.5%) as a white solid. LCMS: m/z (ESI), [M+H]$^+$=43. $^1$H NMR (400 MHz, DMSO, d$_6$) δ 3.41 (s, 3H), 4.25 (s, 2H), 6.36 (d, J=9.2 Hz, 1H), 7.15-7.08 (m, 2H), 7.29-7.26 (m, 1H), 7.44-7.34 (m, 2H), 7.53 (d, J=2.4 Hz, 1H), 8.15-8.05 (brs, 2H), 8.20 (s, 1H).

Compounds listed in the table below were prepared using methods described in Example 22.

| Example/ Compound number | Structure | LCMS [M + H]+ | 1H NMR |
|---|---|---|---|
| 26 | 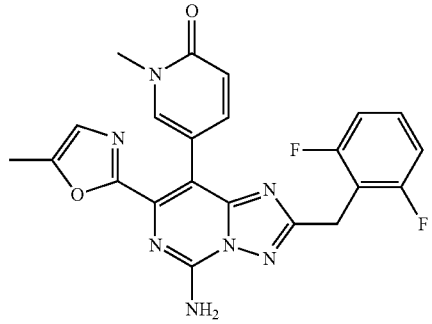 [SMILES: Cc1cnc(-c2nc(N)n3nc(Cc4c(F)cccc4F)nc3c2-c2ccc(=O)n(C)c2)o1] | 450.2 | 1H NMR (400 MHz, DMSO, $d_6$) δ 2.07 (s, 3H), 3.42 (s, 3H), 4.25 (s, 2H), 6.36 (d, J = 9.2 Hz, 1H), 7.15-7.09 (m, 2H), 7.28-7.25 (m, 1H), 7.44-7.36 (m, 1H), 7.79 (d, J = 2.4 Hz, 1H), 7.87 (d, J = 1.2 Hz, 1H), 8.10-8.00(brs, 2H). |
| 27 | 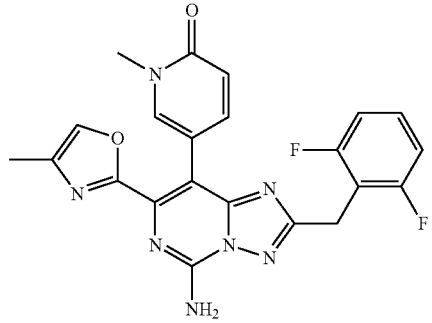 [SMILES: Cc1coc(-c2nc(N)n3nc(Cc4c(F)cccc4F)nc3c2-c2ccc(=O)n(C)c2)n1] | 450.2 | 1H NMR (400 MHz, DMSO-$d_6$) δ 2.32 (s, 3H), 3.47 (s, 3H), 4.24 (s, 2H), 6.35 (d, J = 5.2 Hz, 1H), 6.94 J = 1.2 Hz, 2H), 7.15-7.08 (m, 2H), 7.28 (d, J = 2.4 Hz, 1H), 7.43-7.41 (m, 1H), 7.76 (d, J = 2.4 Hz, 1H), 8.10-8.08(brs, 2H). |
| 44 | 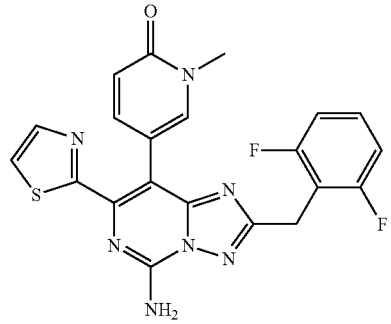 [SMILES: Cn1cc(-c2c(-c3nccs3)nc(N)n3nc(Cc4c(F)cccc4F)nc23)ccc1=O] | 452.2 | 1H NMR (400 MHz, DMSO-$d_6$) δ 3.43 (s, 2H), 4.24 (s, 1H), 6.36 (d, J = 9.3 Hz, 1H), 7.12 (t, J = 7.9 Hz, 1H), 7.32 (dd, J = 9.3, 2.6 Hz, 1H), 7.32-7.44 (m, 1H), 7.77 (d, J = 2.5 Hz, 1H), 7.83 (s, 1H), 8.03 (s, 1H). |

Example 23

Preparation of 5-(5-amino-2-(2,6-difluorobenzyl)-7-(4-fluorophenyl)-[1,2,4]triazolo[1,5-c]pyrimidin-8-yl)-1-(tetrahydrofuran-3-yl)pyridin-2(1H)-one (Cmpd. 23)

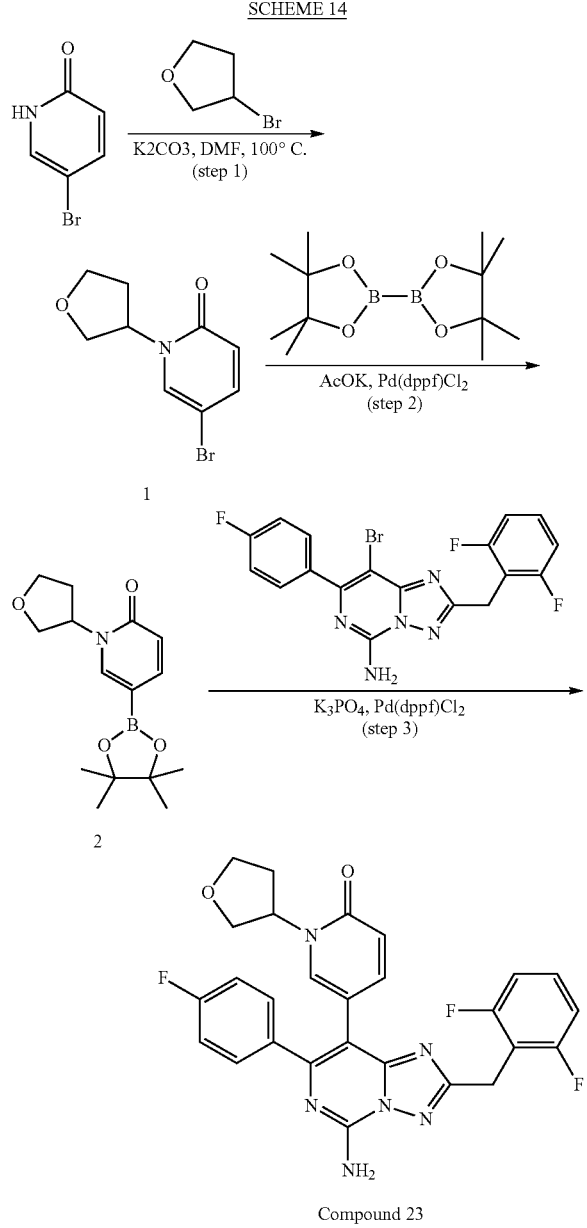

Step 1. 5-bromo-1-(oxolan-3-yl)-1,2-dihydropyridin-2-one

Into a 40 mL sealed tube were added K$_2$CO$_3$ (4.8 g, 34.5 mmol, 3 equiv), 3-bromooxolane (5.2 g, 34.5 mmol, 3.00 equiv) and 5-bromo-1,2-dihydropyridin-2-one (2 g, 11.5 mmol, 1 equiv) in DMF (3 mL) at 80° C. for 6 hours. Desired product could be detected by LCMS. The resulting mixture was concentrated under reduced pressure. The residue was purified by silica gel column chromatography, eluted with PE/EtOAc (1:1) to afford 5-bromo-1-(oxolan-3-yl)-1,2-dihydropyridin-2-one (600 mg, 22.1%) as a yellow solid. LCMS: m/z (ESI), [M+H]$^+$=244.1. $^1$H NMR (400 MHz, DMSO-d$_6$) δ 1.24 (1H, s), 1.99 (1H, m), 2.42 (1H, dtd), 3.84-3.66 (2H, m), 3.88 (1H, dd), 4.06 (1H, td), 5.31 (1H, ddt), 6.39 (1H, d), 7.53 (1H, dd), 7.70 (1H, d).

Step 2. 1-(oxolan-3-yl)-5-(4,4,5,5-tetramethyl-1,3,2-dioxaborolan-2-yl)-1,2-dihydropyridin-2-one Into a 30 mL sealed tube were added 5-bromo-1-(oxolan-3-yl)-1,2-dihydropyridin-2-one (600 mg, 2.5 mmol, 1 equiv), 4,4,5,5-tetramethyl-2-(4,4,5,5-tetramethyl-1,3,2-dioxaborolan-2-yl)-1,3,2-dioxaborolane (936.3 mg, 3.7 mmol, 1.50 equiv), AcOK (482.5 mg, 4.92 mmol, 2 equiv) and Pd(dppf)Cl$_2$ CH$_2$Cl$_2$(200.7 mg, 0.3 mmol, 0.1 equiv) in dioxane (2 mL) at 90° C. for 2 hours. The resulting mixture was concentrated under vacuum. The residue was purified by Prep-TLC (PE/EtOAc 1:1) to afford 1-(oxolan-3-yl)-5-(4,4,5,5-tetramethyl-1,3,2-dioxaborolan-2-yl)-1,2-dihydropyridin-2-one (500 mg, 69.9%) as a yellow solid. LCMS: m/z (ESI), [M+H]$^+$=292.2.

Step 3. 5-(5-amino-2-(2,6-difluorobenzyl)-7-(4-fluorophenyl)-[1,2,4]triazolo[1,5-c]pyrimidin-8-yl)-1-(tetrahydrofuran-3-yl)pyridin-2(1H)-one (Cmpd. 23)

Into a 10 mL sealed tube were added 8-bromo-2-[(2,6-difluorophenyl)methyl]-7-(4-fluorophenyl)-[1,2,4]triazolo[1,5-c]pyrimidin-5-amine (100 mg, 0.2 mmol, 1 equiv), 1-(oxolan-3-yl)-5-(4,4,5,5-tetramethyl-1,3,2-dioxaborolan-2-yl)-1,2-dihydropyridin-2-one (134.1 mg, 0.5 mmol, 2.0 equiv), K$_3$PO$_4$ (122.2 mg, 0.6 mmol, 2.5 equiv) and Pd(dppf)Cl$_2$ CH$_2$Cl$_2$ (18.8 mg, 0.023 mmol, 0.1 equiv) in dioxane (7 mL) and water (0.7 mL) at 80° C. for 2 hours. Desired product could be detected by LCMS. The crude product (50 mg) was purified by Prep-HPLC with the following conditions (Column: XBridge Prep C18 OBD Column, 5 μm, 19*150 mm; Mobile Phase A: Water (10 MMOL/L NH$_4$HCO$_3$+0.1% NH$_3$.H$_2$O), Mobile Phase B: ACN; Flow rate: 20 mL/min; Gradient: 39% B to 39% B in 8 min; 254/220 nm; Rt: 7.7 min) to afford 5-(5-amino-2-(2,6-difluorobenzyl)-7-(4-fluorophenyl)-[1,2,4]triazolo[1,5-c]pyrimidin-8-yl)-1-(tetrahydrofuran-3-yl)pyridin-2(1H)-one (Cmpd. 23) (30 mg, 25.0%) as a white solid. LCMS: m/z (ESI), [M+H]$^+$=519.3. $^1$H NMR (400 MHz, DMSO-d$_6$) δ 1.54-1.55 (1H, m), 2.33 (1H, dq), 3.53-3.59 (3H, m), 3.74 (1H, dd), 4.24 (2H, s), 5.35 (1H, td), 6.30 (1H, d), 7.07-7.18 (3H, m), 7.18-7.26 (2H, m), 7.34-7.45 (1H, m), 7.42-7.51 (3H, m), 8.00 (2H, s).

Example 24

Preparation of 5-[5-amino-2-[(2,6-difluorophenyl)methyl]-7-(6-methylpyridin-3-yl)-[1,2,4]triazolo[1,5-c]pyrimidin-8-yl]-1-methyl-1,2-dihydropyridin-2-one (Cmpd. 24)

SCHEME 15

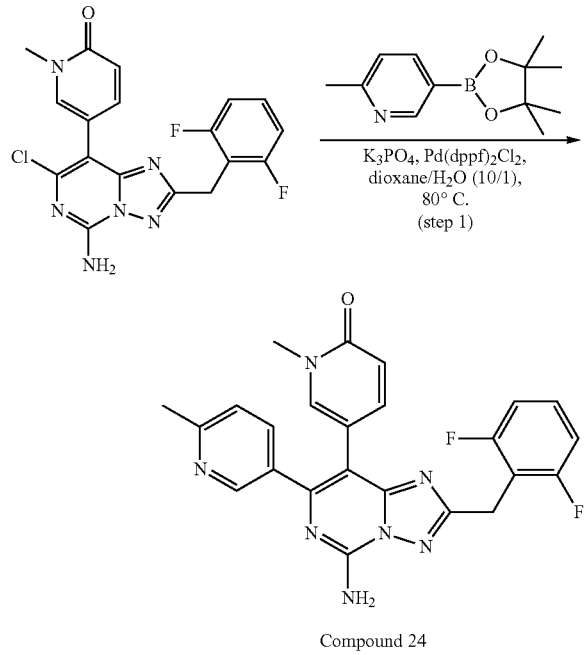

Compound 24

Step 1. 5-[5-amino-2-[(2,6-difluorophenyl)methyl]-7-(6-methylpyridin-3-yl)-[1,2,4]triazolo[1,5-c]pyrimidin-8-yl]-1-methyl-1,2-dihydropyridin-2-one A mixture of 5-[5-amino-7-chloro-2-[(2,6-difluorophenyl)methyl]-[1,2,4]triazolo[1,5-c]pyrimidin-8-yl]-1-methyl-1,2-dihydropyridin-2-one (80 mg, 0.20 mmol, 1 equiv), $K_3PO_4$ (126.5 mg, 0.6 mmol, 3 equiv), Pd(dppf)Cl$_2$ (29.1 mg, 0.04 mmol, 0.2 equiv) and 2-methyl-5-(3,3,4,4-tetramethylborolan-1-yl)pyridine (64.1 mg, 0.3 mmol, 1.5 equiv) in dioxane (1 mL) and water (1 mL) was stirred for 2 hours at 80° C. under nitrogen atmosphere. The resulting mixture was concentrated under reduced pressure. The crude product (80 mg) was purified by Prep-HPLC with the following conditions (Column: XBridge Prep OBD C18 Column 19*250 mm, 5 μm; Mobile Phase A: Water (0.05% NH3H2O), Mobile Phase B: ACN; Flow rate: 20 mL/min; Gradient: 25% B to 45% B in 8 min; 254/220 nm; Rt: 7.5 min) to afford 5-[5-amino-2-[(2,6-difluorophenyl)methyl]-7-(6-methylpyridin-3-yl)-[1,2,4]triazolo[1,5-c]pyrimidin-8-yl]-1-methyl-1,2-dihydropyridin-2-one (Cmpd. 24) (37.7 mg, 41.3%) as a white solid. LCMS: m/z (ESI), [M+H]$^+$=460.2. $^1$H NMR (400 MHz, DMSO-d$_6$) δ 2.4 (s, 3H), 3.3 (d, J=15.8 Hz, 3H), 6.3 (d, J=9.4 Hz, 1H), 7.0-7.2 (m, 3H), 7.2 (d, J=8.1 Hz, 1H), 7.3-7.5 (m, 1H), 7.6-7.7 (m, 2H), 7.9 (s, 1H), 8.5 (dd, J=2.3, 0.8 Hz, 1H).

Example 25

Preparation of 5-[5-amino-2-[(2,6-difluorophenyl)methyl]-7-(2H-1,2,3-triazol-2-yl)-[1,2,4]triazolo[1,5-c]pyrimidin-8-yl]-1-methyl-1,2-dihydropyridin-2-one. (Cmpd. 25)

SCHEME 16

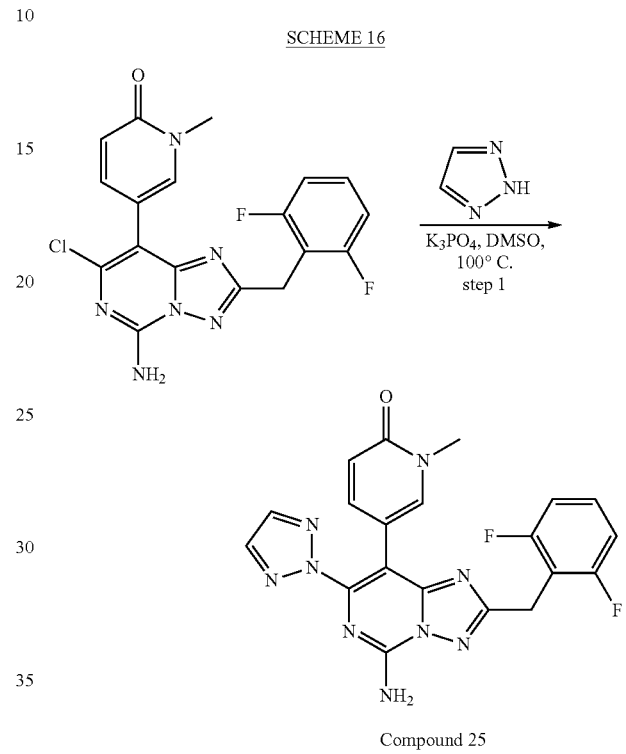

Compound 25

Step 1. 5-[5-amino-2-[(2,6-difluorophenyl)methyl]-7-(2H-1,2,3-triazol-2-yl)-[1,2,4]triazolo[1,5-c]pyrimidin-8-yl]-1-methyl-1,2-dihydropyridin-2-one (Cmpd. 25)

To a stirred mixture of 5-[5-amino-7-chloro-2-[(2,6-difluorophenyl)methyl]-[1,2,4]triazolo[1,5-c]pyrimidin-8-yl]-1-methyl-1,2-dihydropyridin-2-one (step 5, Cmpd. 22, 80 mg, 0.20 mmol, 1 equiv) and 2H-1,2,3-triazole (20.6 mg, 0.30 mmol, 1.5 equiv) in DMSO (5 mL) was added $K_3PO_4$ (126.5 mg, 0.60 mmol, 3 equiv) at room temperature under air atmosphere. The resulting mixture was stirred for 12 hours at 100° C. under air atmosphere. The resulting mixture was concentrated under reduced pressure. The crude product (50 mg) was purified by Prep-HPLC with the following conditions (Column: XBridge Prep OBD C18 Column 30×150 mm 5 μm; Mobile Phase A: Water (0.05% NH$_3$H2), Mobile Phase B: ACN; Flow rate: 60 mL/min; Gradient: 23% B to 30% B in 7 min; 254/220 nm; Rt: 6.28 min) to afford 5-[5-amino-2-[(2,6-difluorophenyl)methyl]-7-(2H-1,2,3-triazol-2-yl)-[1,2,4]triazolo[1,5-c]pyrimidin-8-yl]-1-methyl-1,2-dihydropyridin-2-one (Cmpd. 25) (10 mg) as a white solid. LCMS: m/z (ESI), [M+H]$^+$=436.2. $^1$H NMR: (400 MHz, DMSO) δ 3.35 (s, 3H), 4.28 (s, 2H), 6.25 (d, 1H), 6.84 (dd, 1H), 7.13 (t, 2H), 7.41 (t, 1H), 7.63 (d, 1H), 8.03 (s, 2H).

Example 28

Preparation of 5-(5-amino-7-chloro-2-(2,6-difluorobenzyl)-[1,2,4]triazolo[1,5-c]pyrimidin-8-yl)-1-methylpyridin-2(1H)-one (Cmpd. 28)

SCHEME 17

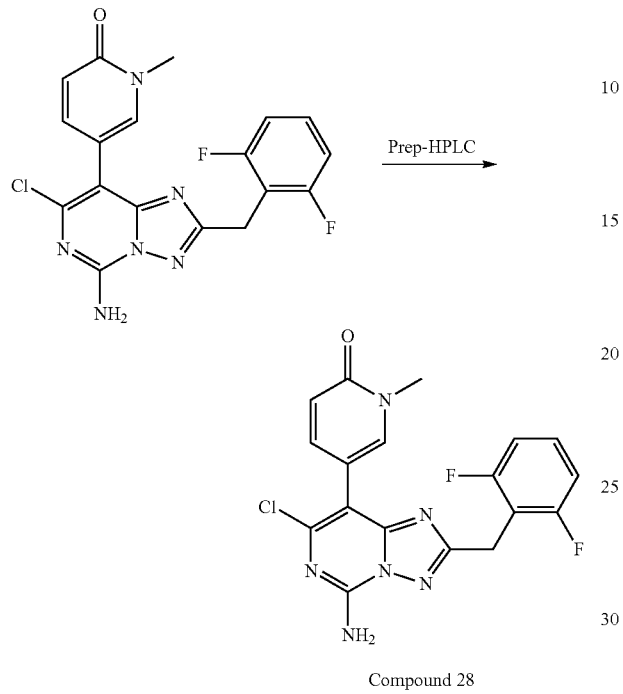

Compound 28

Step 1. 5-(5-amino-7-chloro-2-(2,6-difluorobenzyl)-[1,2,4]triazolo[1,5-c]pyrimidin-8-yl)-1-methylpyridin-2(1H)-one (Cmpd. 28)

The crude product (step 5, Cmpd. 22, 40 mg) was purified by Prep-HPLC with the following conditions (Column: X Bridge Prep OBD C18 Column 19*250 mm, 5 μm; Mobile Phase A: Water (0.05% $NH_3$—$H_2O$), Mobile Phase B: ACN; Flow rate: 20 mL/min; Gradient: 25% B to 50% B in 8 min; 254/220 nm; Rt: 7.48 min) to afford 5-[5-amino-7-chloro-2-[(2,6-difluorophenyl)methyl]-[1,2,4]triazolo[1,5-c]pyrimidin-8-yl]-1-methyl-1,2-dihydropyridin-2-one (Cmpd. 28) (25.8 mg, 64.5%) as a white solid. LCMS: m/z (ESI), $[M+H]^+$=403.1. $^1$H NMR (400 MHz, DMSO-$d_6$) δ 4.20 (2H, s), 6.45 (1H, d), 7.11 (2H, t), 7.39 (1H, tt), 7.50 (1H, dd), 7.87 (1H, d), 8.28 (2H, s).

Example 30

Preparation of 6-(5-amino-7-(4-fluorophenyl)-2-((3-fluoropyridin-2-yl)methyl)-[1,2,4]triazolo[1,5-f]pyrimidin-8-yl)-2-methylpyridazin-3(2H)-one (Cmpd. 30)

SCHEME 18

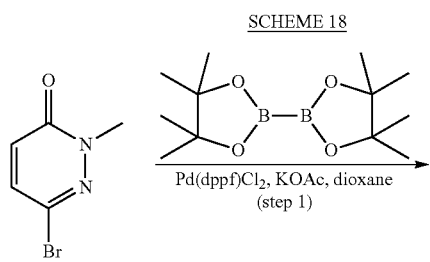

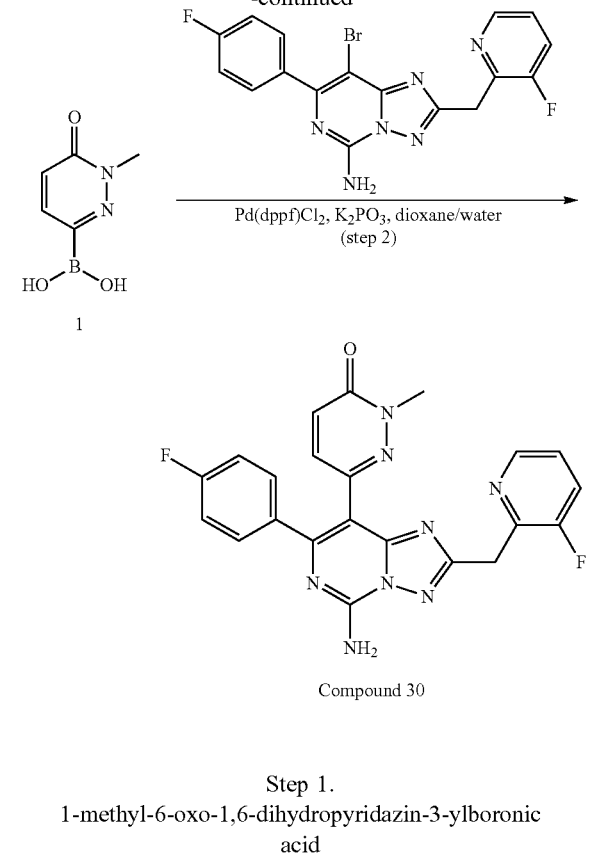

Compound 30

Step 1. 1-methyl-6-oxo-1,6-dihydropyridazin-3-ylboronic acid

Into a 8-mL vial, was placed 6-bromo-2-methyl-2,3-dihydropyridazin-3-one (100 mg, 0.53 mmol, 1 equiv), 4,4,5,5-tetramethyl-2-(4,4,5,5-tetramethyl-1,3,2-dioxaborolan-2-yl)-1,3,2-dioxaborolane (161 mg, 0.63 mmol, 1.20 equiv), Pd(dppp)Cl$_2$ (31 mg, 0.1 mmol, 0.10 equiv) in dioxane (10 mL), KOAc (156 mg, 1.6 mmol, 3.00 equiv). The resulting mixture was stirred for 3 hours at 80° C. under nitrogen atmosphere in an oil bath. The mixture were filtered and the filtrate was concentrated under vacuum. The residue was applied onto a silica gel column with dichloromethane/methanol (10:6). The collected fractions were combined and concentrated under vacuum to afford (1-methyl-6-oxo-1,6-dihydropyridazin-3-yl) boronic acid (174 mg) as an off-white solid. LCMS: m/z (ESI), $[M+H]^+$=155.0. H-NMR (300 MHz, MeOD-$d_4$) δ 3.82 (3H, s), 6.81 (1H, d), 7.53 (1H, d).

Step 2. 6-(5-amino-7-(4-fluorophenyl)-2-((3-fluoropyridin-2-yl)methyl)-[1,2,4]triazolo[1,5-f]pyrimidin-8-yl)-2-methylpyridazin-3(2H)-one (Cmpd. 30)

Into a 40-mL vial, was placed (1-methyl-6-oxo-1,6-dihydropyridazin-3-yl) boronic acid (132.8 mg, 0.86 mmol, 3.00 equiv), 8-bromo-7-(4-fluorophenyl)-2-[(3-fluoropyridin-2-yl)methyl]-[1,2,4]triazolo[1,5-c]pyrimidin-5-amine (120 mg, 0.29 mmol, 1 equiv) in dioxane (10 mL), Pd(dppf)Cl$_2$ (63.1 mg, 0.09 mmol, 0.30 equiv), and a solution of K$_3$PO$_4$ (183.2 mg, 0.86 mmol, 3.00 equiv) in water (2.5 mL). The resulting mixture was stirred for 15 hours at 80° C. under nitrogen atmosphere. The resulting mixture was concentrated under vacuum. The crude product was purified by Prep-HPLC with the following conditions: Column, XBridge RP, 30*150 mm, 5 μm; Mobile Phase A: Water (0.1% NH₄HCO₃), Mobile Phase B: ACN; Flow rate: 60 mL/min; Gradient: 16% B to 45% B in 8 min; 254/220 nm; Rt: 6.12 min. Product was obtained and concentrated under vacuum to afford 6-[5-amino-7-(4-fluorophenyl)-2-[(3-fluoropyridin-2-yl)methyl]-[1,2,4]triazolo[1,5-c]pyrimidin-8-yl]-2-methyl-2,3-dihydropyridazin-3-one (Cmpd. 30) (5 mg, 3.89%) as a white solid. LCMS: m/z (ESI), [M+H]$^+$=447.2. H-NMR (400 MHz, MeOD-d₄) δ 3.70 (3H, s), 4.51 (2H, d), 6.88 (1H, d), 7.06-7.15 (2H, m), 7.34 (1H, d), 7.41 (1H, dt), 7.46-7.56 (2H, m), 7.65 (1H, ddd), 8.32 (1H, dt).

Example 31

Preparation of 2-((3-fluoropyridin-2-yl)methyl)-8-(imidazo[1,2-a]pyridin-6-yl)-7-(oxazol-2-yl)-[1,2,4]triazolo[1,5-c]pyrimidin-5-amine (Cmpd. 31)

SCHEME 19

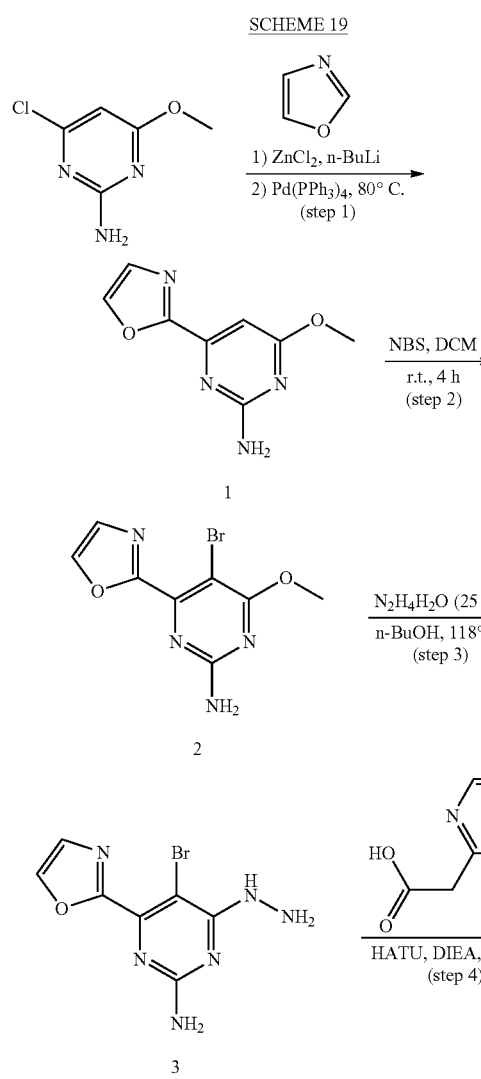

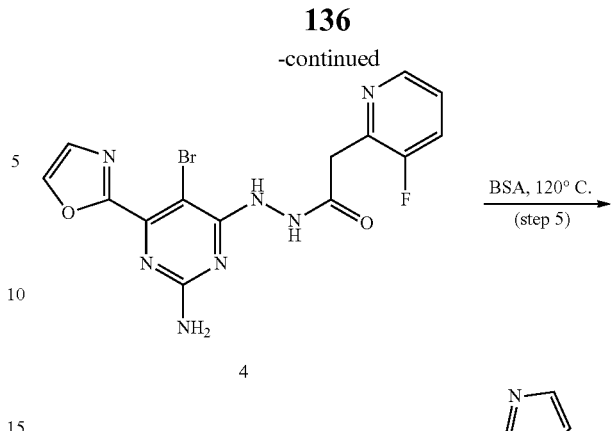

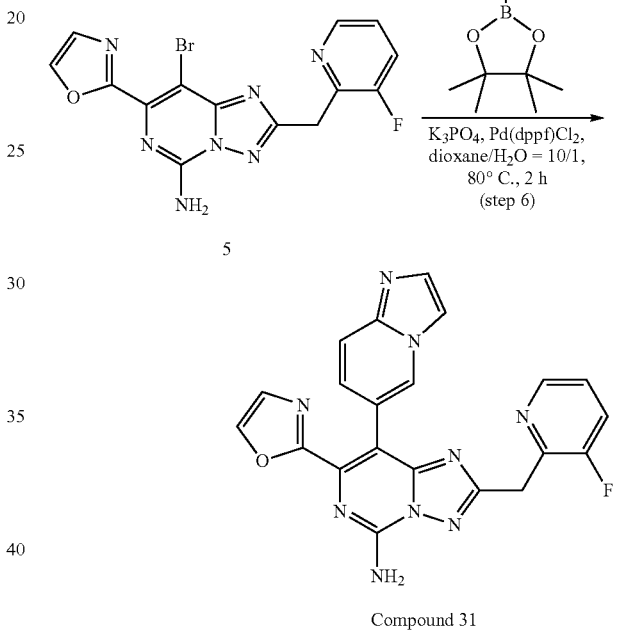

Compound 31

Step 1. 4-methoxy-6-(1,3-oxazol-2-yl)pyrimidin-2-amine

To a stirred solution of 1,3-oxazole (17 g, 248 mmol, 2 equiv) in THF (150 mL) was added n-butyllithium (2.5 M in hexane) (110 mL, 272.8 mmol, 2.2 equiv) dropwise at −78° C. under nitrogen atmosphere, stirred for 30 min, added ZnCl₂ (1 M in THF, 496 mL, 496 mmol, 4.0 equiv) dropwise at −78° C., stirred for 1 hour at −30° C., warmed to room temperature, added 4-chloro-6-methoxy-1,6-dihydropyrimidin-2-amine (20 g, 124 mmol, 1 equiv) and Pd(PPh₃)₄ (7.2 g, 6.2 mmol, 0.05 equiv), degassed under nitrogen, heated overnight at 80° C. The mixture was allowed to cool down to room temperature. The reaction was quenched with Water/Ice at room temperature. The mixture/residue was basified to pH=11 with NH₃.H₂O. The aqueous layer was extracted with EtOAc (3×500 ml) and dried. The residue was purified by silica gel column chromatography, eluted with CH₂Cl₂/MeOH (0-1/20) to afford 4-methoxy-6-(1,3-oxazol-2-yl)pyrimidin-2-amine (21 g) as a white solid. ¹H NMR (400 MHz, DMSO-d₆) δ 3.87 (s, 3H), 6.59 (s, 1H), 6.93 (s, 2H), 7.44 (d, J=0.7 Hz, 1H), 8.27 (d, J=0.8 Hz, 1H).

Step 2. 5-bromo-4-methoxy-6-(oxazol-2-yl)pyrimidin-2-amine

To a stirred mixture of 6-methoxy-4-(1,3-oxazol-2-yl)-1,6-dihydropyrimidin-2-amine (5.6 g, 28.84 mmol, 1 equiv) in DCM (200 mL) was added NBS (7.7 g, 43.26 mmol, 1.5 equiv) in portions at room temperature, stirred for 5 hours. The reaction was quenched by the addition of aq. $Na_2SO_3$ (sat.) at room temperature. The aqueous layer was extracted with $CH_2Cl_2$ (3×50 mL), dried, conce-ntrated under reduced pressure. The residue was washed with EA/MTBE to afford 5-bromo-6-methoxy-4-(1,3-oxazol-2-yl)-1,6-dihydropyrimidin-2-amine (5.6 g, 71.11%) as a light yellow solid. $^1$H NMR: 400 MHz, DMSO-$d_6$) δ 3.94 (s, 3H), 7.08 (s, 2H), 7.49 (d, J=0.7 Hz, 1H), 8.31 (d, J=0.7 Hz, 1H).

Step 3. 5-bromo-4-hydrazineyl-6-(oxazol-2-yl)pyrimidin-2-amine

To a stirred mixture of 5-bromo-4-methoxy-6-(oxazol-2-yl)pyrimidin-2-amine (7 g, 26 mmol, 1 equiv) in n-BuOH (70 mL) was added $NH_2NH_2H_2O$ (32 mL, 648 mmol, 25 equiv) at room temperature, then the mixture was stirred reflux for 10 mins. The mixture was immediately filtrated. The aqueous layer was concentrated under reduced pressure. The residue was washed with DCM/MeOH/MTBE to afford (8 g) as a light yellow solid. LCMS: m/z (ESI), [M+H]$^+$=271.1. $^1$H NMR (400 MHz, DMSO-$d_6$) δ 4.47 (s, 3H), 6.58 (s, 3H), 7.44 (d, J=0.8 Hz, 1H), 8.26 (d, J=0.8 Hz, 2H).

Step 4. N'-(2-amino-5-bromo-6-(oxazol-2-yl)pyrimidin-4-yl)-2-(3-fluoropyridin-2-yl)acetohydrazide To a stirred solution of 5-bromo-6-hydrazinyl-4-(1,3-oxazol-2-yl)-1,6-dihydropyrimidin-2-amine (2.5 g, 9.2 mmol, 1 equiv) and 2-(3-fluoropyridin-2-yl)acetic acid (2840.2 mg, 18.3 mmol, 2.0 equiv) in DMSO (50 mL) were added HATU (6961.5 mg, 18.3 mmol, 2.0 equiv) and DIEA (3549.4 mg, 27.5 mmol, 3.0 equiv) in portions at room temperature, stirred for 1 hour. The residue was purified by reverse flash chromatography with the following conditions: column, C18 silica gel; mobile phase, $CH_3CN$ in water, 0% to 25% gradient in 90 min; detector, UV 220 nm/254 nm, concentrated to afford N'-(2-amino-5-bromo-6-(oxazol-2-yl)pyrimidin-4-yl)-2-(3-fluoropyridin-2-yl)acetohydrazide (2.5 g, 66.6%) as a white solid. $^1$H NMR: (300 MHz, DMSO-$d_6$) δ 3.81 (s, 1H), 6.63 (s, 2H), 7.38 (dt, J=8.6, 4.5 Hz, 1H), 7.45 (d, J=5.4 Hz, 1H), 7.68 (t, J=9.1 Hz, 1H), 8.28 (d, J=5.3 Hz, 1H), 8.35 (d, J=4.7 Hz, 1H), 8.91 (s, 1H), 10.13 (s, 1H).

Step 5. 8-bromo-2-((3-fluoropyridin-2-yl)methyl)-7-(oxazol-2-yl)-[1,2,4]triazolo[1,5-c]pyrimidin-5-amine Into a 40 ml vessel were added N-[2-amino-5-bromo-6-(1,3-oxazol-2-yl)pyrimidin-4-yl]-2-(3-fluoropyridin-2-yl)acetohydrazide (2.5 g, 6.1 mmol, 1 equiv) and (Z)-(trimethylsilyl N-(trimethylsilyl)ethanimidate) (10 mL) at room temperature, heated for 1 hour at 120° C., poured into methanol (35 ml) slowly, filtered and dried to give 8-bromo-2-((3-fluoropyridin-2-yl)methyl)-7-(oxazol-2-yl)-[1,2,4]triazolo[1,5-c]pyrimidin-5-amine (1.7 g, 71.1%) as an off-white sold. $^1$H NMR: (300 MHz, DMSO-$d_6$) δ 4.44 (d, J=2.1 Hz, 2H), 7.41 (dt, J=8.6, 4.4 Hz, 1H), 7.51 (d, J=0.8 Hz, 1H), 7.73 (ddd, J=9.9, 8.3, 1.4 Hz, 1H), 8.27 (s, 2H), 8.30-8.38 (m, 2H).

Step 6. 2-((3-fluoropyridin-2-yl)methyl)-8-(imidazo[1,2-a]pyridin-6-yl)-7-(oxazol-2-yl)-[1,2,4]triazolo[1,5-c]pyrimidin-5-amine (Cmpd. 31)

To a stirred solution of 8-bromo-2-((3-fluoropyridin-2-yl)methyl)-7-(oxazol-2-yl)-[1,2,4]triazolo[1,5-c]pyrimidin-5-amine (50.0 mg, 0.4 mmol, 2.0 equiv) and 6-(4,4,5,5-tetramethyl-1,3,2-dioxaborolan-2-yl)imidazo[1,2-a]pyridine (62.7 mg, 0.4 mmol, 2.0 equiv) in dioxane/$H_2O$ (5.5 mL) were added Pd(dppf)$Cl_2$(28.1 mg, 0.038 mmol, 0.2 equiv) and $K_3PO_4$ (122.1 mg, 0.6 mmol, 3.0 equiv) in portions at room temperature under nitrogen atmosphere. The resulting mixture was stirred for 2 hours at 80° C. under nitrogen atmosphere. The residue was purified by Prep-TLC ($CH_2Cl_2$/MeOH 20:1) to afford 5-[5-amino-7-(4-fluorophenyl)-2-[(3-fluoropyridin-2-yl)methyl]-[1,2,4]triazolo[1,5-c]pyrimidin-8-yl]-1-ethyl-1,2-dihydropyridin-2-one (50.0 mg, 22.7%) as a dark brown solid. The crude product (50 mg) was purified by Prep-HPLC with the following conditions (Column: X Bridge Prep OBD C18 Column 30×150 mm 5 μm; Mobile Phase A: Water (0.05% $NH_3$—$H_2O$), Mobile Phase B: ACN; Flow rate: 60 mL/min; Gradient: 25% B to 40% B in 7 min; 254, 220 nm; Rt: 6.35 min) to afford 2-[(3-fluoropyridin-2-yl)methyl]-8-[imidazo[1,2-a]pyridin-6-yl]-7-(1,3-oxazol-2-yl)-[1,2,4]triazolo[1,5-c]pyrimidin-5-amine (Cmpd. 31) (8.9 mg) as a white solid. LCMS: m/z (ESI), [M+H]$^+$=428.2. $^1$H NMR (300 MHz, DMSO-$d_6$) δ 4.42 (2H, d), 7.05 (1H, dd), 7.26 (1H, d), 7.38 (1H, dt), 7.52-7.77 (3H, m), 7.95 (1H, s), 8.11-8.41 (4H, m), 8.54-8.64 (1H, m).

Compounds listed in the table below were prepared using methods described in Example 31.

| Example/Compound number | Structure | LCMS [M + H]$^+$ | $^1$H NMR |
|---|---|---|---|
| 80 | 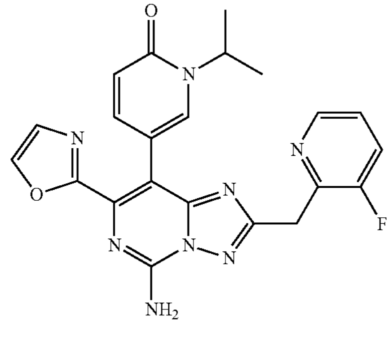 [SMILES: CC(C)n1cc(-c2c(-c3ncco3)nc(N)n3nc(Cc4ncccc4F)nc23)ccc1=O] | 447.3 | $^1$H NMR (400 MHz, DMSO-$d_6$) δ 1.15 (d, J =6.8 Hz, 6H), 4.43 (d, J = 2.1 Hz, 2H), 5.04 (hept, J = 6.9 Hz, 1H), 6.35 (d, J = 9.3 Hz, 1H), 7.25-7.35 (m, 2H), 7.40 (dt, J = 8.6, 4.4 Hz, 1H), 7.65-7.77 (m, 2H), 8.16 (s, 1H), 8.21 (d, J = 0.8 Hz, 1H), 8.34 (dt, J = 4.7, 1.5 Hz, 1H). |

-continued

| Example/ Compound number | Structure | LCMS [M + H]+ | 1H NMR |
|---|---|---|---|
| 82 | 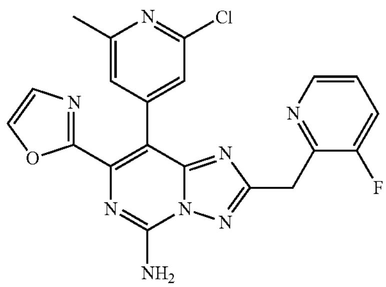 [SMILES: Cc1cc(-c2c(-c3ncco3)nc(N)n3nc(Cc4ncccc4F)nc23)cc(Cl)n1] | 437.2 | 1H NMR (400 MHz, DMSO-d6) δ 2.42 (s, 3H), 4.43 (d, J = 2.1 Hz, 2H), 7.17 (d, J = 1.3 Hz, 1H), 7.23 (s, 1H), 7.31 (s, 1H), 7.39 (dt, J = 8.6, 4.4 Hz, 1H), 7.71 (ddd, J = 9.9, 8.3, 1.4 Hz, 1H), 8.20 (s, 1H), 8.33 (dt, J = 4.8, 1.6 Hz, 2H). |
| 86 | 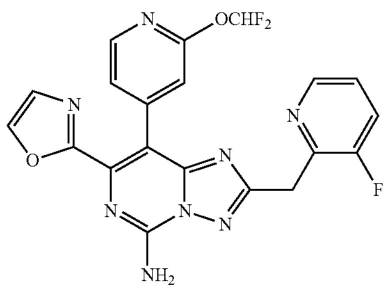 | 455.2 | 1H NMR (400 MHz, DMSO-d6) δ 4.4 (d, J = 2.1 Hz, 2H), 7.0 (d, J = 1.3 Hz, 1H), 7.1 (dd, J = 5.2, 1.4 Hz, 1H), 7.3 (d, J = 0.8 Hz, 1H), 7.4 (dt, J = 8.6, 4.4 Hz, 1H), 7.6-7.7 (m, 1H), 8.2-8.3 (m, 2H), 8.33 (dt, J = 4.7, 1.6 Hz, 1H). |
| 87 | 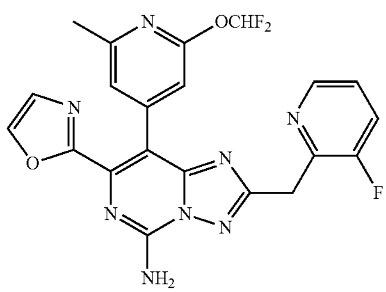 [SMILES: Cc1cc(-c2c(-c3ncco3)nc(N)n3nc(Cc4ncccc4F)nc23)cc(OC(F)F)n1] | 469.2 | 1H NMR (400 MHz, DMSO-d6) δ 2.39 (s, 3H), 4.42 (d, J = 2.2 Hz, 2H), 6.80 (s, 1H), 7.00 (d, J = 1.2 Hz, 1H), 7.31 (d, J = 0.8 Hz, 1H), 7.39 (dt, J = 8.6, 4.4 Hz, 1H), 7.65-7.76 (m, 1H), 8.19 (d, J = 0.8 Hz, 1H), 8.33 (dt, J = 4.7, 1.6 Hz, 2H). |
| 90 | 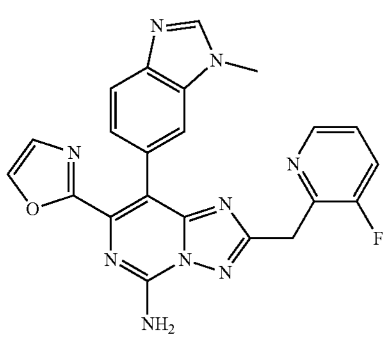 [SMILES: Cn1cnc2ccc(-c3c(-c4ncco4)nc(N)n4nc(Cc5ncccc5F)nc34)cc21] | 442.2 | 1H NMR (400 MHz, DMSO-d6) δ 3.7 (s, 3H), 4.4 (d, J = 2.1 Hz, 2H), 7.1 (dd, J = 8.3, 1.6 Hz, 1H), 7.2 (d, J = 0.8 Hz, 1H), 7.4 (dt, J = 8.6, 4.4 Hz, 1H), 7.5 (d, J = 1.6 Hz, 1H), 7.5 (d, J = 8.3 Hz, 1H), 8.0 (s, 1H), 8.1 (s, 1H), 8.2 (s, 1H), 8.3 (dt, J = 4.7, 1.6 Hz, 1H). |
| 99 | 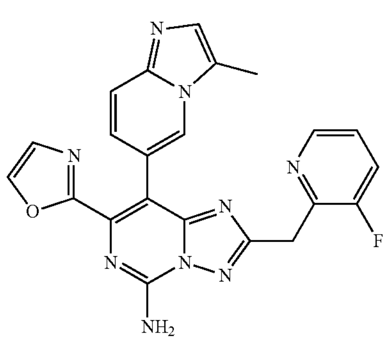 [SMILES: Cc1cnc2ccc(-c3c(-c4ncco4)nc(N)n4nc(Cc5ncccc5F)nc34)cn12] | 442.2 | 1H NMR (400 MHz, DMSO-d6) δ 2.36 (s, 3H), 4.42 (d, J = 2.1 Hz, 2H), 7.06 (dd, J = 9.3, 1.7 Hz, 1H), 7.27 (s, 1H), 7.32-7.42 (m, 2H), 7.46-7.53 (m, 1H), 7.70 (ddd, J = 9.9, 8.3, 1.4 Hz, 1H), 8.17 (s, 1H), 8.24 (d, J = 1.6 Hz, 1H), 8.27-8.35 (m, 1H). |

Example 33

Preparation of 2-[(2,6-difluorophenyl)methyl]-8-(2,6-dimethylpyridin-4-yl)-7-(1,3-oxazol-2-yl)-[1,2,4]triazolo[1,5-c]pyrimidin-5-amine (Cmpd. 33)

SCHEME 20

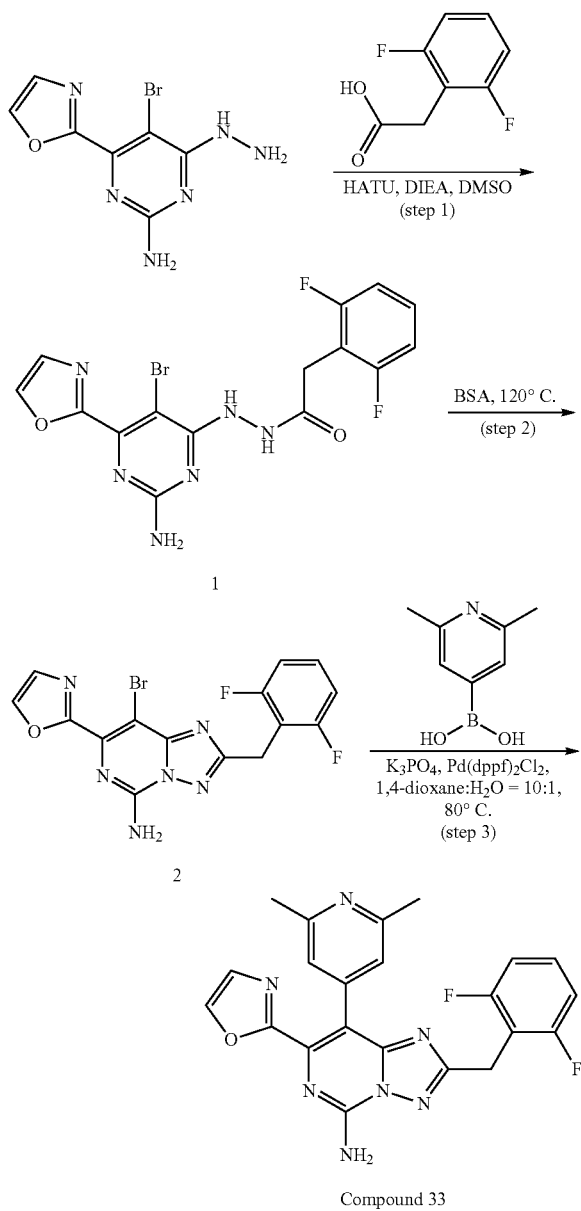

Compound 33

Step 1. Preparation of N'-(2-amino-5-bromo-6-(oxazol-2-yl)pyrimidin-4-yl)-2-(3-fluoropyridin-2-yl)acetohydrazide To a solution of 5-bromo-4-hydrazinyl-6-(1,3-oxazol-2-yl)pyrimidin-2-amine (4 g, 14.756 mmol, 1 equiv), 2-(2,6-difluorophenyl)acetic acid (3.81 g, 22.134 mmol, 1.5 equiv), DIEA (4.77 g, 36.890 mmol, 2.5 equiv) in DMF (50 mL) was added HATU (8.42 g, 22.134 mmol, 1.5 equiv). Stirred at 25° C. for 1 hour. Quenched with water (250 mL). The precipitated solids were collected by filtration and washed with water (2×100 mL) and MTBU:MeOH=5:1(100 mL). The resulting solid was dried under vacuum. The last obtained N-[2-amino-5-bromo-6-(1,3-oxazol-2-yl)pyrimidin-4-yl]-2-(2,6-difluorophenyl)acetohydrazide (4.8 g, 76.50%) as an off-white solid. LCMS: m/z (ESI), [M+H]$^+$=425.1. $^1$H NMR (300 MHz, DMSO-d$_6$) δ 3.63 (s, 2H), 6.60 (s, 2H), 7.09 (d, J=7.6 Hz, 2H), 7.27-7.39 (m, 1H), 7.45 (d, J=6.0 Hz, 1H), 8.27 (s, 1H), 8.90-8.96 (m, 1H), 10.11-10.20 (m, 1H).

Step 2. 8-bromo-2-(2,6-difluorobenzyl)-7-(oxazol-2-yl)-[1,2,4]triazolo[1,5-c]pyrimidin-5-amine Into a 25 ml round-bottom flask were added N-[2-amino-5-bromo-6-(1,3-oxazol-2-yl)pyrimidin-4-yl]-2-(2,6-difluorophenyl)acetohydrazide (2.5 g, 5.880 mmol, 1 equiv) and (Z)-(trimethylsilyl N-(trimethylsilyl)ethanimidate) (10 mL) at room temperature, then heated for 1 hour at 120° C. The mixture was allowed to cool down to room temperature. The mixture was poured into methanol (50 ml) slowly. The resulting mixture was concentrated under reduced pressure. The precipitated solids were collected by filtration and washed with MeOH:MTBU=1:1 (20 mL) and dried to give 8-bromo-2-[(2,6-difluorophenyl)methyl]-7-(1,3-oxazol-2-yl)-[1,2,4]triazolo[1,5-c]pyrimidin-5-amine (1.3 g, 54.30%) as a white sold. LCMS: m/z (ESI), [M+H]$^+$=407.0. $^1$H NMR (300 MHz, DMSO-d$_6$) δ 4.26 (s, 2H), 7.12 (t, J=7.8 Hz, 2H), 7.32-7.53 (m, 2H), 8.21 (s, 2H), 8.33 (d, J=0.8 Hz, 1H).

Step 3. 2-[(2,6-difluorophenylmethyl]-8-(2,6-dimethylpyridin-4-yl)-7-(1,3-oxazol-2-yl)-[1,2,4]triazolo[1,5-c]pyrimidin-5-amine To a solution of 8-bromo-2-[(2,6-difluorophenyl)methyl]-7-(1,3-oxazol-2-yl)-[1,2,4]triazolo[1,5-c]pyrimidin-5-amine (50 mg, 0.1 mmol, 1 equiv) and (2,6-dimethylpyridin-4-yl)boronic acid (27.8 mg, 0.2 mmol, 1.5 equiv) in dioxane (3 mL) and H$_2$O (0.3 mL) were added K$_3$PO$_4$ (78.2 mg, 0.4 mmol, 3 equiv) and Pd(dppf)Cl$_2$ (18.0 mg, 0.02 mmol, 0.2 equiv). After stirring for 2 hours at 80° C. under a nitrogen atmosphere, the resulting mixture was concentrated under reduced pressure. The residue was purified by Prep-TLC/silica gel column chromatography, eluted with CH$_2$Cl$_2$/MeOH (15:1). The crude product (50 mg) was purified by Prep-HPLC with the following conditions (Column: XBridge Prep OBD C18 Column 30×150 mm 5 μm; Mobile Phase A: Water (0.05% NH$_3$H$_2$O), Mobile Phase B: ACN; Flow rate: 60 mL/min; Gradient: 30% B to 40% B in 7 min; 254, 220 nm; Rt: 5.9 min) to afford 2-[(2,6-difluorophenyl)methyl]-8-(2,6-dimethylpyridin-4-yl)-7-(1,3-oxazol-2-yl)-[1,2,4]triazolo[1,5-c]pyrimidin-5-amine (Cmpd. 33) (8.6 mg, 16.2%) as a white solid. LCMS: m/z (ESI), [M+H]$^+$=434.2. $^1$H NMR (400 MHz, DMSO-d$_6$) δ 2.4 (s, 6H), 4.2 (s, 2H), 6.9 (s, 2H), 7.1 (t, J=7.8 Hz, 2H), 7.3 (d, J=0.8 Hz, 1H), 7.3-7.4 (m, 1H), 8.1 (d, J=0.8 Hz, 1H), 8.2 (s, 1H).

Compounds listed in the table below were prepared using methods described in Example 33.

| Example/ Compound number | Structure | LCMS [M + H]+ | 1H NMR |
|---|---|---|---|
| 79 | 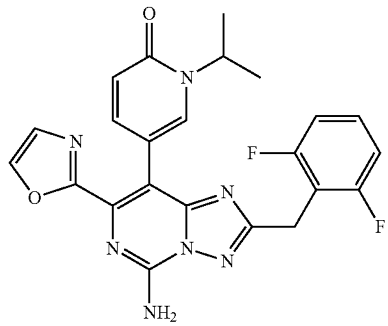 [SMILES: CC(C)n1cc(-c2c(-c3ncco3)nc(N)n3nc(Cc4c(F)cccc4F)nc23)ccc1=O] | 464.2 | 1H NMR (400 MHz, DMSO-$d_6$) δ 1.2 (d, J = 6.8 Hz, 6H), 4.3 (s, 2H), 5.0 (p, J = 6.8 Hz, 1H), 6.3 (d, J = 9.3 Hz, 1H), 7.1 (t, J = 7.8 Hz, 2H), 7.2 (dd, J = 9.3, 2.6 Hz, 1H), 7.3 (d, J = 0.8 Hz, 1H), 7.4-7.5 (m, 1H), 7.7 (d, J = 2.6 Hz, 1H), 8.1 (s, 1H), 8.2 (d, J = 0.7 Hz, 1H). |
| 81 | 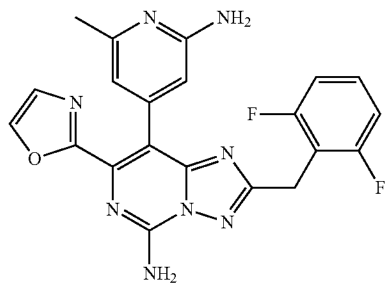 [SMILES: Cc1cc(-c2c(-c3ncco3)nc(N)n3nc(Cc4c(F)cccc4F)nc23)cc(N)n1] | 435.2 | 1H- NMR (300 MHz, DMSO-$d_6$) δ 2.17 (3H, s), 4.25 (2H, s), 5.80 (2H, s), 6.17 (2H, d), 7.12 (2H, t), 7.30 (1H, d), 7.33-7.54 (1H, m), 8.14 (3H, d). |
| 84 | 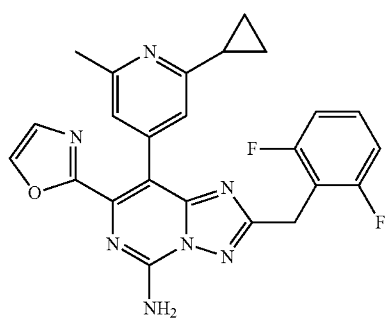 [SMILES: Cc1cc(-c2c(-c3ncco3)nc(N)n3nc(Cc4c(F)cccc4F)nc23)cc(C2CC2)n1] | 460.2 | 1H NMR (400 MHz, DMSO-$d_6$) δ 0.83 (dt, J = 4.9, 2.7 Hz, 1H) 0.89 (dt, J = 8.1, 2.8 Hz, 1H), 1.91-2.01 (m, 1H), 2.33 (s, 2H), 4.25 (s, 1H), 6.83 (d, J = 1.5 Hz, 1H), 6.89 (d, J = 1.5 Hz, 1H), 7.11 (t, J = 7.9 Hz, 1H), 7.29 (d, J = 0.8 Hz, 1H), 7.39 (tt, J = 8.5, 6.7 Hz, 1H), 8.15 (d, J = 0.8 Hz, 2H). |
| 85 | 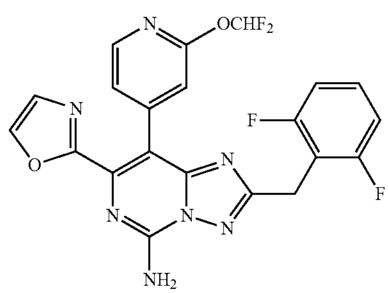 [SMILES: Nc1nc(-c2ncco2)c(-c2ccnc(OC(F)F)c2)c2nc(Cc3c(F)cccc3F)nn12] | 472.2 | 1H NMR (400 MHz, DMSO-$d_6$) δ 4.3 (s, 2H), 7.0 (s, 1H), 7.1-7.2 (m, 3H), 7.3 (s, 1H), 7.3-7.5 (m, 1H), 8.2-8.3 (m, 2H). |
| 91 | 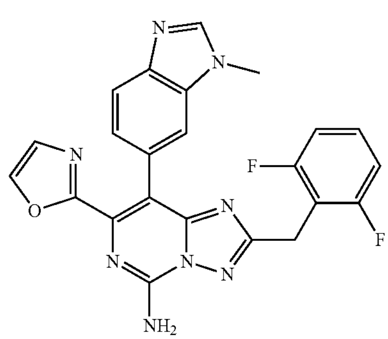 [SMILES: Cn1cnc2ccc(-c3c(-c4ncco4)nc(N)n4nc(Cc5c(F)cccc5F)nc34)cc21] | 459.2 | 1H NMR (400 MHz, Methanol-$d_4$) δ 2.8 (s, 2H), 3.6 (s, 2H), 4.5 (s, 1H), 6.4 (d, J = 8.2 Hz, 1H), 6.5-6.6 (m, 1H), 7.3-7.5 (m, 1H), 7.5 (dd, J = 9.3, 2.6 Hz, 1H), 8.0 (d, J = 2.5 Hz, 1H), 8.1 (d, J = 0.8 Hz, 1H). |

Example 34

Preparation of 5-(5-amino-7-(4-fluorophenyl)-2-((3-fluoropyridin-2-yl)methyl)-[1,2,4]triazolo[1,5-c]pyrimidin-8-yl)-1-ethylpyridin-2(1H)-one (Cmpd. 34)

SCHEME 21

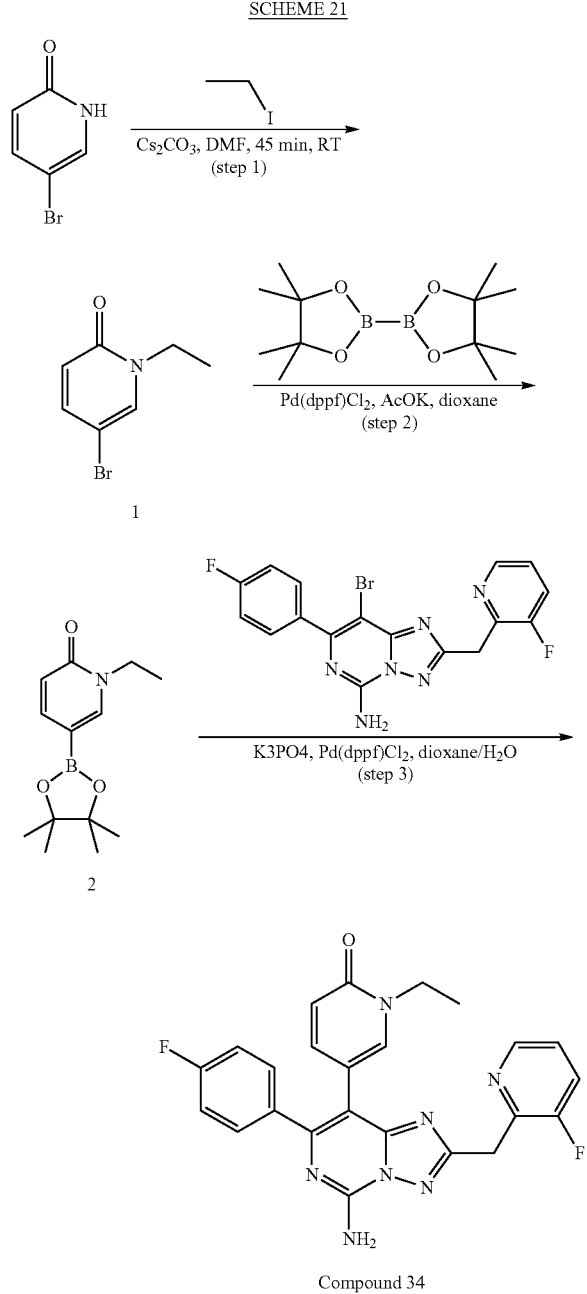

Compound 34

Step 1. 5-bromo-1-ethylpyridin-2(1H)-one

A mixture of 5-bromo-1,2,5,6-tetrahydropyridin-2-one (3.0 g, 17.0 mmol, 1.0 equiv) and Cs$_2$CO$_3$ (16.7 g, 51.3 mmol, 3.0 equiv) in DMF was stirred for 5 min at room temperature under nitrogen atmosphere. To the above mixture was added iodoethane (8.0 g, 51.3 mmol, 3.0 equiv) dropwise over 5 min at room temperature. The resulting mixture was stirred for additional 40 min at room temperature. The residue was purified by Prep-TLC (PE/EtOAc 5:1) to afford 5-bromo-1-ethyl-1,2,5,6-tetrahydropyridin-2-one (1.4 g, 41.7%) as a light yellow solid. LCMS: m/z (ESI), [M+H]$^+$=202.1.

Step 2. 1-ethyl-5-(4,4,5,5-tetramethyl-1,3,2-dioxaborolan-2-yl)pyridin-2(1H)-one To a stirred solution of 5-bromo-1-ethyl-1,2-dihydropyridin-2-one (500.0 mg, 2.5 mmol, 1 equiv) and 4,4,5,5-tetramethyl-2-(4,4,5,5-tetramethyl-1,3,2-dioxaborolan-2-yl)-1,3,2-dioxaborolane (1256.8 mg, 4.9 mmol, 2.0 equiv) in dioxane (20 mL) were added Pd(dppf)Cl$_2$(362.1 mg, 0.5 mmol, 0.2 equiv) and KOAc (728.6 mg, 7.4 mmol, 3.0 equiv) in portions at room temperature under nitrogen atmosphere. The resulting mixture was stirred for 2 hours at 80° C. under nitrogen atmosphere. The residue was purified by Prep-TLC (PE/EtOAc 1:1) to afford 1-ethyl-5-(4,4,5,5-tetramethyl-1,3,2-dioxaborolan-2-yl)-1,2-dihydropyridin-2-one (460.0 mg, 74.6%) as a yellow green solid. LCMS: m/z (ESI), [M+H]$^+$=250.3.

Step 3. 5-(5-amino-7-(4-fluorophenyl)-2-((3-fluoropyridin-2-yl)methyl)-[1,2,4]triazolo[1,5-c]pyrimidin-8-yl)-1-ethylpyridin-2(1H)-one (Cmpd. 34)

To a stirred solution of 1-ethyl-5-(4,4,5,5-tetramethyl-1,3,2-dioxaborolan-2-yl)-1,2-dihydropyridin-2-one (95.5 mg, 0.4 mmol, 2.0 equiv) and 8-bromo-7-(4-fluorophenyl)-2-[(3-fluoropyridin-2-yl)methyl]-[1,2,4]triazolo[1,5-c]pyrimidin-5-amine (80.0 mg, 0.2 mmol, 1 equiv) in 1,4-dioxane/H$_2$O (5.5 mL) were added Pd(dppf)Cl$_2$ (28.1 mg, 0.038 mmol, 0.2 equiv) and K$_3$PO$_4$ (122.1 mg, 0.6 mmol, 3.0 equiv) in portions at room temperature under nitrogen atmosphere. The resulting mixture was stirred for 2 hours at 80° C. under nitrogen atmosphere. The residue was purified by Prep-TLC (CH$_2$Cl$_2$/MeOH 20:1) to afford 5-[5-amino-7-(4-fluorophenyl)-2-[(3-fluoropyridin-2-yl)methyl]-[1,2,4]triazolo[1,5-c]pyrimidin-8-yl]-1-ethyl-1,2-dihydropyridin-2-one (50.0 mg, 22.7%) as a dark brown solid. The crude product (20 mg) was purified by Prep-HPLC with the following conditions (Column: X Bridge Prep OBD C18 Column 30×150 mm 5 µm; Mobile Phase A: Water (10 MMOL/LNH$_4$HCO$_3$+0.1% NH$_3$.H$_2$O) to afford 5-[5-amino-7-(4-fluorophenyl)-2-[(3-fluoropyridin-2-yl)methyl]-[1,2,4]triazolo[1,5-c]pyrimidin-8-yl]-1-ethyl-1,2-dihydropyridin-2-one (Cmpd. 34) (2.0 mg) as a white solid. LCMS: m/z (ESI), [M+H]$^+$=460.1. $^1$H NMR (300 MHz, DMSO-d$_6$) δ 1.00 (3H, t), 3.76 (2H, q), 4.42 (2H, d), 6.31 (1H, d), 7.14-7.27 (3H, m), 7.43 (4H, ddd), 7.72 (1H, t), 7.99 (2H, s), 8.34 (1H, d).

Example 35

Preparation of 5-(5-amino-2-((6-aminopyridin-2-yl)methyl)-7-(4-fluorophenyl)-[1,2,4]triazolo[1,5-c]pyrimidin-8-yl)-1-methylpyridin-2(1H)-one (Cmpd. 35)

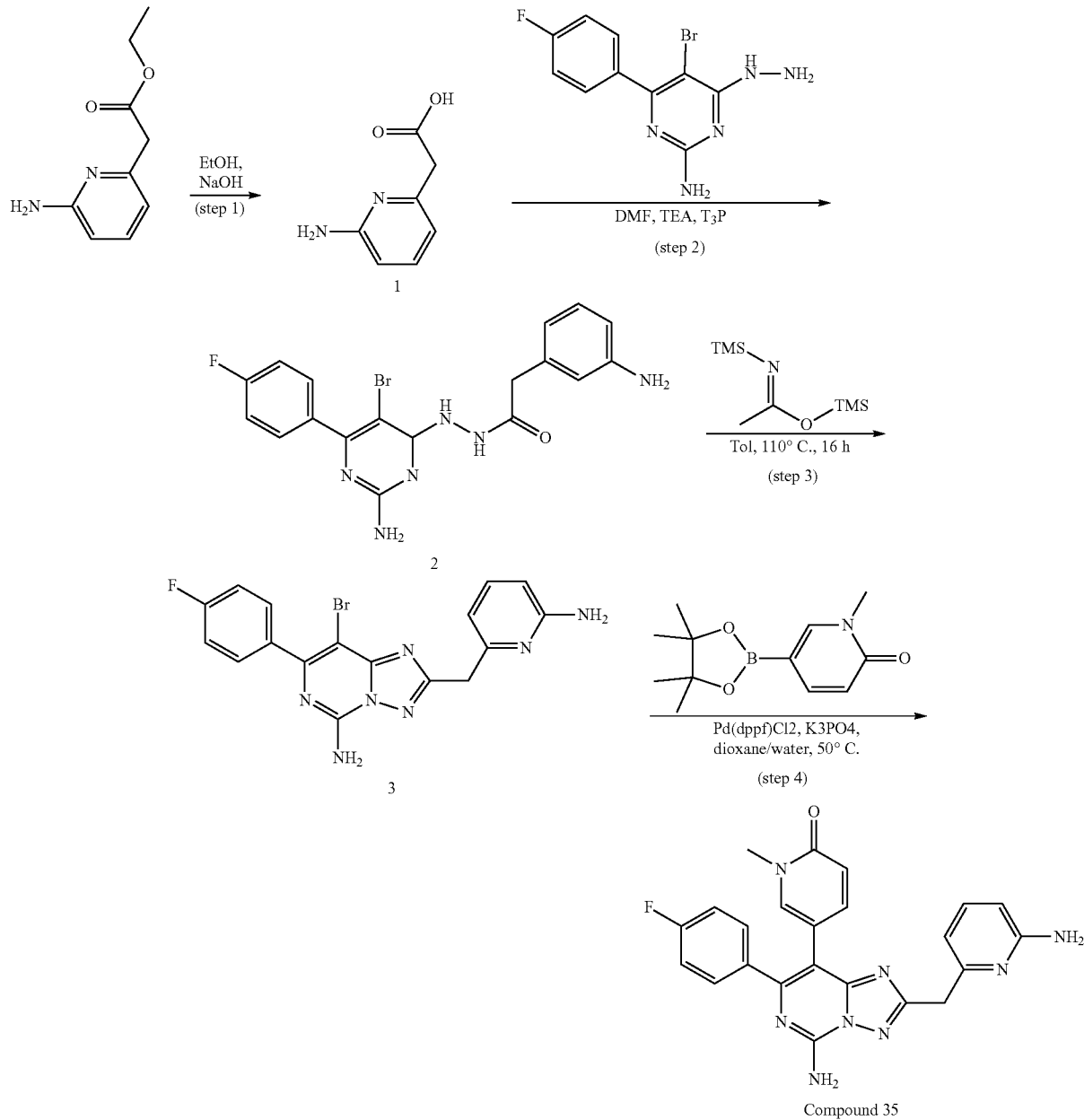

Compound 35

Step 1. 2-(6-aminopyridin-2-yl)acetic acid

To a stirred solution of ethyl 2-(6-aminopyridin-2-yl) acetate (1 g, 5.55 mmol, 1 equiv) in EtOH (20 mL) was added NaOH (0.3 g, 8.32 mmol, 1.5 equiv) in portions at room temperature. The resulting mixture was stirred for 3 hours at 50° C. under nitrogen atmosphere. The precipitated solids were collected by filtration to afford sodium 2-(6-aminopyridin-2-yl)acetate (0.8 g, 82.79%) as white solid. $^1$H NMR (Deuterium Oxide, 400 MHz) δ 3.48 (2H, s), 6.54 (1H, d), 6.65 (1H, d), 7.49 (1H, t).

Step 2. N'-(2-amino-5-bromo-6-(4-fluorophenyl) pyrimidin-4-yl)-2-(6-aminopyridin-2-yl)acetohydrazide A mixture of 5-bromo-4-(4-fluorophenyl)-6-hydrazinylpyrimidin-2-amine (0.8 g, 2.68 mmol, 1 equiv), T3P (1.3 g, 4.0 mmol, 1.5 equiv), TEA (0.8 g, 8.0 mmol, 3 equiv) and sodium 2-(6-aminopyridin-2-yl)acetate (0.5 g, 2.7 mmol, 1 equiv) in DMF (15 mL) was stirred for 2 hours at room temperature under nitrogen atmosphere. The product was precipitated by the addition of water. The resulting solid was dried under vacuum to afford N-[2-amino-5-bromo-6-(4-fluorophenyl)pyrimidin-4-yl]-2-(6-aminopyridin-2-yl)acetohydrazide (0.31 g, 26.7%) as a grey solid. LCMS: m/z (ESI), [M+H]$^+$=432.0.

Step 3. 2-((6-aminopyridin-2-yl)methyl)-8-bromo-7-(4-fluorophenyl)-[1,2,4]triazolo[1,5-c]pyrimidin-5-amine A mixture of N-[2-amino-5-bromo-6-(4-fluorophenyl)pyrimidin-4-yl]-2-(6-aminopyridin-2-yl)acetohydrazide (310 mg, 0.7 mmol, 1 equiv) and (E)-(trimethylsilyl N-(trimethylsilyl)ethanimidate) (729.5 mg, 3.6 mmol, 5 equiv) in Toluene (15 mL) was stirred for 12 hours at 110° C. under nitrogen atmosphere. The resulting mixture was concentrated under vacuum. The crude product was re-crystallized from MeOH/MTBE (1/1, 12 mL) to afford 6-[[5-amino-8-bromo-7-(4-fluorophenyl)-[1,2,4]triazolo[1,5-c]pyrimidin-2-yl]methyl]pyridin-2-amine (150 mg, 50.5%) as a grey solid. LCMS: m/z (ESI), [M+H]$^+$=416.2.

Step 4. 5-(5-amino-2-((6-aminopyridin-2-yl)methyl)-7-(4-fluorophenyl)-[1,2,4]triazolo[1,5-c]pyrimidin-8-yl)-1-methylpyridin-2(1H)-one A mixture of 6-[[5-amino-8-bromo-7-(4-fluorophenyl)-[1,2,4]triazolo[1,5-c]pyrimidin-2-yl]methyl]pyridin-2-amine (140 mg, 0.3 mmol, 1 equiv), Pd(dppf)Cl$_2$ CH$_2$Cl$_2$ (27.6 mg, 0.03 mmol, 0.1 equiv), K$_3$PO$_4$ (215.2 mg, 1.01 mmol, 3 equiv) and 1-methyl-5-(4,4,5,5-tetramethyl-1,3,2-dioxaborolan-2-yl)-1,2-dihydropyridin-2-one (158.9 mg, 0.7 mmol, 2 equiv) in 1,4-dioxane (6 mL) and water (1 mL) was stirred for 15 hours at 50° C. under nitrogen atmosphere. The resulting mixture was concentrated under vacuum. The residue was purified by Prep-TLC (CH$_2$Cl$_2$/MeOH 10:1) to afford crude product (80 mg), which was purified by Prep-HPLC with the following conditions (Column: XBridge Prep OBD C18 Column 30×150 mm 5 μm; Mobile Phase A: Water (0.05% NH$_3$H$_2$O), Mobile Phase B: ACN; Flow rate: 60 mL/min; Gradient: 15% B to 35% B in 7 min; 254, 220 nm; Rt: 6.35 min) to afford 5-[5-amino-2-[(6-aminopyridin-2-yl)methyl]-7-(4-fluorophenyl)-[1,2,4]triazolo[1,5-c]pyrimidin-8-yl]-1-methyl-1,2-dihydropyridin-2-one (Cmpd. 35) (50 mg, 33.2%) as a white solid. LCMS: m/z (ESI), [M+H]$^+$=443.2. $^1$H NMR (400 MHz, DMSO-d$_6$) δ 4.08 (2H, s), 5.84 (2H, s), 6.28 (2H, t), 6.40 (1H, d), 7.13 (1H, dd), 7.20 (2H, t), 7.28 (1H, t), 7.44-7.53 (2H, m), 7.67 (1H, d), 8.00 (2H, s).

Example 36

Preparation of 5-(5-amino-7-(4-fluorophenyl)-2-((3-fluoropyridin-2-yl)methyl)-[1,2,4]triazolo[1,5-c]pyrimidin-8-yl)-1-cyclopropylpyridin-2(1H)-one (Cmpd. 36)

SCHEME 23

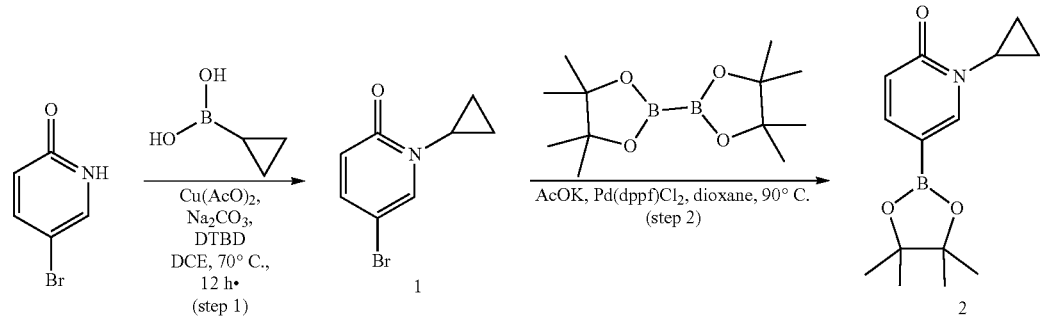

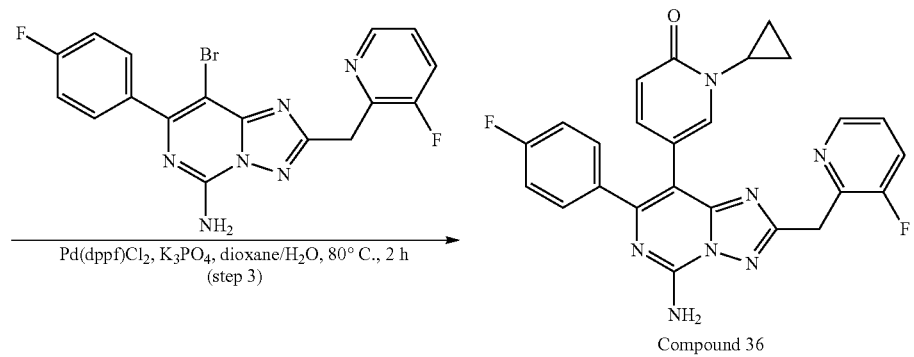

Compound 36

Step 1.
5-bromo-1-cyclopropyl-1,2-dihydropyridin-2-one

A mixture of 5-bromo-1,2-dihydropyridin-2-one (2 g, 11.49 mmol, 1 equiv) and cyclopropylboronic acid (2.0 g, 23.3 mmol, 2.0 equiv), Cu(AcO)$_2$(2.1 g, 0.01 mmol, 1 equiv), Na$_2$CO$_3$ (2.4 g, 22.6 mmol, 2 equiv), 4,4-DI-TERT-BUTYL-2,2-DIPYRIDYL (3.1 g, 0.01 mmol, 1 equiv) in CH$_2$ClCH$_2$Cl (50 mL). The resulting mixture was stirred for 12 hours at 70° C. under nitrogen atmosphere. The solvent was removed under reduced pressure. The residue was purified by silica gel column chromatography, eluted with CH$_2$Cl$_2$/MeOH (20:1) to afford 5-bromo-1-cyclopropyl-1,2-dihydropyridin-2-one (600.0 mg, 24.4%) as a white solid. LCMS: m/z (ESI), [M+H]$^+$=214.0. $^1$H NMR (400 MHz, DMSO-d$_6$) δ (300 MHz, CDCl3) δ 0.86 (2H, tdd), 1.13 (2H, m), 3.31 (1H, tt), 6.48 (1H, m), 7.34 (2H, m).

Step 2. 1-cyclopropyl-5-(4,4,5,5-tetramethyl-1,3,2-dioxaborolan-2-yl)-1,2-dihydropyridin-2-one Into a 40 mL sealed tube were added 5-bromo-1-cyclopropyl-1,2-dihydropyridin-2-one (200 mg, 0.9 mmol, 1 equiv), 4,4,5,5-tetramethyl-2-(4,4,5,5-tetramethyl-1,3,2-dioxaborolan-2-yl)-1,3,2-dioxaborolane (355.89 mg, 1.4 mmol, 1.5 equiv), AcOK (183.4 mg, 1.9 mmol, 2 equiv) and Pd(dppf)Cl$_2$ CH$_2$Cl$_2$(76.3 mg, 0.1 mmol, 0.1 equiv) in dioxane (10 mL) at 90° C. for 2 hours. The resulting mixture was concentrated under vacuum. The residue was purified by Prep-TLC (PE/EtOAc 1:1) to afford 1-cyclopropyl-5-(4,4,5,5-tetramethyl-1,3,2-dioxaborolan-2-yl)-1,2-dihydropyridin-2-one (100 mg, 41.0%) as a yellow solid. LCMS: m/z (ESI), [M+H]$^+$=262.3.

Step 3. 5-[5-amino-7-(4-fluorophenyl)-2-[(3-fluoropyridin-2-yl)methyl]-[1,2,4]triazolo[1,5-c]pyrimidin-8-yl]-1-cyclopropyl-1,2-dihydropyridin-2-one (Cmpd. 36)

Into a 20 mL sealed tube were added 8-bromo-7-(4-fluorophenyl)-2-[(3-fluoropyridin-2-yl)methyl]-[1,2,4]triazolo[1,5-c]pyrimidin-5-amine (100 mg, 0.24 mmol, 1 equiv), 1-cyclopropyl-5-(4,4,5,5-tetramethyl-1,3,2-dioxaborolan-2-yl)-1,2-dihydropyridin-2-one (125.2 mg, 0.48 mmol, 2.0 equiv), K$_3$PO$_4$ (101.8 mg, 0.48 mmol, 2 equiv) and Pd(dppf)Cl$_2$ CH$_2$Cl$_2$(19.6 mg, 0.024 mmol, 0.1 equiv) in dioxane (5 mL) and water (0.5 mL) at 80° C. The resulting mixture was concentrated under reduced pressure. The residue was purified by Prep-TLC (CH$_2$Cl$_2$/MeOH 12:1) to afford 5-[5-amino-7-(4-fluorophenyl)-2-[(3-fluoropyridin-2-yl)methyl]-[1,2,4]triazolo[1,5-c]pyrimidin-8-yl]-1-cyclopropyl-1,2-dihydropyridin-2-one (Cmpd. 36) (5 mg, 4.42%) as a white solid. LCMS: m/z (ESI), [M+H]$^+$=472.2. $^1$H NMR: (400 MHz, DMSO-d$_6$) δ 1.24-0.83 (m, 4H), 1.48 (s, 2H), 3.07 (s, 1H), 3.51 (1H, s), 4.22 (1H, s), 4.39 (8H, dd), 5.00 (2H, d), 5.73 (2H, ddt), 6.35 (2H, d), 7.23 (1H, s), 7.32-7.13 (6H, m), 7.41 (8H, ddd), 7.72 (2H, t), 8.01 (4H, s), 8.34 (2H d).

Example 37

Preparation of 2-((6-aminopyridin-2-yl)methyl)-7-(4-fluorophenyl)-8-(imidazo[1,2-a]pyridin-6-yl)-[1,2,4]triazolo[1,5-c]pyrimidin-5-amine (Cmpd. 37)

SCHEME 24

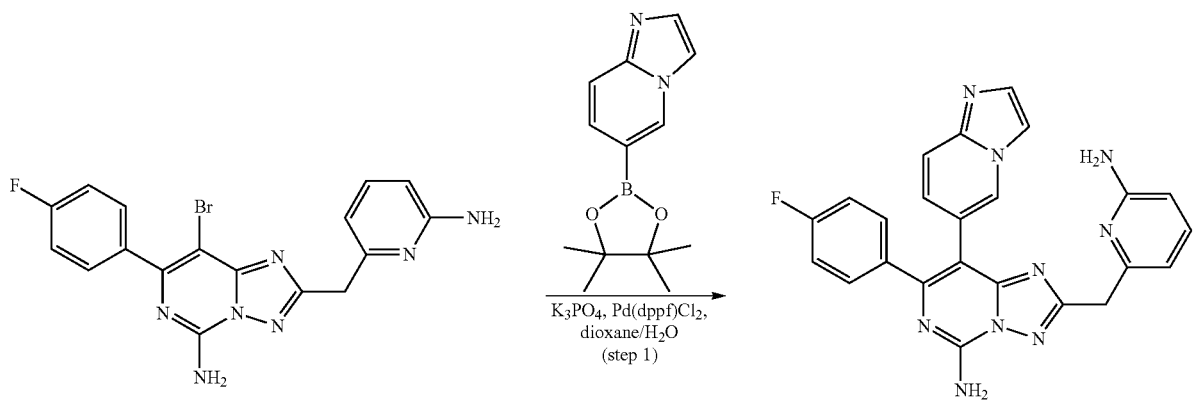

Compound 37

Step 1. 6-[[5-amino-7-(4-fluorophenyl)-8-[imidazo[1,2-a]pyridin-6-yl]-[1,2,4]triazolo[1,5-c]pyrimidin-2-yl]methyl]pyridin-2-amine To a solution of 6-[[5-amino-8-bromo-7-(4-fluorophenyl)-[1,2,4]triazolo[1,5-c]pyrimidin-2-yl]methyl]pyridin-2-amine (100 mg, 0.24 mmol, 1 equiv) and 6-(4,4,5,5-tetramethyl-1,3,2-dioxaborolan-2-yl)imidazo[1,2-a]pyridine (88.4 mg, 0.4 mmol, 1.5 equiv) in dioxane (10 mL) and H$_2$O (1 mL) were added K$_3$PO$_4$ (153.7 mg, 0.7 mmol, 3 equiv) and Pd(dppf)Cl$_2$(35.3 mg, 0.05 mmol, 0.2 equiv). After stirring for 2 hours at 80° C. under a nitrogen atmosphere, the resulting mixture was concentrated under reduced pressure. The residue was purified by Prep-TLC/silica gel column chromatography, eluted with CH$_2$Cl$_2$/MeOH (15:1). The crude product (100 mg) was further purified by Prep-HPLC with the following conditions (Column: XBridge Prep OBD C18 Column 30×150 mm 5 µm; Mobile Phase A: Water (0.05% NH$_3$H$_2$O), Mobile Phase B: ACN; Flow rate: 60 mL/min; Gradient: 25% B to 35% B in 7 min; 254/220 nm; Rt: 6.1 min) to afford 2-((6-aminopyridin-2-yl)methyl)-7-(4-fluorophenyl)-8-(imidazo[1,2-a]pyridin-6-yl)-[1,2,4]triazolo[1,5-c]pyrimidin-5-amine (Cmpd. 37) (58.1 mg, 53.1%) as a white solid. LCMS: m/z (ESI), [M+H]$^+$=452.2. $^1$H NMR (400 MHz, DMSO-d$_6$) δ 4.3 (s, 2H), 6.6 (d, J=6.9 Hz, 2H), 7.1-7.2 (m, 2H), 7.3 (d, J=9.4 Hz, 1H), 7.4-7.5 (m, 2H), 7.6 (t, J=7.8 Hz, 1H), 7.7 (d, J=9.4 Hz, 1H), 7.9 (s, 1H), 8.2 (d, J=1.7 Hz, 2H), 8.8 (s, 1H).

Example 39

Preparation of 5-[5-amino-7-(3,4-difluorophenyl)-2-[(3-fluoropyridin-2-yl)methyl]-[1,2,4]triazolo[1,5-c]pyrimidin-8-yl]-1-methyl-1,2-dihydropyridin-2-one (25 mg, 27.89%) (Cmpd. 39)

SCHEME 25

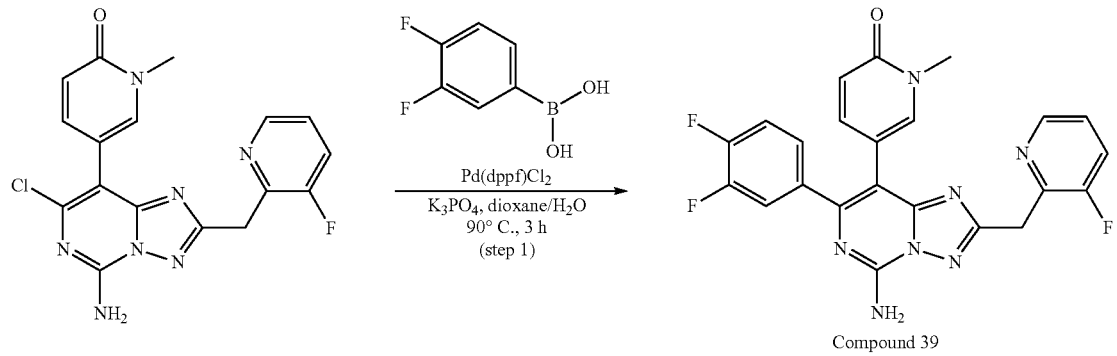

Step 1. 5-[5-amino-7-(3,4-difluorophenyl)-2-[(3-fluoropyridin-2yl)methyl]-[1,2,4]triazolo[1,5-c]pyrimidin-8-yl]-1-methyl-1,2-dihydropyridin-2-one (Cmpd. 39)

Into a 10 mL vial were added 5-[5-amino-7-chloro-2-[(3-fluoropyridin-2-yl)methyl]-[1,2,4]triazolo[1,5-c]pyrimidin-8-yl]-1-methyl-1,2-dihydropyridin-2-one (90 mg, 0.233 mmol, 1 equiv), and (3,4-difluorophenyl)boronic acid (73.68 mg, 0.467 mmol, 2 equiv), Pd(dppf)Cl$_2$ (31.6 mg, 0.04 mmol, 0.2 equiv), K$_3$PO$_4$ (148.56 mg, 0.700 mmol, 3 equiv), dioxane (1 mL), H$_2$O (0.2 mL) at room temperature. Then the mixture was stirred at 100° C. under nitrogen atmosphere for 3 hours. The resulting mixture was extracted with EtOAc (3×50 mL). The combined organic layers were washed with brine (3×10 mL), dried over anhydrous Na$_2$SO$_4$. After filtration, the filtrate was concentrated under reduced pressure. The crude product (50 mg) was purified by Prep-HPLC with the following conditions Column: XBridge Prep OBD C18 Column 30×150 mm 5 μm; Mobile Phase A: Water (10 mmol/L NH$_4$HCO$_3$+0.1% NH$_3$.H$_2$O), Mobile Phase B: ACN; Flow rate: 60 mL/min; Gradient: 22% B to 32% B in 7 min; 254/220 nm; Rt: 6.55 min) to afford 5-[5-amino-7-(3,4-difluorophenyl)-2-[(3-fluoropyridin-2-yl)methyl]-[1,2,4]triazolo[1,5-c]pyrimidin-8-yl]-1-methyl-1,2-dihydropyridin-2-one (Cmpd. 39) (25 mg, 23.1%) as a white solid. LCMS: m/z (ESI), [M+H]$^+$=464.2. $^1$H NMR (300 MHz, DMSO-d$_6$) δ 4.41 (s, 2H), 6.29 (d, J=8.9 Hz, 1H), 7.18 (d, J=26.0 Hz, 2H), 7.43 (d, J=24.3 Hz, 3H), 7.68 (d, J=13.2 Hz, 2H), 8.02 (s, 2H), 8.32 (s, 1H).

Compounds listed in the table below were prepared using methods described in Example 39.

| Example/Compound number | Structure | LCMS [M + H]$^+$ | $^1$H NMR |
|---|---|---|---|
| 40 | 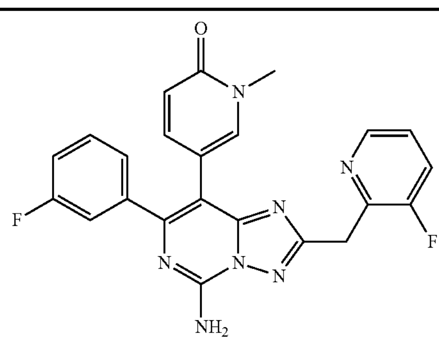 | 446.2 | $^1$H NMR (300 MHz, Methanol-d$_4$) δ 3.55 (s, 3H), 6.42 (d, J = 9.3 Hz, 1H), 7.04-7.17 (m, 1H), 7.17-7.39 (m, 4H), 7.44 (dt, J = 8.8, 4.5 Hz, 1H), 7.69 (t, J = 9.0 Hz, 1H), 7.78 (d, J = 2.5 Hz, 1H), 8.34 (d, J = 4.8 Hz, 1H). |

| Example/Compound number | Structure | LCMS [M + H]+ | 1H NMR |
|---|---|---|---|
| 41 | 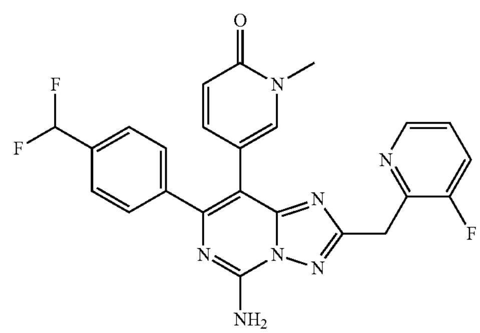 [SMILES: Cn1cc(-c2c(-c3ccc(C(F)F)cc3)nc(N)n3nc(Cc4ncccc4F)nc23)ccc1=O] | 478.2 | 1H NMR (300 MHz, Methanol-d4) δ 3.53 (s, 3H), 4.51 (d, J = 5.1 Hz, 1H), 6.41 (d, J = 9.3 Hz, 1H), 6.77 (t, J = 56.1 Hz, 1H), 7.19 (dd, J = 9.3, 2.6 Hz, 1H), 7.44 (dt, J = 8.8, 4.6 Hz, 1H), 7.52 (d, J = 8.1 Hz, 2H), 7.63 (d, J = 8.1 Hz, 2H), 7.71 (d, J = 8.8 Hz, 1H), 7.78 (d, J = 2.5 Hz, 1H), 8.34 (d, J = 4.9 Hz, 1H). |
| 56 | 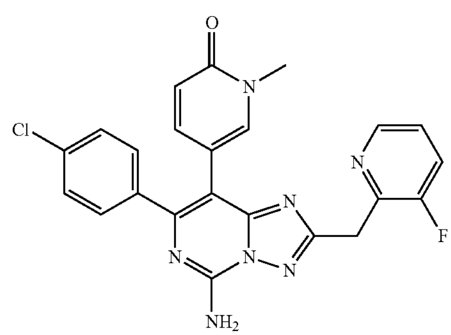 [SMILES: Cn1cc(-c2c(-c3ccc(Cl)cc3)nc(N)n3nc(Cc4ncccc4F)nc23)ccc1=O] | 462.2 | 1H NMR (300 MHz, DMSO-d6) δ 3.33 (s, 3H), 4.39 (d, J = 2.0 Hz, 2H), 6.27 (d, J = 9.3 Hz, 1H), 7.09 (dd, J = 9.3, 2.6 Hz, 1H), 7.37-7.47 (m, 5H), 7.62-7.74 (m, 2H), 7.95 (s, 2H), 8.31 (dt, J = 4.8, 1.6 Hz, 1H). |
| 57 | 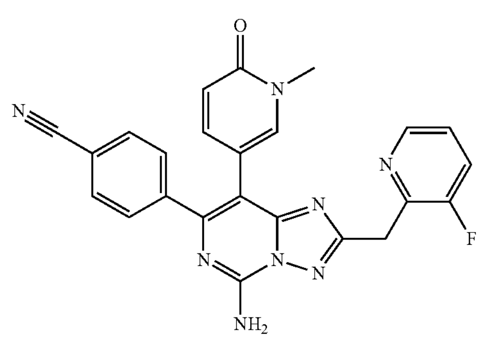 [SMILES: Cn1cc(-c2c(-c3ccc(C#N)cc3)nc(N)n3nc(Cc4ncccc4F)nc23)ccc1=O] | 453.1 | 1H NMR (400 MHz, Methanol-d4) δ: 3.56 (s, 3H), 4.52 (d, J = 2.1 Hz, 2H), 6.44 (d, J = 9.3 Hz, 1H), 7.20 (dd, J = 9.3, 2.5 Hz, 1H), 7.42 (dt, J = 8.6, 4.5 Hz, 1H), 7.60-7.78 (m, 5H), 7.80 (d, J = 2.5 Hz, 1H), 8.32 (d, J = 2.5 Hz, 1H). |
| 59 | 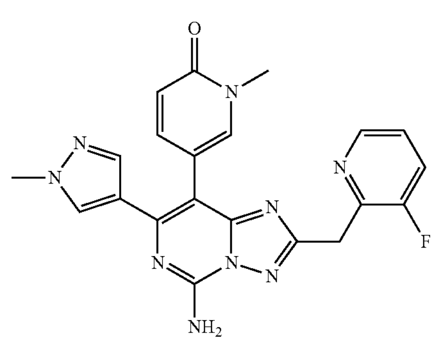 [SMILES: Cn1cc(-c2nc(N)n3nc(Cc4ncccc4F)nc3c2-c2ccc(=O)n(C)c2)cn1] | 432.2 | 1H NMR (300 MHz, Methanol-d4) δ 3.62 (s, 3H), 3.85 (s, 3H), 4.42 (d, J = 2.1 Hz, 2H), 6.63 (d, J = 9.2 Hz, 1H), 7.40 (d, J = 8.3 Hz, 2H), 7.55 (s, 1H), 7.62 (t, J = 9.2, 9.2 Hz, 1H), 7.72 (s, 1H), 7.76-7.81 (m, 1H), 8.30 (d, J = 4.7 Hz, 1H). |

-continued

| Example/ Compound number | Structure | LCMS [M + H]+ | 1H NMR |
|---|---|---|---|
| 61 | 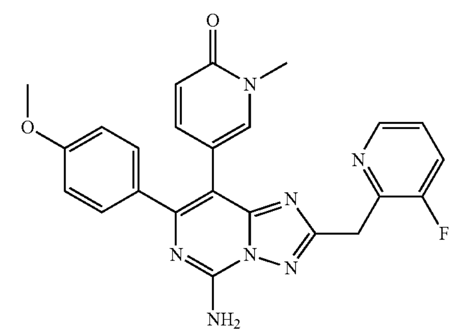 [SMILES: COc1ccc(-c2nc(N)n3nc(Cc4ncccc4F)nc3c2-c2ccc(=O)n(C)c2)cc1] | 458.1 | 1H NMR (300 MHz, Methanol-d4) δ 3.55 (s, 3H), 3.80 (s, 3H), 4.47 (s, 2H), 6.40 (d, J = 9.3 Hz, 1H), 6.82-6.93 (m, 2H), 7.18 (dd, J = 9.3, 2.5 Hz, 1H), 7.34-7.50 (m, 3H), 7.55-7.69 (m, 1H), 7.78 (d, J = 2.5 Hz, 1H), 8.31 (d, J = 4.6 Hz, 1H). |
| 62 | 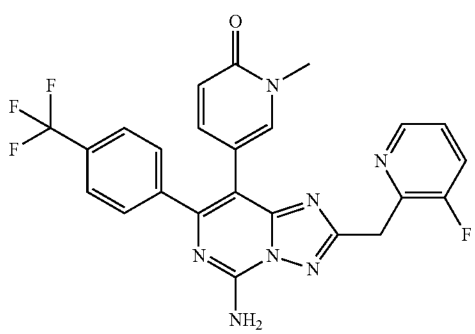 [SMILES: Cn1cc(-c2c(-c3ccc(C(F)(F)F)cc3)nc(N)n3nc(Cc4ncccc4F)nc23)ccc1=O] | 496.3 | 1H NMR (300 MHz, DMSO-d6) δ 4.41 (d, J = 2.1 Hz, 2H), 6.27 (d, J = 9.3 Hz, 1H), 7.10 (dd, J = 9.3, 2.6 Hz, 1H), 7.39 (dt, J = 8.5, 4.4 Hz, 1H), 7.57-7.79 (m, 6H), 7.99 (d, J = 25.8 Hz, 2H), 8.32 (dt, J = 4.7, 1.7 Hz, 1H). |
| 64 | 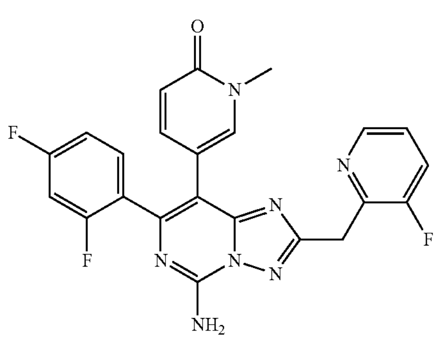 [SMILES: Cn1cc(-c2c(-c3ccc(F)cc3F)nc(N)n3nc(Cc4ncccc4F)nc23)ccc1=O] | 464.2 | 1H NMR (300 MHz, DMSO-d6) δ 4.42 (d, J = 2.1 Hz, 2H), 6.25 (d, J = 9.4 Hz, 1H), 7.09-7.29 (m, 3H), 7.39 (dt, J = 8.6, 4.4 Hz, 1H), 7.46-7.54 (m, 1H), 7.56 (d, J = 2.6 Hz, 1H), 7.71 (ddd, J = 9.9, 8.3, 1.3 Hz, 1H), 8.05 (s, 2H), 8.32 (dt, J = 4.7, 1.6 Hz, 1H). |
| 70 | 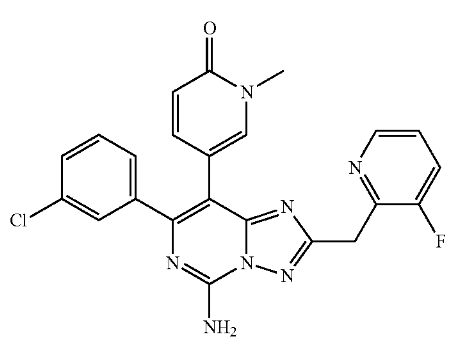 [SMILES: Cn1cc(-c2c(-c3cccc(Cl)c3)nc(N)n3nc(Cc4ncccc4F)nc23)ccc1=O] | 462.1 | 1H NMR (300 MHz, DMSO-d6) δ 4.41 (d, J = 2.1 Hz, 2H), 6.28 (d, J = 9.4 Hz, 1H), 7.14 (dd, J = 9.4, 2.6 Hz, 1H), 7.25-7.44 (m, 4H), 7.54 (d, J = 1.8 Hz, 1H), 7.65 (d, J = 2.5 Hz, 1H), 7.70 (ddd, J = 9.8, 8.3, 1.3 Hz, 1H), 8.02 (s, 2H), 8.32 (dt, J = 4.6, 1.5 Hz, 1H). |

-continued

| Example/ Compound number | Structure | LCMS [M + H]⁺ | ¹H NMR |
|---|---|---|---|
| 76 | 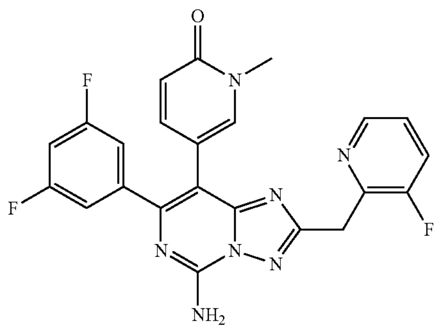 [SMILES: Cn1cc(-c2c(-c3cc(F)cc(F)c3)nc(N)n3nc(Cc4ncccc4F)nc23)ccc1=O] | 464.2 | ¹H NMR (300 MHz, DMSO-d$_6$) δ 4.41 (d, J = 2.1 Hz, 2H), 6.30 (d, J = 9.3 Hz, 1H), 7.04-7.12 (m, 2H), 7.16 (dd, J = 9.4, 2.6 Hz, 1H), 7.20-7.30 (m, 1H), 7.38 (dt, J = 8.5, 4.5 Hz, 1H), 7.62-7.69 (m, 1H), 7.69-7.76 (m, 1H), 8.05 (s, 2H), 8.32 (d, J = 4.7 Hz, 1H). |
| 77 | 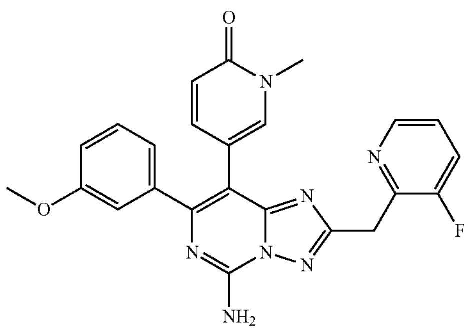 [SMILES: COc1cccc(-c2nc(N)n3nc(Cc4ncccc4F)nc3c2-c2ccc(=O)n(C)c2)c1] | 458.2 | ¹H NMR (300 MHz, DMSO-d$_6$) δ 3.67 (s, 3H), 4.40 (d, J = 2.1 Hz, 2H), 6.26 (d, J = 9.4 Hz, 1H), 6.85-6.92 (m, 1H), 6.92-7.02 (m, 2H), 7.11 (dd, J = 9.3, 2.6 Hz, 1H), 7.24 (t, J = 7.9 Hz, 1H), 7.39 (dt, J = 8.6, 4.4 Hz, 1H), 7.63 (d, J = 2.5 Hz, 1H), 7.70 (ddd, J = 9.9, 8.4, 1.4 Hz, 1H), 7.96 (s, 2H), 8.32 (dt, J = 4.7, 1.6 Hz, 1H), 8.90 (s, 4H). |
| 78 | 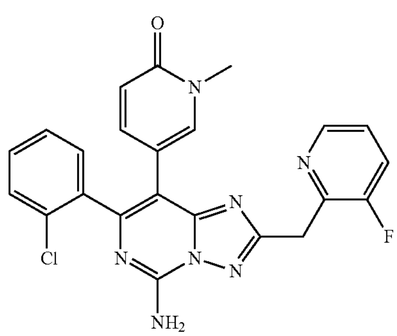 | 462.2 | ¹H NMR (300 MHz, DMSO-d$_6$) δ 3.29 (s, 3H), 4.42 (d, J = 2.1 Hz, 2H), 6.20 (d, J = 9.4 Hz, 1H), 7.13 (dd, J = 9.4, 2.6 Hz, 1H), 7.31-7.47 (m, 5H), 7.50 (d, J = 2.6 Hz, 1H), 7.71 (dd, J = 9.7, 8.1 Hz, 1H), 8.04 (s, 2H), 8.32 (d, J = 4.7 Hz, 1H). |
| 97 | 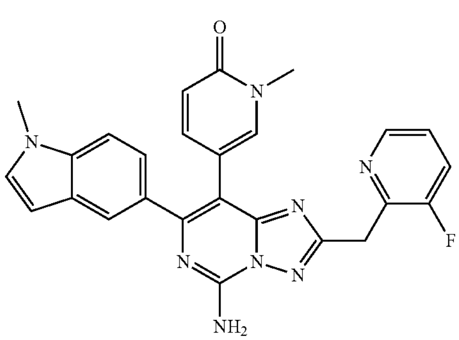 [SMILES: Cn1cc(-c2c(-c3ccc4c(ccn4C)c3)nc(N)n3nc(Cc4ncccc4F)nc23)ccc1=O] | 481.2 | ¹H NMR (300 MHz, DMSO-d$_6$) δ 3.31 (d, 3H), 3.76 (s, 3H), 4.40 (d, J = 2.1 Hz, 2H), 6.18 (d, J = 9.3 Hz, 1H), 6.42 (d, J = 3.1 Hz, 1H), 7.02 (dd, J = 9.3, 2.6 Hz, 1H), 7.20 (dd, J = 8.6, 1.6 Hz, 1H), 7.31 (d, J = 3.1 Hz, 1H), 7.30-7.44 (m, 2H), 7.70 (td, J = 7.2, 1.5 Hz, 3H), 7.85 (s, 2H), 8.32 (dt, J = 4.7, 1.6 Hz, 1H). |

| Example/ Compound number | Structure | LCMS [M + H]+ | 1H NMR |
|---|---|---|---|
| 98 | 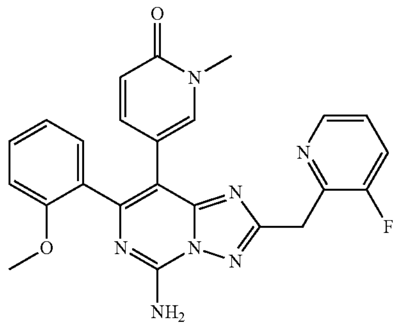 [SMILES: COc1ccccc1-c1nc(N)n2nc(Cc3ncccc3F)nc2c1-c1ccc(=O)n(C)c1] | 458.2 | 1H NMR (300 MHz, DMSO-d6) δ 3.26 (d, J = 14.5 Hz, 5H), 3.52 (s, 3H), 4.40 (d, J = 2.1 Hz, 2H), 6.18 (d, J = 9.3 Hz, 1H), 6.88-7.01 (m, 2H), 7.12 (dd, J = 9.4, 2.6 Hz, 1H), 7.27 (dd, J = 7.1, 5.4 Hz, 1H), 7.26-7.44 (m, 3H), 7.70 (t, J = 9.8 Hz, 1H), 7.89 (s, 2H), 8.32 (d, J = 4.8 Hz, 1H). |

Example 42

Preparation of 5-[5-amino-7-(4-fluorophenyl)-2-[(1,3-thiazol-2-yl)methyl]-[1,2,4]triazolo[1,5-c]pyrimidin-8-yl]-1-methyl-1,2-dihydropyridin-2-one (Cmpd. 42)

(4-fluorophenyl)pyrimidin-4-yl]-2-(1,3-thiazol-2-yl)acetohydrazide (170 mg, 59.9%) as a grey solid. LCMS: m/z (ESI), [M+H]+=423.1. 1H NMR (300 MHz, DMSO-d6) δ 4.05 (s, 2H), 6.44 (s, 2H), 7.28 (t, J=8.9 Hz, 2H), 7.55-7.63 (m, 2H), 7.66 (d, J=3.3 Hz, 1H), 7.75 (d, J=3.3 Hz, 1H), 8.76 (s, 1H), 10.22 (s, 1H).

SCHEME 26

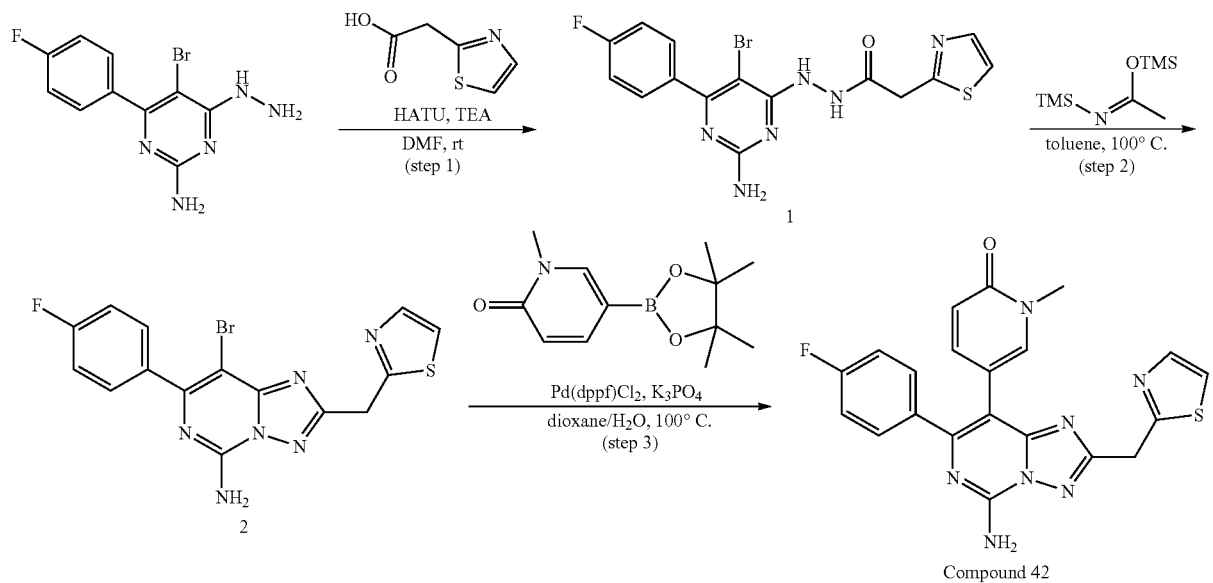

Compound 42

Step 1. N-[2-amino-5-bromo-6-(4-fluorophenyl)pyrimidin-4-yl]-2-(1,3-thiazol-2-yl)acetohydrazide To a stirred mixture of 5-bromo-4-(4-fluorophenyl)-6-hydrazinylpyrimidin-2-amine (200 mg, 0.7 mmol, 1 equiv) and 2-(1,3-thiazol-2-yl)acetic acid (115.3 mg, 0.8 mmol, 1.2 equiv) in DMF (2 mL) were added HATU (382.6 mg, 1.01 mmol, 1.5 equiv) and DIEA (260.1 mg, 2.0 mmol, 3 equiv) in portions at room temperature under nitrogen atmosphere. The resulting mixture was stirred for 3 hours at room temperature under nitrogen atmosphere. The reaction was quenched with water (20 mL) at room temperature. The precipitated solids were collected by filtration and washed with water (3×20 mL). To afford N-[2-amino-5-bromo-6-(4-fluorophenyl)pyrimidin-4-yl]-2-(1,3-thiazol-2-yl)acetohydrazide

Step 2. 8-bromo-7-(4-fluorophenyl)-2-[(1,3-thiazol-2-yl)methyl]-[1,2,4]triazolo[1,5-c]pyrimidin-5-amine To a stirred mixture of N-[2-amino-5-bromo-6-(4-fluorophenyl)pyrimidin-4-yl]-2-(1,3-thiazol-2-yl)acetohydrazide (150 mg, 0.35 mmol, 1 equiv) in toluene (4 mL) was added (Z)-(trimethylsilyl N-(trimethylsilyl)ethanimidate) (216.3 mg, 1.1 mmol, 3 equiv) in portions at room temperature under nitrogen atmosphere. The resulting mixture was stirred for 3 hours at 100° C. under nitrogen atmosphere. The resulting mixture was concentrated under vacuum. The residue was purified by Prep-TLC (CH2Cl2/MeOH 20:1) to afford 8-bromo-7-(4-fluorophenyl)-2-[(1,3-thiazol-2-yl)

methyl]-[1,2,4]triazolo[1,5-c]pyrimidin-5-amine (100 mg, 69.63%) as a grey solid. LCMS: m/z (ESI), [M+H]⁺=405.1. ¹H NMR (400 MHz, Methanol-d₄) δ 4.71 (s, 2H), 7.17-7.25 (m, 2H), 7.57 (d, J=3.4 Hz, 1H), 7.75 (d, J=3.4 Hz, 1H), 7.78-7.84 (m, 2H).

Step 3. 5-[5-amino-7-(4-fluorophenyl)-2-[(1,3-thiazol-2-yl)methyl]-[1,2,4]triazolo[1,5-c]pyrimidin-8-yl]-1-methyl-1,2-dihydropyridin-2-one (Cmpd. 42)

To a stirred mixture of 8-bromo-7-(4-fluorophenyl)-2-[(1,3-thiazol-2-yl)methyl]-[1,2,4]triazolo[1,5-c]pyrimidin-5-amine (100 mg, 0.25 mmol, 1 equiv) and 1-methyl-5-(4,4,5,5-tetramethyl-1,3,2-dioxaborolan-2-yl)-1,2-dihydropyridin-2-one (116.0 mg, 0.49 mmol, 2 equiv) in 1,4-dioxane (3 mL) and H₂O (0.6 mL) were added K₃PO₄ (156.9 mg, 0.74 mmol, 3 equiv) and Pd(dppf)Cl₂ (36.1 mg, 0.05 mmol, 0.2 equiv) in portions at room temperature under nitrogen atmosphere. The resulting mixture was stirred for 3 hours at 100° C. under nitrogen atmosphere. The resulting mixture was concentrated under vacuum. The residue was purified by Column: XBridge Shield RP18 OBD Column, 5 μm, 19*150 mm; Mobile Phase A: Water (10 MMOL/L NH₄HCO₃), Mobile Phase B: ACN; Flow rate: 20 mL/min; Gradient: 25% B to 35% B in 8 min; 254/220 nm; Rt: 6.45 min to afford 5-[5-amino-7-(4-fluorophenyl)-2-[(1,3-thiazol-2-yl)methyl]-[1,2,4]triazolo[1,5-c]pyrimidin-8-yl]-1-methyl-1,2-dihydropyridin-2-one (Cmpd. 42) (35 mg, 32.72%) as a off-white solid. LCMS: m/z (ESI), [M+H]⁺=434.2. ¹H NMR (400 MHz, Methanol-d₄) δ 3.57 (s, 3H), 4.68 (s, 2H), 6.44 (d, J=9.3 Hz, 1H), 7.06-7.14 (m, 2H), 7.22 (dd, J=9.3, 2.5 Hz, 1H), 7.57 (td, J=5.8, 2.5 Hz, 3H), 7.74 (d, J=3.4 Hz, 1H), 7.81 (d, J=2.4 Hz, 1H).

Example 43

Preparation of 7-(4-fluorophenyl)-2-((3-fluoropyridin-2-yl)methyl)-8-(2-(methylamino) pyridin-4-yl)-[1,2,4]triazolo[1,5-c]pyrimidin-5-amine (Cmpd. 43)

Step 1. (2-(methylamino)pyridin-4-yl)boronic acid

Pd(dppf)Cl₂(391.2 mg, 0.5 mmol, 0.2 equiv), K₃PO₄ (1134.9 mg, 5.3 mmol, 2 equiv), 4-bromo-N-methylpyridin-2-amine (500 mg, 2.7 mmol, 1 equiv), 4,4,5,5-tetramethyl-2-(4,4,5,5-tetramethyl-1,3-dioxolan-2-yl)-1,3,2-dioxaborolane (821.7 mg, 3.2 mmol, 1.2 equiv) were dissolved in 10 mL of dioxane. The mixture was stirred at 90° C. for 2 hours. LCMS showed the reaction was completed. The crude product was purified by silica gel column and eluting with MeOH-DCM (1:10) and the product was further purified by prep-HPLC to afford product as a light yellow solid. LCMS: m/z (ESI), [M+H]⁺=153.2.

Step 2. 7-(4-fluorophenyl)-2-((3-fluoropyridin-2-yl)methyl)-8-(2-(methylamino)pyridin-4-yl)-[1,2,4]triazolo[1,5-c]pyrimidin-5-amine (Cmpd. 43)

(2-(methylamino)pyridin-4-yl)boronic acid (100 mg, 0.66 mmol, 1 equiv), 8-bromo-7-(4-fluorophenyl)-2-((3-methylpyridin-2-yl)methyl)-[1,2,4]triazolo[1,5-c]pyrimidin-5-amine, (271.9 mg, 0.66 mmol, 1 equiv), Pd(dppf)Cl₂(96.3 mg, 0.13 mmol, 0.2 equiv), K₃PO₄ (419.1 mg, 1.97 mmol, 3 equiv) were dissolved in 5 mL of dioxane/H₂O (5:1). The mixture was stirred at 80° C. for 3 hours. LCMS showed the reaction was completed. The crude product was purified by silica gel column and eluting with MeOH-DCM (1:10) and the product was further purified by prep-HPLC to afford product (Cmpd. 43) 26.6 mg as a white solid. LCMS: m/z (ESI), [M+H]⁺=445.2. ¹H NMR (300 MHz, Methanol-d₄) δ 2.81 (s, 3H), 4.47 (d, J=2.1 Hz, 2H), 6.41 (dd, J=5.7, 1.6 Hz, 1H), 6.61 (s, 1H), 7.03 (t, J=8.8 Hz, 2H), 7.33-7.54 (m, 3H), 7.56-7.69 (m, 1H), 7.74-7.82 (m, 1H), 8.26-8.37 (m, 2H).

SCHEME 27

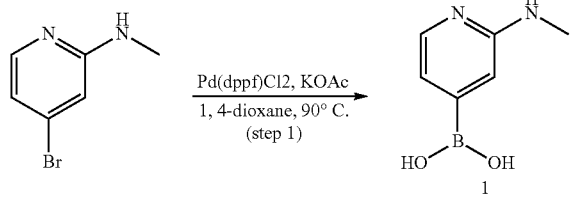

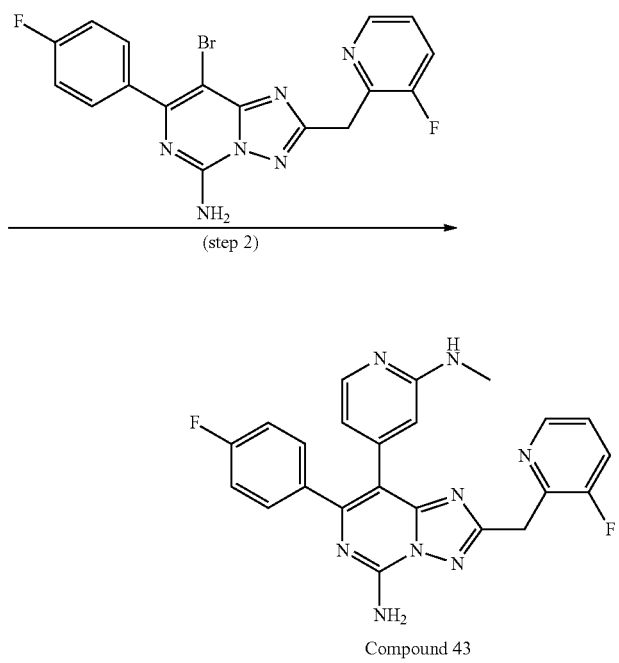

Compound 43

Example 45

Preparation of 7-(4-fluorophenyl)-2-((6-methylpyridin-2-yl)methyl)-8-(2-methylpyridin-4-yl)-[1,2,4]triazolo[1,5-c]pyrimidin-5-amine (Cmpd. 45)

SCHEME 28

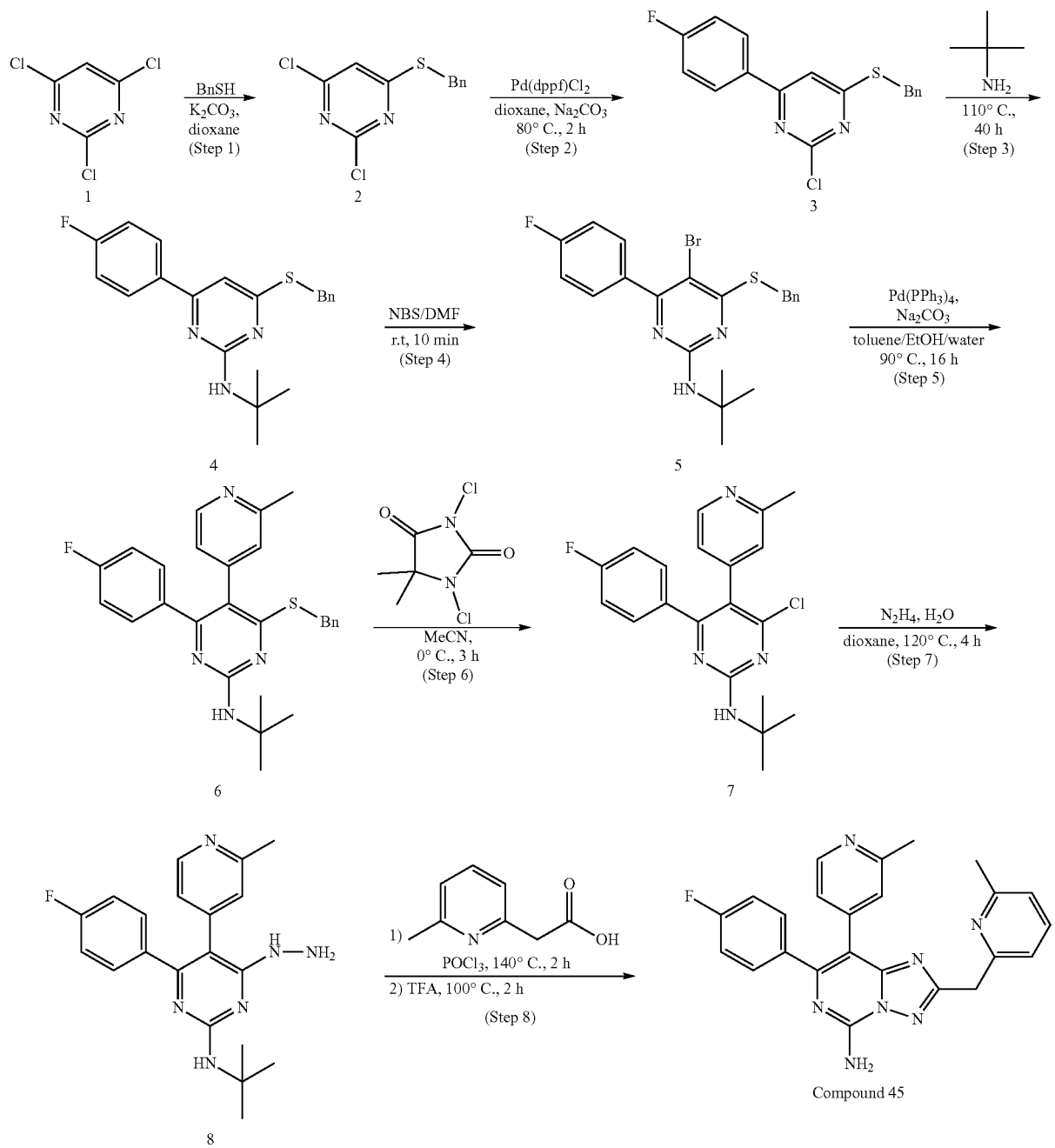

Step 1. Preparation of 4-(benzylthio)-2,6-dichloropyrimidine

To a stirred solution of 2,4,6-trichloropyrimidine (6.5 g, 35.73 mmol) in dioxane (10 mL) was added phenylmethanethiol (4.43 g, 35.73 mmol) and K₂CO₃ (4.93 g, 35.73 mmol) at 0° C. Then the mixture was stirred at room temperature for 16 hours. Then the mixture was concentrated and the residue was poured to water and then extracted with ethyl acetate (2×25 mL). The organic solution was then concentrated to give the crude 4-(benzylthio)-2,6-dichloropyrimidine (9.6 g, yield: 99.5%) as a yellow solid, which can be used for next step without further purification. LCMS m/z (ESI), [M+H]⁺=271.2.

Step 2. Preparation of 4-(benzylthio)-2-chloro-6-(4-fluorophenyl)pyrimidine

The mixture of 4-(benzylthio)-2,6-dichloropyrimidine (9.6 g, 35.6 mmol), 2-(4-fluorophenyl)-4,4,5,5-tetramethyl-1,3,2-dioxaborolane (4.98 g, 35.56 mmol) in dioxane (100 mL) and water (10 mL) were added $Na_2CO_3$ (9.96 g, 71.12 mmol) and $Pd(dppf)Cl_2$ (2.6 g, 3.56 mmol). Then the mixture was stirred at 80° C. for 4 hours under $N_2$ atmosphere. The mixture was concentrated and to the residue was added water (25 mL) and ethyl acetate (100 mL). The organic solution was then concentrated to give the crude product which was further purified by flash column (0-5% ethyl acetate in petro ether) to give the 4-(benzylthio)-2-chloro-6-(4-fluorophenyl)pyrimidine (11.6 g, 98%) as a yellow oil. LCMS: m/z (ESI), $[M+H]^+=331.2$.

Step 3. Preparation of 4-(benzylthio)-N-(tert-butyl)-6-(4-fluorophenyl)pyrimidin-2-amine The solution of 4-(benzylthio)-2-chloro-6-(4-fluorophenyl)pyrimidine (11.6 g, 35.15 mmol) in 2-methylpropan-2-amine (20.55 g, 281.8 mmol) was stirred at 110° C. for 40 hours.

Then the mixture was concentrated and the residue was further purified by flash column (330 g) (0-5% ethyl acetate in petro ether) to give the desired product 4-(benzylthio)-N-(tert-butyl)-6-(4-fluorophenyl)pyrimidin-2-amine (12 g, yield: 93.0%) as a yellowish oil. LCMS: m/z (ESI), $[M+H]^+=368.6$.

Step 4. Preparation of 4-(benzylthio)-5-bromo-N-(tert-butyl)-6-(4-fluorophenyl)pyrimidin-2-amine To the stirred solution of 4-(benzylthio)-N-(tert-butyl)-6-(4-fluorophenyl)pyrimidin-2-amine (10.0 g, 27.24 mmol) in 50 mL DMF was added NBS (5.3 g, 29.96 mmol). Then the mixture was stirred at room temperature for 1 hour. The mixture was concentrated and the residue was purified by flash column (0-5% ethyl acetate in petro ether) to give the desired 4-(benzylthio)-5-bromo-N-(tert-butyl)-6-(4-fluorophenyl)pyrimidin-2-amine (5.50 g, yield: 41%) as a white solid. LCMS: m/z (ESI), $[M+H]^+=446.2$.

Step 5. Preparation of 4-(benzylthio)-N-(tert-butyl)-6-(4-fluorophenyl)-5-(2-methylpyridin-4-yl)pyrimidin-2-amine The mixture of 4-(benzylthio)-5-bromo-N-(tert-butyl)-6-(4-fluorophenyl)pyrimidin-2-amine (3.7 g, 8.31 mmol), (2-methylpyridin-4-yl)boronic acid (1.71 g, 12.47 mmol) in dioxane (50 mL) and water (50 mL) was added $Na_2CO_3$ (2.28 g, 16.63 mmol) and $Pd(PPh_3)_4$ (0.96 g, 0.83 mmol). Then the mixture was stirred at 80° C. for 8 hours under $N_2$ atmosphere. The mixture was concentrated and to the residue was added water (25 mL) and ethyl acetate (100 mL). The organic phase was then concentrated to give the crude product which was further purified by flash column (0-5% ethyl acetate in petro ether) to give the 4-(benzylthio)-N-(tert-butyl)-6-(4-fluorophenyl)-5-(2-methylpyridin-4-yl)pyrimidin-2-amine (2.2 g, yield: 58%) as a yellow oil. LCMS: m/z (ESI), $[M+H]^+=459.4$.

Step 6. Preparation of N-(tert-butyl)-4-chloro-6-(4-fluorophenyl)-5-(2-methylpyridin-4-yl)pyrimidin-2-amine To a solution of 4-(benzylthio)-N-(tert-butyl)-6-(4-fluorophenyl)-5-(2-methylpyridin-4-yl)pyrimidin-2-amine (1.7 g, 3.71 mmol) in 20 mL acetonitrile was added 1 drop of acetic acid and 1 drop of water. Then solution was cooled to 0° C., and 1,3-dichloro-5,5-dimethylimidazolidine-2,4-dione (1.45 g, 7.42 mmol) was added. The mixture was stirred for 3 hours at this temperature. The solution diluted with 40 mL $Na_2SO_3$ solution in water and then extracted with DCM (20 mL×2). The organic layer was collected and concentrated. The crude was purified by column (0-5% EA in PE) to give the desired N-(tert-butyl)-4-chloro-6-(4-fluorophenyl)-5-(2-methylpyridin-4-yl)pyrimidin-2-amine (1.0 g, 73% yield) as a white solid. LCMS: m/z (ESI), $[M+H]^+=371.2$.

Step 7. Preparation of N-(tert-butyl)-4-(4-fluorophenyl)-6-hydrazineyl-5-(2-methylpyridin-4-yl)pyrimidin-2-amine To a solution of N-(tert-butyl)-4-chloro-6-(4-fluorophenyl)-5-(2-methylpyridin-4-yl)pyrimidin-2-amine (0.9 g, 2.34 mmol) in dioxane (3 mL) was added hydrazine (1.17 g, 23.4 mmol). Then the mixture was stirred a 100° C. for 16 hours. To the solution was added 20 mL sat. brine and the solid which formed was collected, washed with 15 mL 20% ethyl acetate in petro ether, then dried to give the desired N-(tert-butyl)-4-(4-fluorophenyl)-6-hydrazineyl-5-(2-methylpyridin-4-yl)pyrimidin-2-amine (0.79 g, 88% yield) as a white solid. LCMS: m/z (ESI), $[M+H]^+=367.4$.

Step 8. Preparation of 7-(4-fluorophenyl)-2-((6-methylpyridin-2-yl)methyl)-8-(2-methylpyridin-4-yl)-[1,2,4]triazolo[1,5-c]pyrimidin-5-amine (Cmpd. 45)

The mixture of N-(tert-butyl)-4-(4-fluorophenyl)-6-hydrazineyl-5-(2-methylpyridin-4-yl)pyrimidin-2-amine (0.020 g, 0.05 mmol), 2-(6-methylpyridin-2-yl)acetic acid (0.019 g, 0.12 mmol) in $POCl_3$ (0.5 mL) was stirred in a sealed tube at 140° C. for 4 hours. The mixture was concentrated and to the residue was added 2 mL TFA. The resulting mixture was stirred in a sealed tube at 100° C. for 2 hours. The mixture was concentrated and purified by C18-flash chromatography, elution gradient 5% to 60% acetonitrile in water (0.05% ammonia). Pure fractions were evaporated to dryness to afford 7-(4-fluorophenyl)-2-((6-methylpyridin-2-yl)methyl)-8-(2-methylpyridin-4-yl)-[1,2,4]triazolo[1,5-c]pyrimidin-5-amine (Cmpd. 45) (5 mg, 21.8% yield). LCMS: m/z (ESI), $[M+H]^+=426.4$. $^1$H NMR (500 MHz, DMSO-$d_6$) δ ppm 2.37 (s, 3H) 2.41 (s, 3H) 4.29 (s, 2H) 7.00 (d, J=5.39 Hz, 1H) 7.07-7.18 (m, 5H) 7.35 (t, J=6.64 Hz, 2H) 7.60 (t, J=7.57 Hz, 1H) 8.15 (br s, 2H) 8.31 (d, J=5.04 Hz, 1H).

Example 46

Preparation of 7-(4-fluorophenyl)-8-(2-methylpyridin-4-yl)-$N^2$-(pyridin-2-yl)-[1,2,4]triazolo[1,5-c]pyrimidine-2,5-diamine (Cmpd. 46)

SCHEME 29

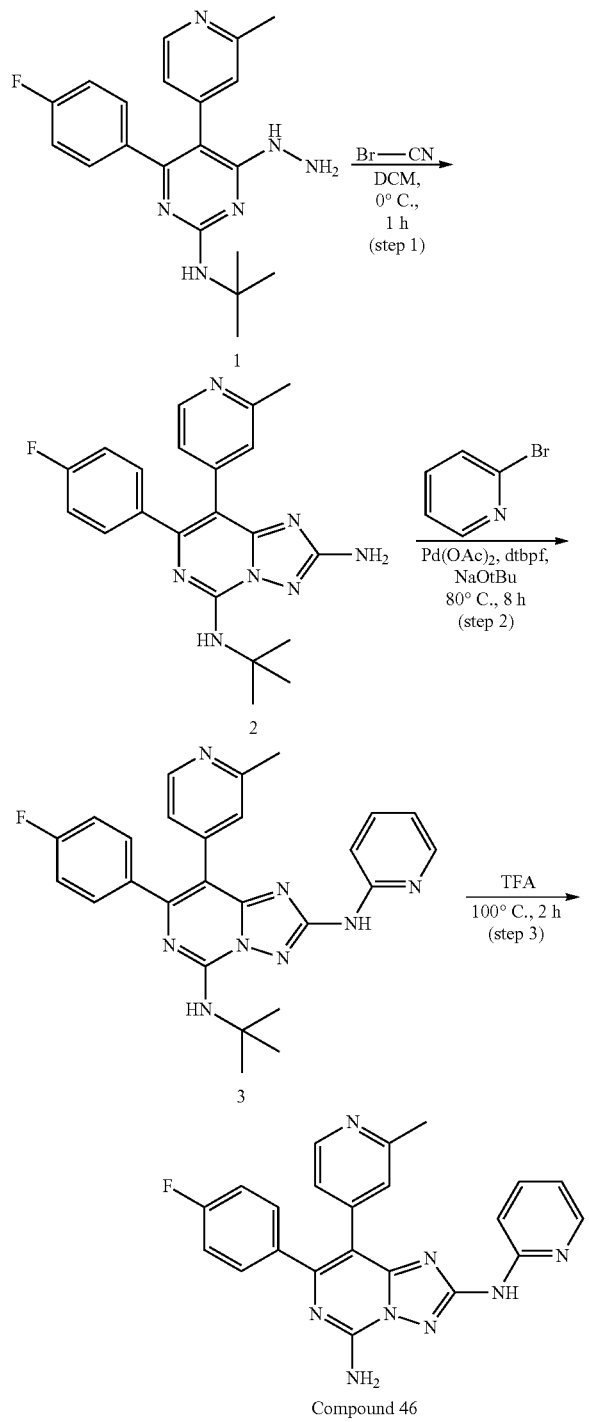

Step 1. Preparation of N5-(tert-butyl)-7-(4-fluorophenyl)-8-(2-methylpyridin-4-yl)-[1,2,4]triazolo[1,5-c]pyrimidine-2,5-diamine To a solution of N-(tert-butyl)-4-(4-fluorophenyl)-6-hydrazineyl-5-(2-methylpyridin-4-yl)pyrimidin-2-amine (0.2 g, 0.55 mmol) in dichloromethane (1.5 mL) was added cyanic bromide (0.06 g, 0.6 mmol) at 0° C. Then the mixture was stirred at this temperature for 1 hour. The mixture was concentrated and to the residue was added 0.2 mL DIEA and 5 mL ethyl acetate. The solid was then collected and dried to afford N5-(tert-butyl)-7-(4-fluorophenyl)-8-(2-methylpyridin-4-yl)-[1,2,4]triazolo[1,5-c]pyrimidine-2,5-diamine (0.15 g, 70.2%) as a yellow solid. LCMS: m/z (ESI), [M+H]⁺=392.4.

Step 2. Preparation of 3-amino-6-(2,6-dimethylpyridin-4-yl)-5-(4-fluorophenyl)pyrazine-2-carbonitrile The mixture of N5-(tert-butyl)-7-(4-fluorophenyl)-8-(2-methylpyridin-4-yl)-[1,2,4]triazolo[1,5-c]pyrimidine-2,5-diamine (0.050 g, 0.13 mmol), 2-bromopyridine (0.041 g, 0.26 mmol) in 5 ml dioxane was added Pd(OAc)₂ (0.058 g, 0.026 mmol), 1,1'-Bis(di-t-butylphosphino)ferrocene (0.014 g, 0.026 mmol) and tBuONa (0.036 g, 0.38 mmol). Then the mixture was stirred at 80° C. for 8 hours under N₂ atmosphere. Then the mixture was concentrated and residue was poured to water (20 mL) and then extracted with ethyl acetate (3×20 mL). The organic solution was then concentrated and the residue was purified by silica flash chromatography, elution gradient 10% to 50% ethyl acetate in petro ether. Pure fractions were evaporated to dryness to afford 3-amino-6-(2,6-dimethylpyridin-4-yl)-5-(4-fluorophenyl)pyrazine-2-carbonitrile (0.04 g, 68% yield) as a yellow solid. LCMS: m/z (ESI), [M+H]⁺=459.4.

Step 3. Preparation of 7-(4-fluorophenyl)-8-(2-methylpyridin-4-yl)-$N^2$-(pyridin-2-yl)-[1,2,4]triazolo[1,5-c]pyrimidine-2,5-diamine (Cmpd. 46)

A solution of 3-amino-6-(2,6-dimethylpyridin-4-yl)-5-(4-fluorophenyl)pyrazine-2-carbonitrile (60 mg, 0.188 mmol) in TFA (2 mL) was stirred at 90° C. for 1 hour in a microwave reactor. Then the solution was concentrated and the crude was washed with 30 mL methanol to give the desired 7-(4-fluorophenyl)-8-(2-methylpyridin-4-yl)-$N^2$-(pyridin-2-yl)-[1,2,4]triazolo[1,5-c]pyrimidine-2,5-diamine (Cmpd. 46) (0.023 g, 32.9% yield) as a gray solid. LCMS: m/z (ESI), [M+H]+=413.5 [M+H]; ¹H NMR (500 MHz, DMSO-d₆) δ ppm 2.37-2.43 (m, 3H) 6.88-7.06 (m, 2H) 7.14 (br s, 2H) 7.22-7.28 (m, 1H) 7.35-7.45 (m, 2H) 7.68-7.82 (m, 1H) 7.89-8.15 (m, 2H) 8.18-8.28 (m, 1H) 8.30-8.43 (m, 2H) 10.11-10.22 (m, 1H).

Example 47

Preparation of 7-(4-fluorophenyl)-2-((6-methylpyridin-2-yl)methyl)-8-(2,6-dimethylpyridin-4-yl)-[1,2,4]triazolo[1,5-c]pyrimidin-5-amine (Cmpd. 47)

SCHEME 30

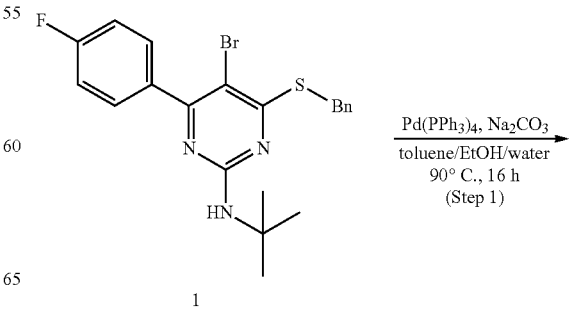

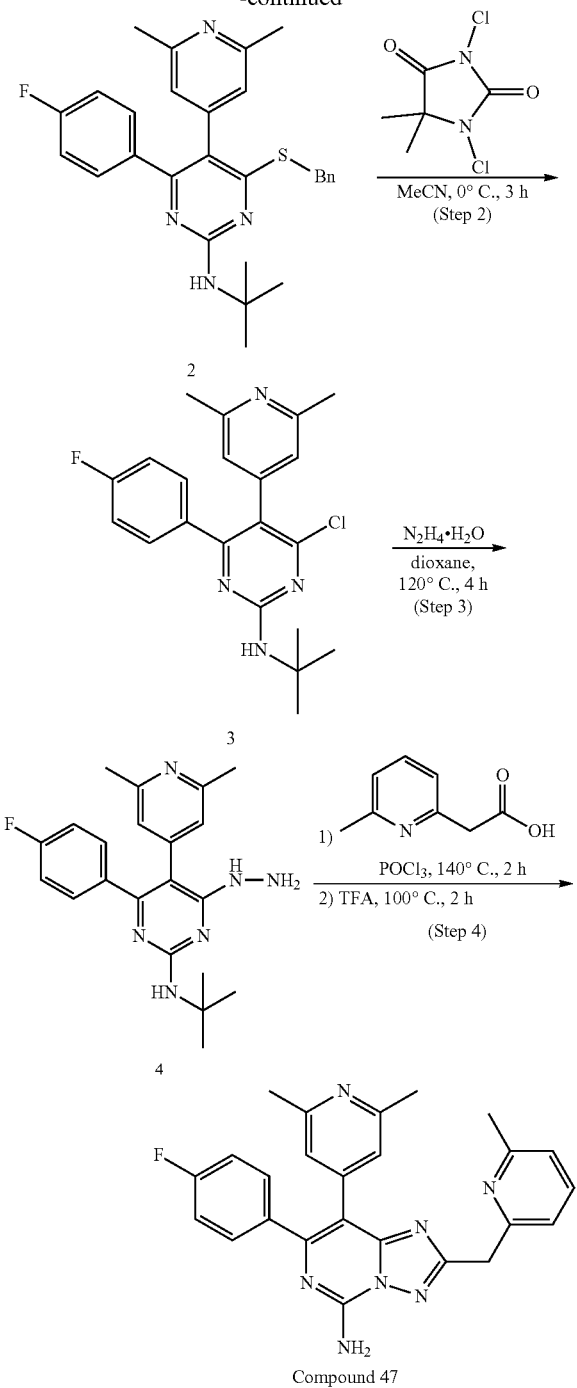

Step 1. Preparation of 4-(benzylthio)-N-(tert-butyl)-5-(2,6-dimethylpyridin-4-yl)-6-(4-fluorophenyl)pyrimidin-2-amine The mixture of 4-(benzylthio)-5-bromo-N-(tert-butyl)-6-(4-fluorophenyl)pyrimidin-2-amine (3.2 g, 7.19 mmol), (2,6-dimethylpyridin-4-yl)boronic acid (1.63 g, 10.79 mmol) in dioxane (50 mL) and water (50 mL) was added $Na_2CO_3$ (1.52 g, 14.38 mmol) and $Pd(PPh_3)_4$ (0.83 g, 0.72 mmol). Then the mixture was stirred at 80° C. for 8 hours under $N_2$ atmosphere. The mixture was concentrated and to the residue was added water (25 mL) and ethyl acetate (100 mL). The organic solution was then concentrated to give the crude product which was further purified by flash column (0-5% ethyl acetate in petro ether) to give the 4-(benzylthio)-N-(tert-butyl)-5-(2,6-dimethylpyridin-4-yl)-6-(4-fluorophenyl)pyrimidin-2-amine (2.4 g, yield: 71%) as a yellow oil. LCMS: m/z (ESI), $[M+H]^+$=474.4.

Step 2. Preparation of N-(tert-butyl)-4-chloro-6-(4-fluorophenyl)-5-(2,6-dimethylpyridin-4-yl)pyrimidin-2-amine To a solution of 4-(benzylthio)-N-(tert-butyl)-6-(4-fluorophenyl)-5-(2,6-dimethylpyridin-4-yl)pyrimidin-2-amine (1.35 g, 2.86 mmol) in 20 mL acetonitrile was added 1 drop AcOH and 1 drop water. Then solution was cooled to 0° C., and 1,3-dichloro-5,5-dimethylimidazolidine-2,4-dione (1.23 g, 6.29 mmol) was added. The mixture was stirred for 3 hours at this temperature. The solution was then poured to 40 mL $Na_2SO_3$ solution in water and then extracted with DCM (2×20 mL). The organic layer was collected and concentrated. The crude was purified by column (0-5% EA in PE) to give the desired N-(tert-butyl)-4-chloro-6-(4-fluorophenyl)-5-(2,6-dimethylpyridin-4-yl)pyrimidin-2-amine (0.90 g, 82% yield) as a white solid. LCMS: m/z (ESI), $[M+H]^+$=385.2.

Step 3. Preparation of N-(tert-butyl)-4-(4-fluorophenyl)-6-hydrazineyl-5-(2,6-dimethylpyridin-4-yl)pyrimidin-2-amine To a solution of N-(tert-butyl)-4-chloro-6-(4-fluorophenyl)-5-(2,6-dimethylpyridin-4-yl)pyrimidin-2-amine (0.9 g, 2.34 mmol) in dioxane (3 mL) was added hydrazine (1.17 g, 23.4 mmol). Then the mixture was stirred a 100° C. for 16 hours. To the solution was added 20 mL sat. brine and the solid which formed was collected, washed with 15 mL 20% ethyl acetate in petro ethyl, then dried to give the desired N-(tert-butyl)-4-(4-fluorophenyl)-6-hydrazineyl-5-(2,6-dimethylpyridin-4-yl)pyrimidin-2-amine (0.8 g, 88%) as a white solid. LCMS: m/z (ESI), $[M+H]^+$=381.3.

Step 4. Preparation of 7-(4-fluorophenyl)-2-((6-methylpyridin-2-yl)methyl)-8-(2,6-dimethylpyridin-4-yl)-[1,2,4]triazolo[1,5-c]pyrimidin-5-amine (Cmpd. 47)

The mixture of N-(tert-butyl)-4-(4-fluorophenyl)-6-hydrazineyl-5-(2,6-dimethylpyridin-4-yl)pyrimidin-2-amine (0.060 g, 0.16 mmol), 2-(6-methylpyridin-2-yl)acetic acid (0.054 g, 0.36 mmol) in $POCl_3$ (1 mL) was stirred in a sealed tube at 140° C. for 2 hours. The mixture was concentrated and to the residue was added 2 mL TFA. The resulting mixture was stirred in a sealed tube at 100° C. for 2 hours. The mixture was concentrated and the residue was purified by C18-flash chromatography, elution gradient 5% to 60% acetonitrile in water (0.05% ammonia). Pure fractions were evaporated to dryness to afford 7-(4-fluorophenyl)-2-((6-methylpyridin-2-yl)methyl)-8-(2,6-dimethylpyridin-4-yl)-[1,2,4]triazolo[1,5-c]pyrimidin-5-amine (Cmpd. 47) (0.02 g, 37.1% yield). LCMS: m/z (ESI), $[M+H]+$=440.5. $^1$H NMR (500 MHz, DMSO-$d_6$) δ ppm 2.31 (s, 6H) 2.39-2.45 (m, 3H) 4.29 (s, 2H) 6.89 (s, 2H) 7.04-7.19 (m, 4H) 7.35 (t, J=6.48 Hz, 2H) 7.59 (t, J=7.72 Hz, 1H) 8.13 (br s, 2 H).

Compounds listed in the table below were prepared using methods described in Example 47.

| Example/ Compound number | Structure | LCMS [M + H]+ | 1H NMR |
|---|---|---|---|
| 48 | 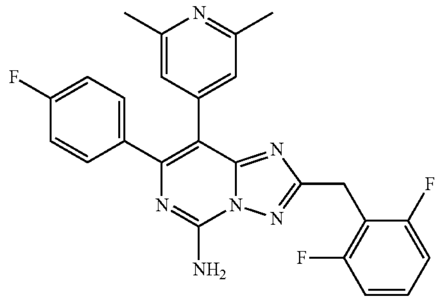 [SMILES: Cc1cc(-c2c(-c3ccc(F)cc3)nc(N)n3nc(Cc4c(F)cccc4F)nc23)cc(C)n1] | 461.3 | 1H NMR (500 MHz, DMSO-d6) δ 2.05 (s, 3 H) 4.15 (s, 2 H) 5.70 (s, 2 H) 6.09 (s, 2 H) 7.00-7.10 (m, 4 H) 7.28-7.39 (m, 3 H) 7.85 (br s, 1 H) |
| 51 | 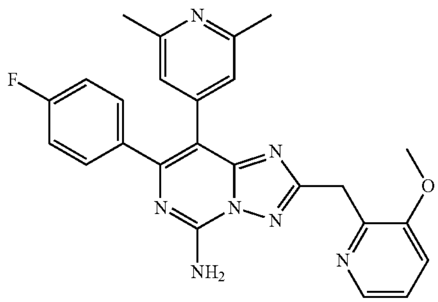 [SMILES: COc1cccnc1Cc1nc2c(-c3cc(C)nc(C)c3)c(-c3ccc(F)cc3)nc(N)n2n1] | 456.3 | 1H NMR (500 MHz, DMSO-d6) δ 2.31 (s, 3 H) 3.82 (s, 3 H) 4.30 (s, 2 H) 6.90 (s, 2 H) 7.13 (t, J = 8.25 Hz, 2 H) 7.26 (dd, J = 8.20, 4.73 Hz, 2 H) 7.33-7.39 (m, 2 H) 7.39-7.45 (m, 1 H) 7.99 (dd, J = 4.73, 0.95 Hz, 1H) 8.07 (br s, 2H) |
Example 50
Preparation of 5-(5-amino-2-(2,6-difluorobenzyl)-7-(4-fluorophenyl)-[1,2,4]triazolo[1,5-c]pyrimidin-8-yl)-1-(oxetan-3-yl)pyridin-2(1H)-one (Cmpd. 50)
SCHEME 31
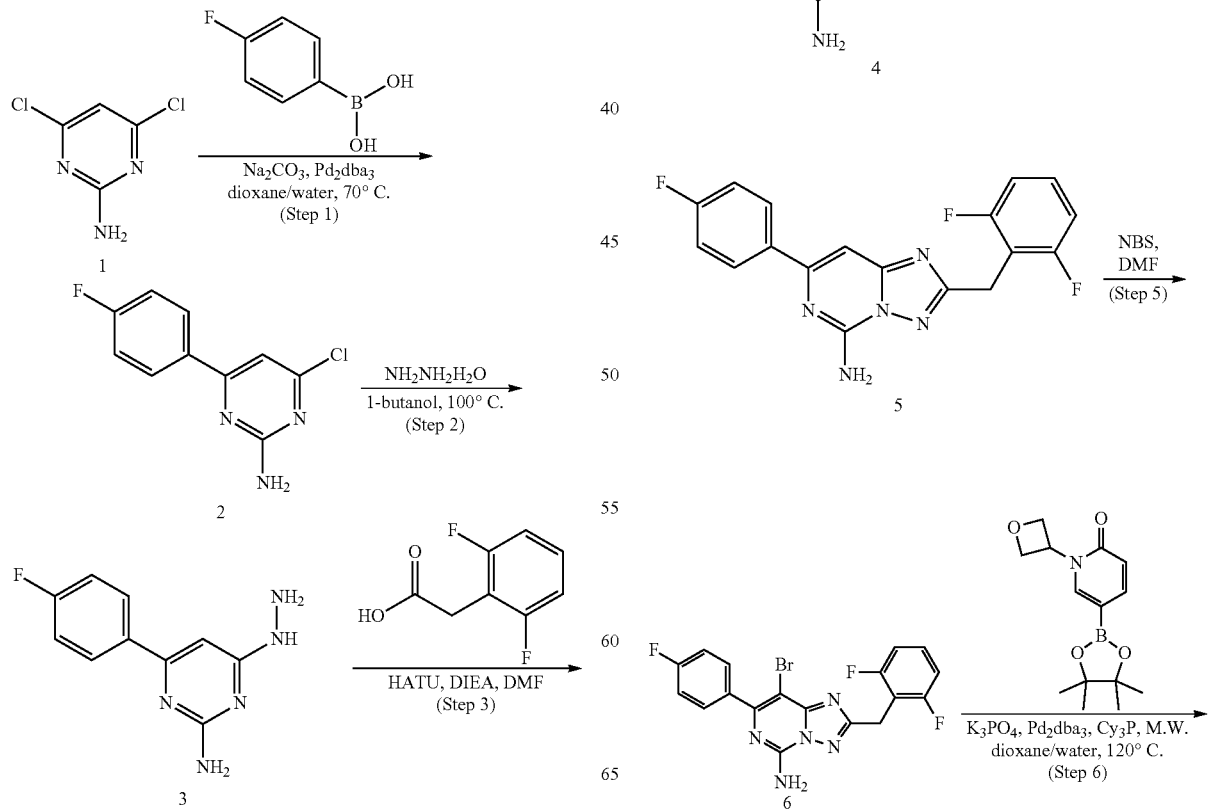

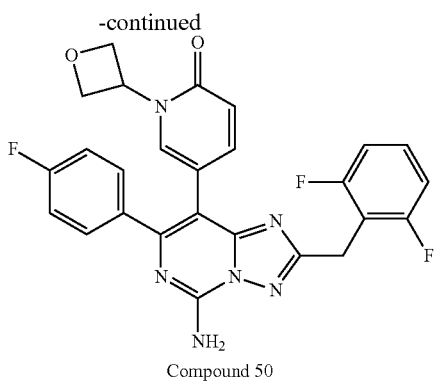

Compound 50

Step 1. Preparation of 4-chloro-6-(4-fluorophenyl)pyrimidin-2-amine

To a mixture of 4,6-dichloropyrimidin-2-amine (10 g, 61 mmol), (4-fluorophenyl)boronic acid (8.8 g, 63 mmol), Pd$_2$(dba)$_3$ (50 mg, 0.055 mmol), in dioxane (80 mL), 1,3,5,7-Tetramethyl-6-phenyl-2,4,8-trioxa-6-phosphaadamantane (40 mg, 0.14 mmol) in dioxane (80 mL) was added water (15 mL). The resulting mixture was heated at 70° C. for 30 min under N$_2$ atmosphere. Then the mixture was diluted by water (300 mL) and filtered. The solid was washed by water (100 mL), then dried to afford the crude product (14 g, 102% yield) as a yellow solid which was used for next step without further purification. LCMS: m/z (ESI), [M+H]$^+$=224.3.

Step 2. Preparation of 4-(4-fluorophenyl)-6-hydrazineylpyrimidin-2-amine

To a mixture of 4-chloro-6-(4-fluorophenyl)pyrimidin-2-amine (600 mg, 2.7 mmol) in 1-butanol (4 mL) was added hydrazine hydrate (2 mL). The resulting mixture was heated at 100° C. for 30 min. Then the mixture was filtered. The solid was washed by 1-butanol (5 mL) and dried to afford 4-(4-fluorophenyl)-6-hydrazineylpyrimidin-2-amine (550 mg, 93% yield) as a white solid. LCMS: m/z (ESI), [M+H]$^+$=220.3.

Step 3. Preparation of N'-(2-amino-6-(4-fluorophenyl)pyrimidin-4-yl)-2-(2,6-difluorophenyl) acetohydrazide To a mixture of 4-(4-fluorophenyl)-6-hydrazineylpyrimidin-2-amine (550 mg, 2.5 mmol) and 2-(2,6-difluorophenyl) acetic acid (450 mg, 2.6 mmol) in DMF (6 mL) was added HATU (1.1 g, 2.9 mmol) and DIEA (500 mg, 3.9 mmol) at 20° C. The resulting mixture was stirred at 20° C. for 10 min. The mixture was purified by C$_{18-40}$ g (MeCN/water=5%-70%) to afford N'-(2-amino-6-(4-fluorophenyl)pyrimidin-4-yl)-2-(2,6-difluorophenyl)acetohydrazide (720 mg, 77% yield) as a yellow solid. LCMS: m/z (ESI), [M+H]$^+$=374.3.

Step 4. Preparation of 2-(2,6-difluorobenzyl)-7-(4-fluorophenyl)-[1,2,4]triazolo[1,5-c]pyrimidin-5-amine A mixture of N'-(2-amino-6-(4-fluorophenyl)pyrimidin-4-yl)-2-(2,6-difluorophenyl) acetohydrazide (700 mg, 1.9 mmol) in POCl$_3$ (10 mL) was heated at 140° C. for 45 min in microwave. Then the mixture was concentrated. The residue was purified by C$_{18-40}$ g (MeCN/water=5%-80%) to afford 4-(4-fluorophenyl)-6-hydrazineylpyrimidin-2-amine (360 mg, 54% yield) as a white solid. LCMS: m/z (ESI), [M+H]$^+$=356.3.

Step 5. Preparation of 8-bromo-2-(2,6-difluorobenzyl)-7-(4-fluorophenyl)-[1,2,4]triazolo[1,5-c]pyrimidin-5-amine To a mixture of 2-(2,6-difluorobenzyl)-7-(4-fluorophenyl)-[1,2,4]triazolo[1,5-c]pyrimidin-5-amine (300 mg, 0.84 mmol) in DMF (10 mL) was added NBS (200 mg, 1.1 mmol). The resulting mixture was stirred at 20° C. for 30 min. Then the mixture was diluted by water and filtered. The solid was purified by C$_{18-40}$ g (MeCN/water=5%-90%) to afford 8-bromo-2-(2,6-difluorobenzyl)-7-(4-fluorophenyl)-[1,2,4]triazolo[1,5-c]pyrimidin-5-amine (320 mg, 87% yield) as a white solid. LCMS: m/z (ESI), [M+H]$^+$=434.1, 436.1.

Step 6. Preparation of 5-(5-amino-2-(2,6-difluorobenzyl)-7-(4-fluorophenyl)-[1,2,4]triazolo[1,5-c]pyrimidin-8-yl)-1-(oxetan-3-yl)pyridin-2(1H)-one (Cmpd. 50)

To a mixture of 8-bromo-2-(2,6-difluorobenzyl)-7-(4-fluorophenyl)-[1,2,4]triazolo[1,5-c]pyrimidin-5-amine (30 mg, 0.069 mmol), 1-(oxetan-3-yl)-5-(4,4,5,5-tetramethyl-1,3,2-dioxaborolan-2-yl)pyridin-2(1H)-one (25 mg, 0.090 mmol), Pd$_2$(dba)$_3$ (5 mg, 0.0055 mmol), Tricyclohexylphosphine (3 mg, 0.011 mmol) and K$_3$PO$_4$ (30 mg, 0.014 mmol) in dioxane (3 mL) was added water (1 mL). The resulting mixture was sealed and heated at 120° C. for 15 min in Microwave. The mixture was filtered and the filtrate was purified by C$_{18-40}$ g (MeCN/water=5%-80%) to afford 5-(5-amino-2-(2,6-difluorobenzyl)-7-(4-fluorophenyl)-[1,2,4]triazolo[1,5-c]pyrimidin-8-yl)-1-(oxetan-3-yl)pyridin-2(1H)-one (Cmpd. 50) (13 mg, 37% yield) as a white solid. LCMS: m/z (ESI), [M+H]$^+$=505.3. $^1$H NMR (500 MHz, DMSO-d$_6$) δ ppm 4.56 (t, J=6.94 Hz, 2H) 4.72 (s, 2H) 4.91-4.95 (m, 2H) 5.59 (quin, J=7.01 Hz, 1H) 6.42 (d, J=9.46 Hz, 1H) 6.99 (br t, J=8.04 Hz, 2H) 7.11-7.19 (m, 2H) 7.31-7.37 (m, 1H) 7.52 (dd, J=9.46, 2.21 Hz, 1H) 7.57 (br dd, J=8.51, 5.36 Hz, 2H) 7.72-7.78 (m, 1H).

Compound listed in the table below was prepared using methods described in Example 50.

| Example/ Compound number | Structure | LCMS [M + H]+ | 1H NMR |
|---|---|---|---|
| 52 | 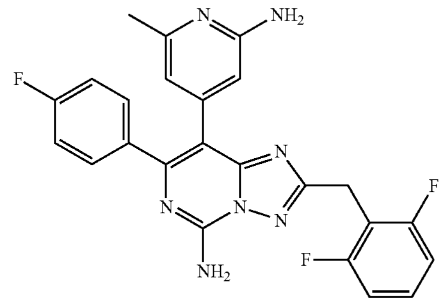 [SMILES: Cc1cc(-c2c(-c3ccc(F)cc3)nc(N)n3nc(Cc4c(F)cccc4F)nc23)cc(N)n1] | 462.3 | 1H NMR (500 MHz, DMSO-d6) δ 2.05 (s, 3 H) 4.15 (s, 2 H) 5.70 (s, 2 H) 6.09 (s, 2 H) 7.00-7.10 (m, 4H) 7.28-7.39 (m, 3 H) 7.85 (br s, 1H) |

Example 55

Preparation of 5-(5-amino-7-(4-fluorophenyl)-2-((3-fluoropyridin-2-yl)methyl)-[1,2,4]triazolo[1,5-c]pyrimidin-8-yl)-1-isopropylpyridin-2(1H)-one (Cmpd. 55)

SCHEME 32

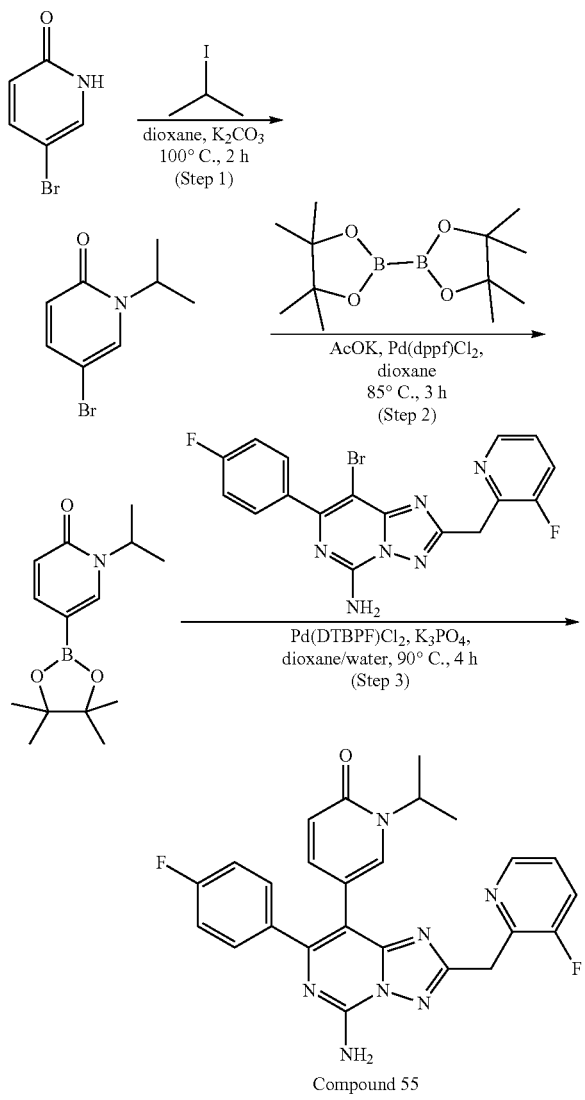

Compound 55

Step 1. 5-bromo-1-isopropylpyridin-2(1H)-one

Into a 40 mL sealed tube were added 5-bromo-1,2-dihydropyridin-2-one (1 g, 5.74 mmol, 1 equiv), 2-iodopropane (1.95 g, 11.48 mmol, 2.00 equiv) and $K_2CO_3$ (2.38 g, 17.22 mmol, 3.00 equiv) in 1,4-dioxane (25 mL) at 80° C. for 2 hours. The resulting mixture was concentrated under reduced pressure. The residue was purified by silica gel column chromatography, eluted with PE/EtOAc (5:1) to afford 5-bromo-1-(propan-2-yl)-1,2-dihydropyridin-2-one (1 g, 80.53%) as a white solid.

Step 2. 1-isopropyl-5-(4,4,5,5-tetramethyl-1,3,2-dioxaborolan-2-yl)pyridin-2(1H)-one Into a 50 mL 3-necked round-bottom flask were added 5-bromo-1-(propan-2-yl)-1,2-dihydropyridin-2-one (1 g, 4.63 mmol, 1 equiv), 4,4,5,5-tetramethyl-2-(4,4,5,5-tetramethyl-1,3,2-dioxaborolan-2-yl)-1,3,2-dioxaborolane (1.76 g, 6.94 mmol, 1.50 equiv), AcOK (0.91 g, 9.26 mmol, 2 equiv) and $Pd(dppf)Cl_2$ $CH_2Cl_2$ (0.38 g, 0.463 mmol, 0.1 equiv) in 1,4-dioxane (10 mL) at 85° C. for 3 hours. The resulting mixture was concentrated under reduced pressure. The residue was purified by silica gel column chromatography, eluted with PE/EtOAc (5:1) to afford 1-(propan-2-yl)-5-(4,4,5,5-tetramethyl-1,3,2-dioxaborolan-2-yl)-1,2-dihydropyridin-2-one (0.9 g, 73.90%) as a white solid.

Step 3. 5-(5-amino-7-(4-fluorophenyl)-2-((3-fluoropyridin-2-yl)methyl)-[1,2,4]triazolo[1,5-c]pyrimidin-8-yl)-1-isopropylpyridin-2(1H)-one (Cmpd. 55)

Into a 100 mL round-bottom flask were added 8-bromo-7-(4-fluorophenyl)-2-((3-fluoropyridin-2-yl)methyl)-[1,2,4]triazolo[1,5-c]pyrimidin-5-amine (500 mg, 1.19 mmol, 1 equiv), 1-(propan-2-yl)-5-(4,4,5,5-tetramethyl-1,3,2-dioxaborolan-2-yl)-1,2-dihydropyridin-2-one (630 mg, 2.395 mmol, 2.00 equiv), $Pd(DtBPF)Cl_2$ (775 mg, 0.119 mmol, 0.10 equiv) and $K_3PO_4$ (762.5 mg, 3.59 mmol, 3.00 equiv) in 1,4-dioxane (12.5 mL) and water (2 mL) at 90° C. for 6 hours under nitrogen atmosphere. Desired product could be detected by LCMS. The resulting mixture was concentrated under reduced pressure. The residue was purified by silica gel column chromatography, eluted with $CH_2Cl_2$/MeOH (20:1) to afford crude product 450 mg. It was dissolved in DCM/EtOH (1/1, 10 mL), then DCM was removed under reduced pressure, the precipitated solids were collected by filtration and washed with EtOH (2×5 mL), to afford 5-(5-amino-7-(4-fluorophenyl)-2-((3-fluoropyridin-2-yl)methyl)-[1,2,4]triazolo[1,5-c]pyrimidin-8-yl)-1-isopropylpyridin-2(1H)-one (Cmpd. 55) (350 mg, 61%) as a white solid. LCMS: m/z (ESI), [M+H]⁺=474.2. ¹H NMR (400 MHz, DMSO-d₆) δ 0.9 (d, J=6.8 Hz, 6H), 4.4 (d, J=2.1 Hz, 2H), 4.9 (p, J=6.8 Hz, 1H), 6.3 (d, J=9.3 Hz, 1H), 7.1-7.2 (m, 2H), 7.3 (dd, J=9.3, 2.5 Hz, 1H), 7.3-7.5 (m, 4H), 7.71 (ddd, J=9.8, 8.3, 1.3 Hz, 1H), 7.97 (s, 2H), 8.3 (dt, J=4.7, 1.6 Hz, 1H).

Example 58

Preparation of 5-[5-amino-7-(4-fluorophenyl)-2-[(1,3-thiazol-4-yl)methyl]-[1,2,4]triazolo[1,5-c]pyrimidin-8-yl]-1-methyl-1,2-dihydropyridin-2-one (Cmpd. 58)

SCHEME 33

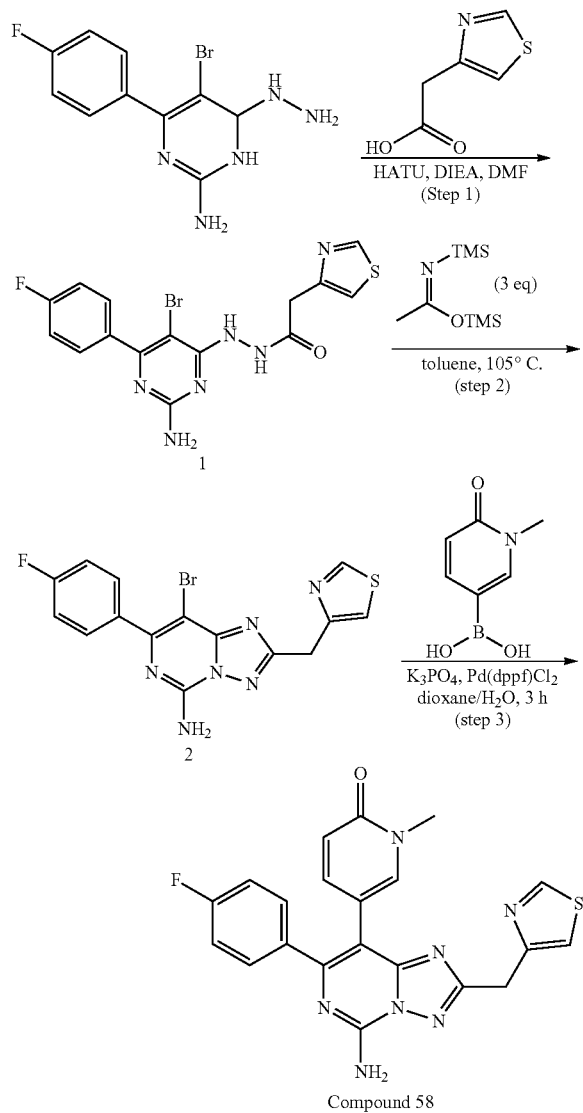

Step 1. Preparation of N-[2-amino-5-bromo-6-(4-fluorophenyl)-3,4-dihydropyrimidin-4-yl]-2-(1,3-thiazol-4-yl)acetohydrazide Into a 40 mL vial were added 5-bromo-4-(4-fluorophenyl)-6-hydrazinyl-1,6-dihydropyrimidin-2-amine (314.48 mg, 1.048 mmol, 1.50 equiv) and 2-(1,3-thiazol-4-yl)acetic acid (100 mg, 0.699 mmol, 1 equiv), HATU (398.40 mg, 1.048 mmol, 1.50 equiv), DIEA (361.12 mg, 2.794 mmol, 4 equiv), DMF (10 mL) at room temperature. Then the mixture was stirred at 25° C. for 3 hours. The product was precipitated by the addition of water. The precipitated solids were collected by filtration and washed with MeOH (10 mL×3) to afford N-[2-amino-5-bromo-6-(4-fluorophenyl)-3,4-dihydropyrimidin-4-yl]-2-(1,3-thiazol-4-yl)acetohydrazide (140 mg, 47.13%) as a white solid. LCMS: m/z (ESI), [M+H]⁺=425.1.

Step 2. Preparation of 8-bromo-7-(4-fluorophenyl)-2-[(1,3-thiazol-4-yl)methyl]-[1,2,4]triazolo[1,5-c]pyrimidin-5-amine Into a 40 mL vial were added N-[2-amino-5-bromo-6-(4-fluorophenyl)-3,4-dihydropyrimidin-4-yl]-2-(1,3-thiazol-4-yl)acetohydrazide (110 mg, 0.259 mmol, 1 equiv) and (Z)-(trimethylsilyl N-(trimethylsilyl)ethanimidate) (157.85 mg, 0.776 mmol, 3.00 equiv), toluene (5 mL) at room temperature. Then the mixture was stirred at 105° C. for 15 hours. The resulting mixture was concentrated under vacuum. The residue was purified by Prep-TLC (CH₂Cl₂/MeOH 12:1) to afford 8-bromo-7-(4-fluorophenyl)-2-[(1,3-thiazol-4-yl)methyl]-[1,2,4]triazolo[1,5-c]pyrimidin-5-amine (50 mg, 47.7%) as a white solid. LCMS: m/z (ESI), [M+H]⁺=407.1.

Step 3. Preparation of 5-[5-amino-7-(4-fluorophenyl)-2-[(1,3-thiazol-4-yl)methyl]-[1,2,4]triazolo[1,5-c]pyrimidin-8-yl]-1-methyl-1,2-dihydropyridin-2-one (Cmpd. 58)

Into a 10 mL vial were added 8-bromo-7-(4-fluorophenyl)-2-[(1,3-thiazol-4-yl)methyl]-[1,2,4]triazolo[1,5-c]pyrimidin-5-amine (40 mg, 0.10 mmol, 1 equiv) and (1-methyl-6-oxo-1,6-dihydropyridin-3-yl)boronic acid (22.6 mg, 0.15 mmol, 1.5 equiv), Pd(dppf)Cl₂ (14.4 mg, 0.02 mmol, 0.2 equiv), K₃PO₄ (41.9 mg, 0.20 mmol, 2 equiv), dioxane (1 mL), H₂O (0.2 mL) at room temperature. Then the mixture was stirred at 100° C. under nitrogen atmosphere for 3 h. The resulting mixture was extracted with EtOAc (20 mL×3). The combined organic layers were washed with brine (10 mL×3), dried over anhydrous Na₂SO₄. After filtration, the filtrate was concentrated under reduced pressure. The residue/crude product was purified by reverse phase flash with the following conditions (column, C18 silica gel; mobile phase, MeOH in water, 10% to 50% gradient in 10 min; detector, UV 254 nm) to afford 5-[5-amino-7-(4-fluorophenyl)-2-[(1,3-thiazol-4-yl)methyl]-[1,2,4]triazolo[1,5-c]pyrimidin-8-yl]-1-methyl-1,2-dihydropyridin-2-one (Cmpd. 58) (10 mg, 23.37%) as an off-white solid. LCMS: m/z (ESI), [M+H]⁺=434.2, ¹H NMR (300 MHz, Methanol-d₄) δ 3.56 (s, 3H), 4.46 (d, J=1.0 Hz, 2H), 6.43 (d, J=9.3 Hz, 1H), 7.02-7.14 (m, 2H), 7.19 (dd, J=9.3, 2.5 Hz, 1H), 7.46-7.61 (m, 3H), 7.79 (d, J=2.5 Hz, 1H), 9.01 (d, J=2.0 Hz, 1H).

Example 60

Preparation of 5-(5-amino-2-(2,6-difluorobenzyl)-7-(4-fluorophenyl)-[1,2,4]triazolo[1,5-c]pyrimidin-8-yl)-1-(1,1-dioxidothietan-3-yl)pyridin-2(1H)-one (Cmpd. 60)

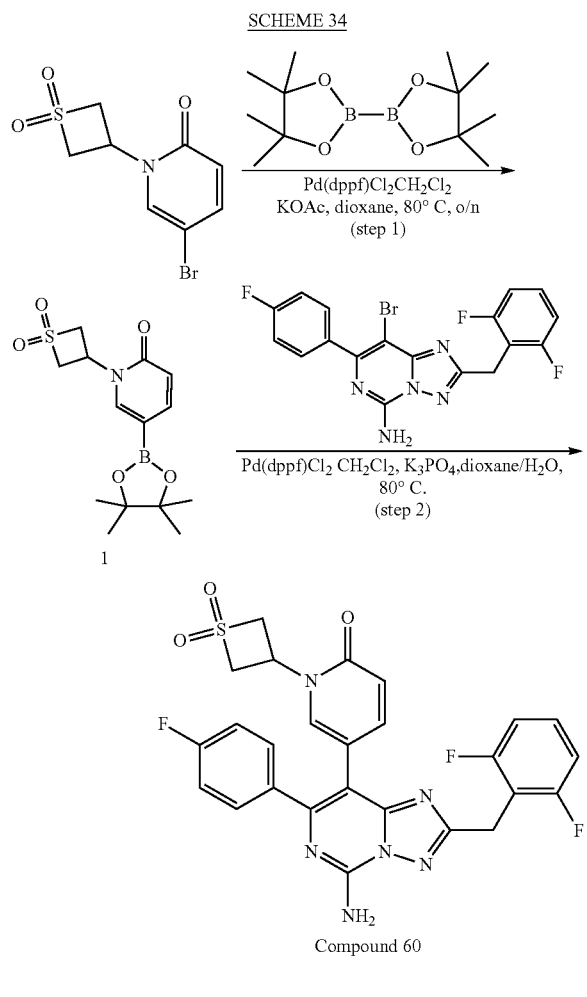

Compound 60

Step 1. 1-(1,1-dioxidothietan-3-yl)-5-(4,4,5,5-tetramethyl-1,3,2-dioxaborolan-2-yl) pyridin-2(1H)-one To a stirred mixture of 3-(5-bromo-2-oxo-1,2-dihydropyridin-1-yl)-1lambda6-thietane-1,1-dione (800 mg, 2.876 mmol, 1 equiv) and 4,4,5,5-tetramethyl-2-(4,4,5,5-tetramethyl-1,3,2-dioxaborolan-2-yl)-1,3,2-dioxaborolane (876.54 mg, 3.452 mmol, 1.2 equiv) in dioxane (20 mL) was added Pd(dppf)Cl$_2$ (234.90 mg, 0.288 mmol, 0.1 equiv) at room temperature under nitrogen atmosphere. The resulting mixture was stirred for 3 hours at 80° C. under nitrogen atmosphere. The residue was purified by Prep-TLC (PE/EtOAc=12:1) to afford 3-[2-oxo-5-(4, 4, 5, 5-tetramethyl-1,3,2-dioxaborolan-2-yl)-1,2-dihydropyridin-1-yl]-1lambda6-thietane-1,1-dion e (380 mg, 40.62%) as an off-white solid. LCMS: m/z (ESI), [M+H]$^+$=326.2.

Step 2. 5-(5-amino-2-(2,6-difluorobenzyl)-7-(4-fluorophenyl)-[1,2,4]triazolo[1,5-c]pyrimidin-8-yl)-1-(1,1-dioxidothietan-3-yl)pyridin-2(1H)-one (Cmpd. 60)

To a stirred solution of 8-bromo-2-[(2,6-difluorophenyl)methyl]-7-(4-fluorophenyl)-[1,2,4]triazolo[1,5-c]pyrimidin-5-amine (80 mg, 0.18 mmol, 1 equiv) and 3-[2-oxo-5-(4,4,5,5-tetramethyl-1,3,2-dioxaborolan-2-yl)-1,2-dihydropyridin-1-yl]-1lambda6-thietane-1, 1-dione (119.8 mg, 0.37 mmol, 2 equiv) in dioxane (6 mL) and H$_2$O (1 mL) were added Pd(dppf)Cl$_2$ (15.0 mg, 0.02 mmol, 0.1 equiv) and K$_3$PO$_4$ (117.3 mg, 0.55 mmol, 3 equiv) at room temperature under nitrogen atmosphere. The resulting mixture was stirred for 3 hours at 80° C. under nitrogen atmosphere. The resulting mixture was extracted with EtOAc (5×20 mL). The combined organic layers were dried over anhydrous Na$_2$SO$_4$. After filtration, the filtrate was concentrated under reduced pressure. The crude product was purified by Prep-HPLC with the following conditions (Column: X Bridge Prep OBD C18 Column 30×150 mm 5 μm; Mobile Phase A: Water (0.05% NH$_3$H$_2$O), Mobile Phase B: ACN; Flow rate: 60 mL/min; Gradient: 31% B to 46% B in 7 min; 254/220 nm; t$_R$=6.80 min) to afford 5-(5-amino-2-(2,6-difluorobenzyl)-7-(4-fluorophenyl)-[1,2,4]triazolo[1,5-c]pyrimidin-8-yl)-1-(1,1-dioxidothietan-3-yl)pyridin-2(1H)-one (Cmpd. 60) (18 mg, 17.68%) as an off-white solid. LCMS: m/z (ESI), [M+H]$^+$=553.1. $^1$H NMR (300 MHz, DMSO-d$_6$) δ: 3.72 (s, 1H), 4.23 (s, 4H), 4.67 (s, 2H), 5.52 (s, 1H), 6.31 (d, J=9.5 Hz, 1H), 7.14 (dt, J=26.8, 8.7 Hz, 4H), 7.44 (d, J=38.9 Hz, 3H), 7.94 (d, J=41.8 Hz, 3H).

Example 63

Preparation of 5-[5-amino-2-[(3-fluoropyridin-2-yl)methyl]-7-(1H-pyrazol-1-yl)-[1,2,4]triazolo[1,5-c]pyrimidin-8-yl]-1-methyl-1,2-dihydropyridin-2-one (Cmpd. 63)

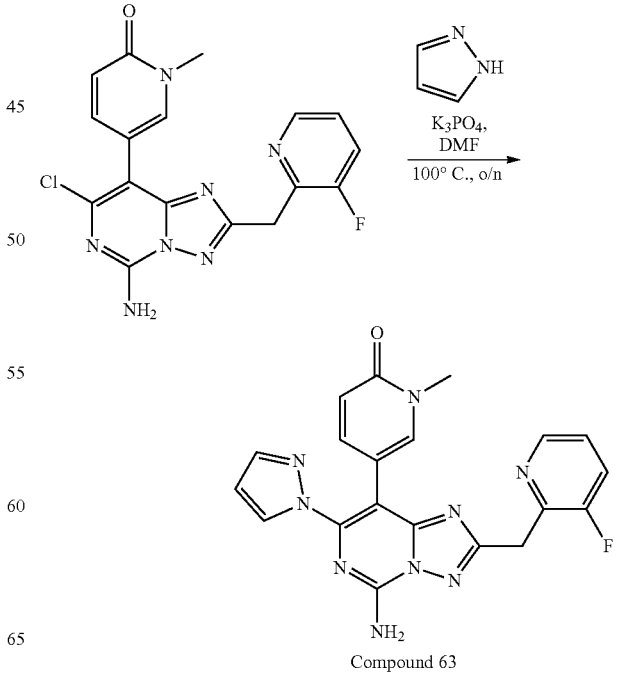

Compound 63

183

Step 1. 5-[5-amino-2-[(3-fluoropyridin-2-yl)methyl]-7-(1H-pyrazol-1-yl)-[1,2,4]triazolo[1,5-c]pyrimidin-8-yl]-1-methyl-1,2-dihydropyridin-2-one (Cmpd. 63)

To a stirred mixture of 5-[5-amino-7-chloro-2-[(3-fluoropyridin-2-yl)methyl]-[1,2,4]triazolo[1,5-c]pyrimidin-8-yl]-1-methyl-1,2-dihydropyridin-2-one (100 mg, 0.3 mmol) and 1H-pyrazole (35.3 mg, 0.5 mmol) in DMF (2 mL) was added $K_3PO_4$ (165.1 mg, 0.8 mmol) in portions at room temperature under nitrogen atmosphere. The resulting mixture was stirred for 3 days at 100° C. under nitrogen atmosphere. The resulting mixture was concentrated under reduced pressure. The crude product (70 mg) was purified by Prep-HPLC with the following conditions (Column: Atlantis Prep T3 OBD Column, 19*250 mm 10 μm; Mobile Phase A: Water (0.05% TFA), Mobile Phase B: ACN; Flow rate: 20 mL/min; Gradient: 16% B to 16% B in 10 min; 254/220 nm; Rt: 8.22 min) to afford 5-[5-amino-2-[(3-fluoropyridin-2-yl)methyl]-7-(1H-pyrazol-1-yl)-[1,2,4]triazolo[1,5-c]pyrimidin-8-yl]-1-methyl-1,2-dihydropyridin-2-one (Cmpd. 63) (15 mg, 13.8%) as an off-white solid. LCMS: m/z (ESI), [M+H]$^+$=418.2. $^1$H NMR (300 MHz, Methanol-$d_4$) δ: 3.57 (s, 3H), 4.44-4.53 (m, 1H), 6.40-6.50 (m, 2H), 7.12 (dd, J=9.3, 2.5 Hz, 1H), 7.43 (dt, J=8.7, 4.5 Hz, 1H), 7.60 (d, J=1.2 Hz, 1H), 7.68 (t, J=9.0 Hz, 1H), 7.77 (d, J=2.4 Hz, 1H), 8.22 (d, J=2.6 Hz, 1H), 8.33 (d, J=4.8 Hz, 1H).

Example 65

Preparation of 5-(5-amino-2-(2,6-difluorobenzyl)-7-(4-fluorophenyl)-[1,2,4]triazolo[1,5-c]pyrimidin-8-yl)-1-(2-hydroxyethyl)pyridin-2(1H)-one (Cmpd. 65)

184

Step 1. 1-(2-hydroxyethyl)-5-(4,4,5,5-tetramethyl-1,3,2-dioxaborolan-2-yl)pyridin-2(1H)-one 4,4,5,5-tetramethyl-2-(4,4,5,5-tetramethyl-1,3,2-dioxaborolan-2-yl)-1,3,2-dioxaborolane) (4.37 g, 17.2 mmol, 1.50 equiv), 5-bromo-1-(2-hydroxyethyl)-1,2-dihydropyridin-2-one) (2.5 g, 11.465 mmol, 1 equiv), KOAc (2.25 g, 22.9 mmol, 2 equiv), Pd(dppf)Cl$_2$ (1.68 g, 2.3 mmol, 0.2 equiv) were dissolved in 30 mL of 1,4-dioxane/H$_2$O (10:1). The mixture was stirred at 90° C. for 3 hours. LCMS showed the reaction was completed. The crude product was purified by silica gel column and eluting with MeOH-DCM (1:10) and the product was further purified by TLC to give 1-(2-hydroxyethyl)-5-(4,4,5,5-tetramethyl-1,3,2-dioxaborolan-2-yl)-1,2-dihydropyridin-2-on e (600.0 mg, 19.74%) as a white solid. LCMS: m/z (ESI), [M+H]$^+$=266.3.

Step 2. 5-(5-amino-2-(2,6-difluorobenzyl)-7-(4-fluorophenyl)-[1,2,4]triazolo[1,5-c]pyrimidin-8-yl)-1-(2-hydroxyethyl)pyridin-2(1H)-one. (Cmpd. 65)

1-(2-hydroxyethyl)-5-(4,4,5,5-tetramethyl-1,3,2-dioxaborolan-2-yl)-1,2-dihydropyridin-2-one (150 mg, 0.57 mmol, 1 equiv), 8-bromo-2-[(2,6-difluorophenyl)methyl]-7-(4-fluorophenyl)-[1,2,4]triazolo[1,5-c]pyrimidin-5-amine (245.7 mg, 0.57 mmol, 1.00 equiv), Pd(dppf)Cl$_2$ (82.8 mg, 0.11 mmol, 0.2 equiv), K$_3$PO$_4$ (240.2 mg, 1.13 mmol, 2.00 equiv) were dissolved in 4 mL of dioxane/H$_2$O (5:1). The mixture was stirred at 90° C. for 2 hours. LCMS showed the reaction was completed. The crude product was purified by silica gel column and eluting with DCM:CH$_3$OH (10:1) and the product was further purified by prep-HPLC to give

SCHEME 36

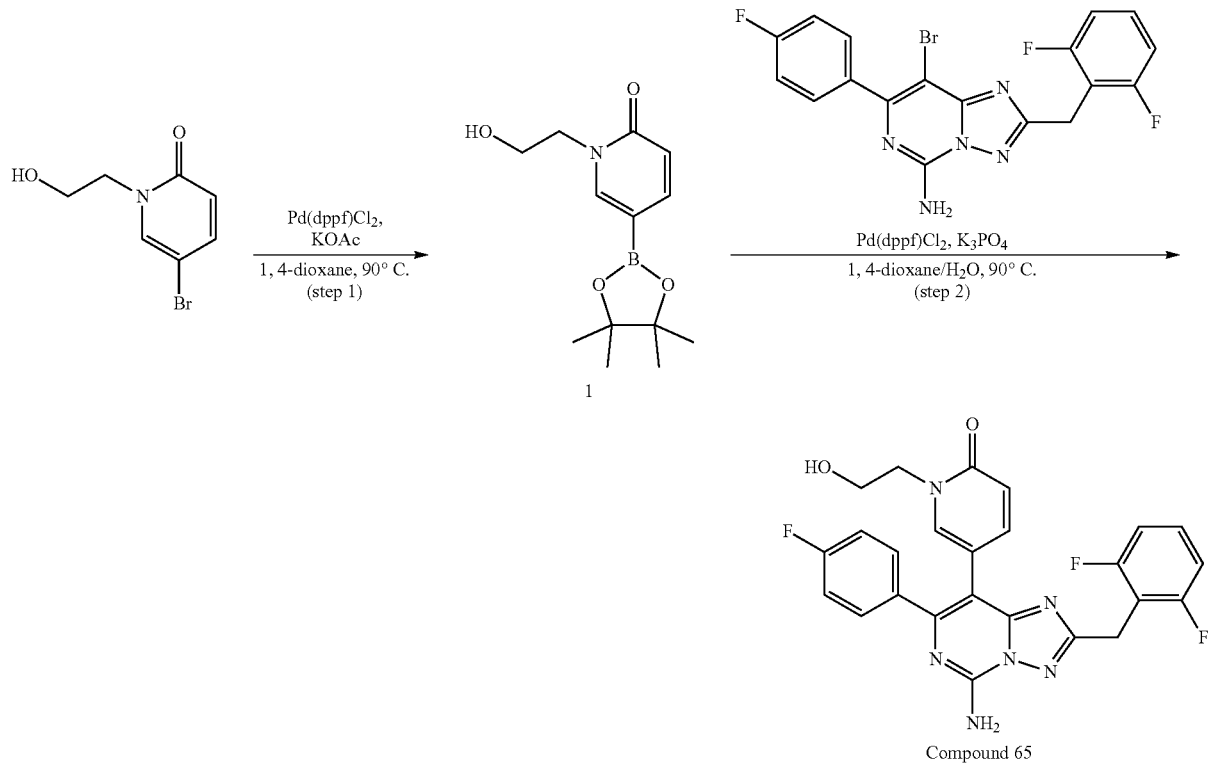

Compound 65

5-(5-amino-2-(2,6-difluorobenzyl)-7-(4-fluorophenyl)-[1,2,4]triazolo[1,5-c]pyrimidin-8-yl)-1-(2-hydroxyethyl)pyridin-2(1H)-one (Cmpd. 65) (16.5 mg, 5.92%) as a white solid. LCMS: m/z (ESI), [M+H]⁺=493.3. ¹H NMR (400 MHz, Methanol-d₄) δ: 3.78 (t, J=5.3 Hz, 2H), 4.06 (t, J=5.3 Hz, 2H), 4.29 (s, 2H), 6.45 (d, J=9.3 Hz, 1H), 6.94-7.07 (m, 4H), 7.08 (d, J=8.8 Hz, 1H), 7.25 (dd, J=9.3, 2.5 Hz, 1H), 7.26-7.40 (m, 1H), 7.54 (dd, J=8.8, 5.4 Hz, 2H), 7.68 (d, J=2.4 Hz, 1H).

Example 66

Preparation of 5-(5-amino-7-(4-fluorophenyl)-2-((3-fluoropyridin-2-yl)methyl)-[1,2,4]triazolo[1,5-c]pyrimidin-8-yl)-1,6-dimethylpyridin-2(1H)-one (Cmpd. 66)

SCHEME 37

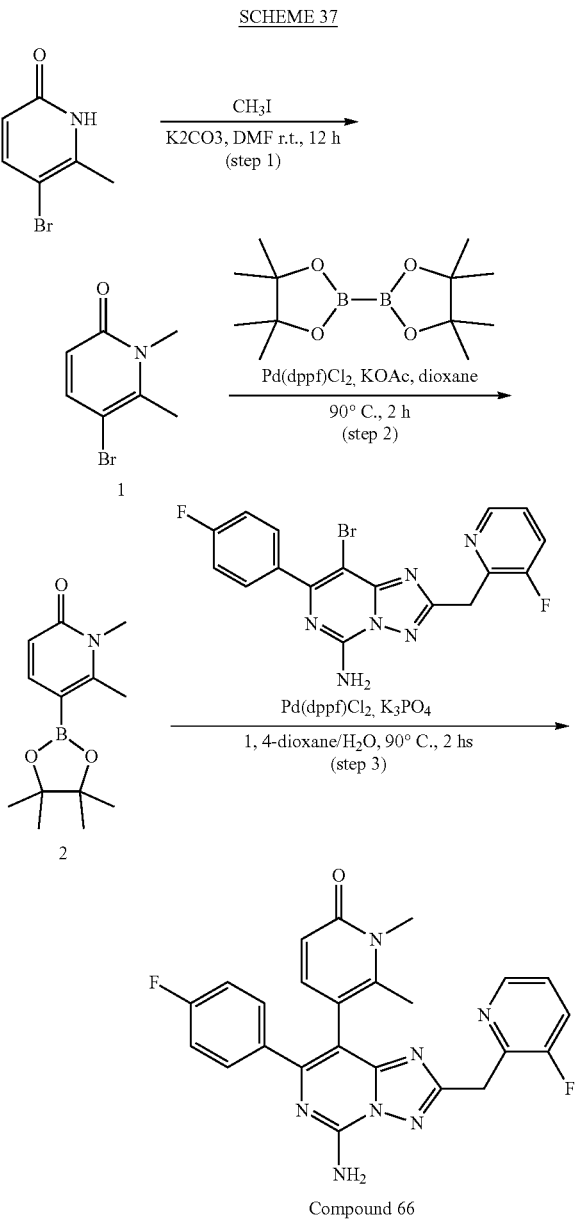

Step 1. 5-bromo-1,6-dimethylpyridin-2(1H)-one 5-bromo-6-methyl-1,2-dihydropyridin-2-one (5 g, 26.592 mmol, 1 equiv), iodomethane (7.55 g, 53.185 mmol, 2.00 equiv), K₂CO₃ (7.35 g, 53.185 mmol, 2.00 equiv) in 10 mL of DMF at room temperature. The mixture was stirred at 80° C. for 2 hours. LCMS showed the reaction was completed. The crude product was purified by silica gel column and eluting with PE:EA=10:1 to afford 5-bromo-1,6-dimethyl-1,2-dihydropyridin-2-one (2.3 g, 42.81%) as a white solid. LCMS: m/z (ESI), [M+H]⁺=202.2.

Step 2. 1,6-dimethyl-5-(4,4,5,5-tetramethyl-1,3,2-dioxaborolan-2-yl)pyridin-2(1H)-one 5-bromo-1,6-dimethyl-1,2-dihydropyridin-2-one (1.5 g, 7.42 mmol, 1 equiv), 4,4,5,5-tetramethyl-2-(4,4,5,5-tetramethyl-1,3,2-dioxaborolan-2-yl)-1,3,2-dioxaborolane (2.26 g, 8.91 mmol, 1 equiv), Pd(dppf)Cl₂(1.09 g, 1.49 mmol, 0.2 equiv), K₃PO₄ (3.15 g, 14.85 mmol, 2 equiv) in 10 mL of DMF at room temperature. The mixture was stirred at 80° C. for 2 hours, LCMS showed the reaction was completed. The crude product was purified by silica gel column and eluting with PE:EA=1:1 to afford 1,6-dimethyl-5-(4,4,5,5-tetramethyl-1,3,2-dioxaborolan-2-yl)-1,2-dihydropyridin-2-one (800 mg, 43.15%) as a white solid. LCMS: m/z (ESI), [M+H]⁺=493.3.

Step 3. 5-(5-amino-7-(4-fluorophenyl)-2-((3-fluoropyridin-2-yl)methyl)-[1,2,4]triazolo[1,5-c]pyrimidin-8-yl)-1,6-dimethylpyridin-2(1H)-one (Cmpd. 66)

1,6-dimethyl-5-(4,4,5,5-tetramethyl-1,3,2-dioxaborolan-2-yl)-1,2-dihydropyridin-2-one (203.0 mg, 0.81 mmol, 1.7 equiv), 8-bromo-7-(4-fluorophenyl)-2-[(3-fluoropyridin-2-yl)methyl]-[1,2,4]triazolo[1,5-c]pyrimidin-5-amine (200 mg, 0.48 mmol, 1 equiv), Pd(AMPHOS)₂Cl₂ (67.9 mg, 0.10 mmol, 0.20 equiv), K₃PO₄ (203.5 mg, 0.96 mmol, 2 equiv) were dissolved in 6 mL of dioxane/H₂O (5:1). The mixture was stirred at 90° C. for 1 hour. LCMS showed the reaction was completed. The crude product was purified by silica gel column and eluting with DCM:CH₃OH (10:1) and the product was further purified by prep-HPLC to give product 5-[5-amino-7-(4-fluorophenyl)-2-[(3-fluoropyridin-2-yl)methyl]-[1,2,4]triazolo[1,5-c]pyrimidin-8-yl]-1,6-dimethyl-1,2-dihydropyridin-2-one (Cmpd. 66) (35.1 mg, 15.94%) as a white solid. LCMS: m/z (ESI), [M+H]⁺=460.3. ¹H NMR (300 MHz, Methanol-d₄) δ: 2.15 (s, 3H), 3.57 (s, 3H), 4.46 (d, J=2.1 Hz, 2H), 6.38 (d, J=9.3 Hz, 1H), 6.99-7.11 (m, 2H), 7.16 (d, J=9.3 Hz, 1H), 7.39 (dt, J=8.6, 4.4 Hz, 1H), 7.44-7.55 (m, 2H), 7.63 (ddd, J=9.7, 8.4, 1.4 Hz, 1H), 8.30 (dt, J=4.8, 1.4 Hz, 1H).

Example 67

Preparation of 5-(5-amino-2-((3,5-difluoropyridin-2-yl)methyl)-7-(4-fluorophenyl)-[1,2,4]triazolo[1,5-c]pyrimidin-8-yl)-1-methylpyridin-2(1H)-one (Cmpd. 67)

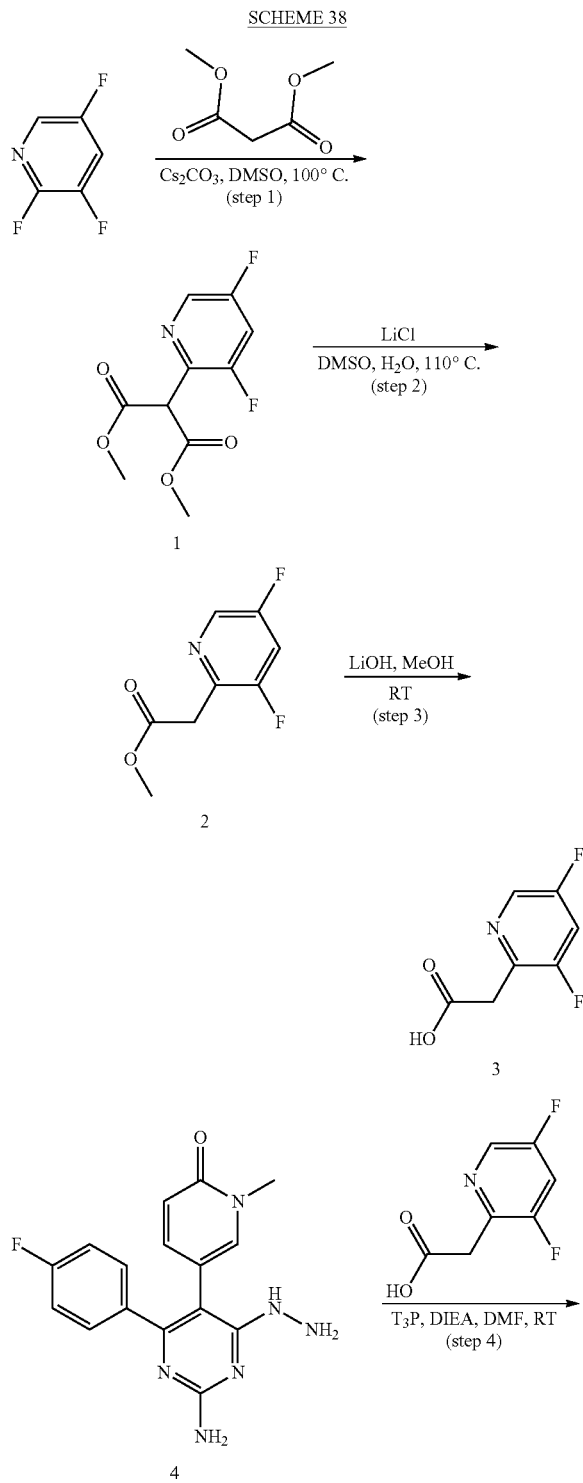

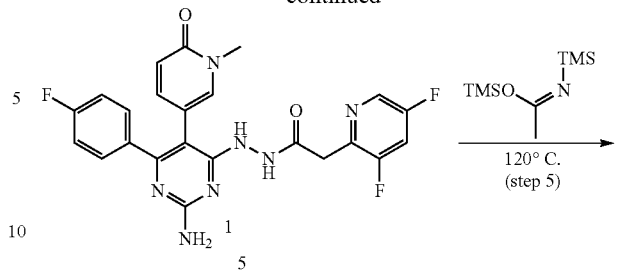

Step 1. 1,3-dimethyl 2-(3,5-difluoropyridin-2-yl)propanedioate

A mixture of 2,3,5-trifluoropyridine (5.0 g, 37.6 mmol, 1.0 equiv) and 1,3-dimethyl propanedioate (7.4 g, 56.0 mmol, 1.5 equiv) and $Cs_2CO_3$ (24.5 g, 75.2 mmol, 2.0 equiv) in DMSO (100.0 mL) was stirred for 10 hours at 100° C. under nitrogen atmosphere. The resulting mixture was extracted with EtOAc (4×50 mL). The combined organic layers were washed with $H_2O$ (3×50 mL), dried over anhydrous $Na_2SO_4$. After filtration, the filtrate was concentrated under reduced pressure. The residue was purified by silica gel column chromatography, eluted with PE/EtOAc (20:1) to afford 1,3-dimethyl 2-(3,5-difluoropyridin-2-yl)propanedioate (8.1 g, 79.13%) as a yellow oil. LCMS: m/z (ESI), $[M+H]^+$=246.2.

Step 2. methyl 2-(3,5-difluoropyridin-2-yl)acetate

A mixture of 1,3-dimethyl 2-(3,5-difluoropyridin-2-yl)propanedioate (8.1 g, 33.0 mmol, 1 equiv) and LiCl (2.8 g, 66.1 mmol, 2.0 equiv) in DMSO (100.0 mL) and $H_2O$ (10.0 mL) was stirred for 10 hours at 110° C. under nitrogen atmosphere. The resulting mixture was extracted with EtOAc (3×100 mL). The combined organic layers were washed with $H_2O$ (4×10 mL), dried over anhydrous $Na_2SO_4$. After filtration, the filtrate was concentrated under reduced pressure. The residue was purified by silica gel column chromatography, eluted with PE/EtOAc (9:1) to afford methyl 2-(3,5-difluoropyridin-2-yl)acetate (3.3 g, 48.04%) as a light yellow oil. LCMS: m/z (ESI), $[M+H]^+$=188.2.

Step 3. 2-(3,5-difluoropyridin-2-yl)acetic acid

A mixture of methyl 2-(3,5-difluoropyridin-2-yl)acetate (3.3 g, 17.6 mmol, 1.0 equiv) and LiGH (0.4 g, 16.7 mmol, 1.0 equiv) in MeOH (30 mL) and $H_2O$ (3.0 mL) was stirred for 6 hours at room temperature under nitrogen atmosphere. The resulting mixture was concentrated under reduced pressure to afford the crude product which was washed with MeCN (10×7 mL). Then dried and obtained 2-(3,5-difluoropyridin-2-yl)acetic acid (3.0 g, 93.4%) as a white solid. LCMS: m/z (ESI), [M+H]⁺=174.2.

Step 4. N-[2-amino-6-(4-fluorophenyl)-5-(1-methyl-6-oxo-1,6-dihydropyridin-3-yl)pyrimidin-4-yl]-2-(3,5-difluoropyridin-2-yl)acetohydrazide A mixture of 5-[2-amino-4-(4-fluorophenyl)-6-hydrazinylpyrimidin-5-yl]-1-methyl-1,2-dihydropyridin-2-one (60 mg, 0.2 mmol, 1 equiv) and 2-(3,5-difluoropyridin-2-yl)acetic acid (63.7 mg, 0.4 mmol, 2.0 equiv) and T3P (117.0 mg, 0.4 mmol, 2.0 equiv) and DIEA (71.3 mg, 0.6 mmol, 3.0 equiv) in DMSO (5.0 mL) was stirred for 1 hour at room temperature under nitrogen atmosphere. The resulting mixture was extracted with CH₂Cl₂ (5×20 mL). The combined organic layers were washed with H₂O (3×5 mL), dried over anhydrous Na₂SO₄. After filtration, the filtrate was concentrated under reduced pressure. The residue was purified by Prep-TLC (CH₂Cl₂/MeOH 20:1) to afford N-[2-amino-6-(4-fluorophenyl)-5-(1-methyl-6-oxo-1,6-dihydropyridin-3-yl)pyrimidin-4-yl]-2-(3,5-difluoropyridin-2-yl)acetohydrazide (80 mg, 89.5%) as a yellow solid. LCMS: m/z (ESI), [M+H]⁺=482.3.

Step 5. 5-[5-amino-2-[(3,5-difluoropyridin-2-yl)methyl]-7-(4-fluorophenyl)-[1,2,4]triazolo[1,5-c]pyrimidin-8-yl]-1-methyl-1,2-dihydropyridin-2-one (Cmpd. 67)

A mixture of N-[2-amino-6-(4-fluorophenyl)-5-(1-methyl-6-oxo-1,6-dihydropyridin-3-yl)pyrimidin-4-yl]-2-(3,5-difluoropyridin-2-yl)acetohydrazide (70.0 mg, 0.2 mmol, 1.0 equiv) and (Z)-(trimethylsilyl N-(trimethylsilyl)ethanimidate) (89.0 mg, 0.4 mmol, 3.0 equiv) was stirred for 2 hours at 120° C. under nitrogen atmosphere. The resulting mixture added into MeOH (20 mL), and filtered, the filter cake was washed with MeOH (5×10 mL). The crude product was purified by Prep-HPLC to afford 5-[5-amino-2-[(3,5-difluoropyridin-2-yl)methyl]-7-(4-fluorophenyl)-[1,2,4]triazolo[1,5-c]pyrimidin-8-yl]-1-methyl-1,2-dihydropyridin-2-one (Cmpd. 67) (18 mg, 26.5%) as a white solid. LCMS: m/z (ESI), [M-t-Bu+H]⁺=464.2. ¹H NMR (400 MHz, DMSO-d₆) δ 4.28 (s, 1H), 6.30 (d, J=9.3 Hz, 1H), 7.11 (dd, J=9.3, 2.6 Hz, 1H), 7.16-7.27 (m, 1H), 7.41-7.52 (m, 1H), 7.70 (d, J=2.6 Hz, 1H), 8.00 (td, J=7.9, 3.1 Hz, 2H), 8.18 (dd, J=3.0, 1.9 Hz, 1H).

Example 68

Preparation of 7-(4-fluorophenyl)-8-[imidazo[1,2-a]pyridin-6-yl]-2-[(2-methyl-1,3-thiazol-4-yl)methyl]-[1,2,4]triazolo[1,5-c]pyrimidin-5-amine (Cmpd. 68)

SCHEME 39

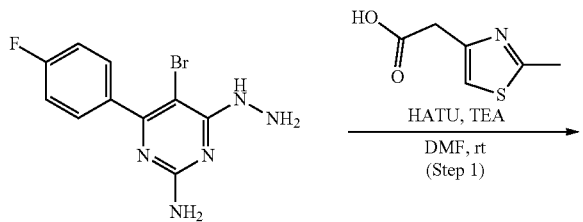

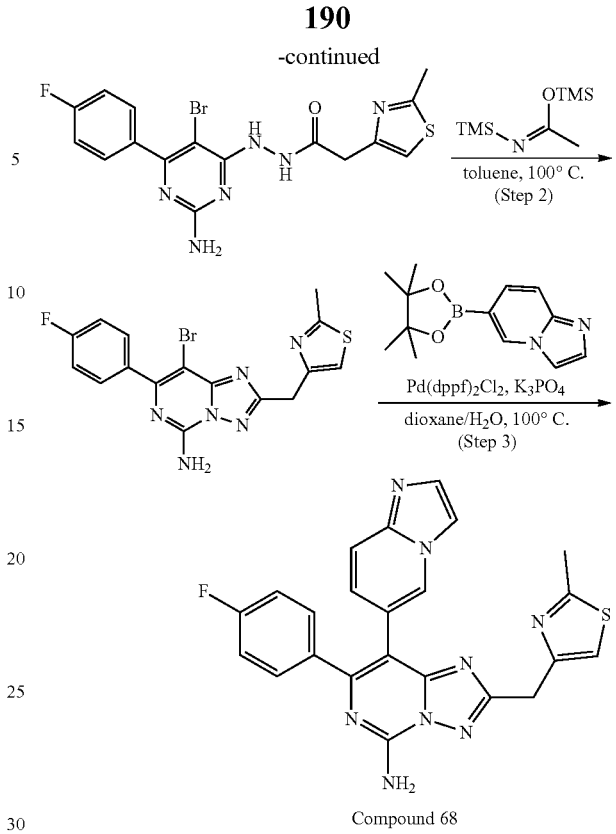

Compound 68

Step 1. N-[2-amino-5-bromo-6-(4-fluorophenyl)pyrimidin-4-yl]-2-(2-methyl-1,3-thiazol-4-yl)acetohydrazide To a stirred mixture of 5-bromo-4-(4-fluorophenyl)-6-hydrazinylpyrimidin-2-amine (200 mg, 0.7 mmol) and 2-(2-methyl-1,3-thiazol-4-yl)acetic acid (126.5 mg, 0.8 mmol) in DMF (5 mL) were added HATU (382.6 mg, 1.0 mmol, 1.5 equiv) and DIEA (260.1 mg, 2.0 mmol) in portions at room temperature under nitrogen atmosphere. The resulting mixture was stirred for 3 hours at room temperature under nitrogen atmosphere. The reaction was quenched with water at room temperature. The precipitated solids were collected by filtration and washed with water (3×20 mL). To afford N-[2-amino-5-bromo-6-(4-fluorophenyl)pyrimidin-4-yl]-2-(2-methyl-1,3-thiazol-4-yl)acetohydrazide (130 mg, 44.3%) as a grey solid. LCMS: m/z (ESI), [M+H]⁺=437.0.

Step 2. 1-[5-amino-8-bromo-7-(4-fluorophenyl)-[1,2,4]triazolo[1,5-c]pyrimidin-2-yl]-2-(2-methyl-1,3-thiazol-4-yl)ethan-1-one To a stirred mixture of N-[2-amino-5-bromo-6-(4-fluorophenyl)pyrimidin-4-yl]-2-(2-methyl-1,3-thiazol-4-yl)acetohydrazide (130 mg, 0.3 mmol) and (E)-(trimethylsilyl N-(trimethylsilyl)ethanimidate) (151.2 mg, 0.7 mmol) in toluene (3 mL). The resulting mixture was stirred for 3 hours at room temperature under nitrogen atmosphere. The reaction was quenched with water at room temperature. The precipitated solids were collected by filtration and washed with water (3×20 mL). To afford 1-[5-amino-8-bromo-7-(4-fluorophenyl)-[1,2,4]triazolo[1,5-c]pyrimidin-2-yl]-2-(2-methyl-1, 3-thiazol-4-yl)ethan-1-one (100 mg, 75.2%) as a light yellow solid. LCMS: m/z (ESI), [M+H]⁺=418.0.

Step 3. 7-(4-fluorophenyl)-8-[imidazo[1,2-a]pyridin-6-yl]-2-[(2-methyl-1,3-thiazol-4-yl)methyl]-[1,2,4]triazolo[1,5-c]pyrimidin-5-amine (Cmpd. 68)

To a stirred mixture of 8-bromo-7-(4-fluorophenyl)-2-[(2-methyl-1,3-thiazol-4-yl)methyl]-[1,2,4]triazolo[1,5-c]pyrimidin-5-amine (80 mg, 0.2 mmol) and 6-(4,4,5,5-tetramethyl-1,3,2-dioxaborolan-2-yl)imidazo[1,2-a]pyridine (93.2 mg, 0.4 mmol) in 1,4-dioxane (3 mL) and H$_2$O (0.6 mL) were added K$_3$PO$_4$ (127.2 mg, 0.6 mmol) and Pd(dppf)Cl$_2$ (27.9 mg, 0.04 mmol, 0.2 equiv) in portions at room temperature under nitrogen atmosphere. The resulting mixture was stirred for 3 hours at 100° C. under nitrogen atmosphere. The resulting mixture was concentrated under vacuum. The residue was purified by Column: XBridge Shield RP18 OBD Column, 5 μm, 19*150 mm; Mobile Phase A: Water (10 mmol/L NH$_4$HCO$_3$), Mobile Phase B: ACN; Flow rate: 20 mL/min; Gradient: 25% B to 35% B in 8 min; 254/220 nm; Rt: 6.45 min to afford 7-(4-fluorophenyl)-8-[imidazo[1,2-a]pyridin-6-yl]-2-[(2-methyl-1,3-thiazol-4-yl)methyl]-[1,2,4]triazolo[1,5-c]pyrimidin-5-amine (Cmpd. 68) (5 mg, 5.7%) as an off-white solid. LCMS: m/z (ESI), [M+H]$^+$=457.2. $^1$H NMR (300 MHz, Methanol-d$_4$) δ: 2.66 (s, 3H), 4.34 (s, 2H), 7.04 (t, J=8.7 Hz, 2H), 7.21 (s, 1H), 7.52 (dd, J=8.7, 5.4 Hz, 2H), 7.63 (d, J=9.7 Hz, 1H), 7.78 (d, J=9.3 Hz, 1H), 8.05 (d, J=2.1 Hz, 1H), 8.20 (s, 1H), 8.96 (s, 1H).

Example 71

Preparation of 5-(5-amino-2-[[3-(difluoromethoxy)pyridin-2-yl]methyl]-7-(1,3-oxazol-2-yl)-[1,2,4]triazolo[1,5-c]pyrimidin-8-yl)-1-methyl-1,2-dihydropyridin-2-one (Cmpd. 71)

SCHEME 40

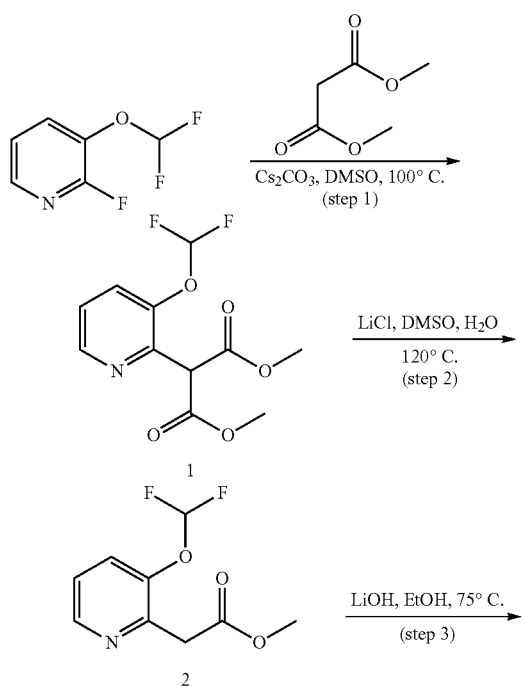

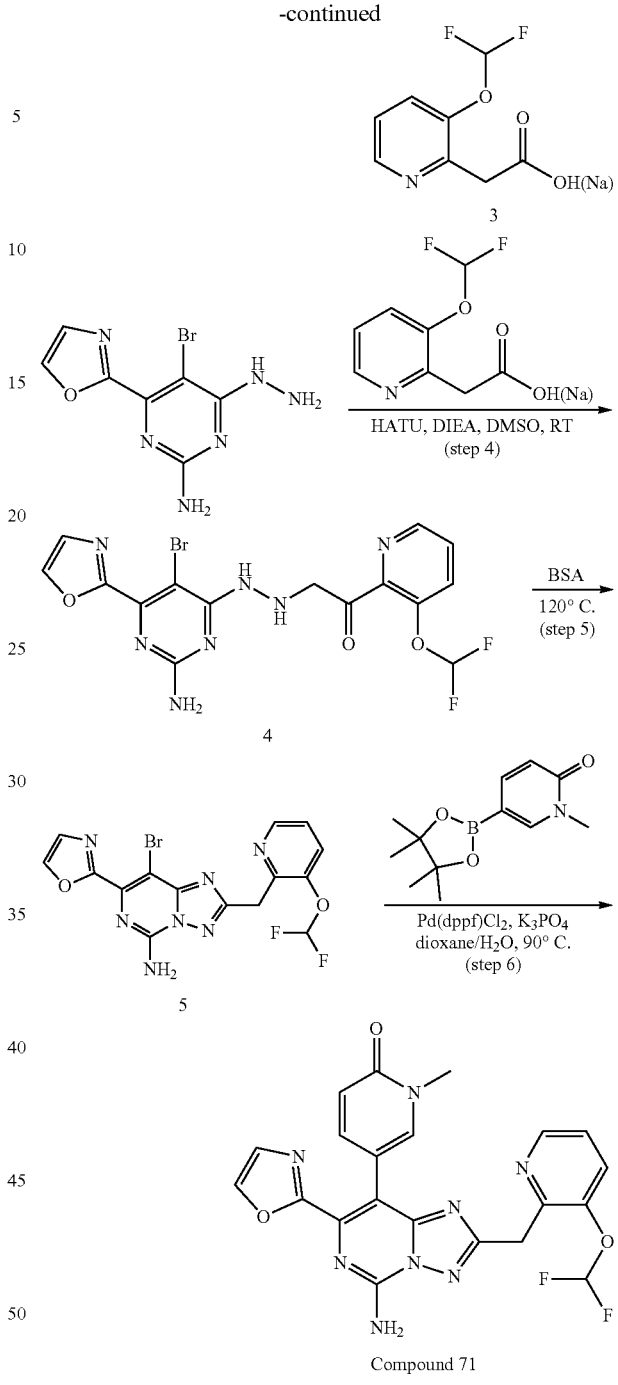

Compound 71

Step 1. 1,3-dimethyl 2-[3-(difluoromethoxy)pyridin-2-yl]propanedioate

A mixture of 3-(difluoromethoxy)-2-fluoropyridine (20 g, 122.6 mmol, 1 equiv) and 1,3-dimethyl propanedioate (24.3 g, 183.9 mmol, 1.5 equiv) and Cs$_2$CO$_3$ (79.9 g, 245.3 mmol, 2.0 equiv) in DMSO (200.0 mL) was stirred for 10 hours at 100° C. under nitrogen atmosphere. The reaction was quenched with H$_2$O (300.0 mL) at room temperature. The resulting mixture was extracted with EA (3×200 mL). The combined organic layers were washed with H$_2$O (2×200 mL), dried over anhydrous Na$_2$SO$_4$. After filtration, the filtrate was concentrated under reduced pressure. The residue was purified by silica gel column chromatography, eluted with (PE:EtOAc=9:1) to afford 1,3-dimethyl 2-[3-(difluoromethoxy)pyridin-2-yl]propanedioate (27.3 g, 72.8%) as a yellow oil. LCMS: m/z (ESI), [M+H]⁺=276.2.

Step 2. methyl 2-[3-(difluoromethoxy)pyridin-2-yl]acetate

A mixture of 1,3-dimethyl 2-[3-(difluoromethoxy)pyridin-2-yl]propanedioate (27.3 g, 99.2 mmol, 1 equiv) and LiCl (8.4 g, 198.1 mmol, 2.0 equiv) in DMSO (250.0 mL) and H₂O (25 mL) was stirred for 10 hours at 110° C. under nitrogen atmosphere. The reaction was quenched with H₂O (300.0 mL) at room temperature. The resulting mixture was extracted with EA (3×250 mL). The combined organic layers were washed with H₂O (2×250 mL), dried over anhydrous Na₂SO₄. After filtration, the filtrate was concentrated under reduced pressure. The residue was purified by silica gel column chromatography, eluted with (PE:EtOAc=20:1) to afford methyl 2-(3-(difluoromethoxy)pyridin-2-yl)acetate (14.5 g, 67.4%) as a yellow oil. LCMS: m/z (ESI), [M+H]⁺=218.2.

Step 3. sodium 2-[3-(difluoromethoxy)pyridin-2-yl]acetate

A mixture of methyl 2-[3-(difluoromethoxy)pyridin-2-yl]acetate (5.0 g, 23.0 mmol, 1 equiv) and LiGH (0.6 g, 25.1 mmol, 1.1 equiv) in MeOH (50.0 mL) and H₂O (5.0 mL) was stirred for 6 hours at room temperature under nitrogen atmosphere. The mixture was acidified to PH=5 with HCl aq (1.1 eq). The resulting mixture was concentrated under vacuum. The residue was redissolved with CH₃CN (100.0 mL). After filtration, the filtrate was concentrated under reduced pressure to afford 2-[3-(difluoromethoxy)pyridin-2-yl]acetic acid (3.0 g, 59.0%) as a white solid. LCMS: m/z (ESI), [M+H]⁺=204.2.

Step 4. 2-[2-[2-amino-5-bromo-6-(1,3-oxazol-2-yl)pyrimidin-4-yl]hydrazin-1-yl]-1-[3-(difluoromethoxy)pyridin-2-yl]ethan-1-one A mixture of 2-[3-(difluoromethoxy)pyridin-2-yl]acetic acid (899.3 mg, 4.4 mmol, 2.0 equiv) and HATU (1683.2 mg, 4.4 mmol, 2.0 equiv) in DMSO (20.0 mL) was stirred for 10 min, then the 5-bromo-4-hydrazinyl-6-(1,3-oxazol-2-yl)pyrimidin-2-amine (600 mg, 2.2 mmol, 1.0 equiv) and DIEA (858.2 mg, 6.6 mmol, 3.0 equiv) were added, and stirred for 1 hour at room temperature under nitrogen atmosphere. The resulting mixture added into H₂O (50 mL), and filtered, the filter cake was washed with H₂O (2×10 mL). This resulted in 2-[2-[2-amino-5-bromo-6-(1,3-oxazol-2-yl)pyrimidin-4-yl]hydrazin-1-yl]-1-[3-(difluoromethoxy)pyridin-2-yl]ethan-1-one (740.0 mg, 67.4%) as a white solid. LCMS: m/z (ESI), [M+H]+=458.1.

Step 5. 8-bromo-2-[[3-(difluoromethoxy)pyridin-2-yl]methyl]-7-(1,3-oxazol-2-yl)-[1,2,4]triazolo[1,5-c]pyrimidin-5-amine A mixture of 2-[2-[2-amino-5-bromo-6-(1,3-oxazol-2-yl)pyrimidin-4-yl]hydrazin-1-yl]-1-[3-(difluoromethoxy)pyridin-2-yl]ethan-1-one (700 mg, 1.53 mmol, 1 equiv) and (Z)-(trimethylsilyl N-(trimethylsilyl)ethanimidate) (939.6 mg, 4.62 mmol, 3.01 equiv) was stirred for 1 hour at 120° C. under nitrogen atmosphere. The resulting mixture was added into MeOH (20 mL) and filtered, the filter cake was washed with MeOH (5×10 mL). This resulted in 8-bromo-2-[[3-(difluoromethoxy)pyridin-2-yl]methyl]-7-(1,3-oxazol-2-yl)-[1,2,4]triazolo[1,5-c]pyrimidin-5-amine (370.0 mg, 53.9%) as a white solid. LCMS: m/z (ESI), [M+H]⁺=440.1.

Step 6. 5-(5-amino-2-[[3-(difluoromethoxy)pyridin-2-yl]methyl]-7-(1,3-oxazol-2-yl)-[1,2,4]triazolo[1,5-c]pyrimidin-8-yl)-1-methyl-1,2-dihydropyridin-2-one (Cmpd. 71)

A mixture of 8-bromo-2-[[3-(difluoromethoxy)pyridin-2-yl]methyl]-7-(1,3-oxazol-2-yl)-[1,2,4]triazolo[1,5-c]pyrimidin-5-amine (150.0 mg, 0.3 mmol, 1.0 equiv) and 1-methyl-5-(4,4,5,5-tetramethyl-1,3,2-dioxaborolan-2-yl)-1,2-dihydropyridin-2-one (160.9 mg, 0.7 mmol, 2.0 equiv) and Pd(dppf)Cl₂ (50.1 mg, 0.1 mmol, 0.2 equiv) and K₃PO₄ (218.0 mg, 1.0 mmol, 3.0 equiv) in dioxane/H₂O (10/1, 0.8 mL) was stirred for 10 hours at 90° C. under nitrogen atmosphere. The residue was purified by Prep-TLC (CH₂Cl₂/MeOH 20:1), the crude product was washed with EtOH (3×8 mL). This resulted in 5-(5-amino-2-[[3-(difluoromethoxy)pyridin-2-yl]methyl]-7-(1,3-oxazol-2-yl)-[1,2,4]triazolo[1,5-c]pyrimidin-8-yl)-1-methyl-1,2-dihydropyridin-2-one (Cmpd. 71) (80.0 mg, 49.1%) as a white solid. LCMS: m/z (ESI), [M+H]⁺=467.2. ¹H NMR (400 MHz, DMSO-d₆) δ 3.43 (s, 3H), 4.41 (s, 2H), 6.28-6.56 (m, 1H), 7.21-7.29 (m, 1H), 7.34 (s, 1H), 7.36-7.48 (m, 1H), 7.67 (d, J=8.2 Hz, 1H), 7.76 (d, J=2.6 Hz, 1H), 8.15 (s, 1H), 8.21 (s, 1H), 8.36 (dd, J=4.7, 1.4 Hz, 1H).

Compounds listed in the table below were prepared using methods described in Example 71.

| Example/Compound number | Structure | LCMS [M + H]⁺ | ¹H NMR |
|---|---|---|---|
| 74 | 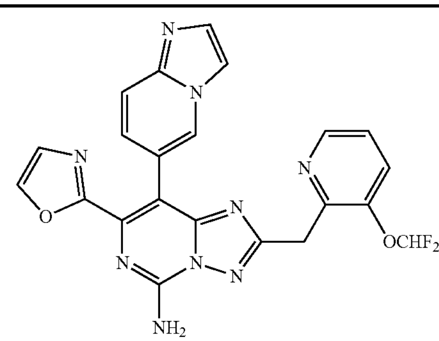 | 476.2 | ¹H NMR (400 MHz, DMSO-d₆) δ 4.39 (s, 1H), 7.04 (dd, J = 9.4, 1.7 Hz, 1H), 7.28-7.20 (m, 1H), 7.43-7.33 (m, 1H), 7.51 (dt, J = 9.3, 0.9 Hz, 1H), 7.58 (d, J = 1.2 Hz, 1H), 7.65 (dt, J = 8.3, 1.2 Hz, 1H), 7.94 (t, J =1.0 Hz, 1H), 8.16 (d, J = 0.8 Hz, 1H), 8.23 (s, 1H), 8.34 (dd, J = 4.7, 1.4 Hz, 1H), 8.58 (dd, J = 1.8, 1.0 Hz, 1H). |

Example 72

Preparation of 8-([1,2,4]triazolo[4,3-a]pyridin-6-yl)-7-(4-fluorophenyl)-2-((3-fluoropyridin-2-yl)methyl)-[1,2,4]triazolo[1,5-c]pyrimidin-5-amine (Cmpd. 72)

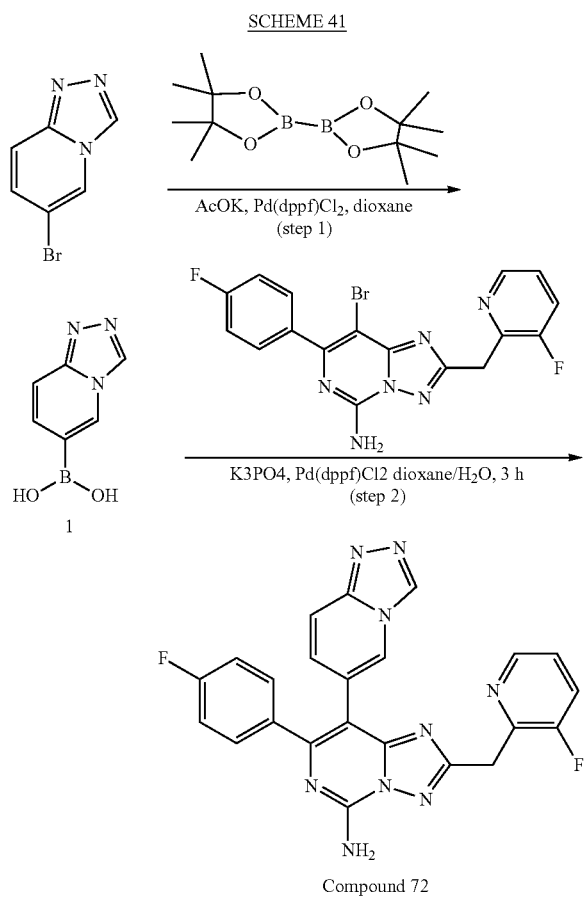

Compound 72

Step 1. Preparation of 6-(4,4,5,5-tetramethyl-1,3,2-dioxaborolan-2-yl)-[1,2,4]triazolo[4,3-a]pyridine Into a 40 mL vial were added 6-bromo-[1,2,4]triazolo[4,3-a]pyridine (500 mg, 2.525 mmol, 1 equiv) and 4,4,5,5-tetramethyl-2-(4,4,5,5-tetramethyl-1,3,2-dioxaborolan-2-yl)-1,3,2-dioxaborolane (705.31 mg, 2.777 mmol, 1.1 equiv), AcOK (495.61 mg, 5.050 mmol, 2 equiv), Pd(dppf)Cl$_2$ (184.75 mg, 0.252 mmol, 0.1 equiv), dioxane (3 mL) at room temperature. Then the mixture was stirred at 100° C. under nitrogen atmosphere for 3 hours. The resulting mixture was concentrated under reduced pressure. The residue was purified by Prep-TLC (CH$_2$Cl$_2$/MeOH 20:1) to afford 6-(4,4,5,5-tetramethyl-1,3,2-dioxaborolan-2-yl)-[1,2,4]triazolo[4,3-a]pyridine (350 mg, 56.56%) as an off-white solid. LCMS: m/z (ESI), [M+H]$^+$=164.

Step 2. Preparation of 7-(4-fluorophenyl)-2-[(3-fluoropyridin-2-yl)methyl]-8-[[1,2,4]triazolo[4,3-a]pyridin-6-yl]-[1,2,4]triazolo[1,5-c]pyrimidin-5-amine (Cmpd. 72)

Into a 10 mL vial were added [[1,2,4]triazolo[4,3-a]pyridin-6-yl]boronic acid (249.95 mg, 1.534 mmol, 8 equiv) and 8-bromo-7-(4-fluorophenyl)-2-[(3-fluoropyridin-2-yl)methyl]-[1,2,4]triazolo[1,5-c]pyrimidin-5-amine (80 mg, 0.192 mmol, 1 equiv), K$_3$PO$_4$ (81.40 mg, 0.383 mmol, 2 equiv), Pd(dppf)Cl$_2$ (28.06 mg, 0.038 mmol, 0.2 equiv), dioxane (2 mL), H$_2$O (0.4 mL) at room temperature. Then the mixture was stirred at 100° C. under nitrogen atmosphere for 3 hours. The resulting mixture was cooled and concentrated under reduced pressure. The residue was purified by Prep-TLC (CH$_2$Cl$_2$/MeOH=10:1) to afford crud product. The crude product was purified by Prep-HPLC with the following conditions (Column: XBridge Shield RP18 OBD Column, 5 μm, 19*150 mm; Mobile Phase A: Water (0.05% TFA), Mobile Phase B: ACN; Flow rate: 25 mL/min; Gradient: 20% B to 40% B in 7 min; 254/220 nm; Rt: 6.67 min) to afford 7-(4-fluorophenyl)-2-[(3-fluoropyridin-2-yl)methyl]-8-[[1,2,4]triazolo[4,3-a]pyridin-6-yl]-[1,2,4]triazolo[1,5-c]pyrimidin-5-amine (Cmpd. 72) (20 mg, 22.90%) as a white solid. LCMS: m/z (ESI), [M+H]$^+$=456.3. $^1$H NMR (300 MHz, DMSO-d$_6$) δ 4.40 (d, J=2.1 Hz, 2H), 7.00-7.20 (m, 3H), 7.37 (dt, J=8.5, 4.4 Hz, 1H), 7.42-7.51 (m, 2H), 7.62-7.74 (m, 2H), 8.12 (s, 2H), 8.30 (dt, J=4.7, 1.6 Hz, 1H), 8.57 (t, J=1.4 Hz, 1H), 9.28 (s, 1H).

Example 83

Preparation of 4-(5-amino-2-(2,6-difluorobenzyl)-7-(oxazol-2-yl)-[1,2,4]triazolo[1,5-c]pyrimidin-8-yl)-6-methylpicolinonitrile (Cmpd. 83)

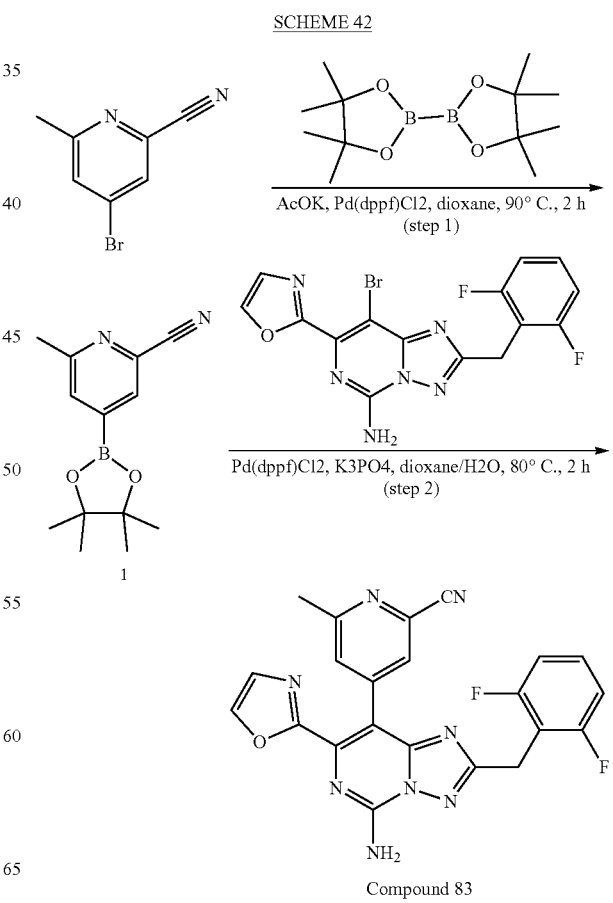

Compound 83

Step 1. 6-methyl-4-(4,4,5,5-tetramethyl-1,3,2-dioxaborolan-2-yl)pyridine-2-carbonitrile Into a 40 mL sealed tube were added AcOK (996.2 mg, 10.2 mmol, 2 equiv), Pd(dppf)Cl₂ CH₂Cl₂ (414.5 mg, 0.51 mmol, 0.1 equiv), 4-bromo-6-methylpyridine-2-carbonitrile (1 g, 5.1 mmol, 1 equiv) and 4,4,5,5-tetramethyl-2-(4,4,5,5-tetramethyl-1,3,2-dioxaborolan-2-yl)-1,3,2-dioxaborolane (1.9 g, 7.6 mmol, 1.5 equiv) in dioxane (20 mL) at 90° C. for 2 hours. Desired product could be detected by LCMS. The resulting mixture was concentrated under reduced pressure. The residue was purified by reverse flash chromatography with the following conditions: column, C18 silica gel; mobile phase, MeOH in water, 10% to 20% gradient in 10 min; detector, UV 254 nm to afford 6-methyl-4-(4,4,5,5-tetramethyl-1,3,2-dioxaborolan-2-yl)pyridine-2-carbonitrile (700 mg, 56.5%) as a white solid. LCMS: m/z (ESI), [M+H]⁺=163.3.

Step 2 4-[5-amino-2-[(2,6-difluorophenyl)methyl]-7-(1,3-oxazol-2-yl)-[1,2,4]triazolo[1,5-c]pyrimidin-8-yl]-6-methylpyridine-2-carbonitrile (Cmpd. 83)

Into a 10 mL sealed tube were added 8-bromo-2-[(2,6-difluorophenyl)methyl]-7-(1,3-oxazol-2-yl)-[1,2,4]triazolo[1,5-c]pyrimidin-5-amine (100 mg, 0.25 mmol, 1 equiv), 6-methyl-4-(4,4,5,5-tetramethyl-1,3,2-dioxaborolan-2-yl)pyridine-2-carbonitrile (120.0 mg, 0.5 mmol, 2 equiv), K₃PO₄ (105 mg, 0.5 mmol, 2 equiv) and Pd(dppf)Cl₂ CH₂Cl₂ (20 mg, 0.025 mmol, 0.1 equiv) in dioxane (10 mL) and water (1 mL) at 80° C. for 2 hours. Desired product could be detected by LCMS. The resulting mixture was concentrated under reduced pressure. The residue was purified by Prep-TLC (PE/EtOAc 1:1) to afford 4-[5-amino-2-[(2,6-difluorophenyl)methyl]-7-(1,3-oxazol-2-yl)-[1,2,4]triazolo[1,5-c]pyrimidin-8-yl]-6-methylpyridine-2-carbonitrile (Cmpd. 83) (50 mg, 45.8%) as a white solid. LCMS: m/z (ESI), [M+H]⁺=445.2. ¹H NMR (400 MHz, DMSO-d₆) δ 2.53 (3H, s), 4.25 (2H, s), 7.12 (2H, t), 7.31 (1H, s), 7.33-7.48 (1H, m), 7.58 (1H, d), 7.80 (1H, d), 8.22 (1H, s), 8.37 (2H, s).

Example 89

Preparation of 7-(4-fluorophenyl)-2-[(3-fluoropyridin-2-yl)methyl]-8-(quinolin-6-yl)-[1,2,4]triazolo[1,5-c]pyrimidin-5-amine (Cmpd. 89)

SCHEME 43

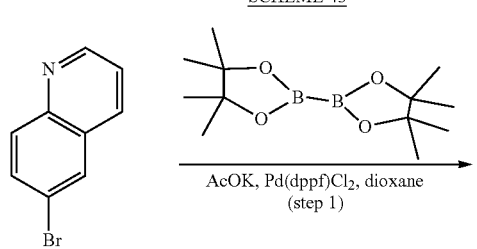

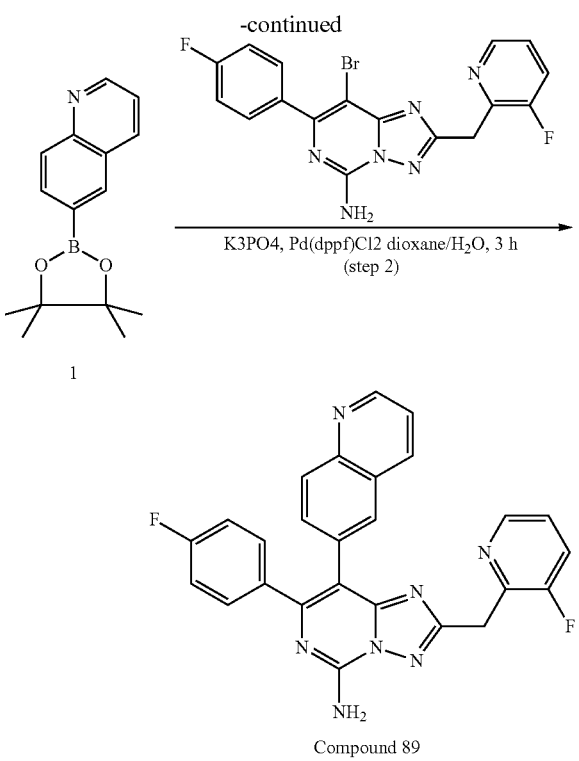

Step 1. Preparation of 6-(4,4,5,5-tetramethyl-1,3,2-dioxaborolan-2-yl)quinoline Into a 40 mL vial were added 6-bromoquinoline (300 mg, 1.442 mmol, 1 equiv) and 4,4,5,5-tetramethyl-2-(4,4,5,5-tetramethyl-1,3,2-dioxaborolan-2-yl)-1,3,2-dioxaborolane (369.82 mg, 1.456 mmol, 1.01 equiv), AcOK (283.02 mg, 2.884 mmol, 2.00 equiv), Pd(dppf)Cl₂ (211.01 mg, 0.288 mmol, 0.20 equiv), dioxane (10 mL) at room temperature. Then the mixture was stirred at 100° C. under nitrogen atmosphere for 3 hours. The resulting mixture was concentrated under reduced pressure. The residue was purified by Prep-TLC (CH₂Cl₂/MeOH=20:1) to afford 6-(4,4,5,5-tetramethyl-1,3,2-dioxaborolan-2-yl)quinoline (150 mg, 40.78%) as an off-white solid. LCMS: m/z (ESI), [M+H]⁺=257.3.

Step 2. Preparation of 7-(4-fluorophenyl)-2-[(3-fluoropyridin-2-yl)methyl]-8-(quinolin-6-yl)-[1,2,4]triazolo[1,5-c]pyrimidin-5-amine (Cmpd. 89)

Into a 10 mL vial were added 6-(4,4,5,5-tetramethyl-1,3,2-dioxaborolan-2-yl)quinoline (97.8 mg, 0.38 mmol, 2 equiv) and 8-bromo-7-(4-fluorophenyl)-2-[(3-fluoropyridin-2-yl)methyl]-[1,2,4]triazolo[1,5-c]pyrimidin-5-amine (80 mg, 0.19 mmol, 1 equiv), K₃PO₄ (81.4 mg, 0.38 mmol, 2 equiv), Pd(dppf)Cl₂ (28.1 mg, 0.04 mmol, 0.2 equiv), dioxane (2 mL), H₂O (0.4 mL) at room temperature. Then the mixture was stirred at 100° C. under nitrogen atmosphere for 3 hours. The resulting mixture was extracted with EtOAc (20 mL×3). The combined organic layers were washed with brine (10 mL×3), dried over anhydrous Na₂SO₄. After filtration, the filtrate was concentrated under reduced pressure. The crude product was purified by Prep-HPLC with the following conditions (Column: XBridge Prep OBD C18 Column 30×150 mm 5 μm; Mobile Phase A: Water (0.05% NH₃ H₂O), Mobile Phase B: ACN; Flow rate: 60 mL/min; Gradient: 30% B to 45% B in 7 min; 254/220 nm; Rt: 7.02 min) to afford 7-(4-fluorophenyl)-2-[(3-fluoropyridin-2-yl) methyl]-8-(quinolin-6-yl)-[1,2,4]triazolo[1,5-c]pyrimidin-5-amine (Cmpd. 89) (30 mg, 33.61%) as a white solid. LCMS: m/z (ESI), [M+H]$^+$=466.2. $^1$H NMR (300 MHz, DMSO-d$_6$) δ 4.39 (d, J=2.0 Hz, 2H), 7.04 (t, J=8.9 Hz, 2H), 7.36 (dd, J=8.7, 5.4 Hz, 3H), 7.44-7.56 (m, 2H), 7.67 (dd, J=9.9, 8.3 Hz, 1H), 7.83-7.92 (m, 2H), 8.02 (s, 2H), 8.22 (d, J=8.3 Hz, 1H), 8.29 (dd, J=4.8, 1.8 Hz, 1H), 8.86 (dd, J=4.2, 1.7 Hz, 1H).

Example 92

Preparation of 5-[5-amino-2-[(2,6-difluorophenyl) methyl]-7-(pvvvyridin-2-yl)-[1,2,4]triazolo[1,5-c] pyrimidin-8-yl]-1-methyl-1,2-dihydropyridin-2-one (Cmpd. 92)

SCHEME 44

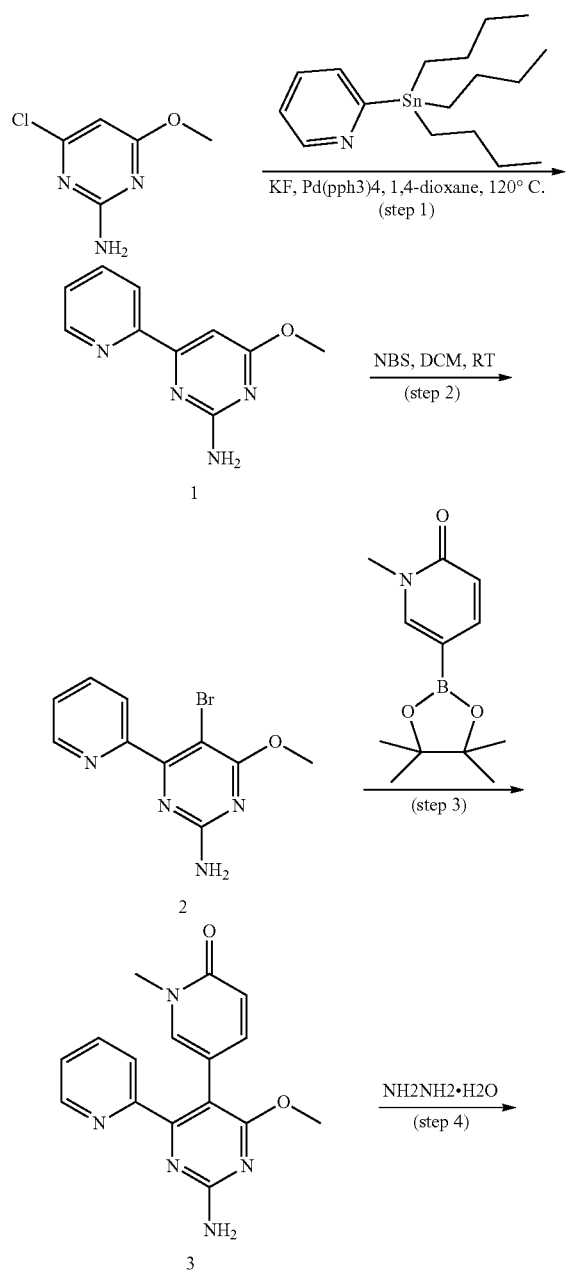

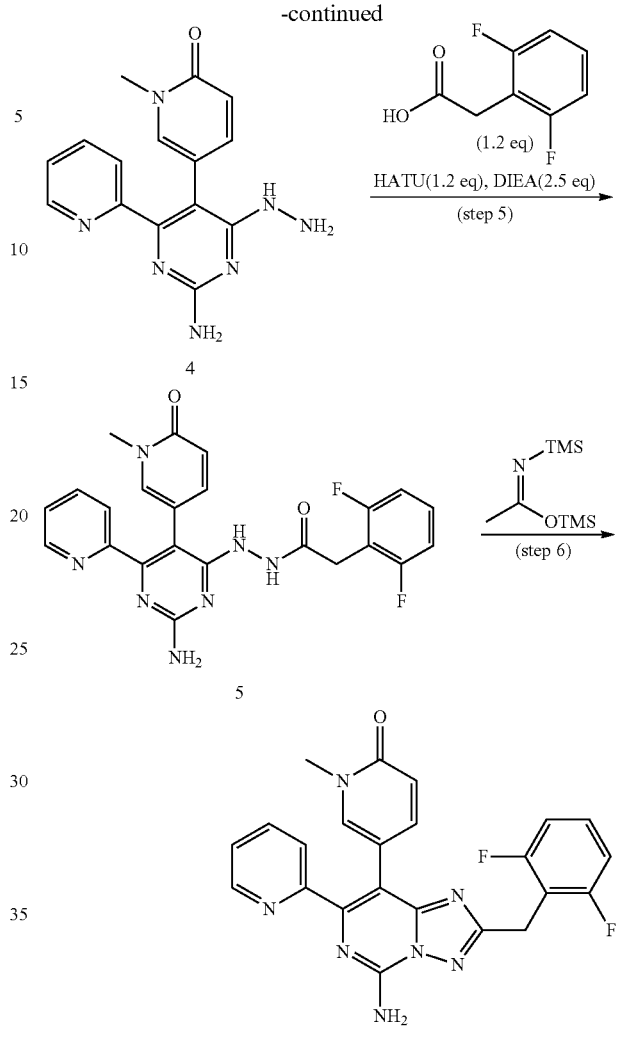

Example 92

Step 1.
4-methoxy-6-(pyridin-2-yl)pyrimidin-2-amine

Into a 1,4-dioxane (25.00 mL) were added 4-chloro-6-methoxypyrimidin-2-amine (500 mg, 3.133 mmol, 1 equiv), 2-(tributylstannyl)pyridine (1730.36 mg, 4.700 mmol, 1.5 equiv), Pd(PPh$_3$)$_4$ (362.09 mg, 0.313 mmol, 0.1 equiv) and KF (364.08 mg, 6.267 mmol, 2 equiv) at room temperature. The resulting mixture was stirred for 3 hours at 120° C. under nitrogen atmosphere. The reaction was quenched by the addition of KF aq (50 mL) at room temperature. The resulting mixture was stirred for 5 hours at room temperature under nitrogen atmosphere. The resulting mixture was extracted with EtOAc (3×35 mL). The combined organic layers were washed with water (3×30 mL), dried over anhydrous Na$_2$SO$_4$. After filtration, the filtrate was concentrated under reduced pressure. The residue was purified by silica gel column chromatography, eluted with PE/EtOAc (4:1~2:1) to afford 4-methoxy-6-(pyridin-2-yl)pyrimidin-2-amine (500 mg, 78.91%) as an off-white solid. LCMS: m/z (ESI), [M+H]$^+$=203.2. $^1$H NMR (400 MHz, DMSO-d$_6$) δ 3.88 (s, 3H), 6.74 (s, 2H), 6.91 (s, 1H), 7.50 (ddd, J=7.6, 4.7, 1.2 Hz, 1H), 7.95 (td, J=7.7, 1.8 Hz, 1H), 8.26 (dt, J=7.8, 1.1 Hz, 1H), 8.68 (ddd, J=4.8, 1.9, 0.9 Hz, 1H).

Step 2. 5-bromo-4-methoxy-6-(pyridin-2-yl)pyrimidin-2-amine

To a stirred solution of 4-methoxy-6-(pyridin-2-yl)pyrimidin-2-amine (500 mg, 2.473 mmol, 1 equiv) in DCM (20 mL) was added NBS (660.12 mg, 3.709 mmol, 1.5 equiv) in portions at room temperature under nitrogen atmosphere. The resulting mixture was stirred for 2 hours. The reaction was monitored by LCMS. The reaction was quenched with Water at room temperature. The resulting mixture was extracted with $CH_2Cl_2$ (2×50 mL). The combined organic layers were washed with water (2×50 mL), dried over anhydrous $Na_2SO_4$. After filtration, the filtrate was concentrated under reduced pressure to afford 5-bromo-4-methoxy-6-(pyridin-2-yl)pyrimidin-2-amine (550 mg, 79.13%) as a light yellow solid. LCMS: m/z (ESI), $[M+H]^+$=281.1. $^1$H NMR (400 MHz, DMSO-$d_6$) δ 3.94 (s, 3H), 6.95 (s, 2H), 7.46 (ddd, J=7.6, 4.9, 1.2 Hz, 1H), 7.54-7.61 (m, 1H), 7.91 (td, J=7.7, 1.8 Hz, 1H), 8.62-8.68 (m, 1H).

Step 3. 5-[2-amino-4-methoxy-6-(pyridin-2-yl)pyrimidin-5-yl]-1-methyl-1,2-dihydropyridin-2-one To a solution of 5-bromo-4-methoxy-6-(pyridin-2-yl)pyrimidin-2-amine (450 mg, 1.601 mmol, 1 equiv) and 1-methyl-5-(4,4,5,5-tetramethyl-1,3,2-dioxaborolan-2-yl)-1,2-dihydropyridin-2-one (564.5 mg, 2.4 mmol, 1.5 equiv) in dioxane (20 mL) and $H_2O$ (2 mL) were added $K_3PO_4$ (1019.4 mg, 4.8 mmol, 3 equiv) and Pd(dppf)$Cl_2$ (234.3 mg, 0.30 mmol, 0.2 equiv). After stirring for 2 hours at 80° C. under a nitrogen atmosphere, the residue was purified by Prep-TLC $CH_2Cl_2$/MeOH (12/1) to afford 5-[2-amino-4-methoxy-6-(pyridin-2-yl)pyrimidin-5-yl]-1-methyl-1,2-dihydropyridin-2-one (230 mg, 33.7%) as a dark yellow solid. LCMS: m/z (ESI), $[M+H]^+$=310.2.

Step 4. 5-[2-amino-4-hydrazinyl-6-(pyridin-2-yl)pyrimidin-5-yl]-1-methyl-1,2-dihydropyridin-2-one To a stirred solution/mixture of 5-[2-amino-4-methoxy-6-(pyridin-2-yl)pyrimidin-5-yl]-1-methyl-1,2-dihydropyridin-2-one (100 mg, 0.3 mmol, 1 equiv) in n-BuOH (3 mL) and $NH_2NH_2 \cdot H_2O$ (1 mL) at 110° C. under nitrogen atmosphere. The resulting mixture was concentrated under vacuum. The resulting mixture was washed with 6 mL of MTBE, to afford 5-[2-amino-4-hydrazinyl-6-(pyridin-2-yl)pyrimidin-5-yl]-1-methyl-1,2-dihydropyridin-2-one (80 mg, 80.0%) as a dark yellow solid. LCMS: m/z (ESI), $[M+H]^+$=310.2.

Step 5. N-[2-amino-5-(1-methyl-6-oxo-1,6-dihydropyridin-3-yl)-6-(pyridin-2-yl)pyrimidin-4-yl]-2-(2,6-difluorophenyl)acetohydrazide To a stirred solution of 5-[2-amino-4-hydrazinyl-6-(pyridin-2-yl)pyrimidin-5-yl]-1-methyl-1,2-dihydropyridin-2-one (90 mg, 0.3 mmol, 1 equiv) and 2-(2,6-difluorophenyl)acetic acid (75.1 mg, 0.4 mmol, 1.5 equiv) in DMF (3 mL) was added HATU (221.25 mg, 0.6 mmol, 2 equiv) and DIEA (112.8 mg, 0.9 mmol, 3 equiv) at 0° C. under nitrogen atmosphere. The mixture was stirred at 0° C.~10° C. for 30 mins. The resulting mixture was washed with 10 mL of MeOH, to afford N-[2-amino-5-(1-methyl-6-oxo-1,6-dihydropyridin-3-yl)-6-(pyridin-2-yl)pyrimidin-4-yl]-2-(2,6-difluorophenyl)acetohydrazide (50 mg, 37.1%) as a dark yellow solid. LCMS: m/z (ESI), $[M+H]^+$=464.2.

Step 6. 5-[5-amino-2-[(2,6-difluorophenyl)methyl]-7-(pyridin-2-yl)-[1,2,4]triazolo[1,5-c]pyrimidin-8-yl]-1-methyl-1,2-dihydropyridin-2-one (Cmpd. 92)

To a stirred solution/mixture of N-[2-amino-5-(1-methyl-6-oxo-1,6-dihydropyridin-3-yl)-6-(pyridin-2-yl)pyrimidin-4-yl]-2-(2,6-difluorophenyl)acetohydrazide (40 mg, 0.09 mmol, 1 equiv) and (Z)-(trimethylsilyl N-(trimethylsilyl) ethanimidate) (351.2 mg, 1.7 mmol, 20.00 equiv) in toluene (3 mL) at 100° C. under nitrogen atmosphere. The crude product (30 mg) was purified by Prep-HPLC to afford 5-[5-amino-2-[(2,6-difluorophenyl)methyl]-7-(pyridin-2-yl)-[1,2,4]triazolo[1,5-c]pyrimidin-8-yl]-1-methyl-1,2-dihydropyridin-2-one (Cmpd. 92) (3 mg, 7.8%) as a yellow solid. LCMS: m/z (ESI), $[M+H]^+$=446.2. $^1$H NMR (400 MHz, Methanol-$d_4$) δ 3.6 (s, 3H), 4.3 (s, 2H), 6.4 (d, J=9.2 Hz, 1H), 6.9-7.1 (m, 2H), 7.2 (dd, J=9.3, 2.6 Hz, 1H), 7.3-7.4 (m, 1H), 7.4-7.5 (m, 1H), 7.7-7.8 (m, 2H), 7.9 (td, J=7.8, 1.8 Hz, 1H), 8.5 (dd, J=3.9, 2.5 Hz, 1H).

Example 93/94

Preparation of 2-[(3-fluoropyridin-2-yl)methyl]-8-[imidazo[1,2-a]pyridin-6-yl]-7-(1H-1,2,3-triazol-1-yl)-[1,2,4]triazolo[1,5-c]pyrimidin-5-amine (Cmpd. 93) and 2-[(3-fluoropyridin-2-yl)methyl]-8-[imidazo[1,2-a]pyridin-6-yl]-7-(2H-1,2,3-triazol-2-yl)-[1,2,4]triazolo[1,5-c]pyrimidin-5-amine (Cmpd. 94)

SCHEME 45

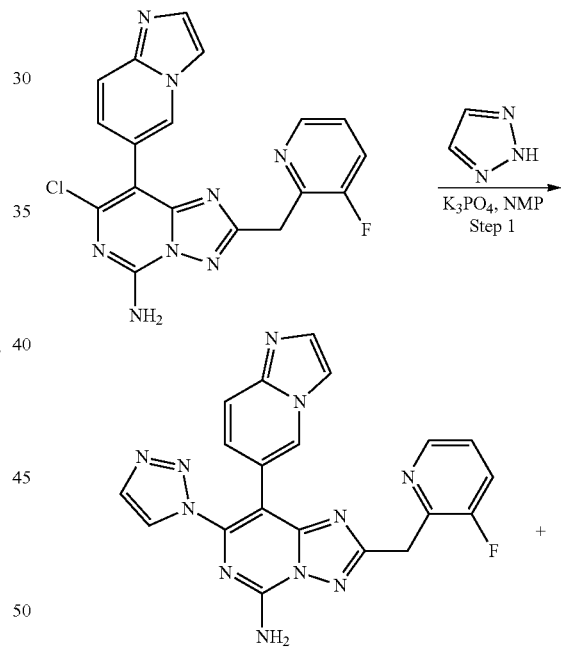

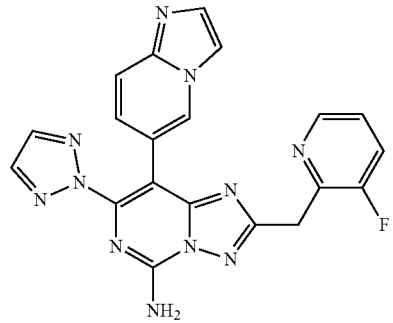

Example 93

Example 94

Step 1. 2-[(3-fluoropyridin-2-yl)methyl]-8-[imidazo[1,2-a]pyridin-6-yl]-7-(1H-1,2,3-triazol-1-yl)-[1,2,4]triazolo[1,5-c]pyrimidin-5-amine Into a 10 mL vial were added 7-chloro-2-[(3-fluoropyridin-2-yl)methyl]-8-[imidazo[1,2-a]pyridin-6-yl]-[1,2,4]triazolo[1,5-c]pyrimidin-5-amine (130 mg, 0.329 mmol, 1 equiv), and 2H-1,2,3-triazole (45.48 mg, 0.659 mmol, 2 equiv), $K_3PO_4$ (244.63 mg, 1.152 mmol, 3.5 equiv), and NMP (5 mL) at room temperature. Then the mixture was stirred at 100° C. under nitrogen atmosphere for 3 hours. The resulting mixture was extracted with EtOAc (3×10 mL). The combined organic layers were washed with brine (3×10 mL), dried over anhydrous $Na_2SO_4$. After filtration, the filtrate was concentrated under reduced pressure. The crude product (30 mg) was purified by Prep-HPLC with the following conditions (Column: XBridge Prep C18 OBD Column, 5 μm, 19*150 mm; Mobile Phase A: Water (0.05% TFA), mobile Phase B: ACN; Flow rate: 20 mL/min; gradient: 14% B to 32% B in 7 min; 254/220 nm; Rt: 4.67 min) to afford 2-[(3-fluoropyridin-2-yl)methyl]-8-[imidazo[1,2-a]pyridin-6-yl]-7-(1H-1,2,3-triazol-1-yl)-[1,2,4]triazolo[1,5-c]pyrimidin-5-amine; trifluoroacetic acid (Cmpd. 93) (7 mg, 3.93%) as a white solid, LCMS: m/z (ESI), [M+H]$^+$=427.1. $^1$H NMR (300 MHz, DMSO-$d_6$) δ 4.43 (d, J=2.1 Hz, 2H), 7.38 (dt, J=8.6, 4.4 Hz, 1H), 7.55 (dd, J=9.4, 1.6 Hz, 1H), 7.70 (ddd, J=9.9, 8.3, 1.4 Hz, 1H), 7.82-7.95 (m, 2H), 8.19 (d, J=2.1 Hz, 1H), 8.31 (dt, J=4.7, 1.6 Hz, 1H), 8.41 (d, J=2.1 Hz, 1H), 8.48 (d, J=1.2 Hz, 1H), 8.67 (s, 2H), 8.95 (t, J=1.3 Hz, 1H) and 2-[(3-fluoropyridin-2-yl)methyl]-8-[imidazo[1,2-a]pyridin-6-yl]-7-(2H-1,2,3-triazol-2-yl)-[1,2,4]triazolo[1,5-c]pyrimidin-5-amine (Cmpd. 94) (8 mg, 5.33%) as a white solid. LCMS: m/z (ESI), [M+H]$^+$=427.1. $^1$H NMR (300 MHz, DMSO-$d_6$) δ 4.43 (d, J=2.1 Hz, 2H), 7.38 (dt, J=8.6, 4.4 Hz, 1H), 7.55 (dd, J=9.4, 1.6 Hz, 1H), 7.70 (ddd, J=9.9, 8.3, 1.4 Hz, 1H), 7.82-7.95 (m, 2H), 8.19 (d, J=2.1 Hz, 1H), 8.31 (dt, J=4.7, 1.6 Hz, 1H), 8.41 (d, J=2.1 Hz, 1H), 8.48 (d, J=1.2 Hz, 1H), 8.67 (s, 2H), 8.95 (t, J=1.3 Hz, 1H).

Example 100

Preparation of 2-[(3-fluoropyridin-2-yl)methyl]-N7,N7-dimethyl-8-[3-methylimidazo[1,2-a]pyridin-6-yl]-[1,2,4]triazolo[1,5-c]pyrimidine-5,7-diamine (Cmpd. 100)

SCHEME 46

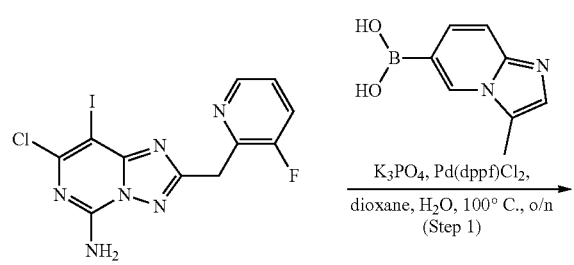

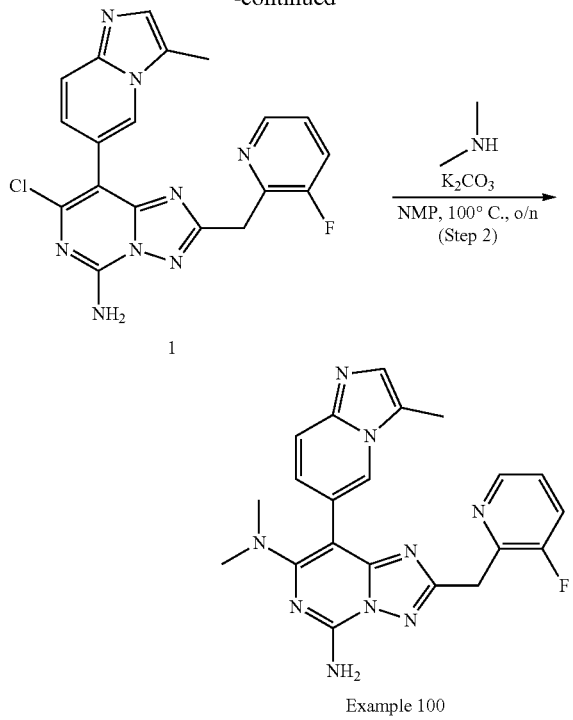

Example 100

Step 1. 7-chloro-2-[(3-fluoropyridin-2-yl)methyl]-8-[3-methylimidazo[1,2-a]pyridin-6-yl]-[1,2,4]triazolo[1,5-c]pyrimidin-5-amine To a stirred mixture of 7-chloro-2-[(3-fluoropyridin-2-yl)methyl]-8-iodo-[1,2,4]triazolo[1,5-c]pyrimidin-5-amine (3 g, 7.415 mmol, 1 equiv), $K_3PO_4$ (6.30 g, 29.661 mmol, 4 equiv) and [3-methylimidazo[1,2-a]pyridin-6-yl]boronic acid (2.61 g, 14.831 mmol, 2 equiv) in dioxane (20 mL) and $H_2O$ (2 mL) was added Pd(dppf)Cl$_2$ (813.86 mg, 1.112 mmol, 0.15 equiv) in portions at room temperature under nitrogen atmosphere. The mixture was stirred overnight at 100° C. under nitrogen atmosphere. The resulting mixture was concentrated under reduced pressure. The resulting mixture was washed with water (50 mL). The resulting mixture was filtered, the filter cake was washed with water (3×20 mL). The filtrate was concentrated under reduced pressure. The resulting mixture was washed with $CH_2Cl_2$ (50 mL). And the resulting mixture was filtered, the filter cake was washed with $CH_2Cl_2$ (3×20 mL). The filtrate was concentrated under reduced pressure to afford 7-chloro-2-[(3-fluoropyridin-2-yl)methyl]-8-[3-methylimidazo[1,2-a]pyridin-6-yl]-[1,2,4]triazolo[1,5-c]pyrimidin-5-amine (2 g, 65.9%) as a brown solid. LCMS: m/z (ESI), [M+H]$^+$=409.2. $^1$H-NMR (300 MHz, DMSO-$d_6$) δ 2.40 (3H, d), 4.35 (2H, d), 7.25 (1H, dd), 7.31-7.44 (2H, m), 7.58 (1H, dd), 7.67 (1H, ddd), 8.21-8.65 (4H, m).

Step 2. 2-[(3-fluoropyridin-2-yl)methyl]-N7,N7-dimethyl-8-[3-methylimidazo[1,2-a]pyridin-6-yl]-[1,2,4]triazolo[1,5-c]pyrimidine-5,7-diamine (Cmpd. 100)

To a stirred mixture of 7-chloro-2-[(3-fluoropyridin-2-yl)methyl]-8-[3-methylimidazo[1,2-a]pyridin-6-yl]-[1,2,4]triazolo[1,5-c]pyrimidin-5-amine (100 mg, 0.245 mmol, 1 equiv) and K₂CO₃ (135.22 mg, 0.978 mmol, 4 equiv) in NMP (1 mL) was added the solution of dimethylamine (165.42 mg, 3.669 mmol, 15 equiv) in THF dropwise at room temperature under nitrogen atmosphere. And the mixture was stirred overnight at 100° C. under nitrogen atmosphere. The resulting mixture was filtered. The crude product was purified by Prep-HPLC with the following conditions (Column: X Bridge Prep OBD C18 Column 30×150 mm 5 μm; Mobile Phase A: Water (0.05% NH₃H₂O), Mobile Phase B: ACN; Flow rate: 60 mL/min; Gradient: 24% B to 34% B in 7 min; 254; 220 nm; Rt: 6.48 min) to afford 2-[(3-fluoropyridin-2-yl)methyl]-N7,N7-dimethyl-8-[3-methylimidazo[1,2-a]pyridin-6-yl]-[1,2,4]triazolo[1,5-c]pyrimidine-5,7-diamine (Cmpd. 100) (29 mg, 28.4%) as a white solid. LCMS: m/z (ESI), [M+H]⁺=418.2. H-NMR (300 MHz, DMSO-d₆) δ 2.36 (3H, d), 2.79 (6H, s), 4.23 (2H, d), 7.25 (1H, dd), 7.30-7.39 (2H, m), 7.49 (1H, dd), 7.54-7.72 (3H, m), 8.28 (2H, ddd).

Compound listed in the table below was prepared using methods described in Example 100.

| Example number | Structure | LCMS [M + H]⁺ | ¹H NMR |
|---|---|---|---|
| 101 | 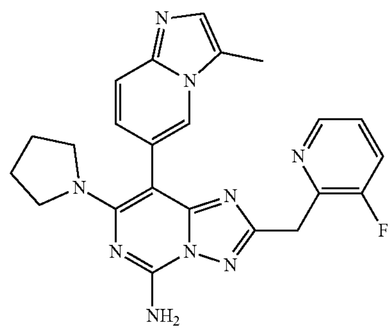 [SMILES: Cc1cnc2ccc(-c3c(N4CCCC4)nc(N)n4nc(Cc5ncccc5F)nc34)cn12] | 444.2 | ¹H-NMR (400 MHz, MeOD-d₄) δ 1.69-1.84 (4H, m), 2.50 (3H, d), 4.26 (2H, d), 3.30 (2H, s), 3.32 (2H, s), 7.27 (1H, dd), 7.33-7.40 (2H, m), 7.50 (1H, dd), 7.58 (1H, ddd,), 8.22 (1H, dd), 8.28 (1H, dt). |
| 102 | 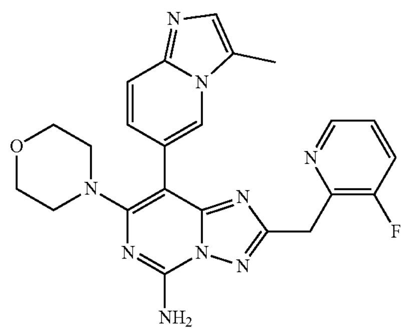 [SMILES: Cc1cnc2ccc(-c3c(N4CCOCC4)nc(N)n4nc(Cc5ncccc5F)nc34)cn12] | 460.3 | ¹H-NMR (400 MHz, MeOD-d₄) δ 2.64 (3H, d), 3.32 (4H, s), 3.59-3.66 (4H, m), 4.9 (2H, s), 7.39 (1H, dt), 7.62 (1H, ddd), 7.82 (1H, d), 7.90 (1H, dd), 8.23 (1H, dd), 8.30 (1H, dt), 8.86-8.92 (1H, m). |
| 110 | 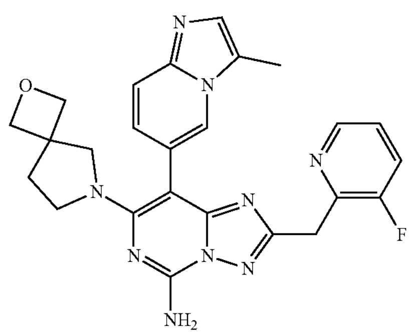 [SMILES: Cc1cnc2ccc(-c3c(N4CCC5(COC5)C4)nc(N)n4nc(Cc5ncccc5F)nc34)cn12] | 486.3 | ¹H-NMR (400 MHz, DMSO-d₆) δ 2.01 (2H, t), 2.39 (3H, d), 3.17 (2H, t), 3.51 (2H, s), 4.21 (2H, d), 4.37-4.50 (4H, m), 7.20 (1H, dd), 7.32-7.40 (2H, m), 7.49 (1H, dd), 7.53-7.62 (2H, m), 7.67 (1H, ddd), 8.17 (1H, t), 8.30 (1H, dt). |
| 112-1 | isomer 1 | 474.3 | ¹H-NMR (400 MHz, DMSO-d₆) δ 0.98 (3H, d), 2.38 (3H, d), 2.53 2.62 (1H, m), 2.78 (1H, td), 3.38-3.48 (2H, m), 3.48 -3.70 (3H, m), 4.29 (2H, d), 7.31-7.42 (2H, m), 7.47 -7.58 (2H, m), 7.70 (1H, ddd), 7.80 (2H, s), 8.32 (1H, dt), 8.43 (1H, t). |

| Example number | Structure | LCMS [M + H]+ | 1H NMR |
|---|---|---|---|
| 112-2 | 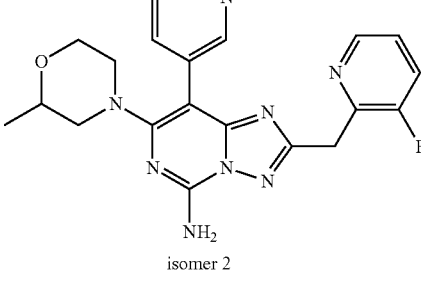 isomer 2 | 474.2 | 1H-NMR (400 MHz, DMSO-d6) δ 0.97 (3H, d), 2.38 (3H, s), 2.53-2.60 (1H, m), 2.72-2.86 (1H, m), 3.39-3.50 (2H, m), 3.50-3.69 (3H, m), 4.29 (2H, d), 7.34-7.41 (2H, m), 7.46-7.57 (2H, m), 7.69 (1H, ddd), 7.81 (2H, s), 8.32 (1H, dt), 8.43 (1H, t). |
| 113-1 | 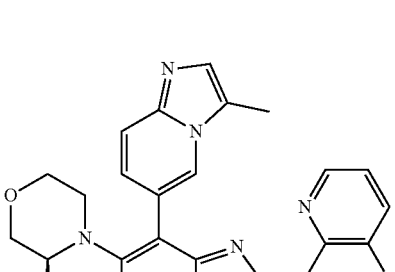 | 474.3 | 1H-NMR (300 MHz, DMSO-d6) δ 1.03 (3H, d), 2.35 (3H, s), 3.14 (2H, q), 3.38 (1H, d), 3.41-3.58 (2H, m), 3.64 (1H, d), 3.73 (1H, dq), 4.27 (2H, d), 7.27-7.41 (2H, m), 7.51 (2H, s), 7.62-7.72 (1H, m), 7.78 (2H, s), 8.30 (1H, dt), 8.38 (1H, d). |
| 113-2 | 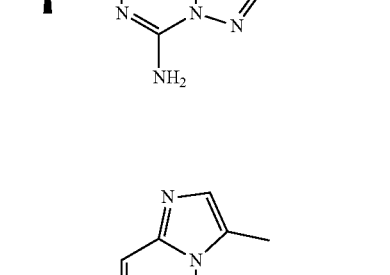 | 474.2 | 1H-NMR (300 MHz, DMSO-d6) δ 1.05 (3H, d), 2.38 (3H, d), 3.17 (2H, q), 3.35-3.43 (1H, m), 3.43-3.53 (1H, m), 3.55 (1H, dd), 3.60-3.70 (1H, m), 3.71-3.81 (1H, m), 4.29 (2H, d), 7.32-7.43 (2H, m), 7.54 (2H, d), 7.70 (1H, ddd), 7.80 (2H, s), 8.32 (1H, dt), 8.40 (1H, t). |
| 116 | 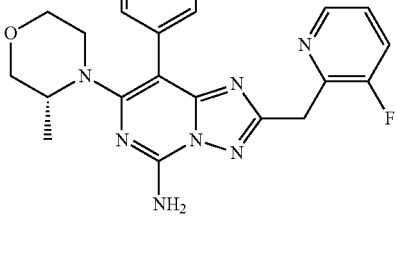 | 459.2 | 1H-NMR (300 MHz, DMSO-d6) δ 2.32 (3H, s), 4.34-4.46 (2H, m), 6.22 (1H, dd), 6.84 (1H, d), 7.34-7.46 (3H, m), 7.69 (1H, t), 8.04 (1H, t), 8.18 (1H, s), 8.27-8.52 (3H, m). |

-continued

| Example number | Structure | LCMS [M + H]+ | 1H NMR |
|---|---|---|---|
| 117 | 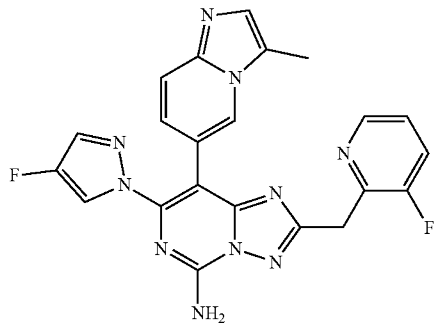 [SMILES: Cc1cnc2ccc(-c3c(-n4cc(F)cn4)nc(N)n4nc(Cc5ncccc5F)nc34)cn12] | 459.2 | 1H-NMR (300 MHz, DMSO-d6) δ 2.31 (3H, d), 4.40 (2H, d), 6.80 (1H, dd), 7.31-7.45 (3H, m), 7.61-7.77 (2H, m), 8.12-8.18 (1H, m), 8.22 (1H, dd), 8.27-8.59 (3H, m) |
| 118 | 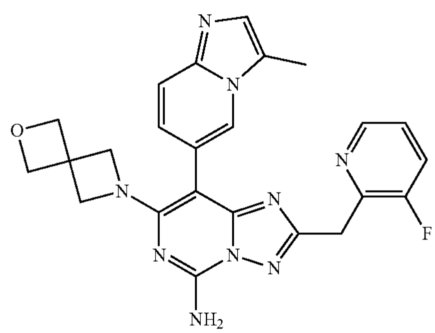 [SMILES: Cc1cnc2ccc(-c3c(N4CC5(COC5)C4)nc(N)n4nc(Cc5ncccc5F)nc34)cn12] | 472.2 | 1H-NMR (400 MHz, DMSO-d6) δ 2.36 -2.48 (3H, m), 3.90 (4H, s), 4.22 (2H, d), 4.56 (4H, s), 7.20 (1H, dd), 7.29-7.43 (2H, m), 7.52 (1H, dd), 7.57-7.82 (3H, m), 8.15 (1H, t), 8.30 (1H, dt). |
| 119 | 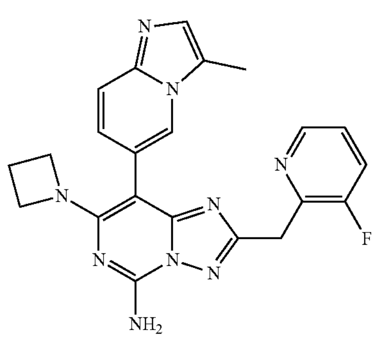 [SMILES: Cc1cnc2ccc(-c3c(N4CCC4)nc(N)n4nc(Cc5ncccc5F)nc34)cn12] | 430.3 | 1H-NMR (400 MHz, DMSO-d6) δ 1.96-2.16 (2H, m), 2.52 (3H, d), 3.73 (4H, t), 4.22 (2H, d), 7.22 (1H, dd), 7.36 (2H, q), 7.50 (1H, d), 7.59-7.80 (3H, m), 8.17 (1H, t), 8.30 (1H, dt). |

Example 103

Preparation of (S)-7-(4-fluorophenyl)-8-(1-methyl-1H-benzo[d]imidazol-6-yl)-2-((1-methylpyrrolidin-2-yl) methyl)-[1,2,4]triazolo[1,5-c]pyrimidin-5-amine (Cmpd. 103)

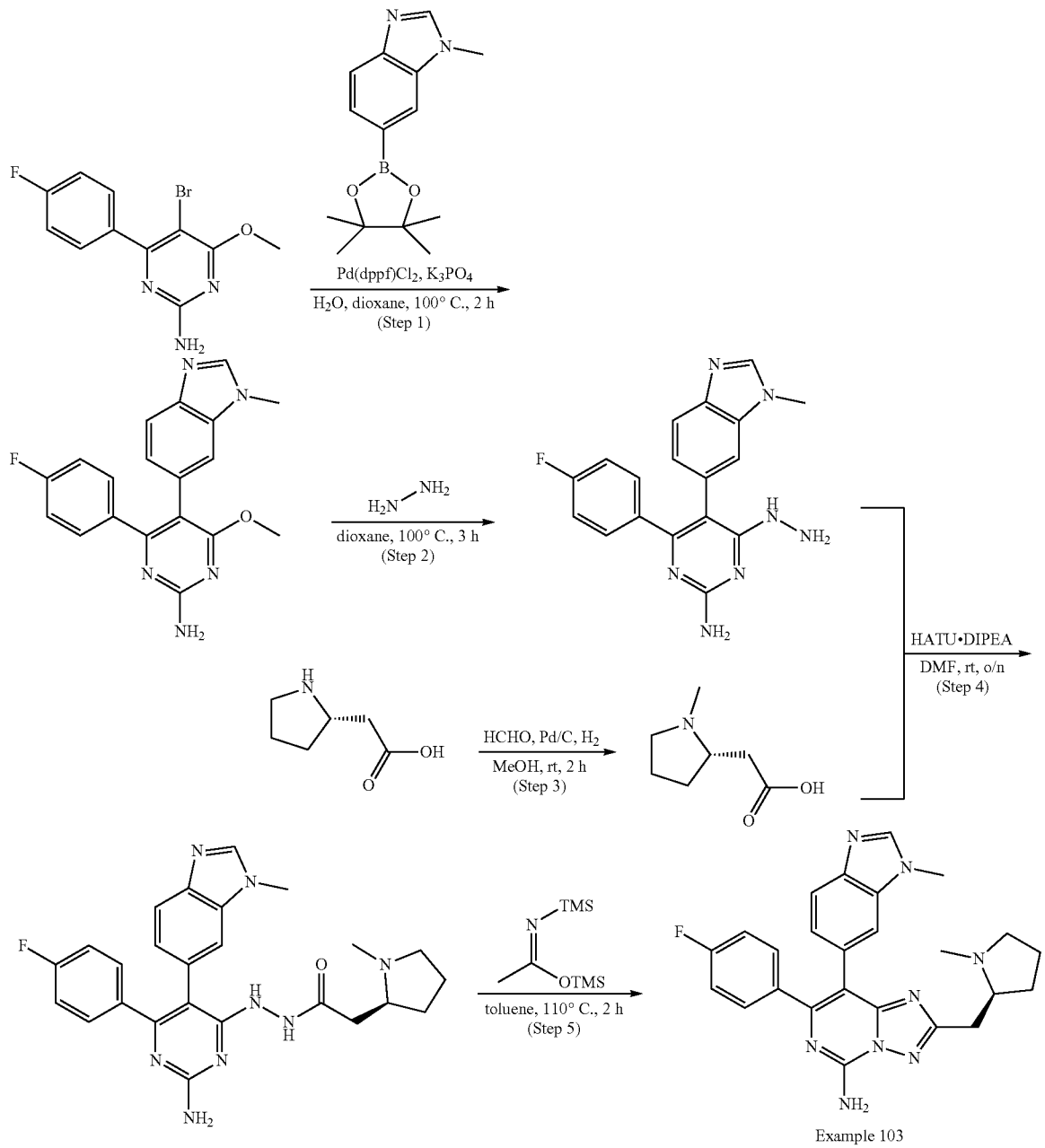

Example 103

Step 1. 4-(4-fluorophenyl)-6-methoxy-5-(1-methyl-1H-1,3-benzodiazol-6-yl)pyrimidin-2-amine To a solution of 5-bromo-4-(4-fluorophenyl)-6-methoxypyrimidin-2-amine (1000 mg, 3.354 mmol, 1 equiv) and 1-methyl-6-(4,4,5,5-tetramethyl-1,3,2-dioxaborolan-2-yl)-1H-1,3-benzodiazole (1298.81 mg, 5.032 mmol, 1.5 equiv) in dioxane (30 mL) and H$_2$O (6 mL) were added K$_3$PO$_4$ (1424.06 mg, 6.709 mmol, 2 equiv) and Pd(dppf)Cl$_2$ (490.88 mg, 0.671 mmol, 0.2 equiv). After stirring for 2 hours at 100° C. under nitrogen atmosphere, the resulting mixture was concentrated under reduced pressure. The residue was purified by silica gel column chromatography, eluting with CH$_2$Cl$_2$/MeOH (10:1) to afford 4-(4-fluorophenyl)-6-methoxy-5-(1-methyl-1H-1,3-benzodiazol-6-yl)pyrimidin-2-amine (847 mg, 72.2%) as a yellow solid. LCMS: m/z (ESI), [M+H]$^+$=350.3.

Step 2. 4-(4-fluorophenyl)-6-hydrazineyl-5-(1-methyl-1H-benzo[d]imidazol-6-yl)pyrimidin-2-amine Into a vial were added 4-(4-fluorophenyl)-6-methoxy-5-(1-methyl-1H-1,3-benzodiazol-6-yl)pyrimidin-2-amine (450 mg, 1.288 mmol, 1 equiv), hydrazine (5 mL) and dioxane (5 mL) at room temperature. The resulting mixture was stirred for 3 hours at 100° C. under air atmosphere. The product was precipitated by the addition of water. The resulting mixture was filtered and the filter cake was washed with methyl t-butyl ether (3×30 mL). The filtrate was concentrated under reduced pressure. The resulting solid was dried under vacuum to afford 4-(4-fluorophenyl)-6-hydrazineyl-5-(1-methyl-1H-benzo[d]imidazol-6-yl)pyrimidin-2-amine (375 mg, 83.3%) as an off-white solid. LCMS: m/z (ESI), [M+H]$^+$=350.3.

Step 3. (S)-2-(1-methylpyrrolidin-2-yl)acetic acid hydrochloride

To a solution of (S)-2-(pyrrolidin-2-yl)acetic acid hydrochloride (500 mg, 3.019 mmol, 1 equiv) and formaldehyde (1.5 mL, 0.050 mmol, 0.02 equiv) in MeOH (10 mL, 0.312 mmol, 0.10 equiv) was added 10% Pd/C (150 mg) under nitrogen atmosphere in a round-bottom flask. The mixture was hydrogenated at room temperature for 2 hours under hydrogen atmosphere using a hydrogen balloon, filtered through a Celite pad and concentrated under reduced pressure to afford (S)-2-(1-methylpyrrolidin-2-yl)acetic acid hydrochloride (446 mg, 82.2%) as a white solid. LCMS: m/z (ESI), [M+H]$^+$=144.3.

Step 4. (S)—N'-(2-amino-6-(4-fluorophenyl)-5-(1-methyl-1H-benzo[d]imidazol-6-yl)pyrimidin-4-yl)-2-(1-methylpyrrolidin-2-yl)acetohydrazide Into a vial were added 4-(4-fluorophenyl)-6-hydrazinyl-5-(1-methyl-1H-1,3-benzodiazol-6-yl)pyrimidin-2-amine (150 mg, 0.429 mmol, 1 equiv), 2-[(2S)-1-methylpyrrolidin-2-yl]acetic acid (153.69 mg, 1.073 mmol, 2.50 equiv), HATU (195.90 mg, 0.515 mmol, 1.20 equiv), DIPEA (166.47 mg, 1.288 mmol, 3.00 equiv) and DMF (5 mL) at room temperature. The resulting mixture was stirred overnight at room temperature under nitrogen atmosphere. The resulting mixture was concentrated under reduced pressure. The residue was purified by Prep-TLC (CH$_2$Cl$_2$/MeOH 12:1) to afford (S)—N'-(2-amino-6-(4-fluorophenyl)-5-(1-methyl-1H-benzo[d]imidazol-6-yl)pyrimidin-4-yl)-2-(1-methylpyrrolidin-2-yl)acetohydrazide (120 mg, 58.9%) as a brown solid. LCMS: m/z (ESI), [M+H]$^+$=475.2.

Step 5. (S)-7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine (Cmpd. 103)

Into a vial were added N-[2-amino-6-(4-fluorophenyl)-5-(1-methyl-1H-1,3-benzodiazol-6-yl)pyrimidin-4-yl]-2-[(2S)-1-methylpyrrolidin-2-yl]acetohydrazide (120 mg, 0.253 mmol, 1 equiv) and (Z)-(trimethylsilyl N-(trimethylsilyl)ethanimidate) (3 mL) at room temperature. The resulting mixture was stirred for 2 hours at 110° C. under nitrogen atmosphere. The resulting mixture was concentrated under reduced pressure. The residue was purified by Prep-HPLC with the following conditions (Column: XBridge Prep OBD C18 Column 19*250 mm, 5 μm; Mobile Phase A: Water (0.05% NH$_3$H$_2$O), Mobile Phase B: ACN; Flow rate: 20 mL/min; Gradient: 29% B to 39% B in 8 min; 254/220 nm; t$_R$: 6.45 min) to afford (S)-7-(4-fluorophenyl)-8-(1-methyl-1H-benzo[d]imidazol-6-yl)-2-((1-methylpyrrolidin-2-yl)methyl)-[1,2,4]triazolo-[1,5-c]pyrimidin-5-amine (Cmpd. 103) (8 mg, 6.9%) as a white solid. LCMS: m/z (ESI), [M+H]$^+$=457.2. $^1$H-NMR (400 MHz, DMSO-d$_6$) δ 1.61 (3H, d), 1.74-1.91 (1H, m), 2.11 (1H, q), 2.26 (3H, s), 2.57-2.70 (2H, m), 2.93 (1H, t), 3.12 (1H, dd), 3.74 (3H, s), 6.96-7.13 (3H, m), 7.36 (2H, dd), 7.48-7.59 (2H, m), 7.95 (2H, s), 8.19 (1H, s).

Example 104

Preparation of (R)-7-(4-fluorophenyl)-8-(1-methyl-1H-benzo[d]imidazol-6-yl)-2-((1-methylpyrrolidin-2-yl) methyl)-[1,2,4]triazolo[1,5-c]pyrimidin-5-amine (Cmpd. 104)

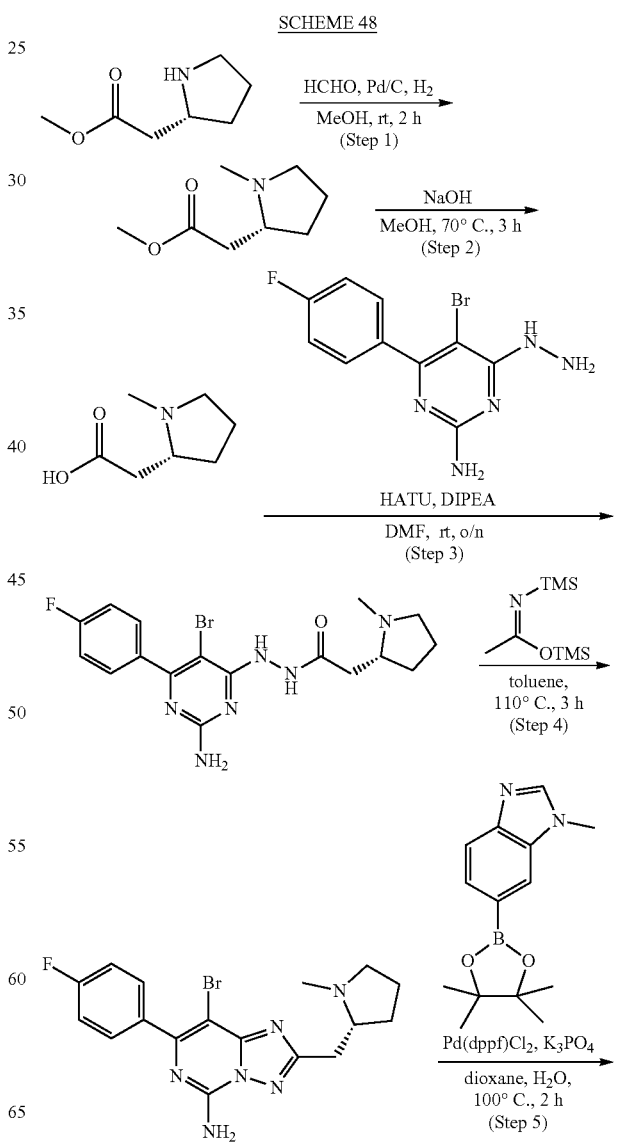

SCHEME 48

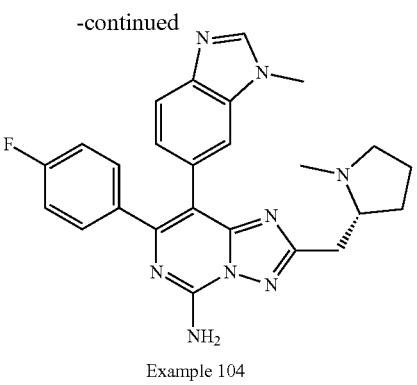

Example 104

Step 1. methyl 2-[(2R)-1-methylpyrrolidin-2-yl]acetate hydrochloride

To a solution of methyl 2-[(2R)-pyrrolidin-2-yl]acetate hydrochloride (20 mg, 0.111 mmol, 1 equiv) and formaldehyde (10.03 mg, 0.334 mmol, 3 equiv, 37%) in MeOH (1 mL) was added Pd/C (20 mg, 0.188 mmol, 1.69 equiv) under nitrogen atmosphere in a round-bottom flask. The mixture was hydrogenated at room temperature for 2 hours under hydrogen atmosphere using a hydrogen balloon, filtered through a Celite pad and concentrated under reduced pressure to afford methyl 2-[(2R)-1-methylpyrrolidin-2-yl]acetate hydrochloride (14 mg, 64.9%) as a white solid. LCMS: m/z (ESI), [M+H]$^+$=158.3.

Step 2. 2-[(2R)-1-methylpyrrolidin-2-yl]acetic acid

Into a vial were added methyl 2-[(2R)-1-methylpyrrolidin-2-yl]acetate (21 mg, 0.134 mmol, 1 equiv), NaOH (6.41 mg, 0.160 mmol, 1.20 equiv) and MeOH (2 mL) at room temperature. The resulting mixture was stirred for 3 hours at 70° C. under nitrogen atmosphere. The mixture was neutralized to pH 7 with acetic acid. The resulting mixture was concentrated under vacuum. The residue was dissolved in acetic acid (5 mL). The resulting mixture was concentrated under vacuum to afford 2-[(2R)-1-methylpyrrolidin-2-yl]acetic acid (12 mg, 62.7%) as a white solid. LCMS: m/z (ESI), [M+H]$^+$=142.3.

Step 3. N-[2-amino-5-bromo-6-(4-fluorophenyl)pyrimidin-4-yl]-2-[(2R)-1-methyl-pyrrolidin-2-yl]acetohydrazide Into a vial were added 5-bromo-4-(4-fluorophenyl)-6-hydrazinylpyrimidin-2-amine (200 mg, 0.671 mmol, 1 equiv), 2-[(2R)-1-methylpyrrolidin-2-yl]acetic acid (288.18 mg, 2.013 mmol, 3.00 equiv), HATU (306.10 mg, 0.805 mmol, 1.20 equiv), DIPEA (173.41 mg, 1.342 mmol, 2.00 equiv) and DMF (7 mL) at room temperature. The resulting mixture was stirred overnight at room temperature under nitrogen atmosphere. The resulting mixture was concentrated under vacuum. The residue was purified by Prep-TLC (CH$_2$Cl$_2$/MeOH 10:1) to afford N-[2-amino-5-bromo-6-(4-fluorophenyl)pyrimidin-4-yl]-2-[(2R)-1-methylpyrrolidin-2-yl]acetohydrazide (130 mg, 45.7%) as a light brown solid. LCMS: m/z (ESI), [M+H]$^+$=423.2

Step 4. 8-bromo-7-(4-fluorophenyl)-2-[[(2R)-1-methylpyrrolidin-2-yl]methyl]-[1,2,4]-triazolo[1,5-c]pyrimidin-5-amine Into a round-bottom flask were added (Z)-(trimethylsilyl N-(trimethyl-silyl)ethanimidate) (288.36 mg, 1.417 mmol, 3 equiv), toluene (5 mL) and N-[2-amino-5-bromo-6-(4-fluorophenyl)pyrimidin-4-yl]-2-[(2R)-1-methylpyrrolidin-2-yl]acet-ohydrazide (200 mg, 0.472 mmol, 1 equiv) at room temperature. The resulting mixture was stirred for 3 hours at 110° C. under nitrogen atmosphere. The resulting mixture was concentrated under reduced pressure. The residue was purified by Prep-TLC (CH$_2$Cl$_2$/MeOH 12:1) to afford 8-bromo-7-(4-fluorophenyl)-2-[[(2R)-1-methylpyrrolidin-2-yl]methyl]-[1,2,4]triazolo[1,5-c]pyrimidin-5-amine (140 mg, 73.1%) as a light brown solid. LCMS: m/z (ESI), [M+H]$^+$=407.2

Step 5. (R)-7-(4-fluorophenyl)-8-(1-methyl-1H-benzo[d]imidazol-6-yl)-2-((1-methylpyrrolidin-2-yl)methyl)-[1,2,4]triazolo[1,5-c]pyrimidin-5-amine (Cmpd. 104)

To a solution of 1-methyl-6-(4,4,5,5-tetramethyl-1,3,2-dioxaborolan-2-yl)-1H-1,3-benzodiazole (248.40 mg, 0.962 mmol, 3.00 equiv) and 8-bromo-7-(4-fluorophenyl)-2-[[(2R)-1-methylpyrrolidin-2-yl]methyl]-[1,2,4]triazolo[1,5-c]pyrimidin-5-amine (130 mg, 0.321 mmol, 1 equiv) in dioxane (3 mL, 0.034 mmol, 0.11 equiv) and H$_2$O (0.5 mL, 0.028 mmol, 0.09 equiv) were added K$_3$PO$_4$ (204.27 mg, 0.962 mmol, 3.00 equiv) and Pd(dppf)Cl$_2$ (46.94 mg, 0.064 mmol, 0.20 equiv). After stirring for 2 hours at 100° C. under a nitrogen atmosphere, the resulting mixture was concentrated under reduced pressure. The residue was purified by Prep-HPLC with the following conditions (Column: XBridge Prep OBD C18 Column 19*250 mm, 5 µm; Mobile Phase A: Water (0.05% NH$_3$H$_2$O), Mobile Phase B:ACN; Flow rate: 20 mL/min; Gradient: 28% B to 39% B in 8 min; 254:220 nm; t$_R$: 6.75 min) to afford (R)-7-(4-fluorophenyl)-8-(3-methyl-3H-benzo[d]imidazol-5-yl)-2-((1-methylpyrrolidin-2-yl) methyl)-[1,2,4]triazolo[1,5-f]pyrimidin-5-amine (Cmpd. 104) (5 mg, 3.4%) as a white solid. LCMS: m/z (ESI), [M+H]$^+$=457.4. $^1$H-NMR (400 MHz, Methanol-d$_4$) δ 1.68-1.86 (3H, m), 1.96-2.05 (1H, m), 2.34 (1H, q), 2.43 (3H, s), 2.75-2.89 (2H, m), 3.08-3.19 (1H, m), 3.22-3.29 (1H, m), 3.88 (3H, s), 6.94 (2H, t), 7.11 (1H, dd), 7.40-7.47 (2H, m), 7.59 (1H, d), 7.62 (1H, d), 8.17 (1H, s).

Example 106-1/106-2

Preparation of 8-(3-methylimidazo[1,2-a]pyridin-6-yl)-7-(oxazol-2-yl)-2-((tetrahydrofuran-2-yl)methyl)-[1,2,4]triazolo[1,5-f]pyrimidin-5-amine (Ex.106-1) and 8-(3-methylimidazo[1,2-a]pyridin-6-yl)-7-(oxazol-2-yl)-2-((tetrahydrofuran-2-yl)methyl)-[1,2,4]triazolo[1,5-f]pyrimidin-5-amine (Ex.106-2)

SCHEME 49

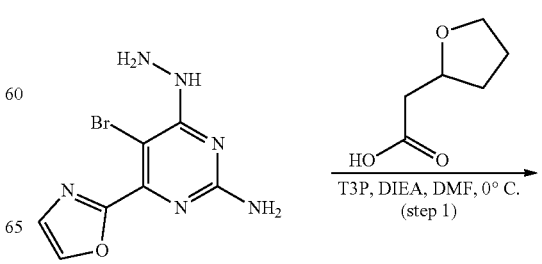

-continued

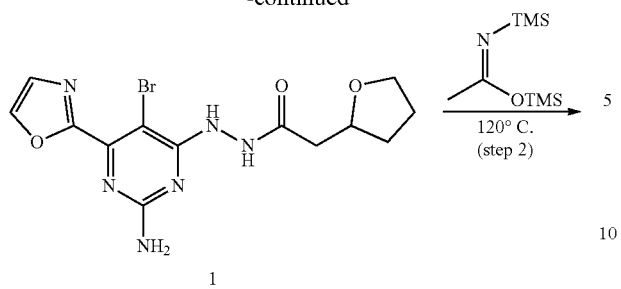

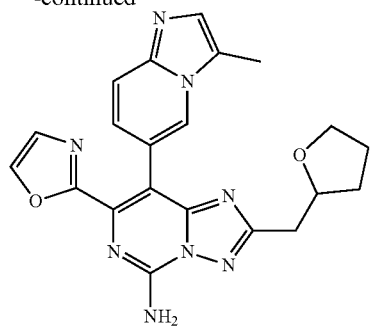

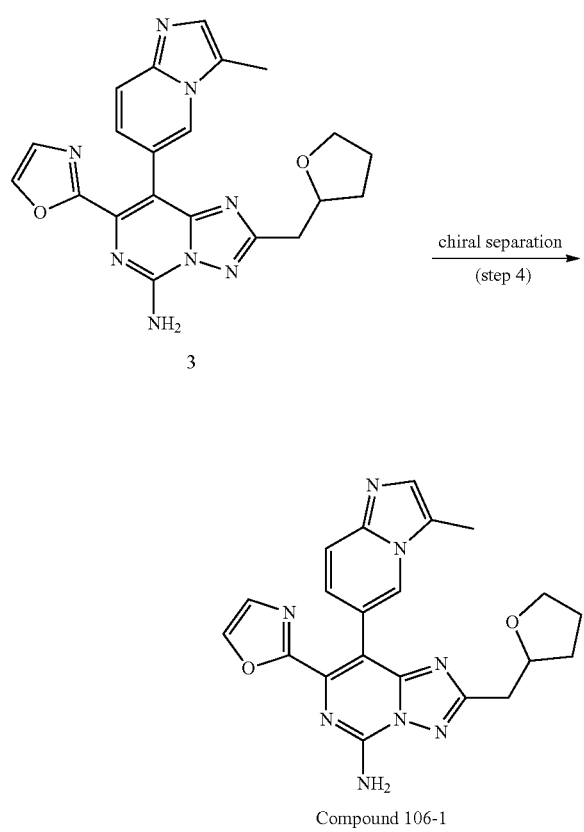

Compound 106-1

Step 1. N'-(2-amino-5-bromo-6-(oxazol-2-yl)pyrimidin-4-yl)-2-(tetrahydrofuran-2-yl)acetohydrazide To a stirred solution of 5-bromo-4-hydrazinyl-6-(1,3-oxazol-2-yl)pyrimidin-2-amine (600 mg, 2.213 mmol, 1 equiv) and 2-(oxolan-2-yl)acetic acid (288.06 mg, 2.213 mmol, 1.00 equiv) in DMF was added DIEA (858.19 mg, 6.640 mmol, 3.00 equiv), T$_3$P (1408.51 mg, 4.427 mmol, 2.00 equiv) dropwise at 0° C. under air atmosphere. The resulting mixture was stirred at room temperature for 4 hours. The resulting mixture was concentrated under vacuum. The residue was purified by Prep-TLC (CH$_2$Cl$_2$/MeOH 20:1) to afford N-[2-amino-5-bromo-6-(1,3-oxazol-2-yl)pyrimidin-4-yl]-2-(oxolan-2-yl)acetohydrazide (500 mg, 58.95%) as a yellow solid. LCMS: m/z (ESI), [M+H]$^+$=385.0. $^1$H-NMR (400 MHz, DMSO-d$_6$) δ 1.54-1.65 (1H, m), 1.85 (2H, hept), 2.00 (1H, dq), 2.30 (1H, dd), 2.46 (1H, t), 3.59 (1H, p), 3.76 (1H, q), 4.13 (1H, h), 6.32-6.72 (1H, m), 7.46 (1H, s), 8.28 (1H, s), 9.39 (1H, d).

Step 2. 8-bromo-7-(oxazol-2-yl)-2-((tetrahydrofuran-2-yl)methyl)-[1,2,4]triazolo[1,5-f]pyrimidin-5-amine Into a 40 mL vial were added N-[2-amino-5-bromo-6-(1,3-oxazol-2-yl)pyrimidin-4-yl]-2-(oxolan-2-yl)acetohydrazide (500 mg, 1.305 mmol, 1 equiv) and (Z)-(trimethylsilyl N-(trimethylsilyl)ethanimidate) (20 mL) at room temperature. The resulting mixture was stirred for 12 hours at 120° C. under air atmosphere. The resulting mixture was concentrated under reduced pressure. The residue was purified by Prep-TLC (CH$_2$Cl$_2$/MeOH 20:1) to afford 8-bromo-7-(1,3-oxazol-2-yl)-2-[(oxolan-2-yl)methyl]-[1,2,4]triazolo[1,5-c]pyrimidin-5-amine (340 mg, 71.35%) as a yellow solid. LCMS: m/z (ESI), [M+H]$^+$=365.0. $^1$H-NMR (400 MHz, DMSO-d$_6$) δ 1.66 (1H, ddt), 1.78-1.96 (2H, m), 1.97-2.13 (1H, m), 2.90-3.11 (2H, m), 3.62 (1H, td), 3.78 (1H, td), 4.32 (1H, p), 7.52 (1H, s), 8.25 (2H, s), 8.35 (1H, s).

Step 3. 8-(3-methylimidazo[1,2-a]pyridin-6-yl)-7-(oxazol-2-yl)-2-((tetrahydrofuran-2-yl)methyl)-[1,2,4]triazolo[1,5-f]pyrimidin-5-amine Into a 40 mL vial were added 8-bromo-7-(1,3-oxazol-2-yl)-2-[(oxolan-2-yl)methyl]-[1,2,4]triazolo[1,5-c]pyrimidin-5-amine (246 mg, 0.674 mmol, 1 equiv) and [3-methylimidazo[1,2-a]pyridin-6-yl]boronic acid (296.36 mg, 1.684 mmol, 2.50 equiv), Pd(dppf)Cl$_2$ (98.58 mg, 0.135 mmol, 0.2 equiv), K$_3$PO$_4$ (428.96 mg, 2.021 mmol, 3.0 equiv) in dioxane (20 mL)/water (3 mL) at room temperature. The resulting mixture was stirred for 15 hours at 100° C. under nitrogen atmosphere, and then concentrated under vacuum. The residue was purified by Prep-TLC (CH₂Cl₂/MeOH 20:1) to afford 8-[3-methylimidazo[1,2-a]pyridin-6-yl]-7-(1,3-oxazol-2-yl)-2-[(oxolan-2-yl)methyl]-[1,2,4]triazolo[1,5-c]pyrimidin-5-amine (100 mg, 35.65%) as a yellow solid. LCMS: m/z (ESI), [M+H]⁺=417.3. ¹H-NMR (400 MHz, DMSO-d₆) δ 1.63 (1H, dq), 1.82 (2H, tq), 2.00 (1H, dq), 2.39 (3H, s), 2.97 (2H, qd), 3.58 (1H, q), 3.75 (1H, q), 4.25 (1H, p), 7.10 (1H, dd), 7.26 (1H, s), 7.40 (1H, d), 7.48-7.57 (1H, m), 8.16 (1H, s), 8.17-8.41 (3H, m).

Step 4. 8-(3-methylimidazo[1,2-a]pyridin-6-yl)-7-(oxazol-2-yl)-2-((tetrahydrofuran-2-yl)methyl)-[1,2,4]triazolo[1,5-f]pyrimidin-5-amine (Ex.106-1) and 8-(3-methylimidazo[1,2-a]pyridin-6-yl)-7-(oxazol-2-yl)-2-((tetrahydrofuran-2-yl)methyl)-[1,2,4]triazolo[1,5-f]py-rimidin-5-amine (Ex.106-2)

The crude product (60 mg) was purified by Prep-Chriral-HPLC with the following conditions (Column: Lux Su Cellulose-4, 2.12*25 cm, 5 μm; Mobile Phase A: Hex (8 mmol/L NH3.MeOH)—HPLC, Mobile Phase B: MeOH:EtOH=1:1-HPLC; Flow rate: 20 mL/min; Gradient: 50 B to 50 B in 21 min; 254/220 nm; RT1:13.027; RT2:17.308) to afford 8-(3-methylimidazo[1,2-a]pyridin-6-yl)-7-(oxazol-2-yl)-2-((tetrahydrofuran-2-yl)methyl)-[1,2,4]triazolo[1,5-f]pyrimidin-5-amine (Ex.106-1) (25 mg, 31.25%) and 8-(3-methylimidazo[1,2-a]pyridin-6-yl)-7-(oxazol-2-yl)-2-((tetrahydrofuran-2-yl)methyl)-[1,2,4]triazolo[1,5-f]pyrimidin-5-amine (Ex.106-2) (25 mg, 31.25%) as a white solid. (Ex.106-1) LCMS: m/z (ESI), [M+H]⁺=417.1. ¹H-NMR (400 MHz, MeOD-d₄) δ 1.74 (1H, ddt), 1.96 (2H, dddd), 2.08-2.20 (1H, m), 2.51 (3H, d), 2.99-3.17 (2H, m), 3.83 (2H, dtd), 4.38-4.49 (1H, m), 7.17 (1H, dd), 7.28 (1H, d), 7.41 (1H, d), 7.55 (1H, dd), 7.90 (1H, d), 8.37 (1H, t); (Ex.106-2) LCMS: m/z (ESI), [M+H]⁺=417.2. ¹H-NMR (400 MHz, MeOD-d₄) δ 1.68-2.17 (4H, m), 2.51 (3H, d), 2.99-3.18 (2H, m), 3.68-3.81 (1H, m), 3.91 (1H, q), 4.43 (1H, p), 7.18 (1H, dd), 7.28 (1H, d), 7.41 (1H, d), 7.55 (1H, dd), 7.90 (1H, d), 8.36 (1H, t).

Example 107-1/107-2

Preparation of 8-(3-methylimidazo[1,2-a]pyridin-6-yl)-7-(oxazol-2-yl)-2-((tetrahydrofuran-3-yl)methyl)-[1,2,4]triazolo[1,5-f]pyrimidin-5-amine (Cmpd. 107-1) and 8-(3-methylimidazo[1,2-a]pyridin-6-yl)-7-(oxazol-2-yl)-2-((tetrahydrofuran-3-yl)methyl)-[1,2,4]triazolo[1,5-f]pyrimidin-5-amine (Cmpd. 107-2)

SCHEME 50

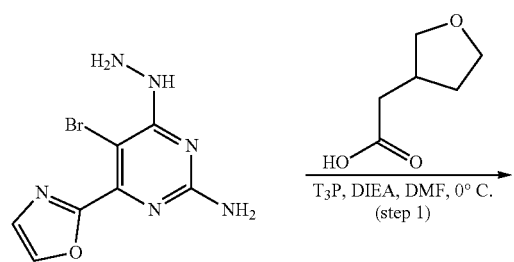

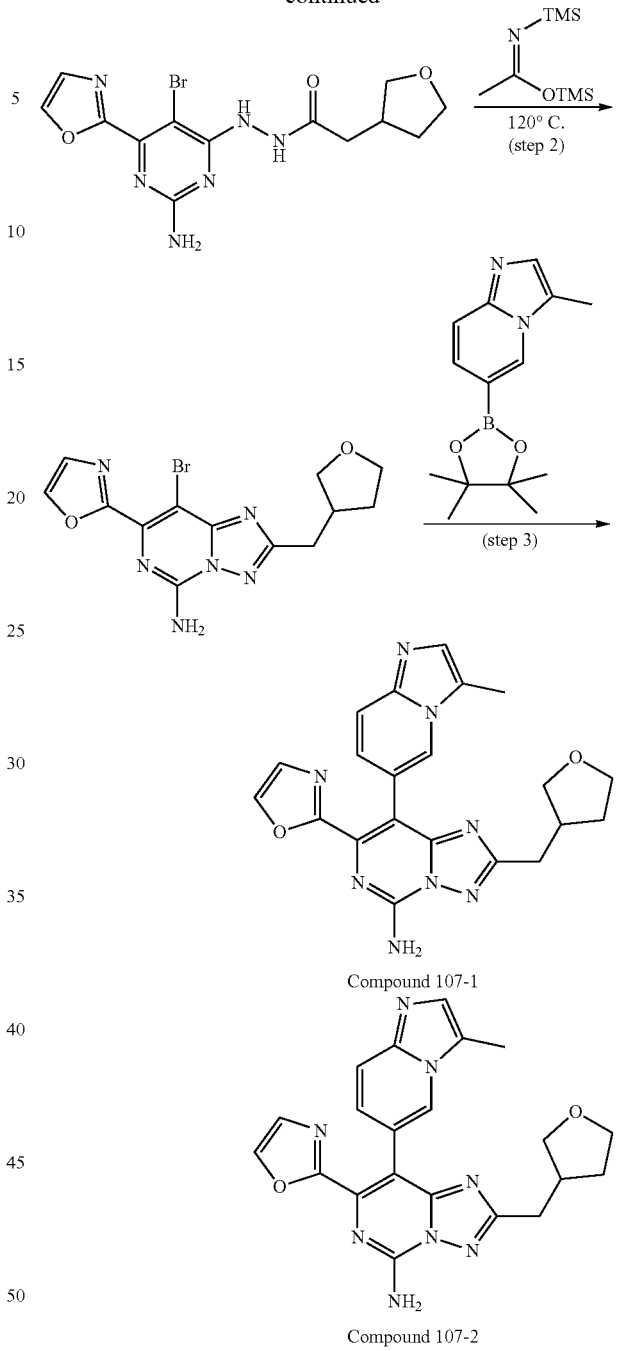

Step 1. N-[2-amino-5-bromo-6-(1,3-oxazol-2-yl)pyrimidin-4-yl]-2-(oxolan-3-yl)acetohydrazide Into a 100 mL 3-necked round-bottom flask were added 5-bromo-4-hydrazinyl-6-(1,3-oxazol-2-yl)pyrimidin-2-amine (400 mg, 1.476 mmol, 1 equiv) and DMF at room temperature. To the above mixture was added T₃P (1878.02 mg, 5.902 mmol, 4 equiv) and DIEA (953.55 mg, 7.378 mmol, 5 equiv) dropwise over 1 min at 0° C. To the above mixture was added 2-(oxolan-3-yl)acetic acid (193 mg, 1.483 mmol, 1.01 equiv) dropwise over 5 min at 0° C. The resulting mixture was stirred for additional 1 hour at −3° C. The resulting mixture was concentrated under reduced pressure. The resulting mixture was washed with 1×12 mL of PE. The precipitated solids were collected by filtration and washed with EtOAc (1×4 mL). This resulted in N-[2-amino-5-bromo-6-(1,3-oxazol-2-yl)pyrimidin-4-yl]-2-(oxolan-3-yl)acetohydrazide (1000 mg, 159.16%, crude) as a yellow oil. LCMS: m/z (ESI), [M+H]⁺=385.0.

Step 2. 8-bromo-7-(1,3-oxazol-2-yl)-2-[(oxolan-3-yl)methyl]-[1,2,4]triazolo[1,5-c]pyrimidin-5-amine Into a 50 mL round-bottom flask were added N-[2-amino-5-bromo-6-(1,3-oxazol-2-yl)pyrimidin-4-yl]-2-(oxolan-3-yl)acetohydrazide (2 g, 5.219 mmol, 1 equiv) and (Z)-(trimethylsilyl N-(trimethylsilyl)ethanimidate) (8 mL) at room temperature. The resulting mixture was stirred for 2 hours at 120° C. under air atmosphere. The mixture was allowed to cool down to 35° C. The resulting mixture was diluted with MeOH (10 mL). The resulting mixture was filtered. This resulted in 8-bromo-7-(1,3-oxazol-2-yl)-2-[(oxolan-3-yl)methyl]-[1,2,4]triazolo[1,5-c]pyrimidin-5-amine (600 mg, 30.82%) as a dark yellow solid. LCMS: m/z (ESI), [M+H]⁺=365.1 ¹H NMR (300 MHz, DMSO-d₆,) δ 1.55-1.77 (2H, m), 2.00-2.09 (1H, m), 2.62-2.77 (1H, m), 2.90 (2H, d), 3.41-3.46 (1H, m), 3.58-3.71 (1H, m), 3.71-3.88 (2H, m), 7.51 (1H, d), 8.20 (2H, s), 8.34 (1H, d).

Step 3. 8-(3-methylimidazo[1,2-a]pyridin-6-yl)-7-(oxazol-2-yl)-2-((tetrahydrofuran-3-yl)methyl-[1,2,4]triazolo[1,5-f]pyrimidin-5-amine (Cmpd. 107-1) and 8-(3-methylimidazo[1,2-a]pyridin-6-yl)-7-(oxazol-2-yl)-2-((tetrahydrofuran-3-yl)methyl)-[1,2,4]triazolo[1,5-f]pyrimidin-5-amine (Cmpd. 107-2)

To a stirred mixture of 8-bromo-7-(1,3-oxazol-2-yl)-2-[(oxolan-3-yl)methyl]-[1,2,4]triazolo[1,5-c]pyrimidin-5-amine (400 mg, 1.095 mmol, 1 equiv) and [3-methylimidazo[1,2-a]pyridin-6-yl]boronic acid (385.51 mg, 2.191 mmol, 2.00 equiv) in solvents (dioxane:H2O=10:1) were added Pd(dppf)Cl₂ (160.29 mg, 0.219 mmol, 0.2 equiv) and K₃PO₄ (813.75 mg, 3.834 mmol, 3.50 equiv) in portions at room temperature under air atmosphere. The resulting mixture was stirred for overnight at 100° C. under nitrogen atmosphere. The resulting mixture was concentrated under reduced pressure. The aqueous layer was extracted with EtOAc (3×20 mL). The residue was purified by reverse flash chromatography with the following conditions: column, C18 silica gel; mobile phase, ACN in water, 50% to 100% gradient in 20 min; detector, UV 254 nm. The crude product was purified by prep Chiral HPLC with the following conditions (Column: CHTRALPAK IG, 2.0 cm I.D*25 cm L (5 μm); Mobile Phase A: Hex:DCM=3:1(10 mM NH₃-MEOH)— HPLC, Mobile Phase B: EtOH—HPLC; Flow rate: 20 mL/min; Gradient: 50 B to 50 B in 36 min; 220/254 nm; RT 1:16.167; RT 2:23.294) to afford 8-(3-methylimidazo[1,2-a]pyridin-6-yl)-7-(oxazol-2-yl)-2-((tetrahydrofuran-3-yl)methyl)-[1,2,4]triazolo[1,5-f]pyrimidin-5-amine (50 mg, 49.70%) as a grey solid and 8-(3-methylimidazo[1,2-a]pyridin-6-yl)-7-(oxazol-2-yl)-2-((tetrahydrofuran-3-yl)methyl)-[1,2,4]triazolo[1,5-f]pyrimidin-5-amine (50 mg, 49.70%) as a grey solid. (Ex.107-1) LCMS: m/z (ESI), [M+H]⁺=417. ¹H-NMR (300 MHz, Methanol-d₄) δ 1.67-1.84 (1H, m), 2.06-2.23 (1H, m), 2.52 (3H, d), 2.80-2.85 (1H, m), 2.94-3.03 (2H, m), 3.56-3.59 (1H, m), 3.77-3.82 (1H, m), 3.85-4.00 (2H, m), 7.16-7.20 (1H, m), 7.28 (1H, d), 7.42 (1H, d), 7.54-7.57 (1H, m), 7.91 (1H, d), 8.36 (1H, d); (Ex.107-2) LCMS: m/z (ESI), [M+H]⁺=417.2 ¹H-NMR (300 MHz, Methanol-d₄) δ 1.75-1.79 (1H, m), 2.06-2.23 (1H, m), 2.51 (3H, d), 2.80-2.84 (1H, m), 2.98 (2H, d), 3.56-3.61 (1H, m), 3.77-3.80 (1H, m), 3.88-3.94 (2H, m), 7.16-7.20 (1H, m), 7.28 (1H, d), 7.42 (1H, d), 7.54-7.57 (1H, m), 7.91 (1H, d), 8.35-8.37 (1H, m).

Compound listed in the table below was prepared using methods described in Example 106-1/106-2 and 107-1/107-2.

| Example number | Structure | LCMS [M + H]⁺ | ¹H NMR |
|---|---|---|---|
| 105-1 | 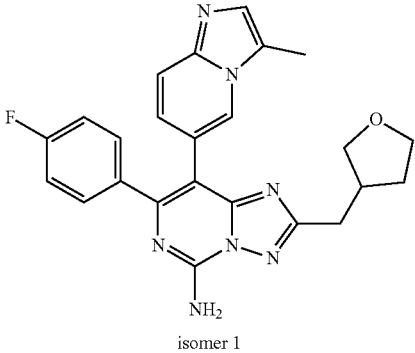 [SMILES: Cc1cnc2ccc(-c3c(-c4ccc(F)cc4)nc(N)n4nc(CC5CCOC5)nc34)cn12] isomer 1 | 444.3 | ¹H-NMR (300 MHz, DMSO-d₆) δ 1.63 (1H, dq), 2.01 (1H, dq), 2.32 (3H, s), 2.64 (1H, p), 2.86 (2H, d), 3.43 (1H, dd), 3.63 (1H, q), 3.73 (1H, dd), 3.81 (1H, t), 6.93 (1H, dd), 7.12 (2H, t), 7.35 (1H, s), 7.37-7.51 (3H, m), 8.04 (2H, s), 8.22 (s, 1H). |
| 105-2 | 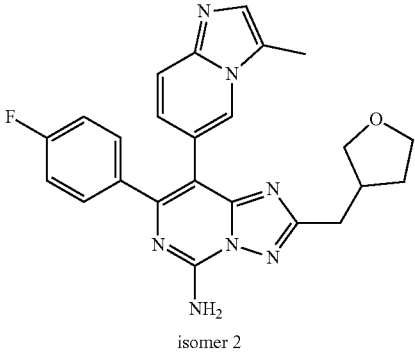 [SMILES: Cc1cnc2ccc(-c3c(-c4ccc(F)cc4)nc(N)n4nc(CC5CCOC5)nc34)cn12] isomer 2 | 444.2 | ¹H-NMR (300 MHz, DMSO-d₆) δ1.63 (1H, dq), 2.01 (1H, dq), 2.32 (3H, d), 2.64 (1H, p), 2.86 (2H, d), 3.43 (1H, dd), 3.63 (1H, q), 3.69-3.87 (2H, m), 6.93 (1H, dd), 7.12 (2H, t), 7.35 (1H, d), 7.37-7.51 (3H, m), 8.04 (2H, s), 8.18 -8.25 (1H, m). |

| Example number | Structure | LCMS [M + H]+ | ¹H NMR |
|---|---|---|---|
| 114 | 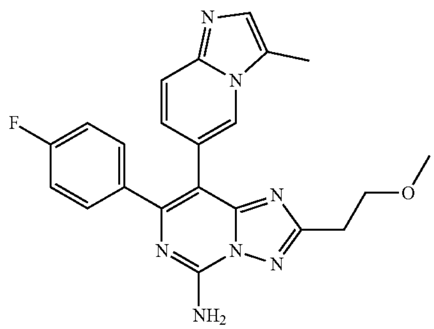 | 418.2 | ¹H-NMR (300 MHz, Methanol-d₄) δ 2.46 (3H, d), 3.12 (2H,t), 3.35 (5H, d), 3.85 (2H, t), 6.94-7.08 (3H, m), 7.33-7.45 (2H, m), 7.45-7.58 (2H, m), 8.25-8.31 (1H, m). |
| 120 | 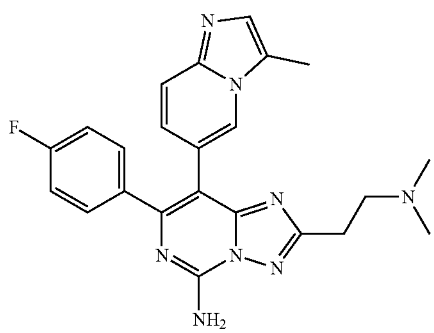 [SMILES: Cc1cnc2ccc(-c3c(-c4ccc(F)cc4)nc(N)n4nc(CCN(C)C)nc34)cn12] | 431.4 | ¹H-NMR (300 MHz, Methanol-d₄) δ 2.60 (3H, d), 3.01 (6H, s), 3.31-3.45 (2H, m), 3.70 (2H, t), 6.98-7.12 (2H, m), 7.47-7.59 (2H, m), 7.64 (1H, dd), 7.79 (1H, dd), 7.86 (1H, d), 8.76-8.83 (1H, m). |
| 122 | 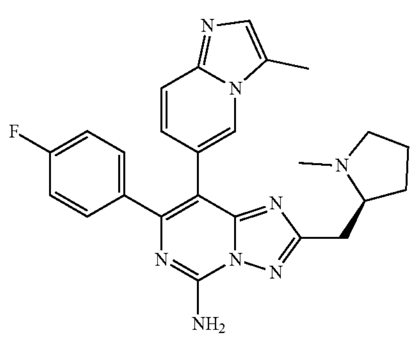 [SMILES: Cc1cnc2ccc(-c3c(-c4ccc(F)cc4)nc(N)n4nc(C[C@@H]5CCCN5C)nc34)cn12] | 457.2 | ¹H-NMR (400 MHz, DMSO-d₆) δ 1.81 (1H, s), 1.87-2.10 (2H, m), 2.29 (1H, s), 2.47 (3H, s), 2.95 (3H, s), 3.09-3.25 (2H, m), 3.53 (1H, s), 3.66 (1H, s), 3.80 (1H, s), 7.17 (2H, t), 7.48 (3H, dd), 7.94 (2H, d), 8.33 (2H, s), 8.73 (1H, s). |
| 125 | 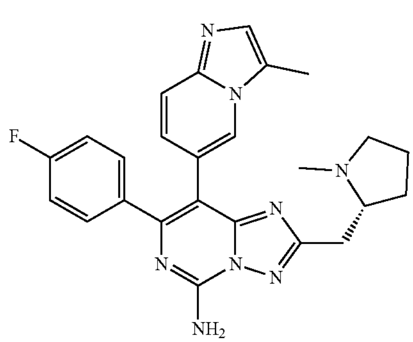 [SMILES: Cc1cnc2ccc(-c3c(-c4ccc(F)cc4)nc(N)n4nc(C[C@H]5CCCN5C)nc34)cn12] | 457.2 | ¹H-NMR (300 MHz, Methanol-d₄) δ 1.75 (3H, dd), 1.93-2.03 (1H, m), 2.26-2.34 (1H, m), 2.39-2.49 (6H, m), 2.74-2.89 (2H, m), 3.10 (1H, d), 3.22 (1H, d), 6.92-7.12 (3H, m), 7.32-7.46 (2H, m), 7.45-7.59 (2H, m), 8.28 (1H, d). |

| Example number | Structure | LCMS [M + H]+ | 1H NMR |
|---|---|---|---|
| 126 | 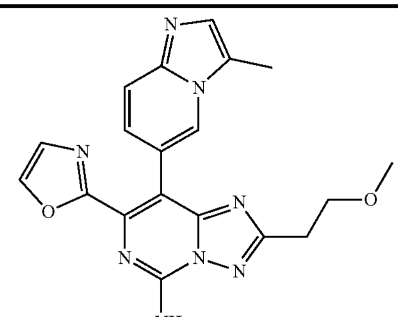 | 391.1 | 1H-NMR (400 MHz, DMSO-d6) δ 2.31-2.62 (3H, s), 3.06 (2H, dt), 3.23 (3H, s), 3.75 (2H, dt), 7.09-7.11 (1H, d), 7.26 (1H, s), 7.39 (1H, s), 7.47-7.62 (1H, d), 8.12-8.48 (4H, d) |

Example 121

Preparation of 2-(2,6-difluorobenzyl)-7-(3-methoxyazetidin-1-yl)-8-(3-methylimidazo[1,2-a]pyridin-6-yl)-[1,2,4]triazolo[1,5-c]pyrimidin-5-amine (Cmpd. 121)

SCHEME 51

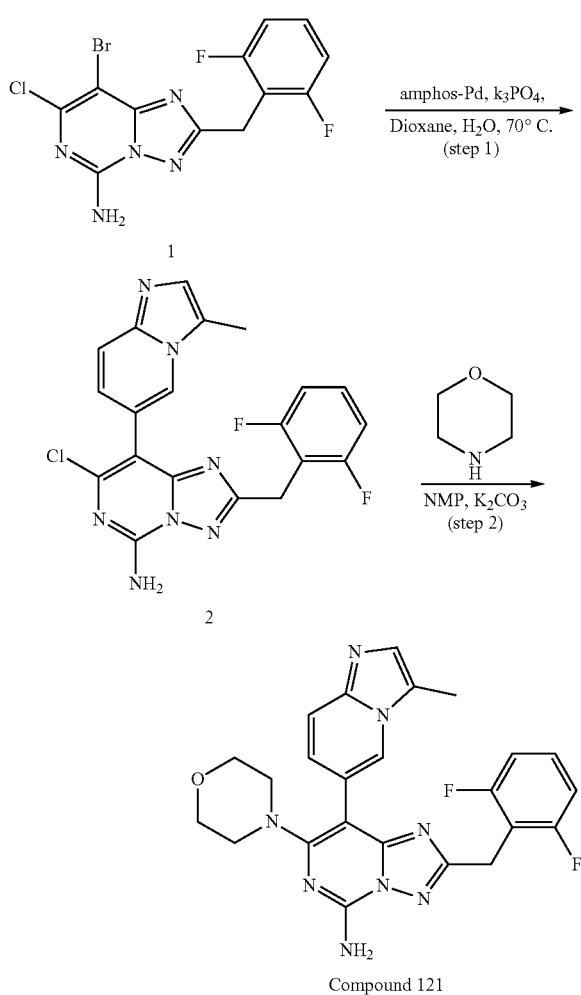

Compound 121

Step 1. 7-chloro-2-(2,6-difluorobenzyl)-8-(3-methylimidazo[1,2-a]pyridin-6-yl)-[1,2,4]triazolo[1,5-c]pyrimidin-5-amine To a stirred mixture of 8-bromo-7-chloro-2-[(2,6-difluorophenyl)methyl]-[1,2,4]triazolo[1,5-c]pyrimidin-5-amine (100 mg, 0.267 mmol, 1 equiv) and [3-methylimidazo[1,2-a]pyridin-6-yl]boronic acid (93.96 mg, 0.534 mmol, 2.00 equiv) in dioxane (5 mL) were added PdAMPHOS (18.90 mg, 0.027 mmol, 0.1 equiv), water (1 mL) and K₃PO₄ (170.01 mg, 0.801 mmol, 3 equiv) in portions at room temperature under nitrogen atmosphere. The resulting mixture was stirred for additional overnight at 70° C. The mixture was allowed to cool down to room temperature. The resulting solid was collected by filtration and washed with EtOAc (5 mL), dried under vacuum to afford 7-chloro-2-[(2,6-difluorophenyl)methyl]-8-[3-methylimidazo[1,2-a]pyridin-6-yl]-[1,2,4]triazolo[1,5-c]pyrimidin-5-amine (60 mg, 52.78%) as a white solid. LCMS: m/z (ESI), [M+H]+=426.2.

Step 2. 2-(2,6-difluorobenzyl)-7-(3-methoxyazetidin-1-yl)-8-(3-methylimidazo[1,2-a]pyridin-6-yl)-[1,2,4]triazolo[1,5-c]pyrimidin-5-amine (Cmpd. 121)

To a stirred mixture of 7-chloro-2-[(2,6-difluorophenyl)methyl]-8-[3-methylimidazo[1,2-a]pyridin-6-yl]-[1,2,4]triazolo[1,5-c]pyrimidin-5-amine (100 mg, 0.235 mmol, 1 equiv) and azetidine (26.82 mg, 0.470 mmol, 2 equiv) in NMP (5 mL) were added K₂CO₃ (64.91 mg, 0.470 mmol, 2 equiv) in portions at room temperature under air atmosphere. The resulting mixture was stirred for additional overnight at 100° C. The mixture was allowed to cool down to room temperature. The resulting mixture was filtered, and the filter cake was washed with MeOH (3×20 mL). The filtrate was concentrated under reduced pressure. The crude product (100 mg) was purified by Prep-HPLC with the following conditions (Column: XBridge Prep OBD C18 Column 30×150 mm 5 µm; Mobile Phase A: Water (0.05% N₃H2O), Mobile Phase B: ACN; Flow rate: 60 mL/min; Gradient: 33% B to 44% B in 7 min; 254; 220 nm; Rt: 6.45 min) to afford 7-(azetidin-1l-yl)-2-[(2,6-difluorophenyl)methyl]-8-[3-methylimidazo[1,2-a]pyridin-6-yl]-[1,2,4]triazolo [1,5-c]pyrimidin-5-amine (10.6 mg, 10.010) as a white solid. LCMS: m/z (ESI), [M+H]+=477.4. 1H NMR (300 MHz, DMSO-d6) δ 2.3 (3H, d), 3.1 (4H, d), 3.5 (4H, d), 4.1 (2H, s), 7.0 (2H, t), 7.3 (2H, d), 7.5 (2H, d), 7.7 (2H, s), 8.4 (1H, s).

Compound listed in the table below was prepared using methods described in Example 121.

| Example number | Structure | LCMS [M + H]+ | 1H NMR |
|---|---|---|---|
| 108 | 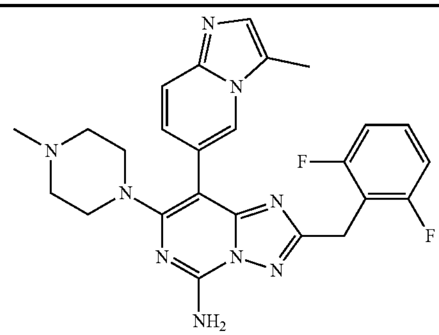 | 490.3 | 1H-NMR (400 MHz, DMSO-d6) δ 2.1 (3H, s), 2.3 (4H, t), 2.4 (3H, s), 3.1-3.3 (4H, m), 4.1 (2H, s), 7.1 (2H, q), 7.3-7.4 (2H, m), 7.5-7.6 (2H, m), 7.7 (2H, s), 8.5 (1H, s) |
| 109 | 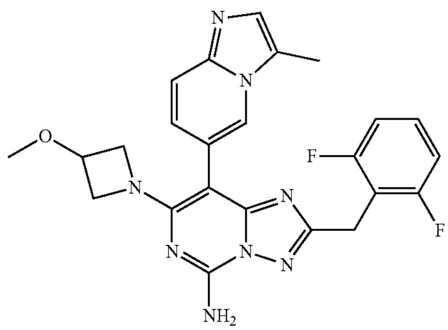 [SMILES: COC1CN(c2nc(N)n3nc(Cc4c(F)cccc4F)nc3c2-c2ccc3ncc(C)n3c2)C1] | 477.2 | 1H-NMR (400 MHz, DMSO-d6) δ 2.4 (3H, d), 3.1 (3H, s), 3.6 (2H, dd), 3.9 (2H, dd), 4.1 (3H, s), 7.1 (2H, t), 7.2 (1H, dd), 7.3-7.4 (2H, m), 7.5 (1H, dd), 7.7 (2H, s), 8.2-8.2 (1H, m) |
| 123 | 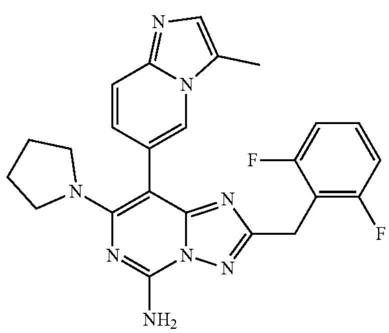 [SMILES: Cc1cnc2ccc(-c3c(N4CCCC4)nc(N)n4nc(Cc5c(F)cccc5F)nc34)cn12] | 461.2 | 1H-NMR (400 MHz, DMSO-d6) δ 1.6-1.8 (4H, m), 2.4 (3H, s), 3.2 (4H, d), 4.0 (2H, s), 7.1 (2H, t), 7.2 (1H, dd), 7.3-7.4 (2H, m), 7.4-7.5 (3H, m), 8.2 (1H, s) |
| 124 | 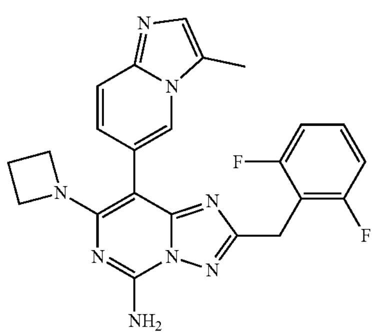 [SMILES: Cc1cnc2ccc(-c3c(N4CCC4)nc(N)n4nc(Cc5c(F)cccc5F)nc34)cn12] | 447.3 | 1H-NMR (400 MHz, DMSO-d6) δ 2.1 (2H, p), 2.4 (3H, s), 3.7 (4H, t), 4.0 (2H, s), 7.1 (2H, t), 7.2 (1H, dd), 7.3-7.4 (2H, m), 7.5 (1H, d), 7.6 (2H, s), 8.2 (1H, s) |

Example 127: Binding Affinities to Different Adenosine Receptors

Binding affinity and specificities of the compounds against different subtype of human adenosine receptors (hA1, hA2A, hA2B and hA3) were characterized with cell membrane chromatography binding analysis.

The compounds at different concentrations were incubate with hA1 membrane (from PerkinElmer) and [3H]-8-Cyclopentyl-1,3-dipropylxanthine (DPCPX) for 50 min at 25° C., meanwhile 100 μL 0.5% PEI solution was added into UNFILTER-96 GF/B filter plate for 60 min at 4° C., then UNIFILTER-96 GF/B filter plate was washed twice with 50 ml wash buffer, the membrane mix was transferred into UNIFILTER-96 GF/B filter plate, and the filter plate was washed 4 times before incubated at 55° C. for 10 min. At last, 40 L ULTIMA GOLD was added into each well, and CPM was read by TopCount.

The compounds at different concentrations were incubate with hA2a membrane (from PerkinElmer) and [3H]-CGS21680 for 90 min at 25° C., meanwhile 100 μL 0.5% PEI solution was added into UNFILTER-96 GF/B filter plate for 60 min at 4° C., then UNIFILTER-96 GF/B filter plate was washed twice with 50 ml wash buffer, the membrane mix was transferred into UNIFILTER-96 GF/B filter plate, and the filter plate was washed 4 times before incubated at 55° C. for 10 min. At last, 40 L ULTIMA GOLD was added into each well, and CPM was read by TopCount.

The compounds at different concentrations were incubate with hA2b membrane (from PerkinElmer) and [$^3$H]-DPCPX for 60 min at 27° C., and the binding reactions were stopped by rapid filtration through 0.5% BSA coated UNIFILTER-96 GF/C plates using cell harvester. The filter plates were then washed three times with ice cold wash buffer, and dried at 37° C. for 120 min. At last, 50 L of scintillation cocktail was added into each well, and CPM was read by TopCount.

The compounds at different concentrations were incubate with hA3 membrane (from PerkinElmer) and [$^{121}$1]-AB-MECA for 60 min at 27° C., the binding reactions were stopped by rapid filtration through 0.50% BSA coated UNIFILTER-96 GF/C plates using cell harvester. The filter plates were then washed three times with ice cold wash buffer, and dried at 37° C. for 120 min. At last, 50 L of scintillation cocktail was added into each well, and CPM was read by TopCount.

Binding affinity and specificities of the exemplary compounds against human A1, A2a, A2b and A3 receptors are shown in Table 3 below. The empty boxes in the tables below indicate data not available.

TABLE 3

Binding Affinities of Exemplary Compounds

| Cmpd. number | Binding Affinity (IC$_{50}$ nM) | | | |
| --- | --- | --- | --- | --- |
| | hA2a | hA1 | hA2b | hA3 |
| 1 | 2.3 | 1.1 | 2.3 | 2873 |
| 9 | 2.1 | 0.2 | | |
| 10 | 0.9 | 2.3 | 0.1 | 4771 |
| 20 | 2.8 | 4.0 | 8.7 | 1067 |
| 21 | 20 | 43 | | |
| 22 | 12 | 6.8 | | |
| 25 | 1.4 | 7.9 | | |
| 31 | 3.0 | 137 | | |
| 32 | 5.5 | 3.4 | | |
| 34 | 2.8 | 0.8 | 0.4 | 10000 |
| 37 | 6.3 | 4.0 | | |
| 41 | 3.4 | 2.2 | | |
| 55 | 4.0 | 0.1 | 2.8 | 7294 |
| 61 | 4.2 | 1.7 | | |
| 62 | 5.2 | 5.1 | | |
| 66 | 7.2 | 46 | | |
| 70 | 4.1 | 0.8 | | |
| 77 | 3.6 | 1.4 | | |
| 85 | 5.5 | 5.4 | | |
| 86 | 8.3 | 21 | | |
| 94 | 3.5 | 52 | | |

Example 128: FLIPR™ and cAMP Inhibition Assay hADORA1/CHO (hA1 expressing) cells (Genscript) were plated at 1×10$^4$ cells/well into 384-well polystyrene plates one day before starting the experiment. On the day of experiment, the supernatant was discard and replaced with 40 L of dye (FLIPR calcium 5 Assay Kit) per well and the plates were incubated for 60 mins at 37° C. plus 5% CO$_2$. Then testing compounds were added at different concentrations for FLIPR™ inhibition assay. After a 400 s incubation with compound, 10 M adenosine was added into the cells, and the signal was captured by FLIPR.

hA2a/CHO, hA2b/CHO and mA2a/CHO (Genscript) were plated at 5×10$^3$ cells/well into 384-well polystyrene plates at the day of experiment. Compounds were pre-incubated with cells for 30 min at 37° C., 5% CO$_2$. Then 10 M adenosine was added to the cells and incubated for 30 min at 37° C., 5% CO$_2$. Detection reagent (CISBIO) was added and the plates were incubated for 60 min at room temperature. The signal was captured by Envision.

FLIPR™ and cAMP inhibition activities of exemplary compounds in different adenosine receptor over-expressing cell lines are shown in Table 4 below.

TABLE 4

FLIPR and cAMP Inhibitory Activity of Exemplary Compounds

| Cmpd. number | cAMP & FLIPR IC$_{50}$ (nM) | | | | |
| --- | --- | --- | --- | --- | --- |
| | hA2a | hA2b | mA2a | hA1 | hA3 |
| 1 | 4.7 | 117 | 10 | 8.5 | >10000 |
| 2 | 59 | 73 | 59 | 23 | >10000 |
| 3 | 56 | 65 | 70 | 42 | >10000 |
| 4 | 52 | 254 | 24 | 511 | |
| 5 | 1.9 | #N/A | 1.5 | #N/A | |
| 6 | 63 | 17 | 182 | 21 | >10000 |
| 7 | 102 | 1601 | 209 | 23 | >10000 |
| 8 | 59 | 2951 | 98 | 162 | >10000 |
| 9 | 0.6 | 56 | 0.8 | 20 | >10000 |
| 10 | 0.2 | 4.4 | 0.4 | 42 | >10000 |
| 11 | 34 | 219 | 78 | 9.7 | >10000 |
| 12 | 46 | 5003 | 316 | 214 | >10000 |
| 13 | 11 | 81 | 56 | 153 | >10000 |
| 14 | 6.9 | 2243 | 18 | 97 | >10000 |
| 15 | 46 | 582 | 88 | 27 | |
| 16 | 174 | 125 | 758 | 205 | |
| 17 | 43 | 4794 | 51 | 22 | |
| 18 | 1.2 | 511 | 9.6 | 49 | >10000 |
| 19 | 102 | 303 | 88 | 23 | >10000 |
| 20 | 3.5 | 84 | 4.9 | 34 | >10000 |
| 21 | 36 | 270 | 41 | 113 | >10000 |
| 22 | 8.2 | 168 | 12 | 25 | |
| 23 | 7.7 | 2055 | 2.9 | 26 | |
| 24 | 58 | 631 | 162 | 12 | |
| 25 | 20 | 582 | 30 | 21 | |
| 26 | 15 | 457 | 34 | 33 | |
| 27 | 139 | 10000 | 245 | 112 | |
| 28 | 158 | 6420 | 217 | 1146 | |
| 29 | 3.8 | 91 | 5.1 | 4.3 | |
| 30 | 5.9 | 160 | 25 | 16 | |
| 31 | 14 | 80 | 51 | 188 | |
| 32 | 0.9 | 19 | 5.4 | 28 | |
| 33 | 18 | 10000 | 109 | 6935 | |
| 34 | 2.1 | 58 | 3.4 | 12 | |
| 35 | 27 | 173 | 23 | 35 | |
| 36 | 20 | 408 | 31 | 45 | |
| 37 | 1.8 | 12 | 7.3 | 12 | |
| 38 | 41 | 38 | 263 | 8.6 | |
| 39 | 18 | 235 | 39 | 15 | |
| 40 | 5.2 | 72 | 15 | 18 | |
| 41 | 70 | 259 | 189 | 17 | |
| 42 | 7.9 | 206 | 13 | 6.6 | |
| 43 | 19 | 12 | 41 | 24 | |
| 44 | 4.3 | 97 | 5.9 | 13 | |
| 55 | 0.7 | 101 | 0.8 | 13 | |
| 56 | 22 | 142 | 36 | 34 | |
| 57 | 120 | 399 | 219 | 76 | |
| 58 | 29 | 2293 | 47 | 25 | |
| 59 | 98 | 1554 | 179 | 37 | |
| 60 | 56 | 3303 | 16 | 40 | |
| 61 | 28 | 122 | 42 | 25 | |
| 62 | 184 | 602 | 318 | 27 | |
| 63 | 122 | 1558 | 125 | 250 | |
| 64 | 68 | 742 | 137 | 97 | |
| 65 | 0.2 | 14 | 0.6 | 17 | |
| 66 | 31 | 109 | 346 | 69 | |
| 67 | 22 | 3199 | 21 | 13 | |
| 68 | 3.2 | 614 | 12 | 29 | |

TABLE 4-continued

FLIPR and cAMP Inhibitory Activity of Exemplary Compounds

| Cmpd. number | cAMP & FLIPR IC$_{50}$ (nM) | | | |
|---|---|---|---|---|
| | hA2a | hA2b | mA2a | hA1 | hA3 |
| 69 | 0.1 | 4.69 | 0.3 | 22 | |
| 70 | 5.5 | 68 | 13 | 14 | |
| 71 | 11 | 102 | 6.4 | 8.9 | |
| 72 | 37 | 1049 | 107 | 9.7 | |
| 73 | 0.1 | 4.80 | 0.4 | 11 | |
| 74 | 0.8 | 14 | 1.2 | 11 | |
| 75 | 1.7 | 38 | 17 | 31 | |
| 76 | 7.9 | 253 | 19 | 8.8 | |
| 77 | 6.7 | 51 | 17 | 13 | |
| 78 | 135 | 1262 | 324 | 1157 | |
| 79 | 0.7 | 45 | 0.9 | 28 | |
| 80 | 3.6 | 186 | 4.9 | 25 | |
| 81 | 49 | 9086 | 164 | 5323 | |
| 82 | 25 | 2909 | 63 | 2643 | |
| 83 | 18 | 10000 | 76 | 923 | |
| 84 | 60 | 10000 | 428 | 2724 | |
| 85 | 15 | 48 | 11 | 27 | |
| 86 | 71 | 83 | 48 | 59 | |
| 87 | 27 | 5801 | 90 | 4046 | |
| 88 | 0.7 | 47 | 2.6 | 110 | |
| 89 | 0.4 | 82 | 1.3 | 132 | |
| 90 | 1.8 | 48 | 3.5 | 72 | |
| 91 | 2.6 | 102 | 5.1 | 206 | |
| 92 | 8.0 | 680 | 11 | 13 | |
| 93 | 103 | 1112 | 170 | 779 | |
| 94 | 7.7 | 94 | 20 | 41 | |
| 95 | 3.7 | 241 | 8.9 | 27 | |
| 96 | 25 | 3804 | 123 | 681 | |
| 97 | 47 | 1724 | 120 | 19 | |
| 98 | 88 | 1536 | 224 | 333 | |
| 99 | 0.5 | 21 | 0.8 | 3.5 | |
| 100 | 1.2 | 38 | 3.5 | 11.8 | |
| 101 | 8.2 | 202.9 | 58.1 | 6.6 | |
| 102 | 2.6 | 121.0 | 11.2 | 27.2 | |
| 103 | 8.3 | >8109 | 30.3 | 263.7 | |
| 104 | 1.0 | 1631.3 | 5.7 | 34.1 | |
| 105-1 | 0.1 | 47.5 | 1.0 | 14.0 | |
| 105-2 | 0.1 | 71.6 | 1.0 | 11.8 | |
| 106-1 | 0.5 | | | 53.2 | |
| 106-2 | 0.2 | | | 34.9 | |
| 107-1 | 0.5 | 416.5 | 32.7 | 54.6 | |
| 107-2 | 0.5 | 473.2 | 27.7 | 34.5 | |
| 108 | 42.3 | | | 131 | |
| 109 | 3.5 | | | 30.6 | |
| 110 | 794.9 | >10000 | 7192 | 85.9 | |
| 112-1 | 91.6 | | | 965.5 | |
| 112-2 | 3.2 | | | 119.5 | |
| 113-1 | 42.4 | | | 3274 | |
| 113-2 | 73.0 | | | >10000 | |
| 114 | 0.2 | 40.9 | 0.4 | 5.7 | |
| 116 | 0.2 | 12.2 | 0.2 | 7.9 | |
| 117 | 0.2 | 16.4 | 0.5 | 9.7 | |
| 118 | 227.9 | | | >8093 | |
| 119 | 1.9 | | | 48.6 | |
| 120 | 0.6 | 146.3 | 9.5 | 66.7 | |
| 121 | 0.2 | 44.5 | 2.9 | 71.5 | |
| 122 | 0.3 | 93.5 | 2.6 | 67.7 | |
| 123 | 0.4 | 80.5 | 16.5 | 42.4 | |
| 124 | 0.1 | 23.3 | 3.9 | 16.0 | |
| 125 | 0.4 | | | 34.1 | |
| 126 | 1.1 | | | 83.6 | |

What is claimed is:

1. A compound of Formula (Ia):

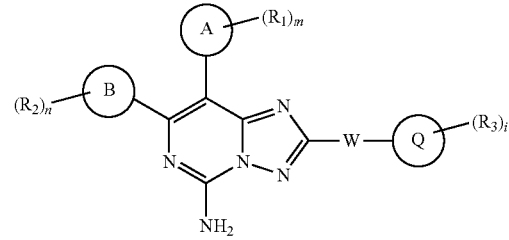

Formula (Ia)

or a pharmaceutically acceptable salt thereof, wherein, ring A is

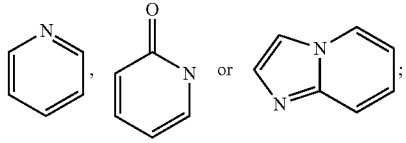

ring B is

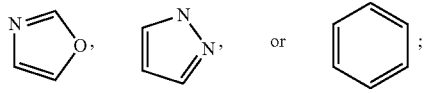 [SMILES: c1cocn1 ; c1cn[nH]c1 ; c1ccccc1]

ring Q is

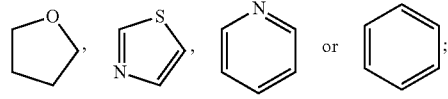

W is methylene,
each $R_1$ is independently amino, or $C_{1-12}$ alkyl;
each $R_2$ is independently selected from halogen;
each $R_3$ is independently selected from halogen; and
m is 0, 1, or 2;
n is 0, or 1;
i is 0, or 1.

2. The compound of claim 1, wherein each $R_1$ is independently amino, methyl, or ethyl.

3. The compound of claim 1, wherein each $R_2$ is independently fluoro, or chloro.

4. The compound of claim 1, wherein each $R_3$ is independently fluoro, or chloro.

5. The compound of claim 1, wherein the compound is selected from the group consisting of:
8-(2,6-dimethylpyridin-4-yl)-7-(4-fluorophenyl)-2-[(3-fluoropyridin-2-yl)methyl]-[1,2,4]triazolo[1,5-c]pyrimidin-5-amine,
2-((3-fluoropyridin-2-yl)methyl)-8-(imidazo[1,2-a]pyridin-6-yl)-7-(oxazol-2-yl)-[1,2,4]triazolo[1,5-c]pyrimidin-5-amine, 5-[5-amino-7-(4-fluorophenyl)-2-[(1,3-thiazol-2-yl)methyl]-[1,2,4]triazolo[1,5-c]pyrimidin-8-yl]-1-methyl-1,2-dihydropyridin-2-one, 8-(2-amino-6-methylpyridin-4-yl)-2-(2,6-difluorobenzyl)-7-(oxazol-2-yl)-[1,2,4]triazolo[1,5-c]pyrimidin-5-amine, 2-[(3-fluoropyridin-2-yl)methyl]-8-[imidazo[1,2-a]pyridin-6-yl]-7-(2H-1,2,3-triazol-2-yl)-[1,2,4]triazolo[1,5-c]pyrimidin-5-amine, 8-(3-methylimidazo[1,2-a]pyridin-6-yl)-7-(oxazol-2-yl)-2-((tetrahydrofuran-3-yl)methyl)-[1,2,4]triazolo[1,5-c]pyrimidin-5-amine (isomer 1), 8-(3-methylimidazo[1,2-a]pyridin-6-yl)-7-(oxazol-2-yl)-2-((tetrahydrofuran-3-yl)methyl)-[1,2,4]triazolo[1,5-c]pyrimidin-5-amine (isomer 2).

6. A pharmaceutical composition comprising one or more compounds according to claim 1, and a pharmaceutically acceptable carrier.

7. A compound of formula (I), or a pharmaceutically acceptable salt thereof, as claimed in claim 1, in combination with immunotherapeutics or chemotherapeutics.

8. The compound of claim 7, wherein said immunotherapeutics is selected from the group consisting of anti-PD-1/PD-L1 antibody, anti-CTLA-4 antibody, anti-CD73 antibody, anti-CD39 antibody, anti-CCR2 antibody and any combination thereof.

9. The compound of claim 7, wherein said chemotherapeutics is selected from the group consisting of Platinum based chemotherapeutics (CISPLATIN, OXALIPLATION, Docetaxel, Paclitaxel, Doxorubicin, Etoposide, Mitoxantrone and any combination thereof.

* * * * *